United States Patent
Li et al.

(10) Patent No.: US 12,227,769 B2
(45) Date of Patent: Feb. 18, 2025

(54) METHODS AND COMPOSITIONS FOR TREATING NEGATIVE-SENSE SINGLE-STRANDED RNA VIRUS

(71) Applicants: The University of Chicago, Chicago, IL (US); Nationwide Children's Hospital, Columbus, OH (US); The Ohio State University, Columbus, OH (US)

(72) Inventors: Jianrong Li, Dublin, OH (US); Mark E. Peeples, Bexley, OH (US); Chuan He, Chicago, IL (US); Stefan Niewiesk, Dublin, OH (US); Mijia Lu, Columbus, OH (US); Miaoge Xue, Columbus, OH (US); Zijie Zhang, Chicago, IL (US); Boxuan Zhao, Palo Alto, CA (US)

(73) Assignees: The University of Chicago, Chicago, IL (US); Nationwide Children's Hospital, Columbus, OH (US); The Ohio State University, Columbus, OH (US)

( * ) Notice: Subject to any disclaimer, the term of this patent is extended or adjusted under 35 U.S.C. 154(b) by 958 days.

(21) Appl. No.: 17/309,038

(22) PCT Filed: Oct. 18, 2019

(86) PCT No.: PCT/US2019/056942
§ 371 (c)(1),
(2) Date: Apr. 16, 2021

(87) PCT Pub. No.: WO2020/081937
PCT Pub. Date: Apr. 23, 2020

(65) Prior Publication Data
US 2022/0033783 A1    Feb. 3, 2022

Related U.S. Application Data

(60) Provisional application No. 62/748,175, filed on Oct. 19, 2018.

(51) Int. Cl.
*A61K 35/76* (2015.01)
*C12N 7/00* (2006.01)

(52) U.S. Cl.
CPC .............. *C12N 7/00* (2013.01); *A61K 35/76* (2013.01); *C12N 2760/18522* (2013.01)

(58) Field of Classification Search
None
See application file for complete search history.

(56) References Cited

FOREIGN PATENT DOCUMENTS

| WO | WO 98/18324 | 5/1998 |
| WO | WO 2017/177029 | 10/2017 |

OTHER PUBLICATIONS

Gokhale et al. N6-Methyladenosine in Flaviviridae Viral RNA Genomes Regulates Infection. Cell Host & Microbe 20, 654-665, Nov. 9, 2016.*
Imam et al. N6-methyladenosine modification of hepatitis B virus RNA differentially regulates the viral life cycle. PNAS, 115(35): 8829-8834, Aug. 28, 2018.*
Gonzales-van Horn et al. Making the Mark: The Role of Adenosine Modifications in the Life Cycle of RNA Viruses. Cell Host & Microbe 21, Jun. 14, 2017, p. 661-669.*
Zhang et al. Rational Design of Human Metapneumovirus Live Attenuated Vaccine Candidates by Inhibiting Viral mRNA Cap Methyltransferase. Journal of Virology, 2014, 88(19): 11411-11429.*
"17th NSV 2018." *NSV*, Sep. 21, 2018, http://library.ctr.utexas.edu/digitized/TexasArchive/phase2/9028-01-1.pdf. Feb. 2020.
Canaani et al., "Identification and mapping of N6-methyladenosine containing sequences in simian virus 40 RNA." *Nucleic Acids Res* 1979, 6(8), 2879-99.
Collins et al., "Production of infectious human respiratory syncytial virus from cloned cDNA confirms an essential role for the transcription elongation factor from the 5' proximal open reading frame of the M2 mRNA in gene expression and provides a capability for vaccine development" *Proc Natl Acad Sci U S A* 1995, 92(25): 11563-7.
Furuichi et al., "Blocked, methylated 5'-terminal sequence in avian sarcoma virus RNA" *Nature* 1975. 257(5527), 618-20.
Gokhale et al., "N6-Methyladenosine in Flaviviridae Viral RNA Genomes Regulates Infection" *Cell Host & Microbe* 2016, 20(5), 654-665.
Hesser et al., "N6-methyladenosine modification and the YTHDF2 reader protein play cell type specific roles in lytic viral gene expression during Kaposi's sarcoma-associated herpesvirus infection." *PLoS Pathog* 2018, 14(4): e1006995, 23 pages.
International Search Report and Written Opinion issued in Corresponding PCT Application No. PCT/US2019/056942, dated Mar. 17, 2020.
Kane et al., "Inhibition of Methylation at Two Internal $N^6$-Methyladenosine Sites Caused by GAC to GAU Mutations" *The Journal of Biological Chemistry* 1987, 262(7), 3422-3427.
Kane et al., "Precise localization of m6A in Rous sarcoma virus RNA reveals clustering of methylation sites: implications for RNA processing." *Mol Cell Biol* 1985, 5(9), 2298-306.

(Continued)

*Primary Examiner* — Nianxiang Zou
(74) *Attorney, Agent, or Firm* — Norton Rose Fulbright US LLP

(57) ABSTRACT

The current disclosure relates to methods, compositions and kits for detecting modified adenosine in a target RNA molecule. Aspects relate to a method for detecting modified adenosine in a target ribonucleic acid (RNA) comprising contacting the target RNA with an adenosine deaminase enzyme (adenosine deaminase, RNA-specific) to generate a target RNA with deaminated adenosines and sequencing the target RNA with deaminated adenosines; wherein the modified adenosine is detected when the nucleotide sequence includes adenosine within a m6A motif.

25 Claims, 98 Drawing Sheets
Specification includes a Sequence Listing.

(56) References Cited

OTHER PUBLICATIONS

Kennedy et al., "Posttranscriptional m(6)A Editing of HIV-1 mRNAs Enhances Viral Gene Expression." *Cell Host Microbe* 2016, 19(5), 675-85.
Krug et al., "Influenza viral mRNA contains internal N6-methyladenosine and 5'-terminal 7-methylguanosine in cap structures." *J Virol* 1976, 20(1), 45-53.
Li, A., et al., "Cytoplasmic m6A reader YTHDF3 promotes mRNA translation." *Cell Res* 2017. 27(3): p. 444-447.
Moss et al., "5'-Terminal and internal methylated nucleosides in herpes simplex virus type 1 mRNA." *J Virol* 1977, 23(2), 234-9.
Shi, H., et al., "YTHDF3 facilitates translation and decay of N6-methyladenosinemodified RNA." *Cell Res* 2017, 27(3): p. 315-328.
Tirumuru et al., "N(6)-methyladenosine of HIV-1 RNA regulates viral infection and HIV-1 Gag protein expression." *Elife* 2016, 5:e15528, 20 pages.
Tsai et al., "Addition of m6A to SV40 late mRNAs enhances viral structural gene expression and replication" *PLoS Pathog* 2018, 14(2): p. e1006919, 23 pages.
Winkler et al., "m(6)A modification controls the innate immune response to infection by targeting type I interferons." *Nature Immunology* 2019, 20:173-182.
Xue et al., "Viral N6-methyladenosine upregulates replication and pathogenesis of human respiratory syncytial virus" *Nature Communications* 2019, 10(4595), 1-18.
Ye et al., "Kaposi's Sarcoma-Associated Herpesvirus Utilizes and Manipulates RNA N(6)-Adenosine Methylation To Promote Lytic Replication." *J Virol.* 2017, 91(16), 21 pages.
Yue et al., "RNA N6-methyladenosine methylation in post-transcriptional gene expression regulation." *Genes Dev* 2015, 29(13), p. 1343-1355.

\* cited by examiner

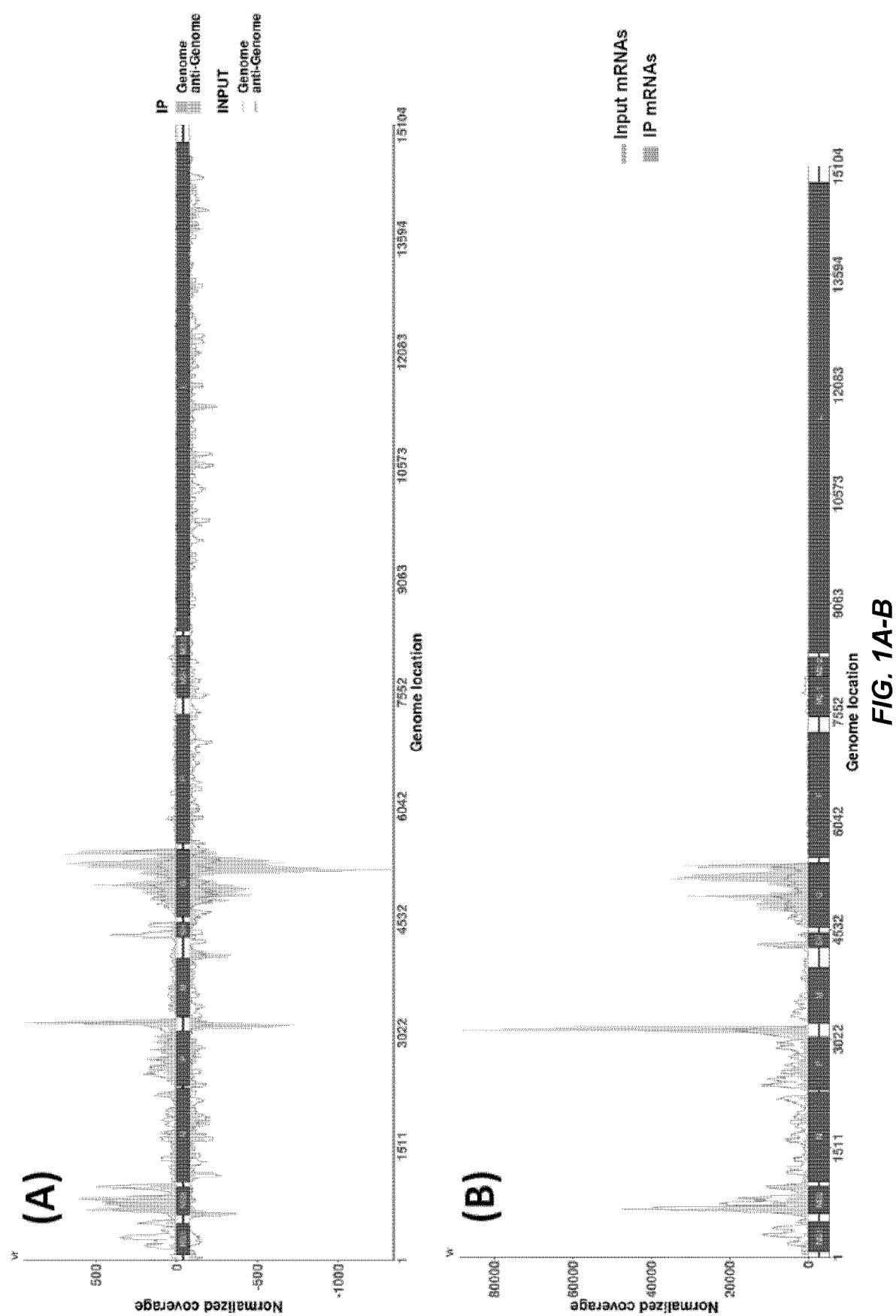
FIG. 1A-B

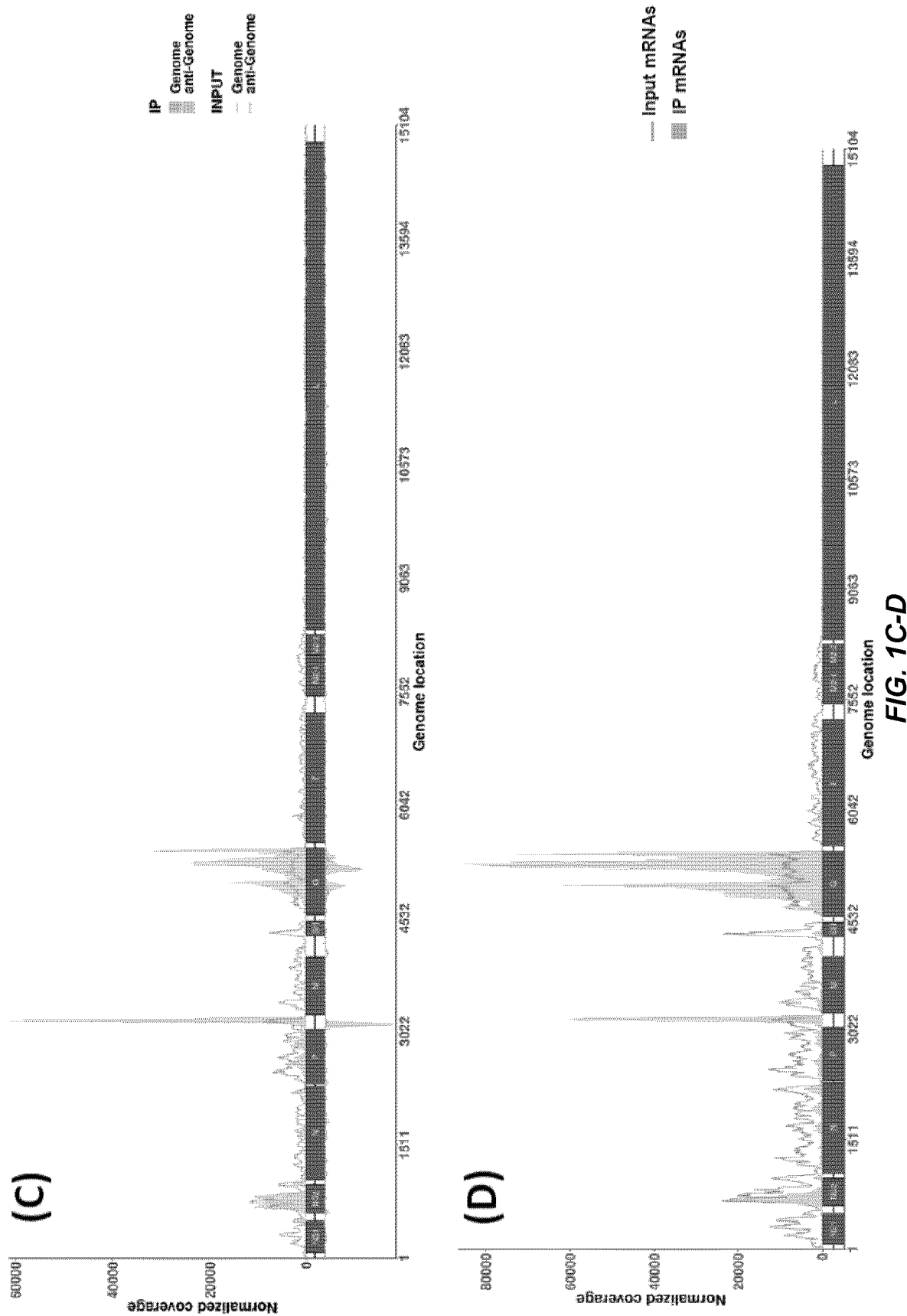
FIG. 1C-D

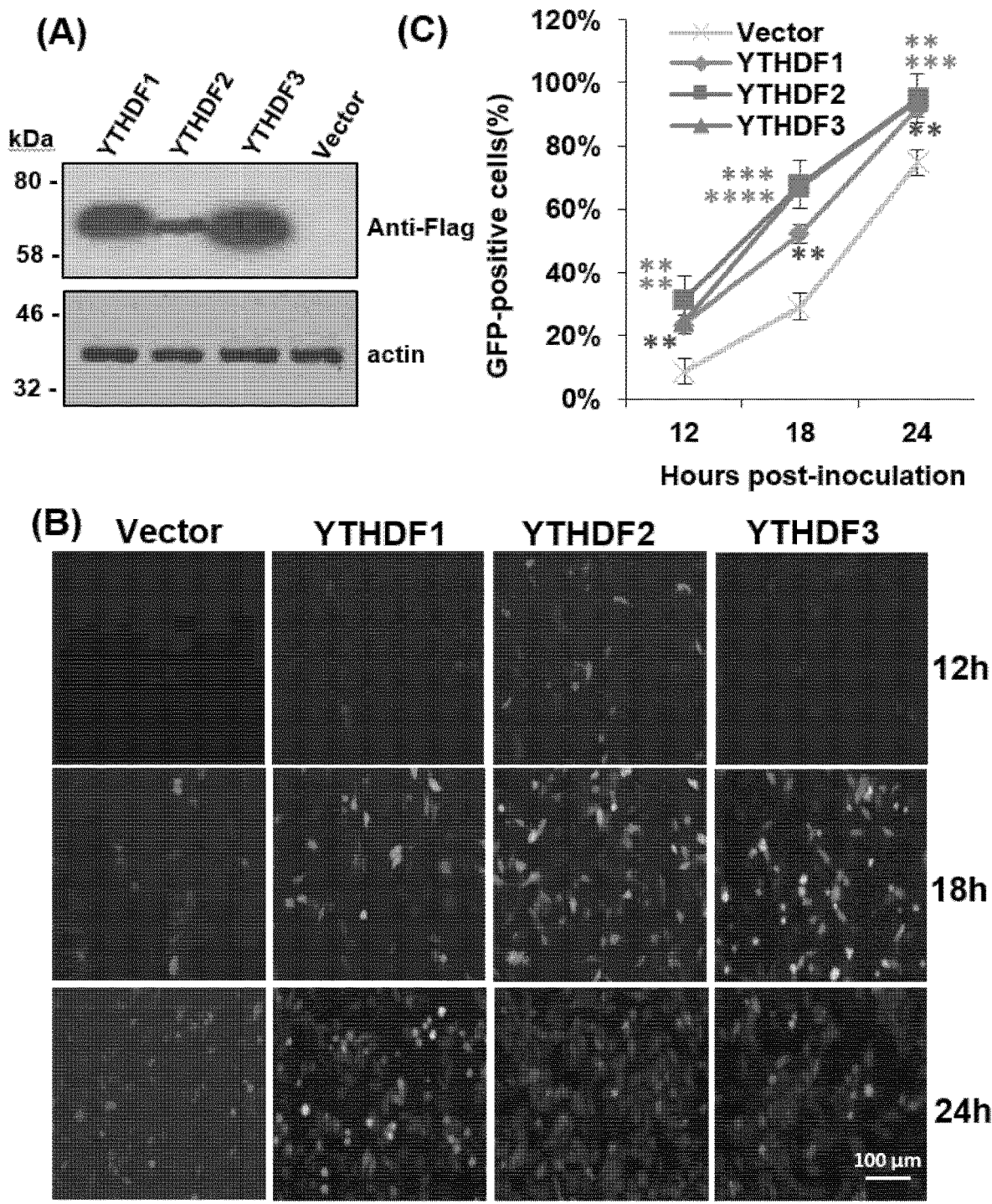
FIG. 2A-C

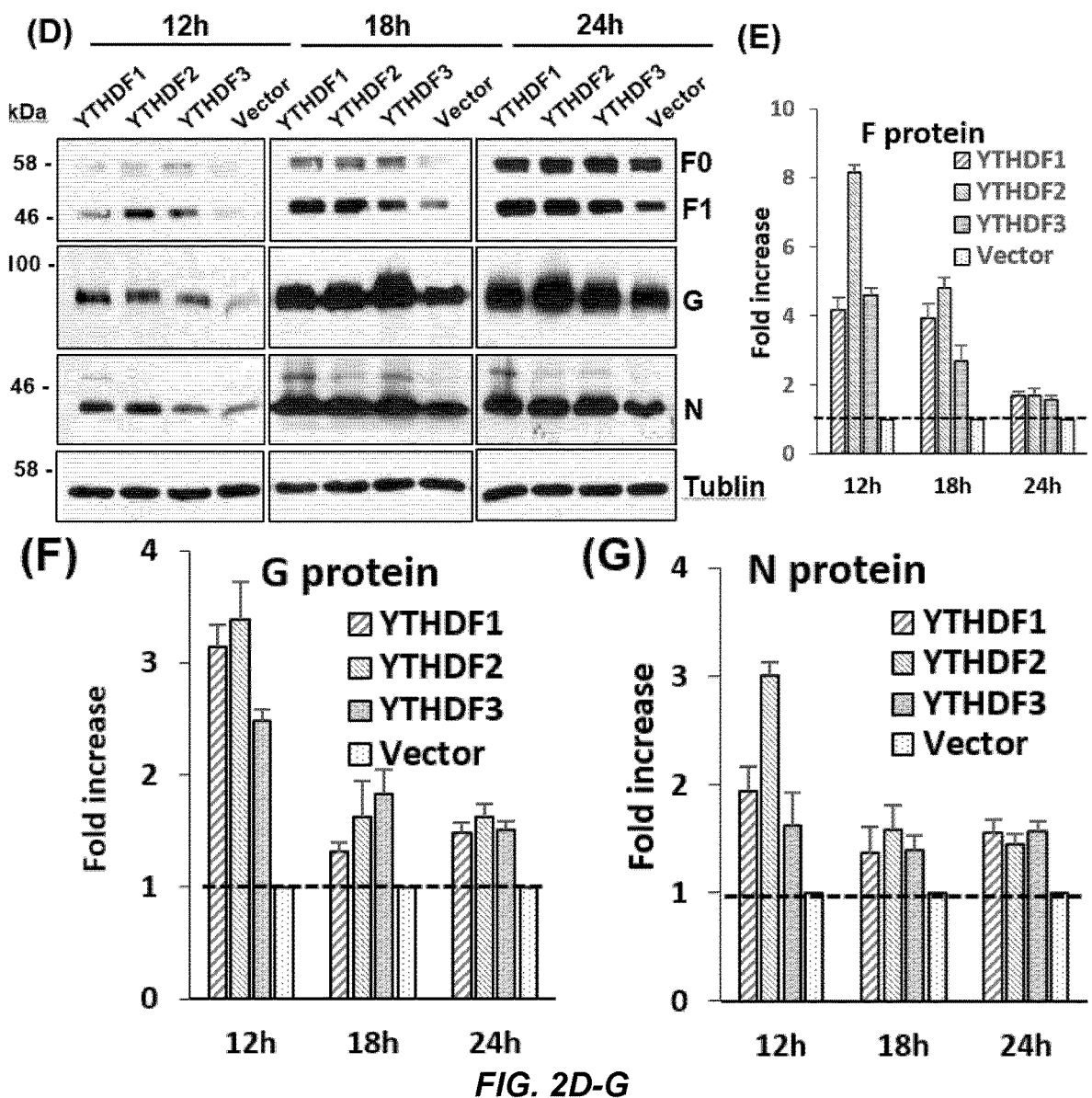
FIG. 2D-G

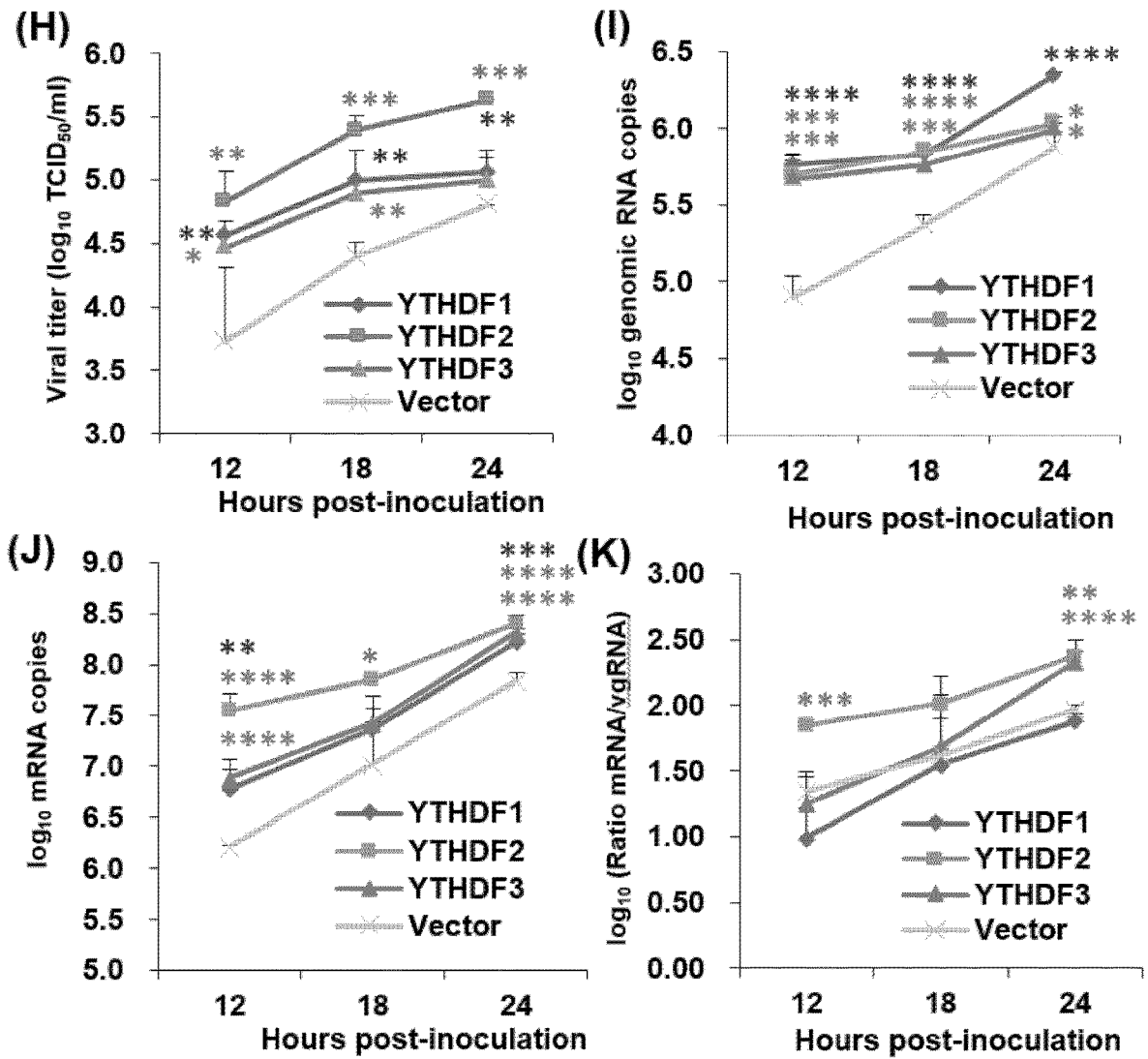
FIG. 2H-K

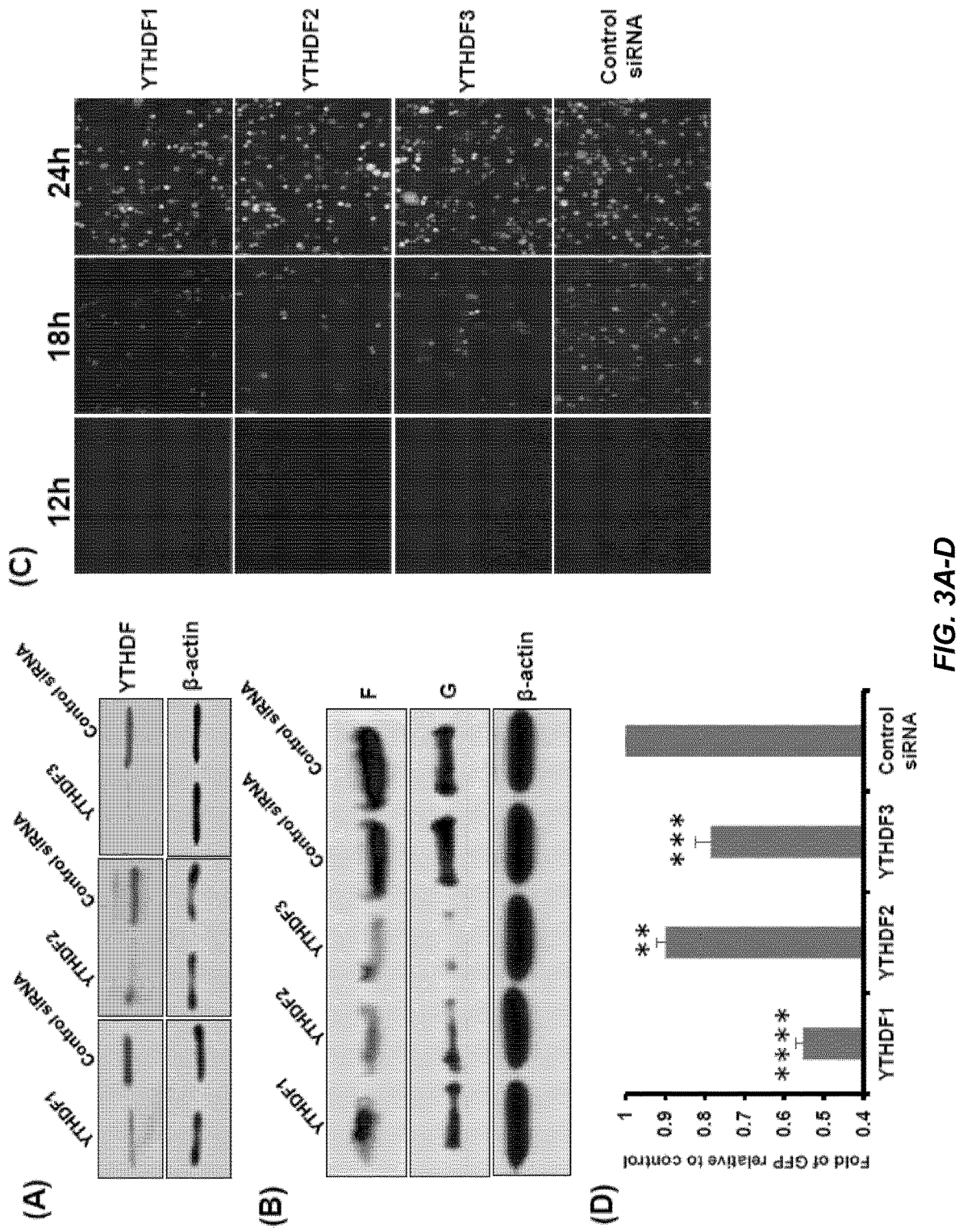
FIG. 3A-D

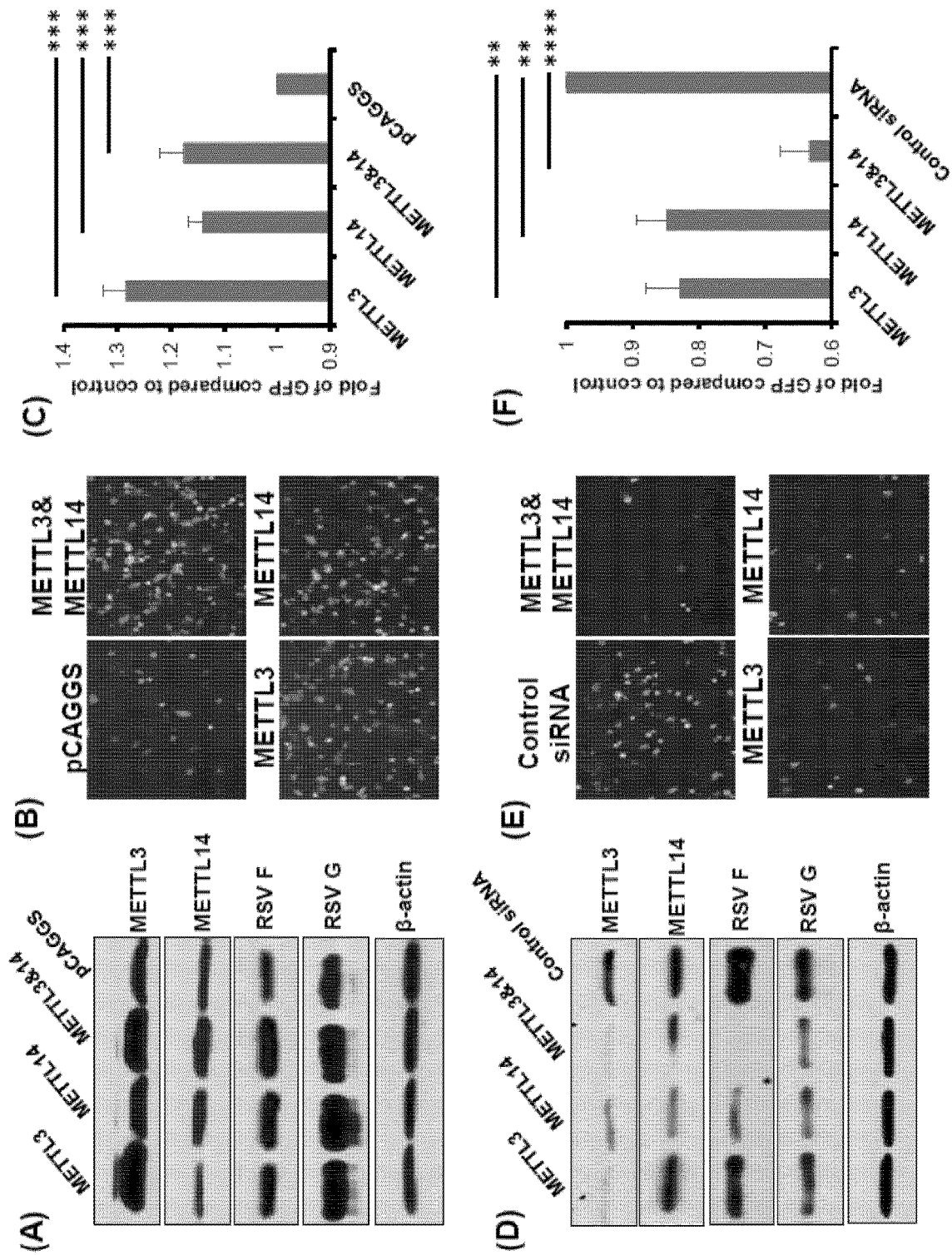
FIG. 4A-F

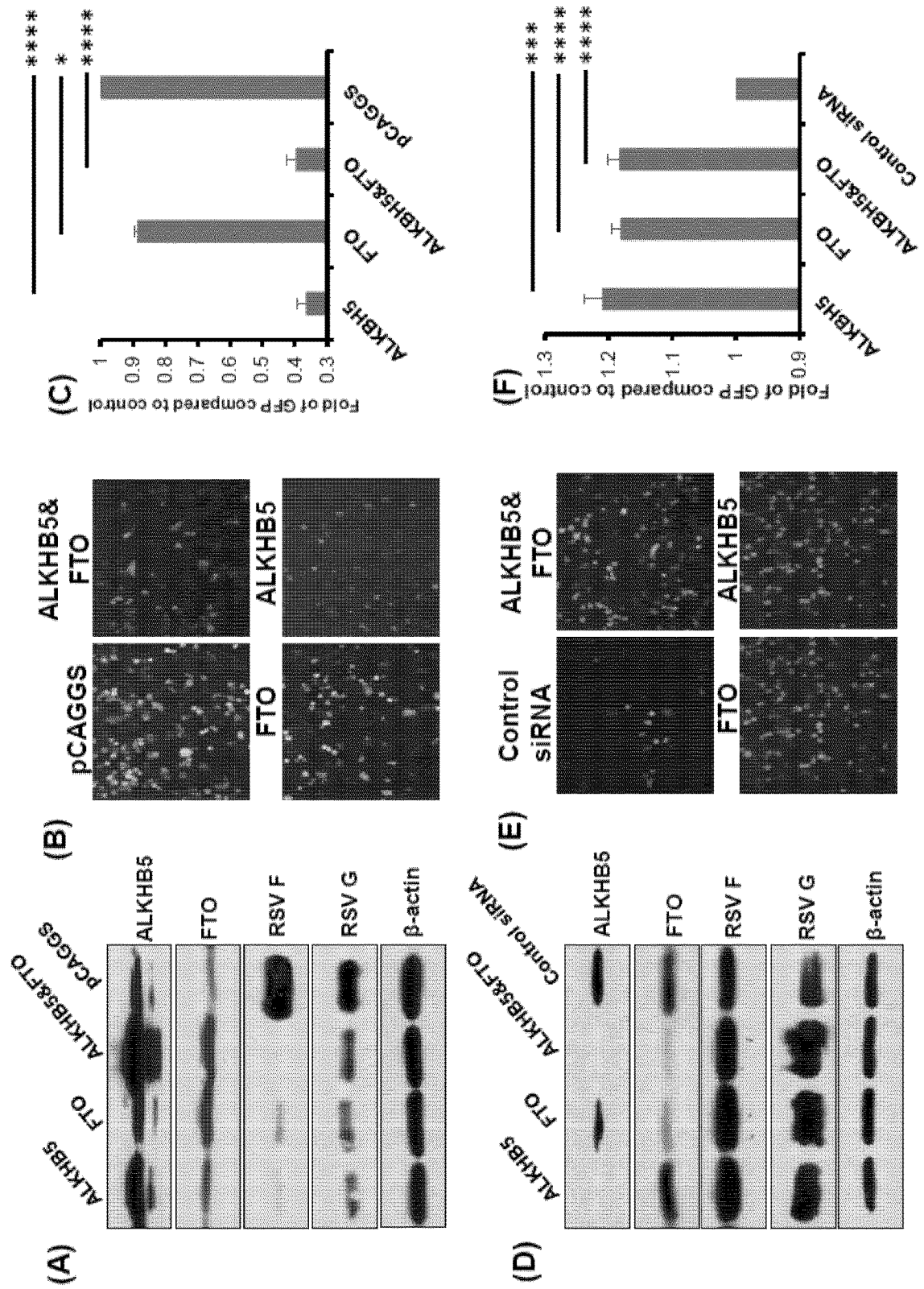
FIG. 5A-F

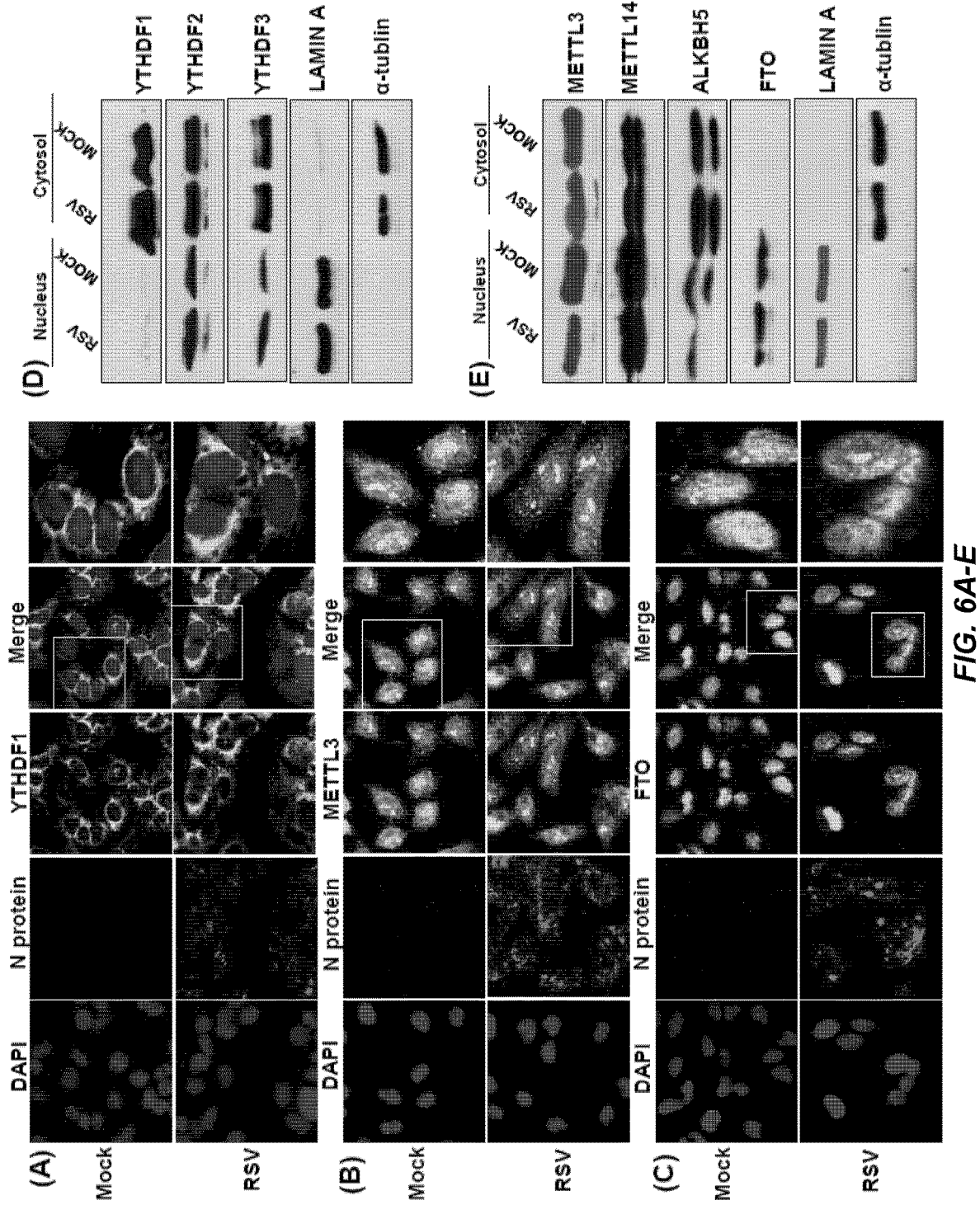
FIG. 6A-E

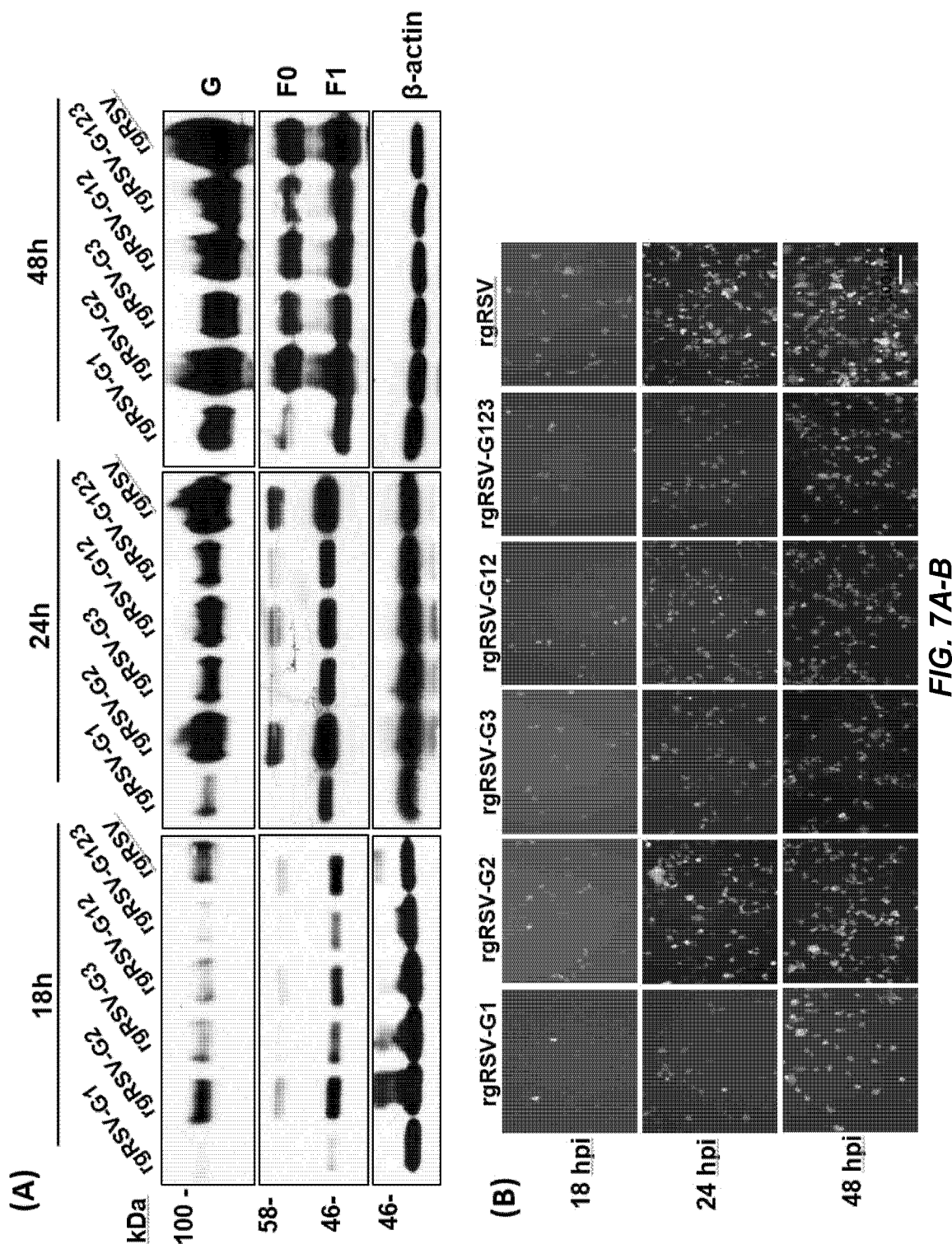
FIG. 7A-B

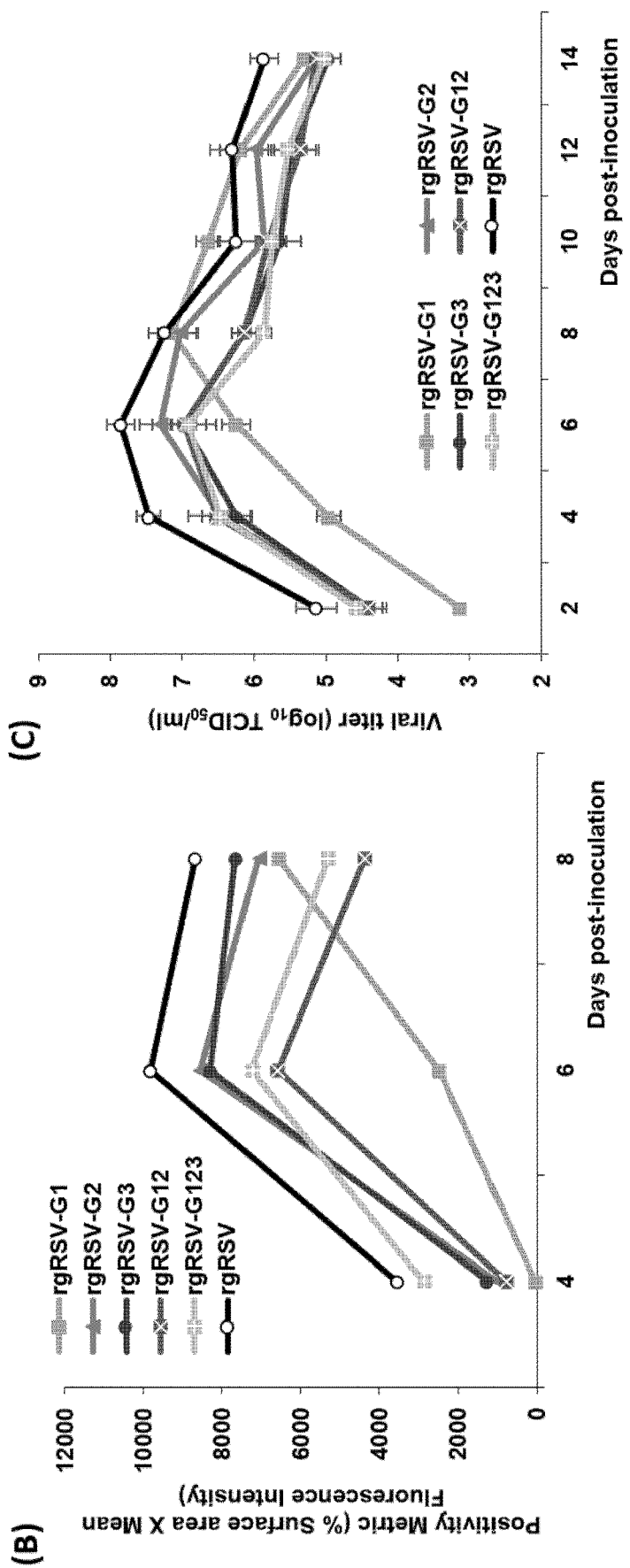
FIG. 8B-C

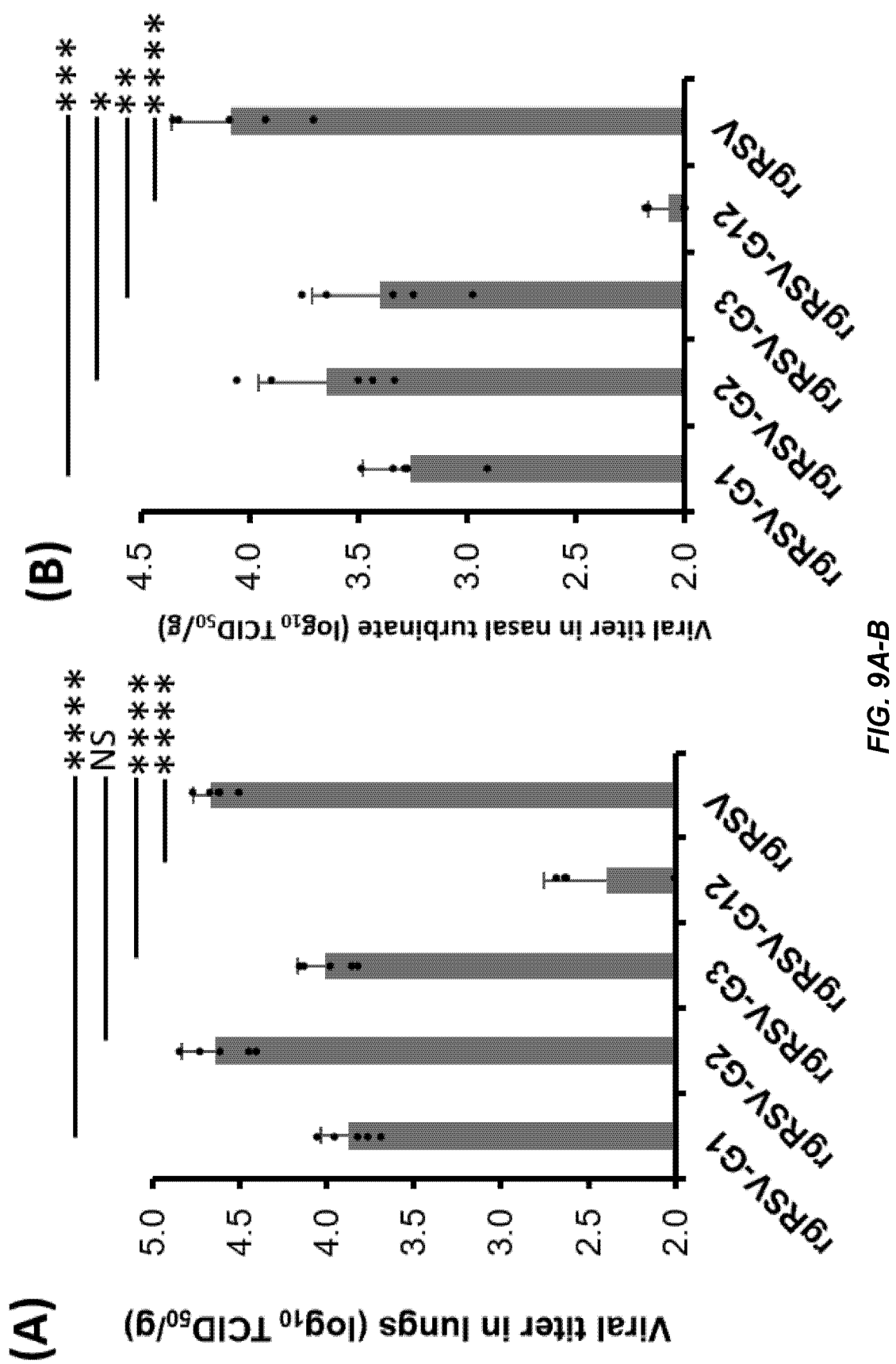
FIG. 9A-B

FIG. 9D-E

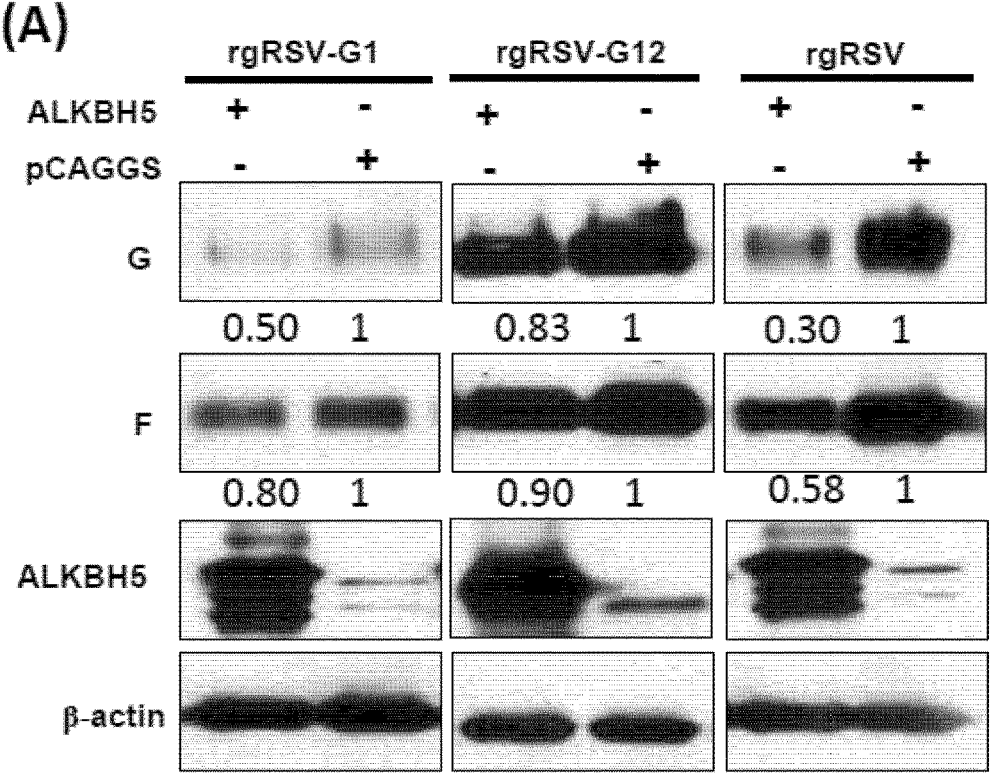
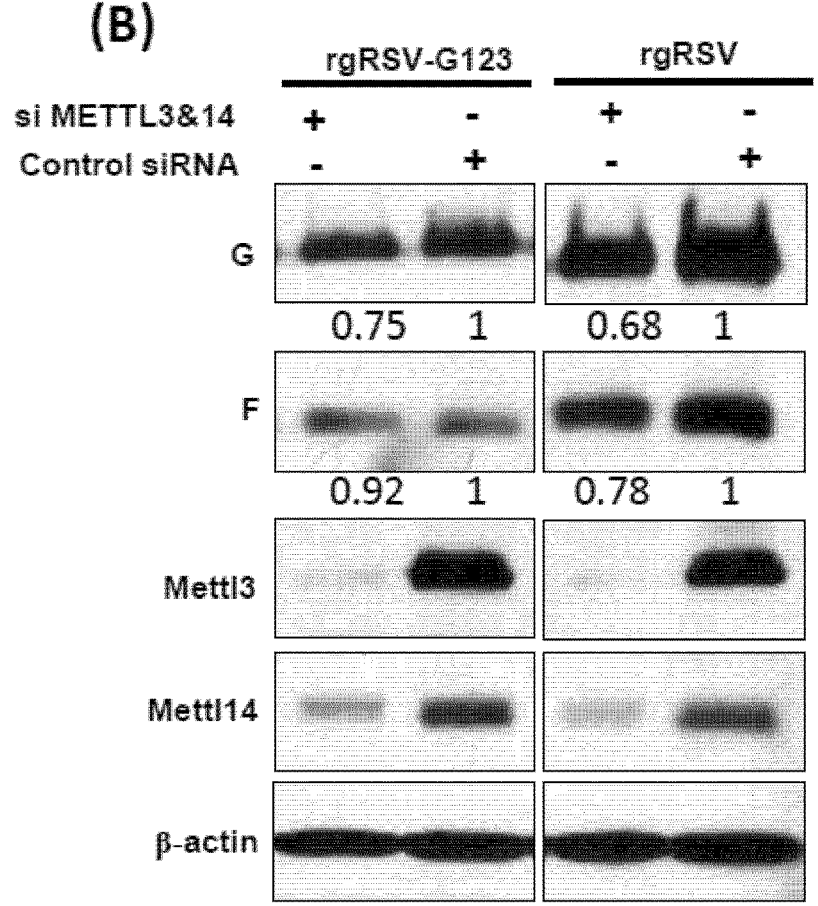
*FIG. 10A-B*

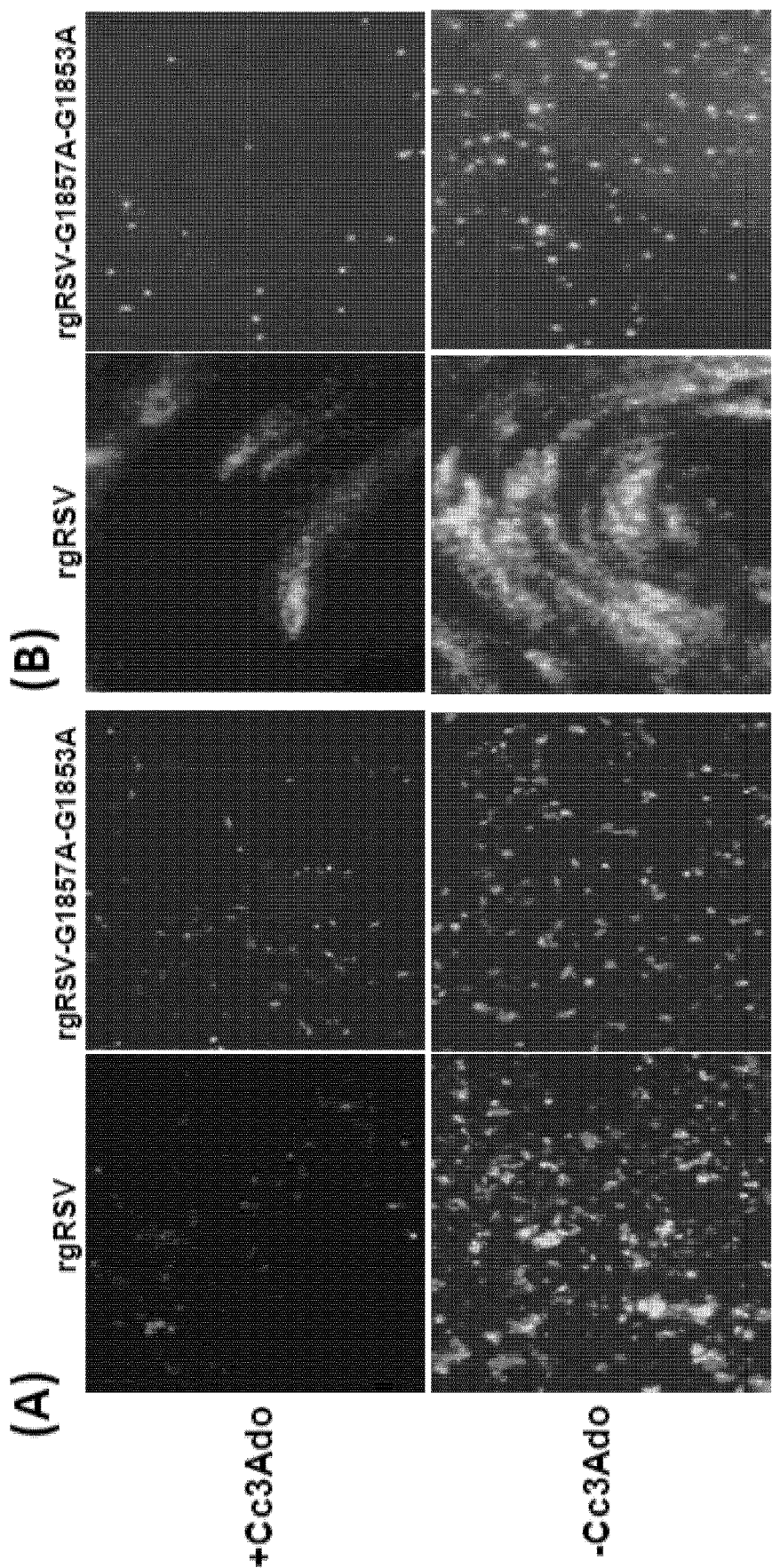
FIG. 11A-B

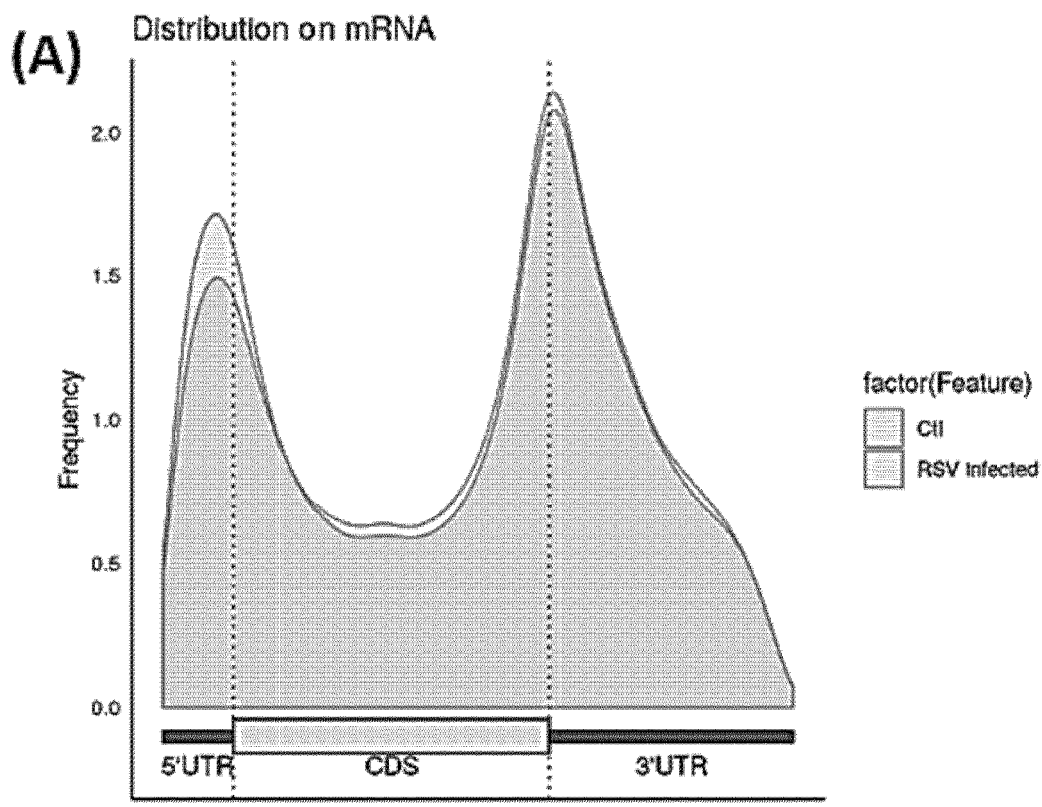
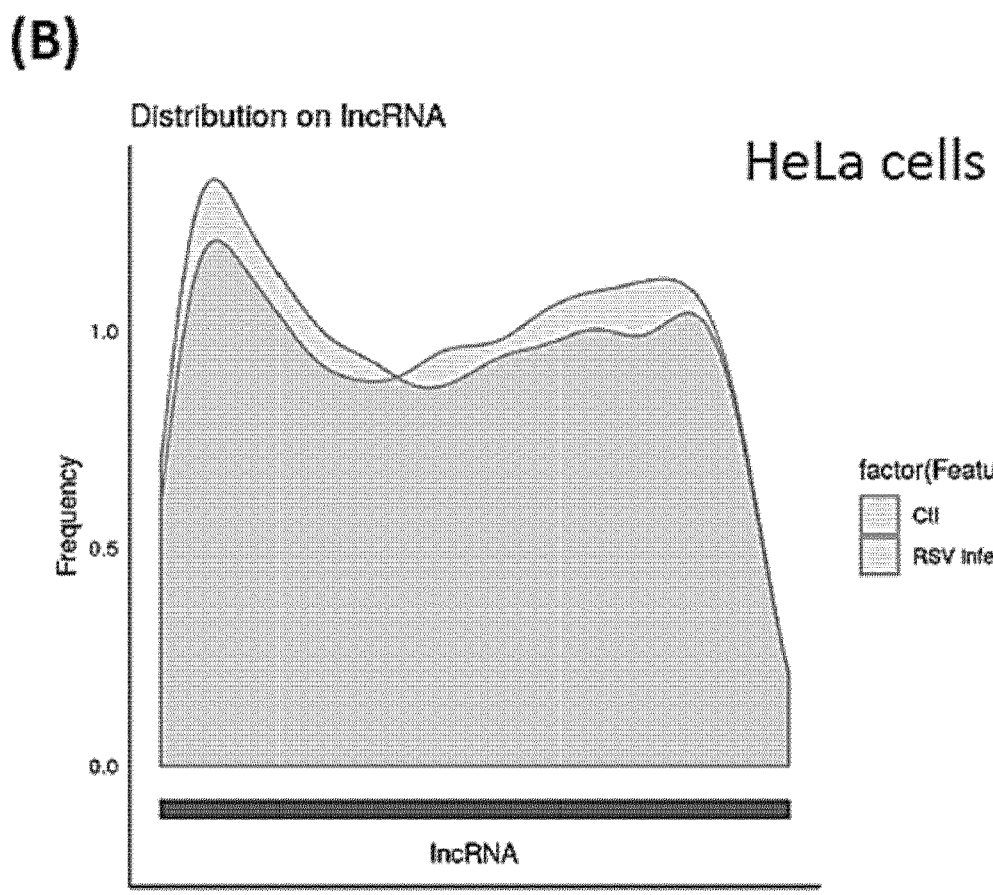
FIG. 12A-B

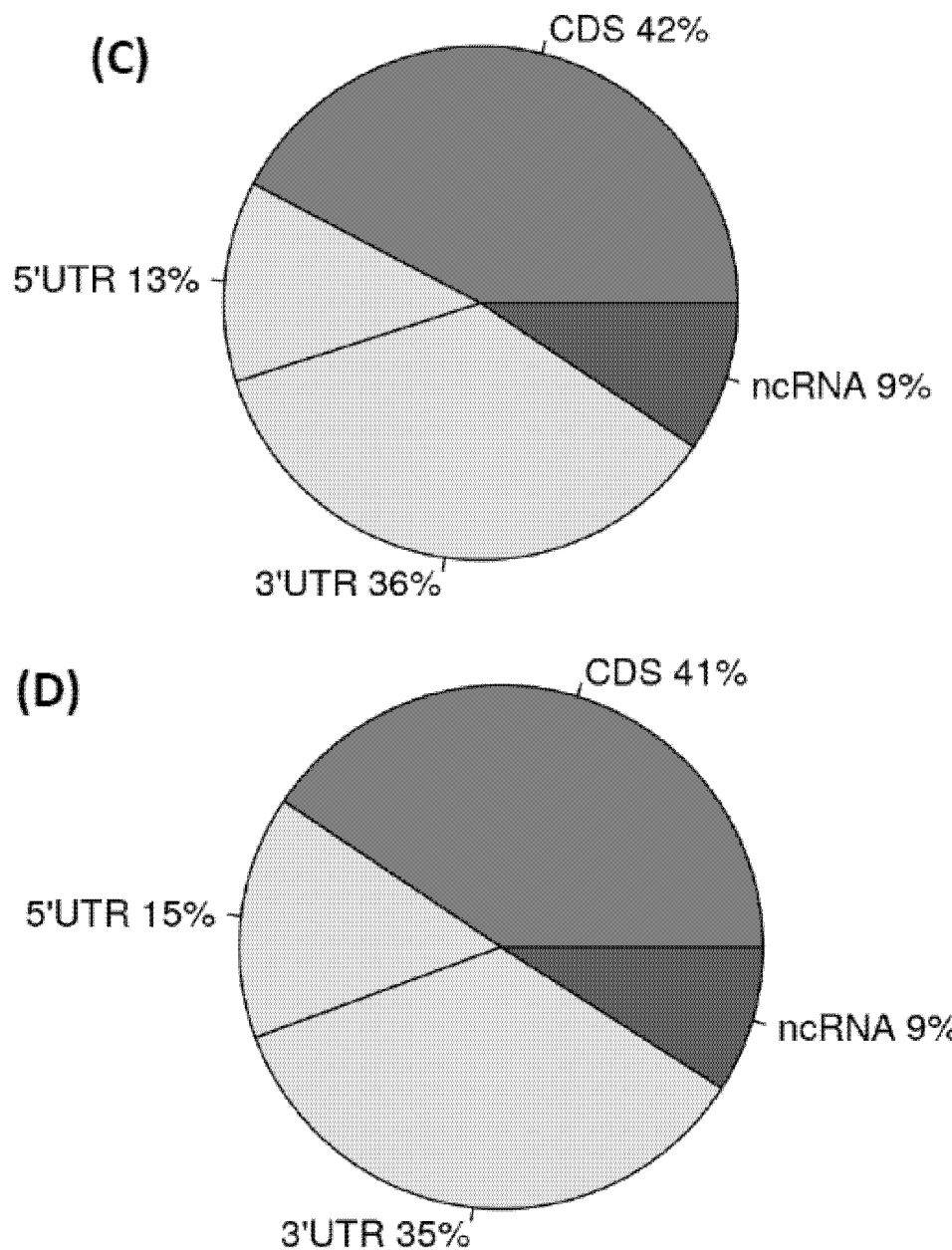
FIG. 12C-D

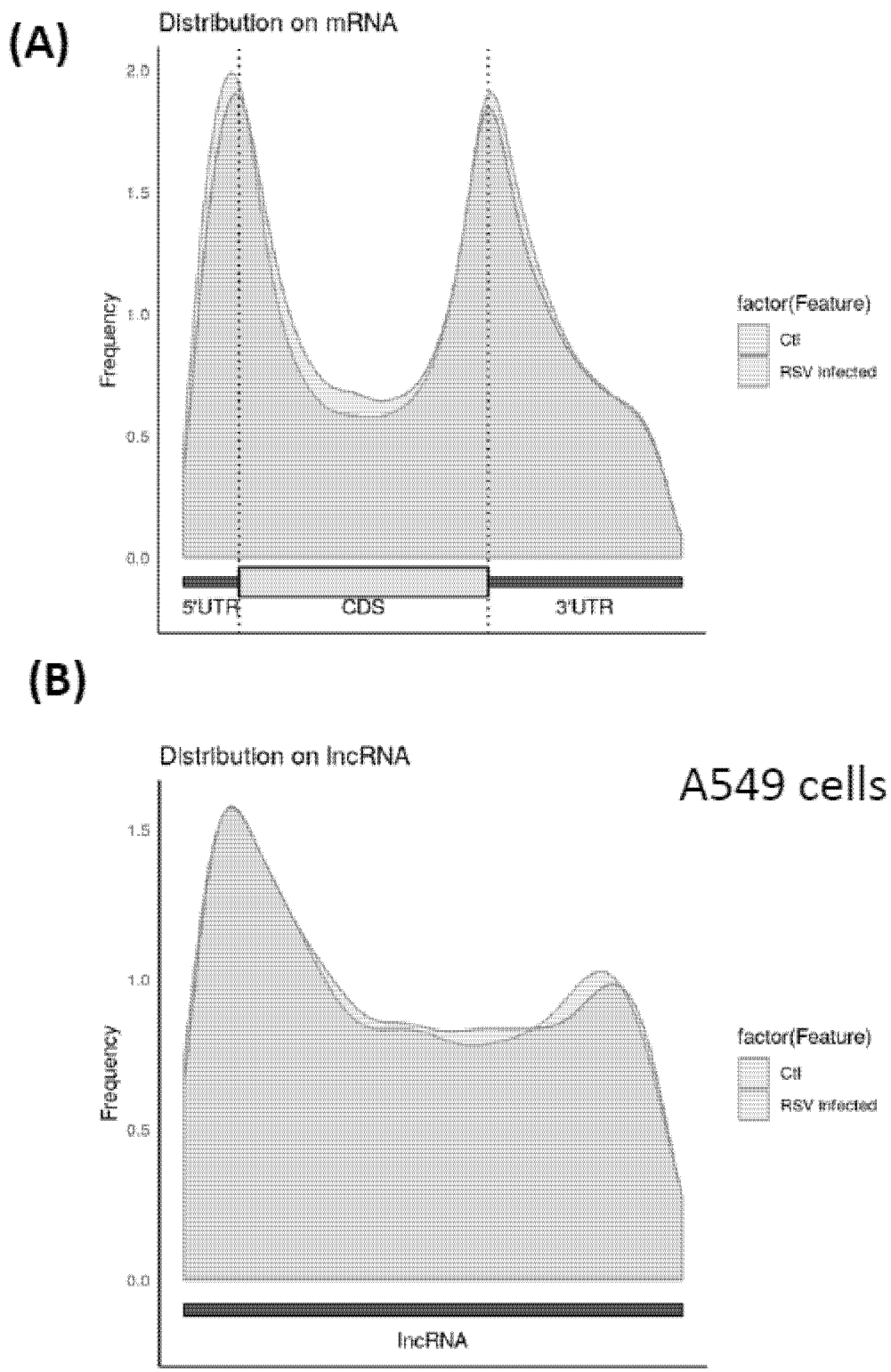
FIG. 13A-B

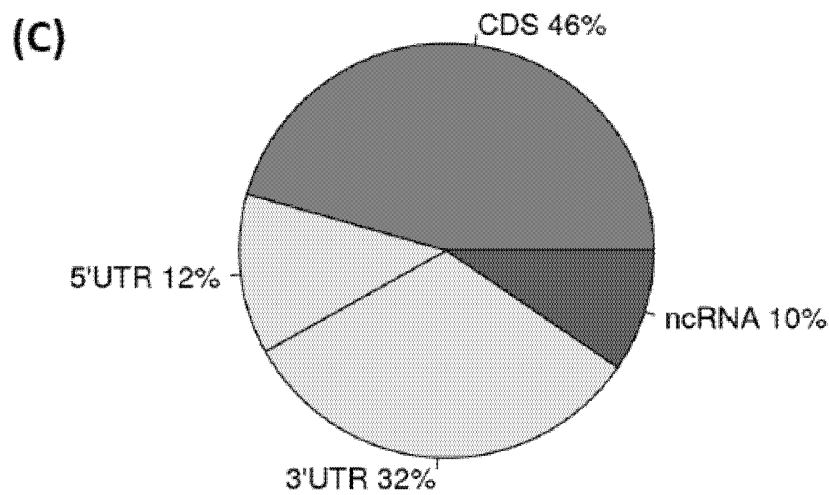
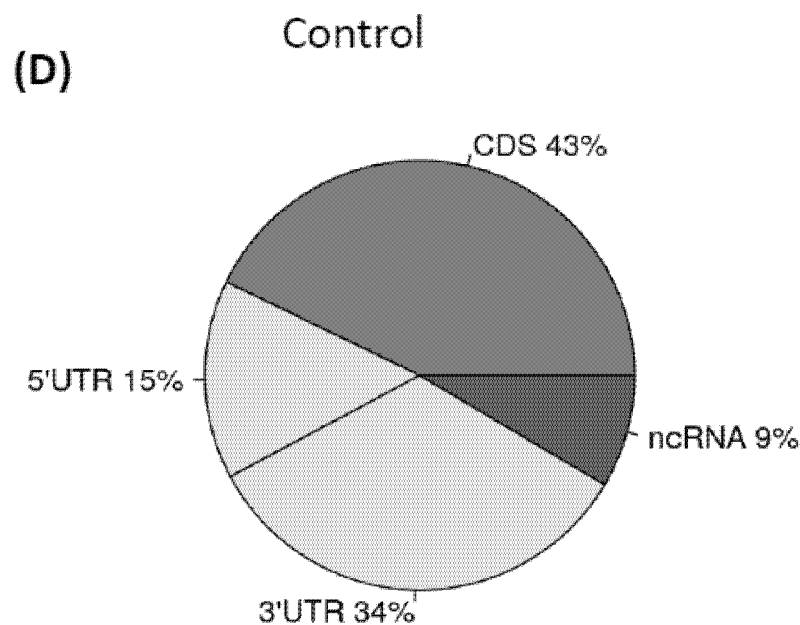
FIG. 13C-D

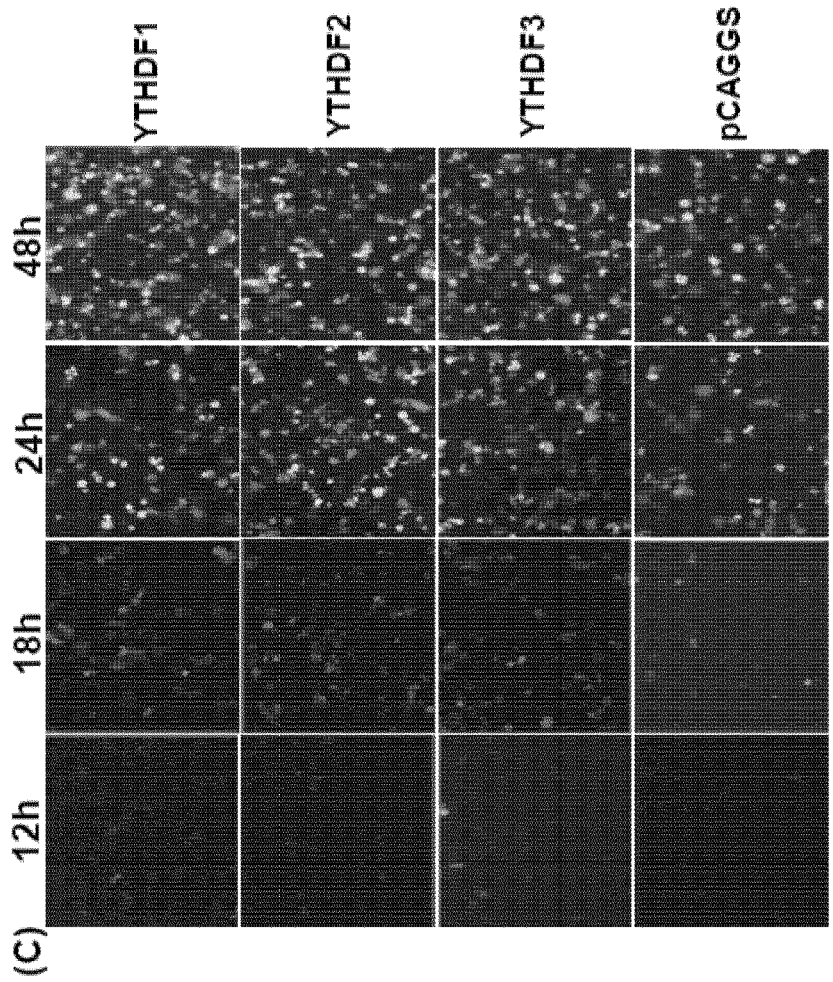
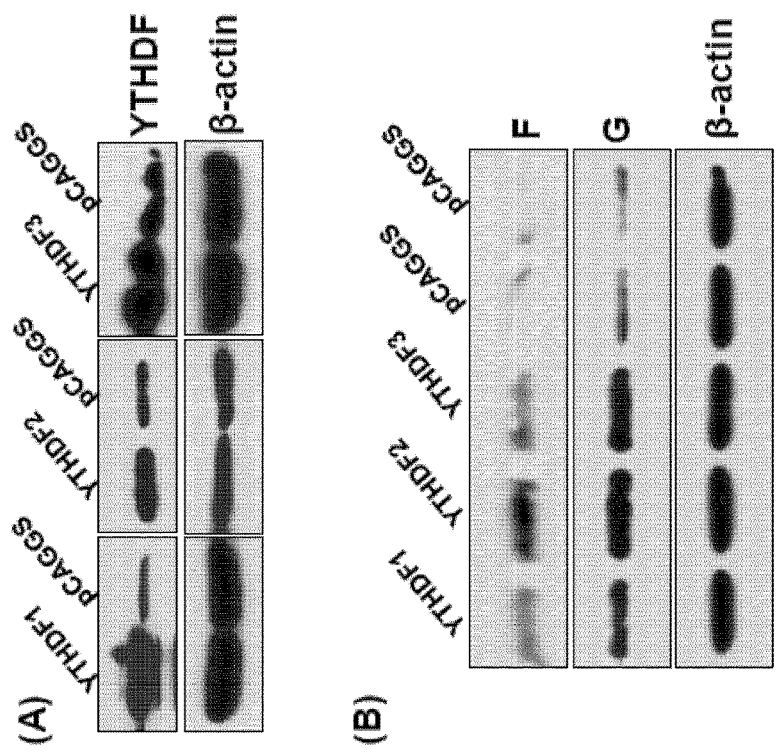
FIG. 14A-C

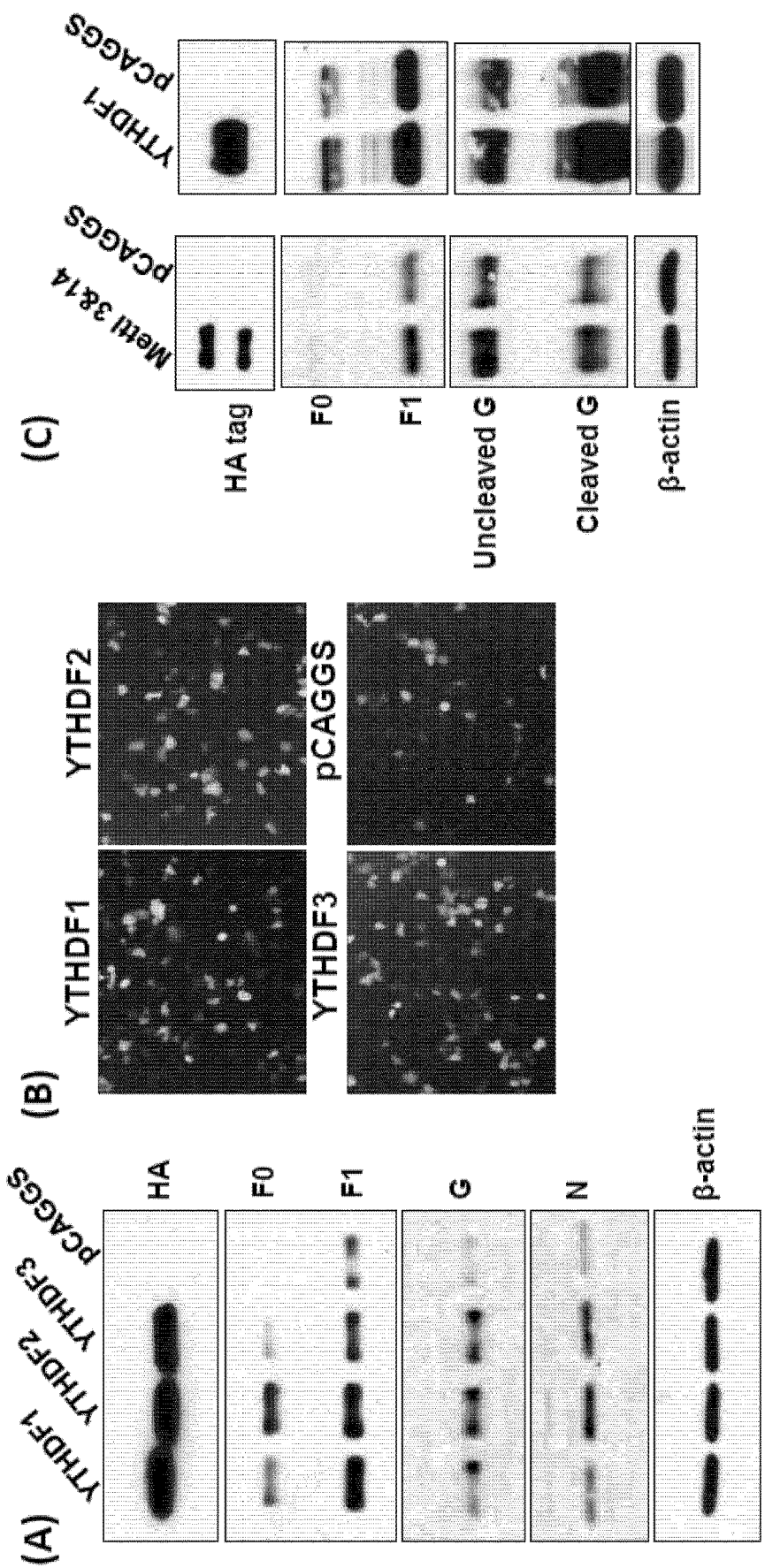
FIG. 15A-C

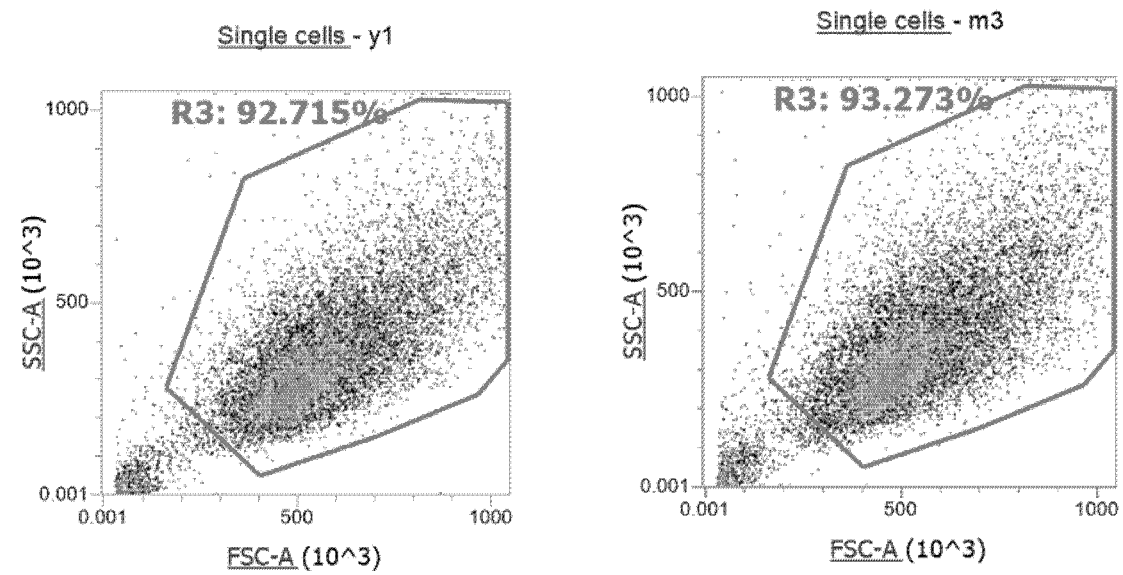
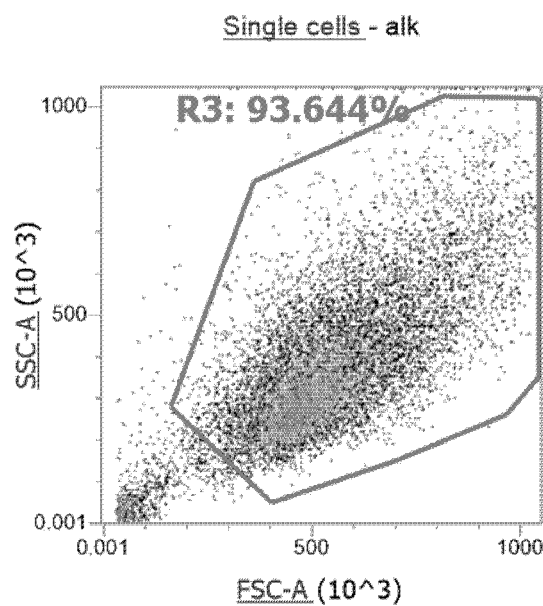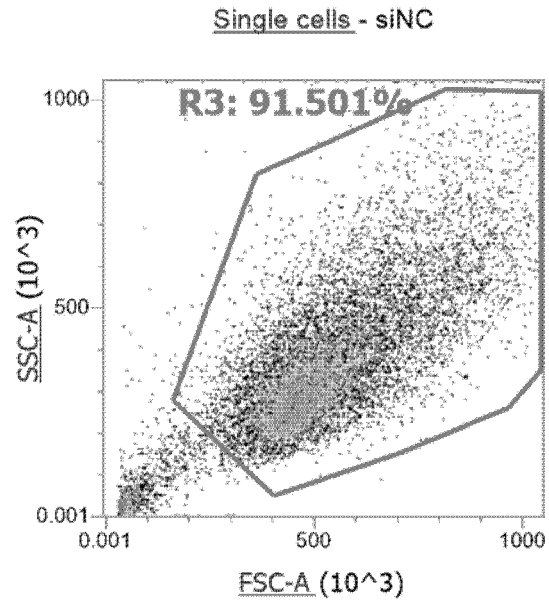
*FIG. 16D*

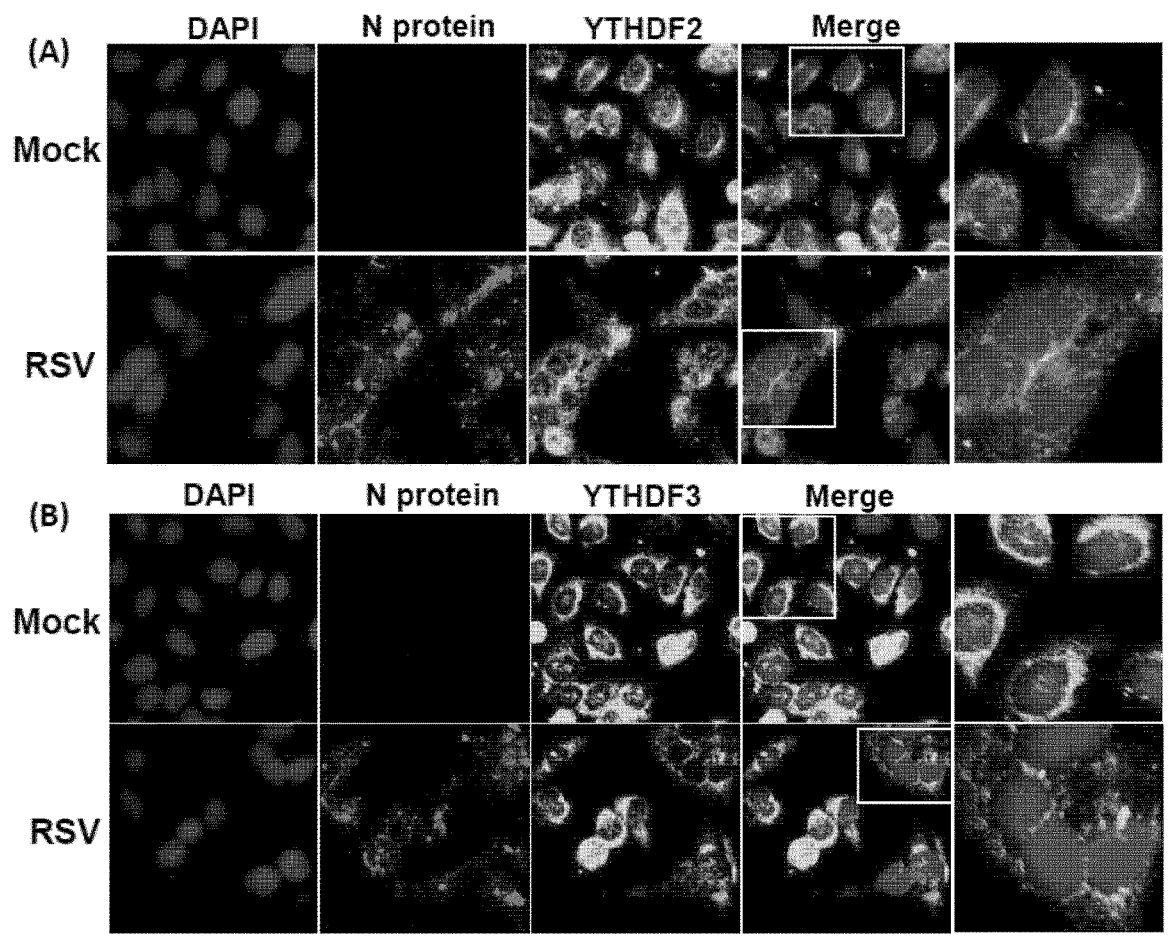
*FIG. 17A-B*
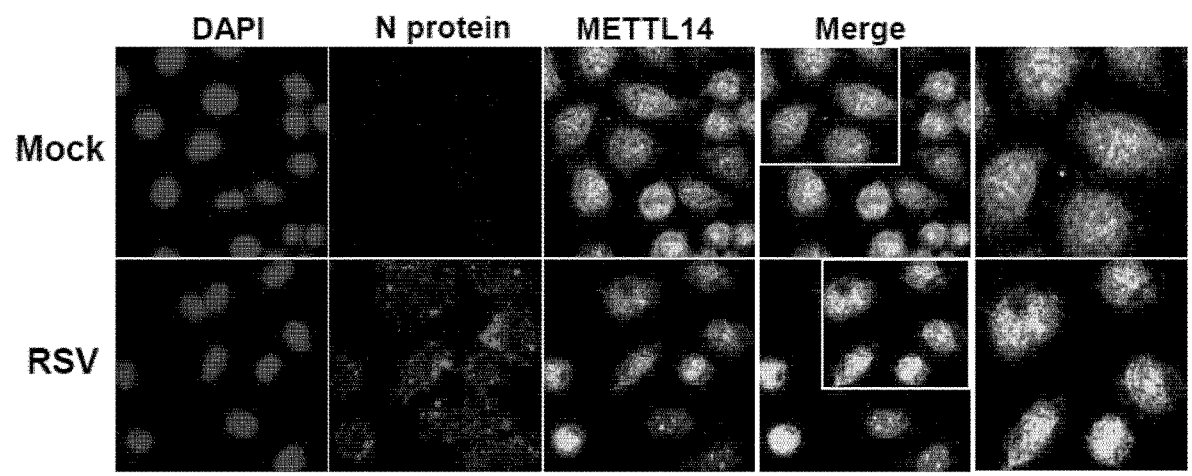
*FIG. 18*

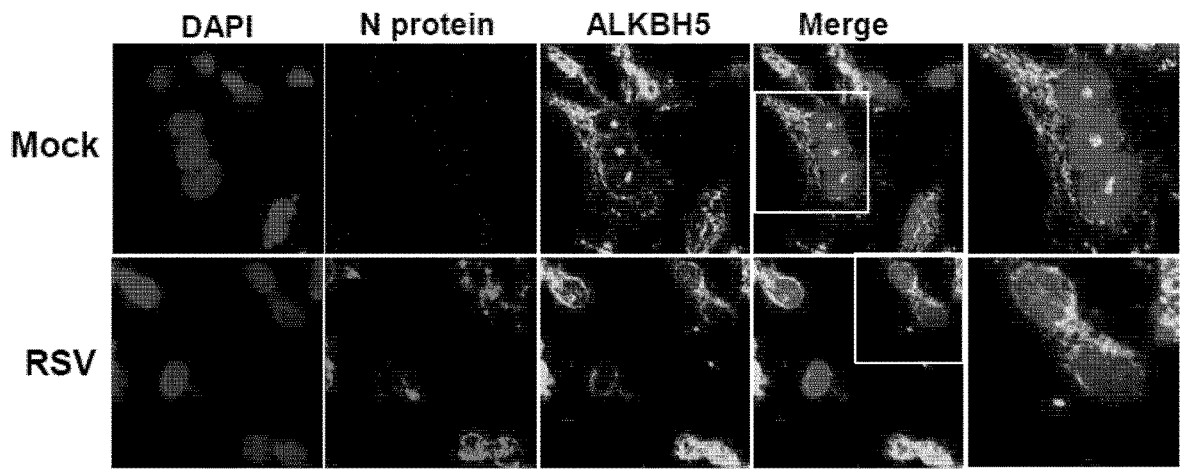
FIG. 19
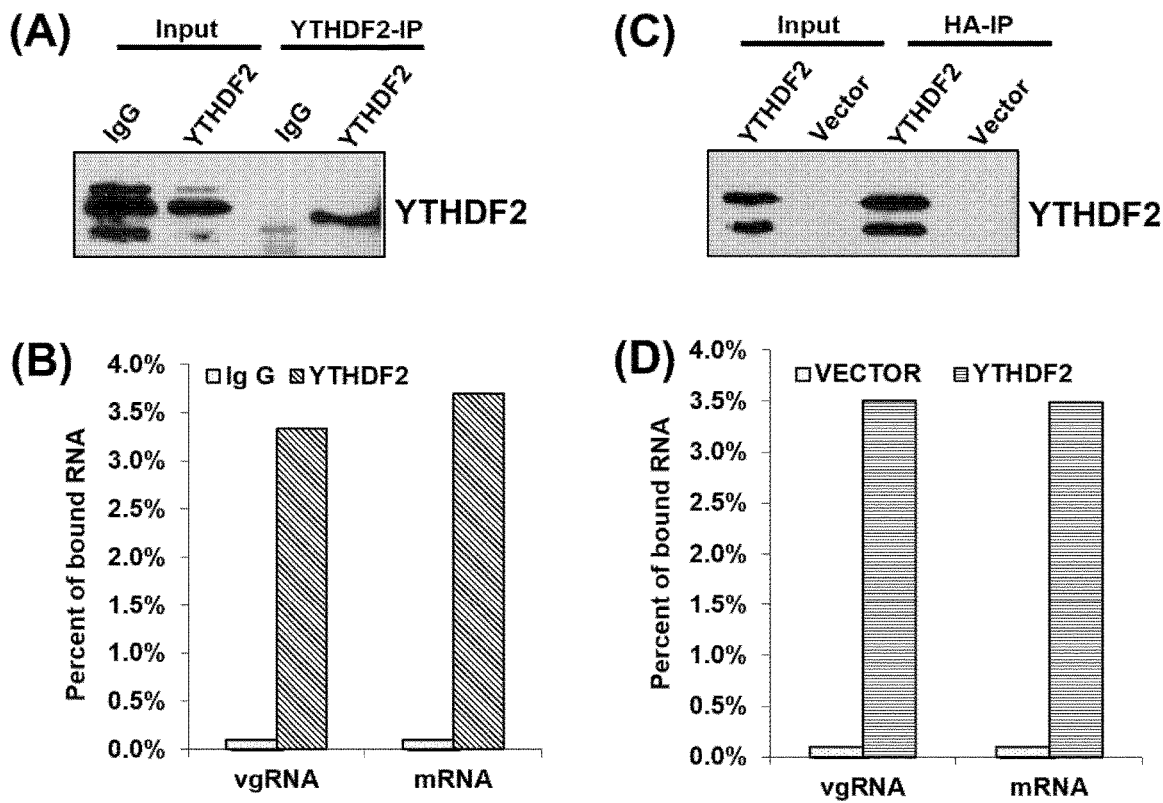
FIG. 20A-D

FIG. 22A-B

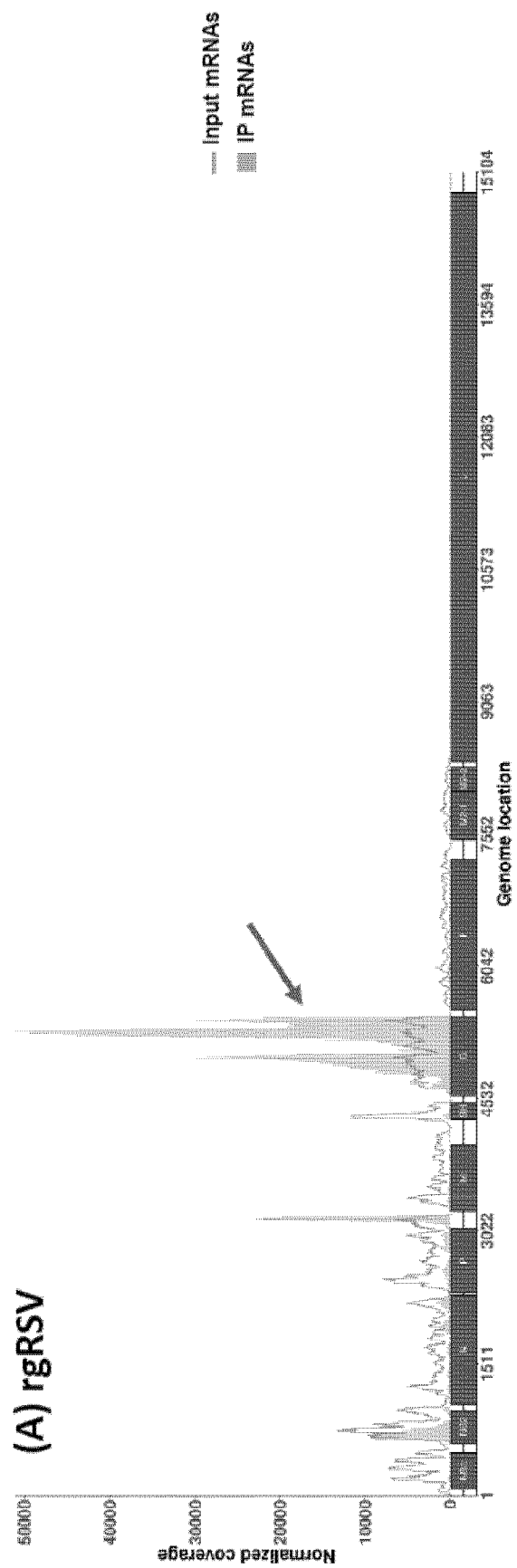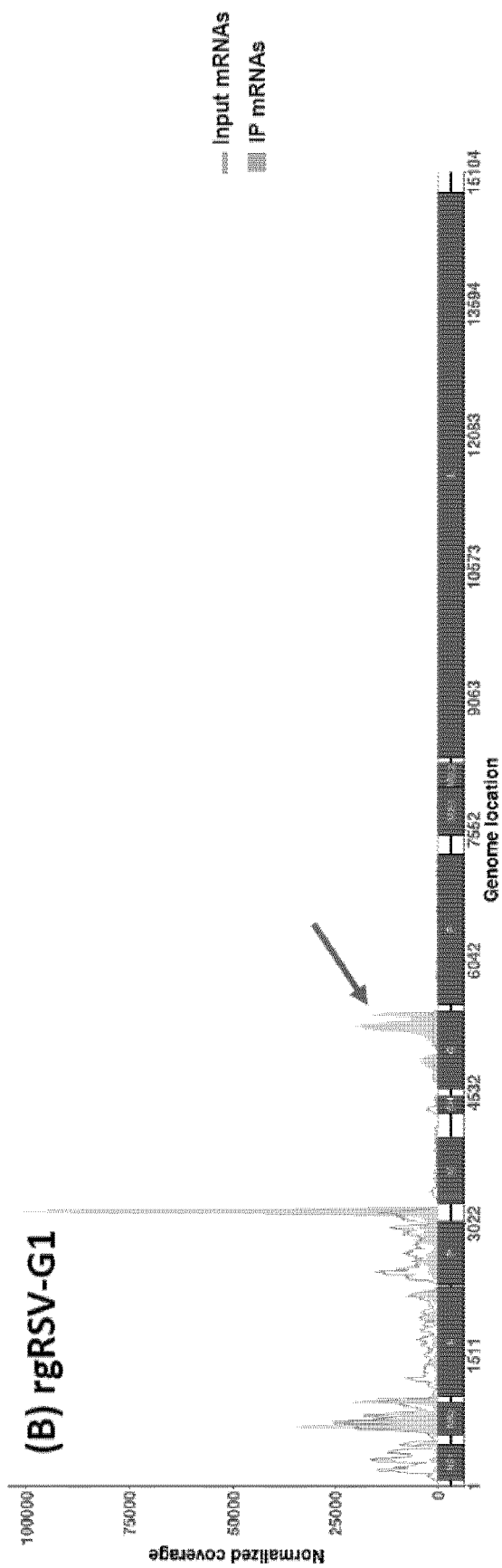
FIG. 24A-B

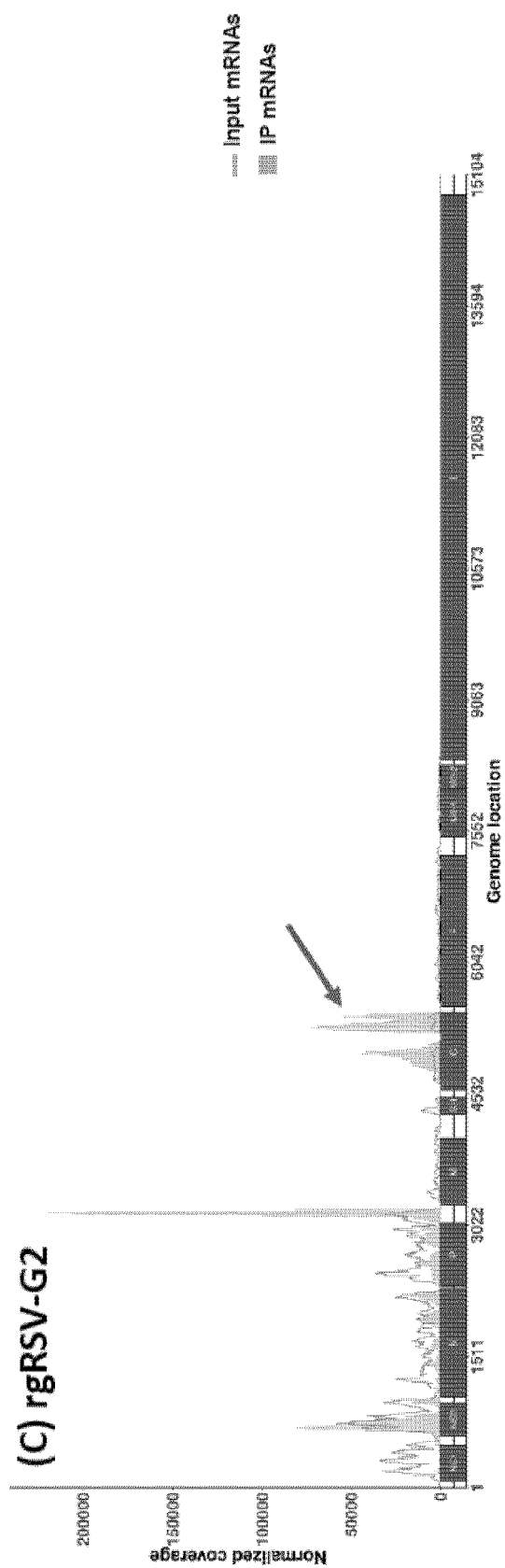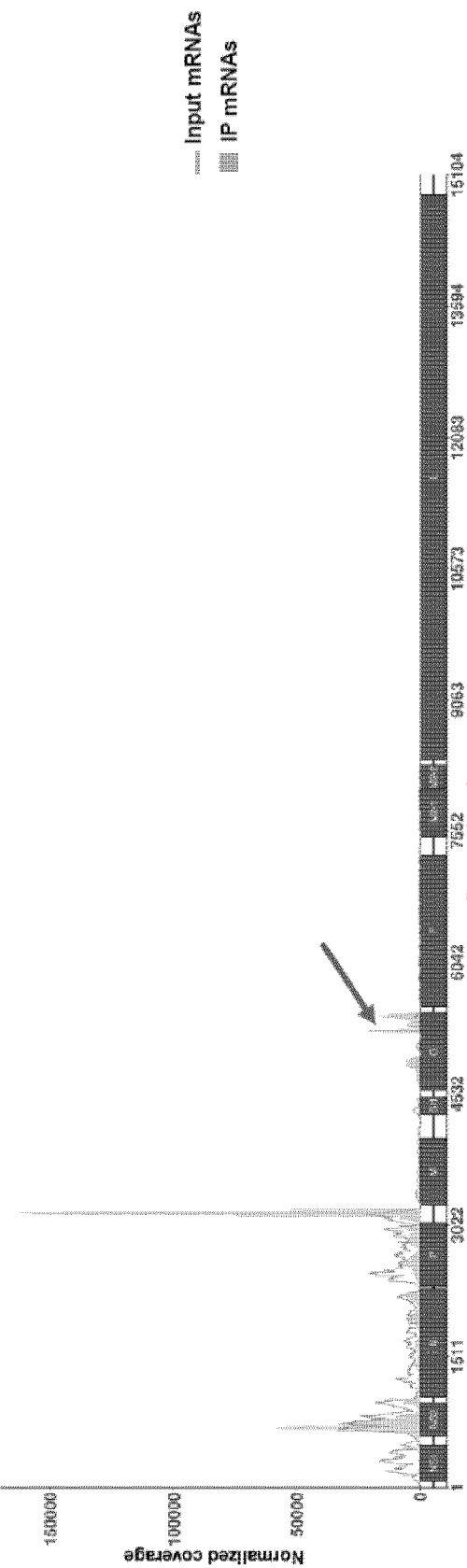
FIG. 24C-D

FIG. 25

| hMPV RNAs | Peak no. | Peak range (nt) [a] | P value | Gene location [b] | Peak size (nt) | Enrichment Fold [c] |
|---|---|---|---|---|---|---|
| Genome | 1 | 1498-1617 | $7.23 \times 10^{-10}$ | P | 119 | 1.59 |
| | 2 | 1887-1916 | $2.23 \times 10^{-8}$ | P | 29 | 2.15 |
| | 3 | 2097-2126 | $2.26 \times 10^{-4}$ | P | 29 | 2.33 |
| | 4 | 6499-6558 | $4.53 \times 10^{-68}$ | G | 59 | 3.06 |
| | 5 | 6649-6947 | $1.0 \times 10^{-128}$ | G | 298 | 2.79 |
| Antigenome | 1 | 241-389 | $4.47 \times 10^{-127}$ | N | 148 | 2.35 |
| | 2 | 420-449 | $2.10 \times 10^{-2}$ | N | 29 | 1.16 |
| | 3 | 1468-1587 | $1.0 \times 10^{-128}$ | P | 119 | 3.12 |
| | 4 | 1768-1916 | $1.0 \times 10^{-128}$ | P | 148 | 2.96 |
| | 5 | 2816-2935 | $4.47 \times 10^{-65}$ | M | 119 | 1.86 |
| | 6 | 3265-3294 | $9.62 \times 10^{-13}$ | F | 29 | 2.05 |
| | 7 | 3325-3414 | $2.58 \times 10^{-75}$ | F | 89 | 2.42 |
| | 8 | 3534-3623 | $2.84 \times 10^{-7}$ | F | 89 | 1.36 |
| | 9 | 3954-4042 | $4.65 \times 10^{-12}$ | F | 88 | 1.53 |
| | 10 | 4373-4492 | $1.99 \times 10^{-33}$ | F | 119 | 1.96 |
| | 11 | 6404-6902 | $1.0 \times 10^{-128}$ | G | 498 | 3.12 |
| | 12 | 10691-10780 | $6.19 \times 10^{-22}$ | L | 89 | 2.08 |
| mRNA | 1 | 1513-1572 | $1.0 \times 10^{-128}$ | P | 59 | 1.78 |
| | 2 | 6459-6577 | $1.0 \times 10^{-128}$ | G | 118 | 12.31 |
| | 3 | 6637-6844 | $1.16 \times 10^{-5}$ | G | 207 | 14.808 |
| | 4 | 10735-10764 | $1.0 \times 10^{-128}$ | L | 29 | 1.22 |

FIG. 26C

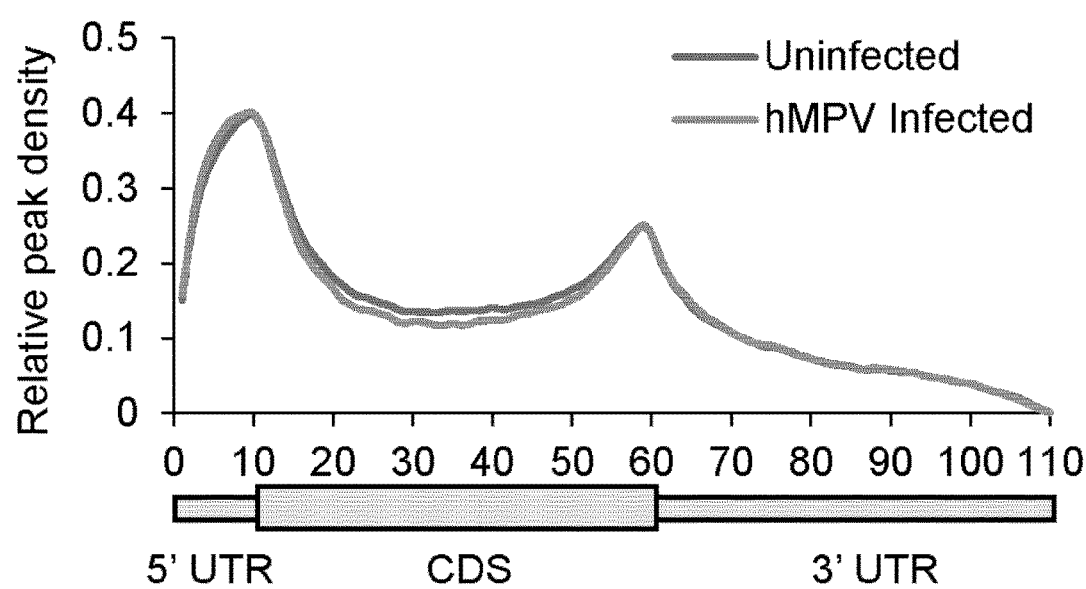
*FIG. 27A-B*

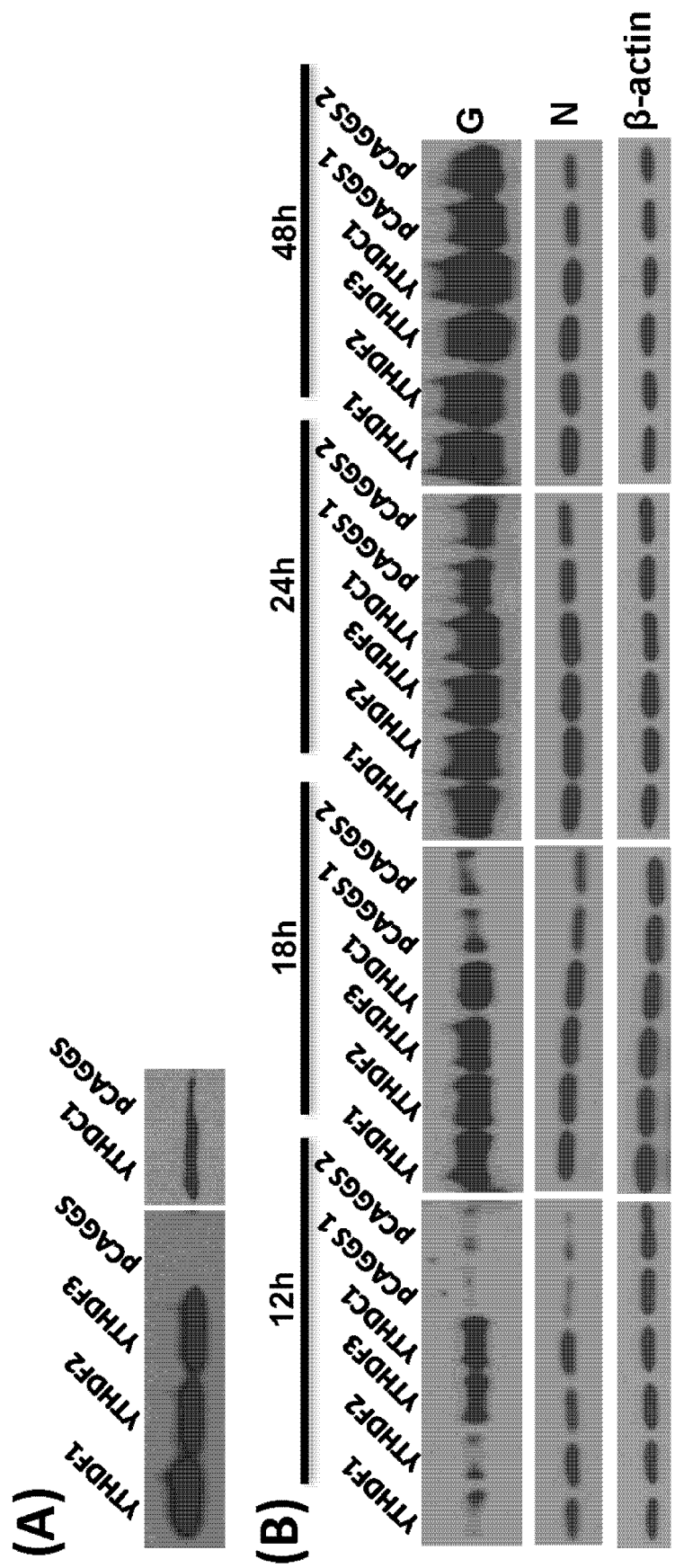
FIG. 28A-B

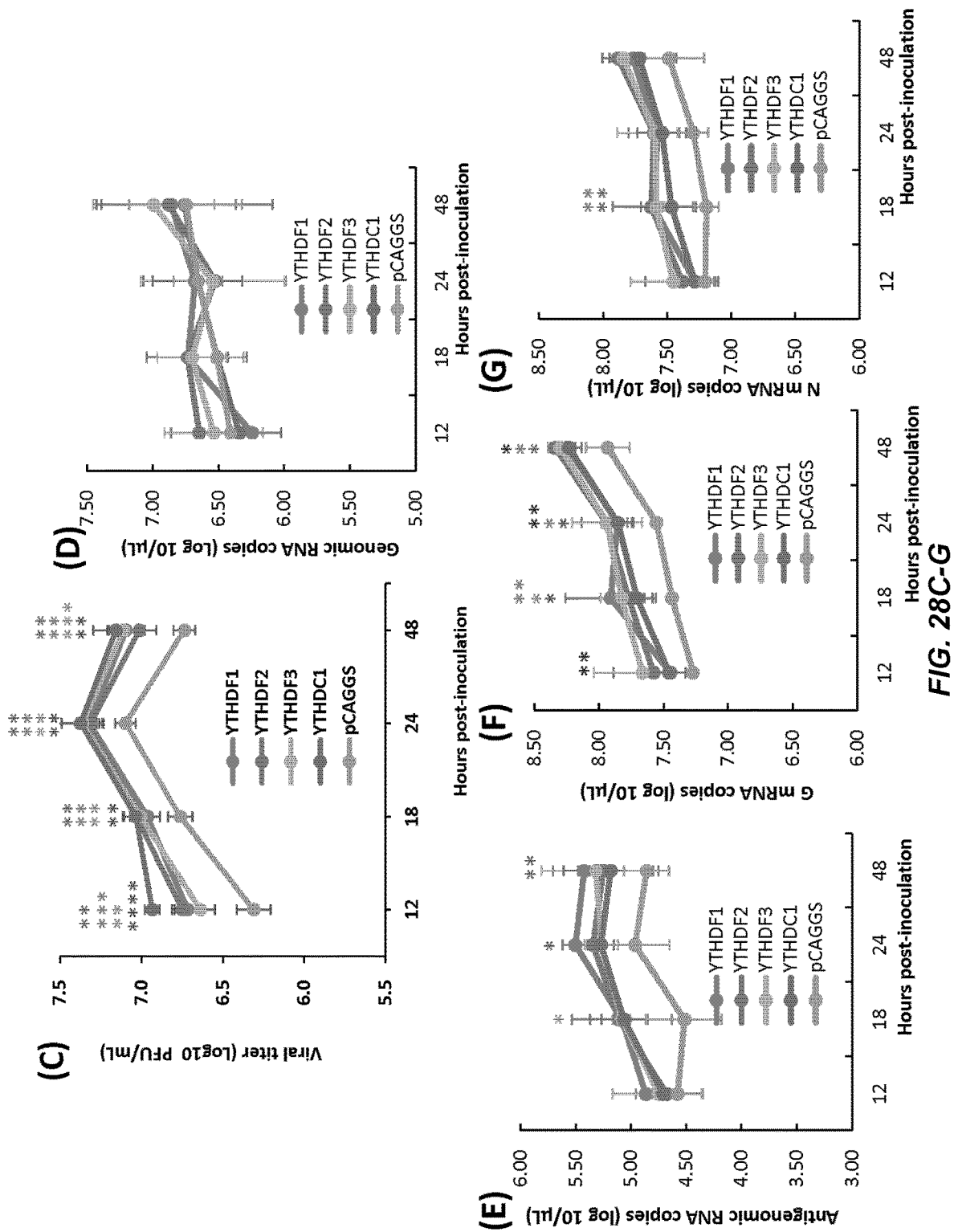
FIG. 28C-G

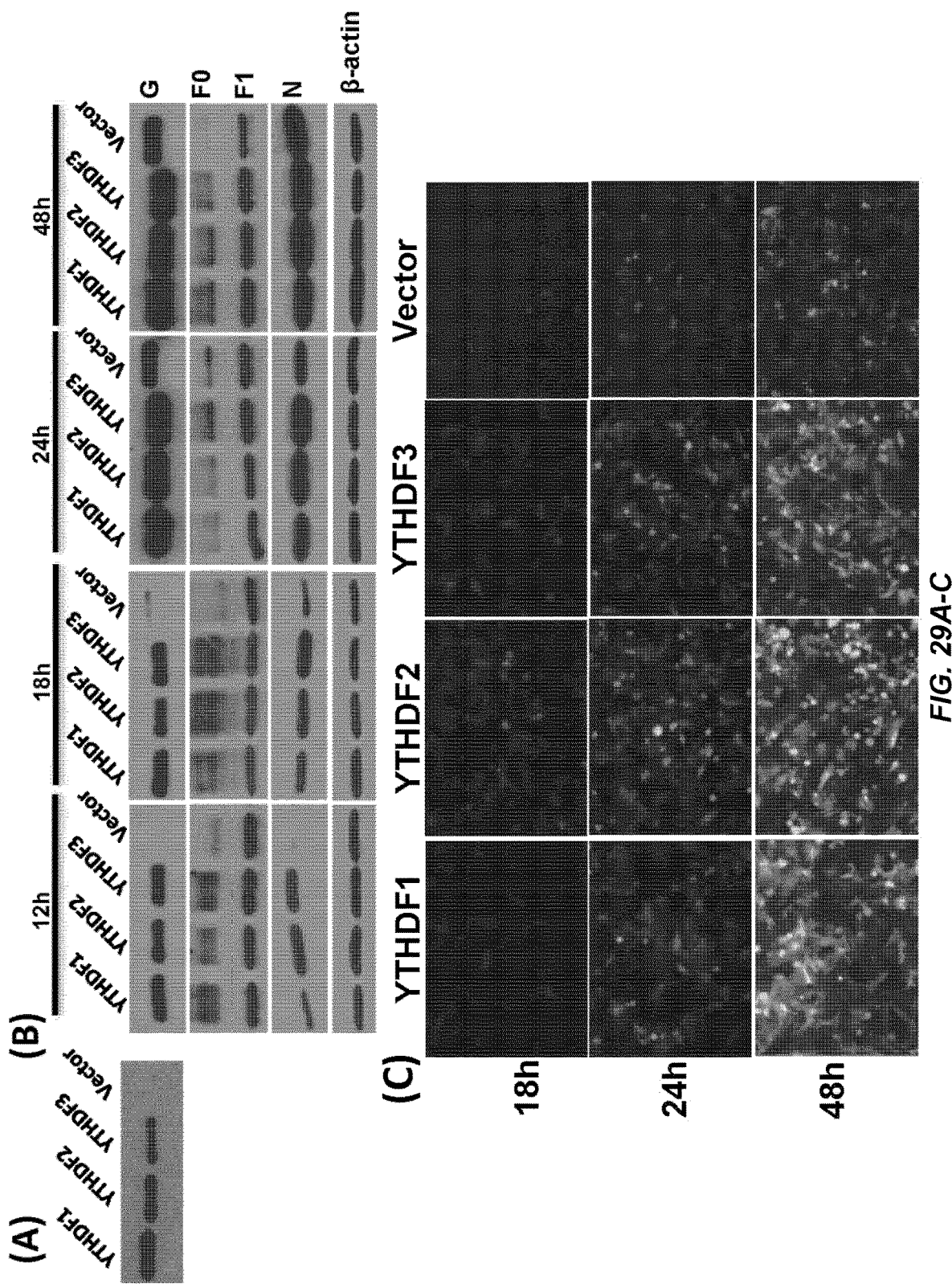
FIG. 29A-C

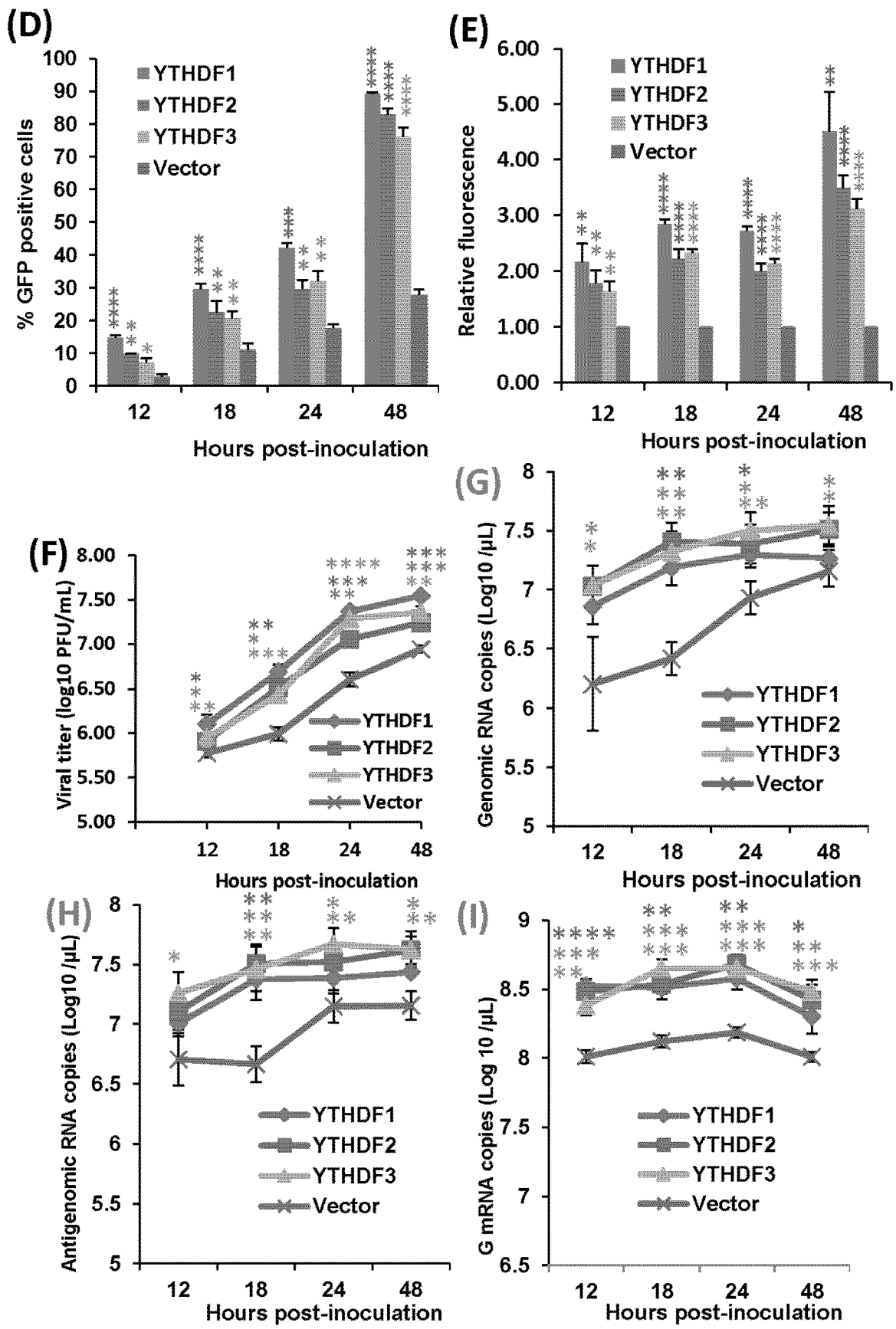
FIG. 29D-I

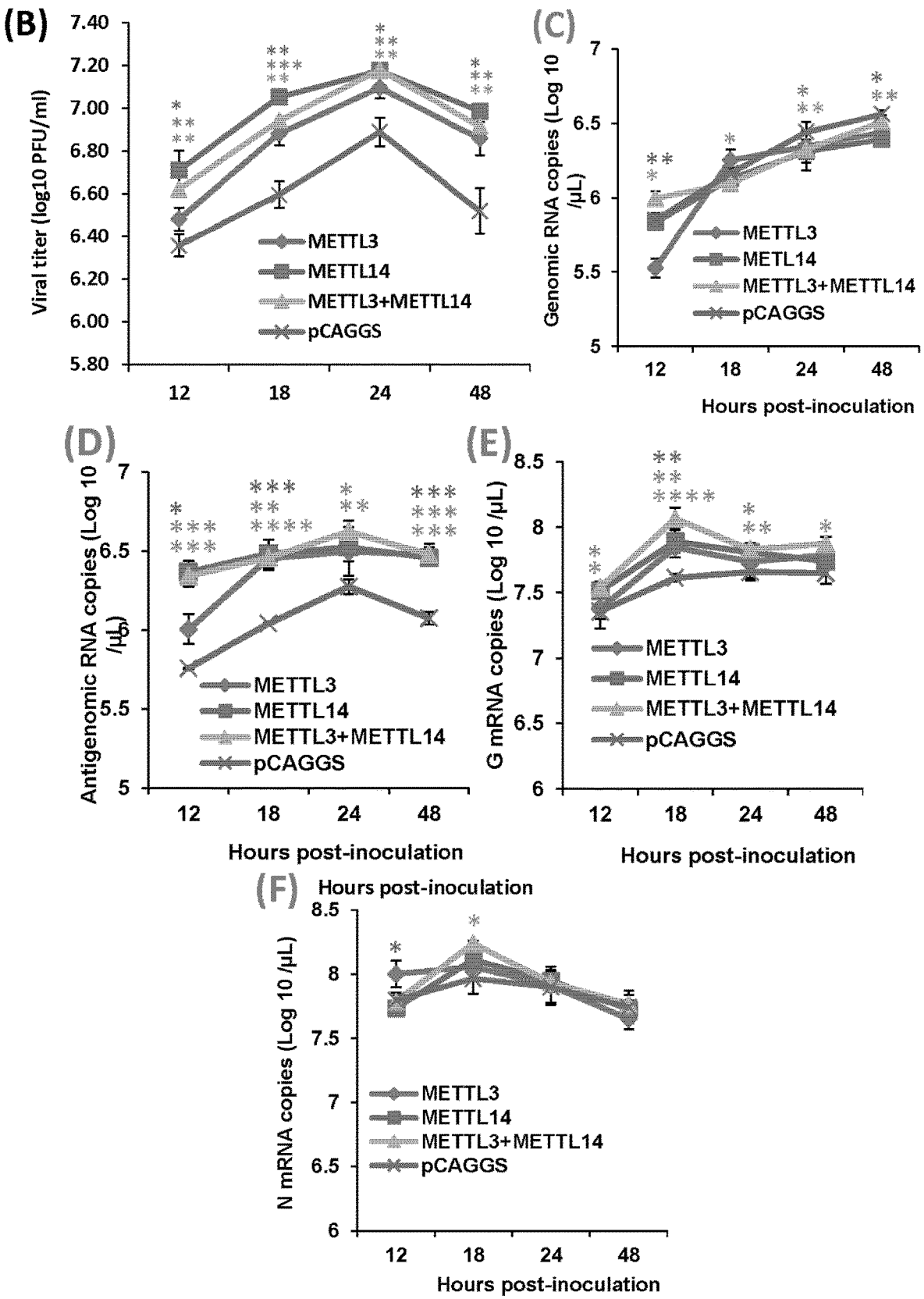
FIG. 30B-F

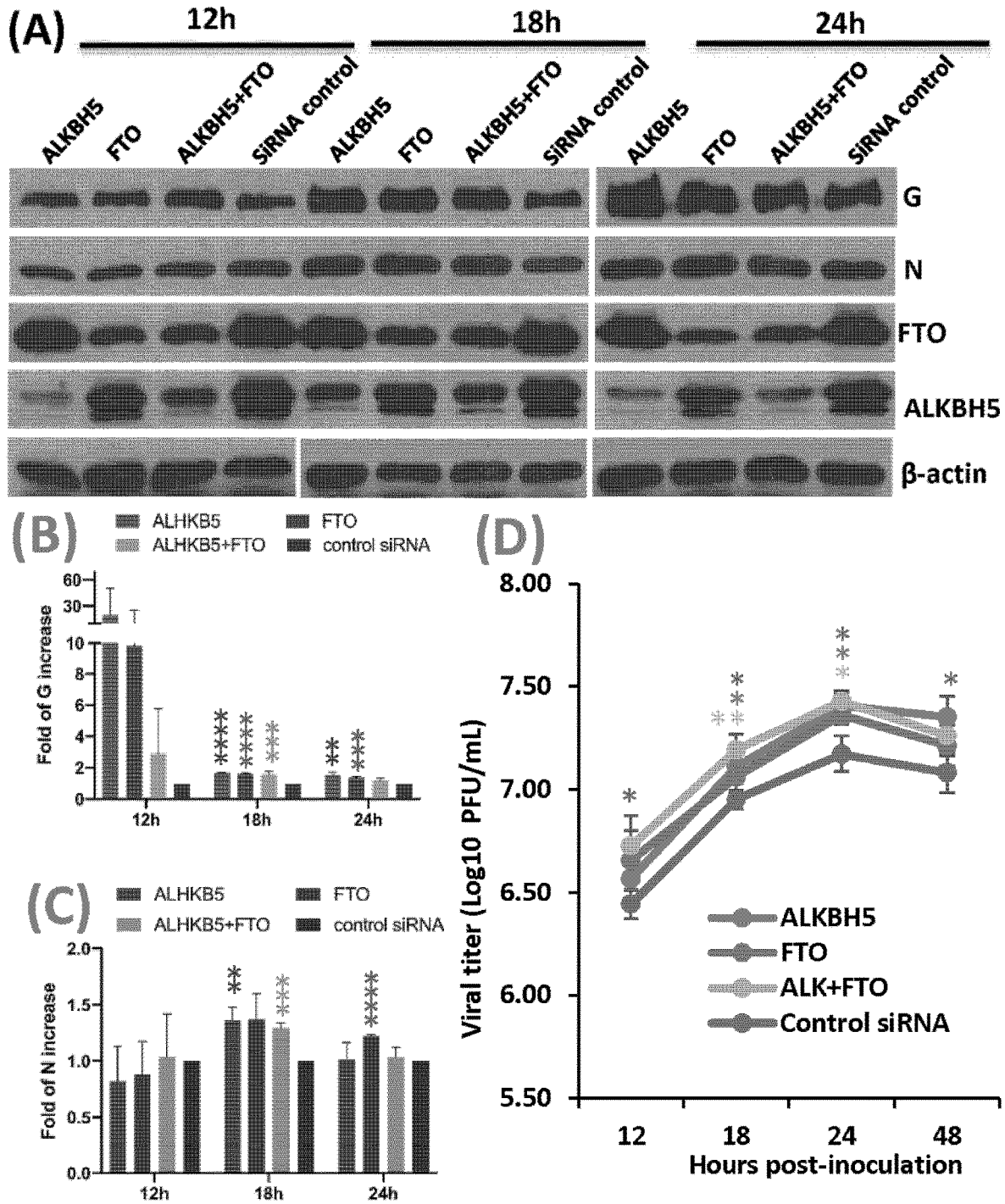
FIG. 31A-D

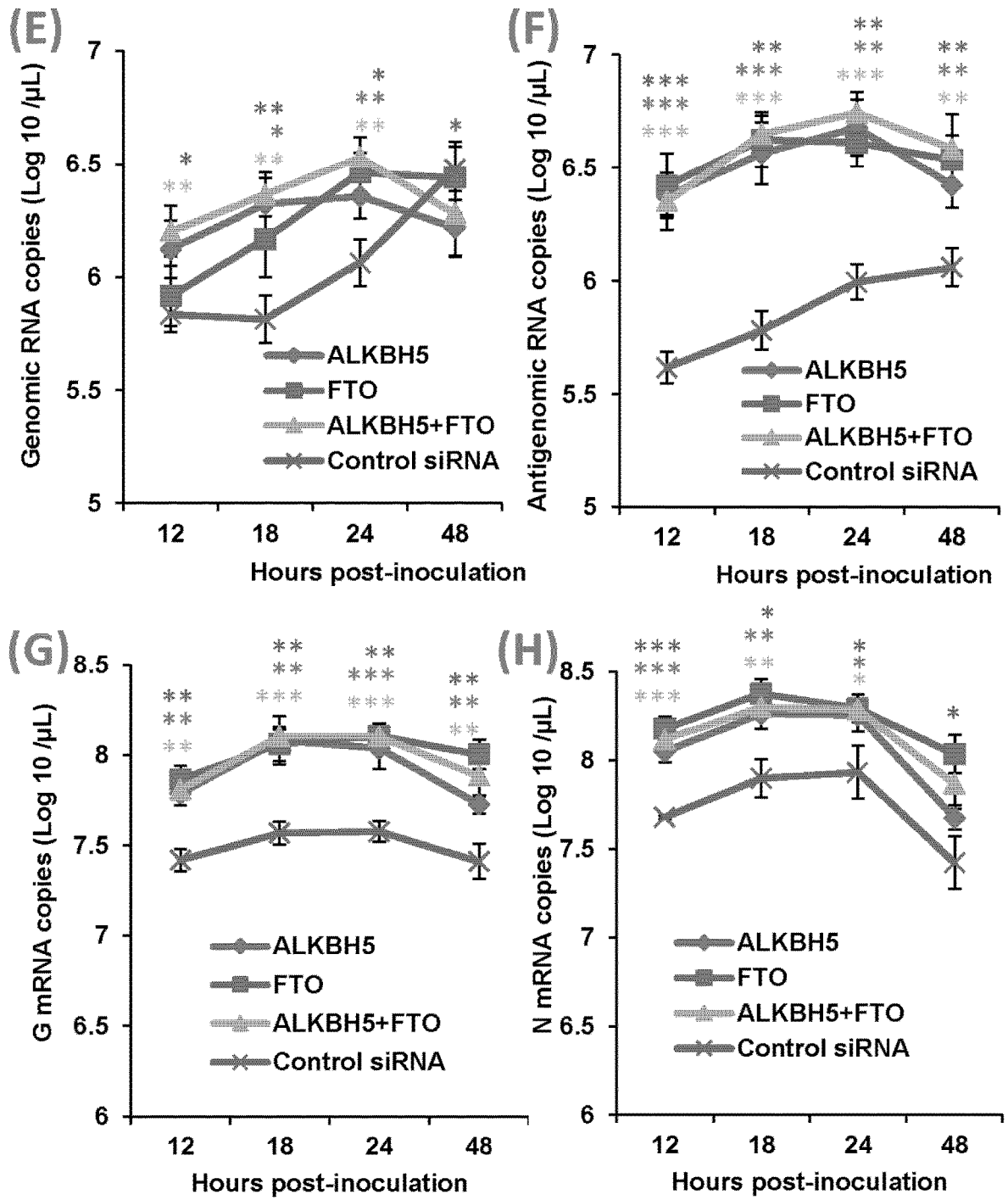
FIG. 31E-H

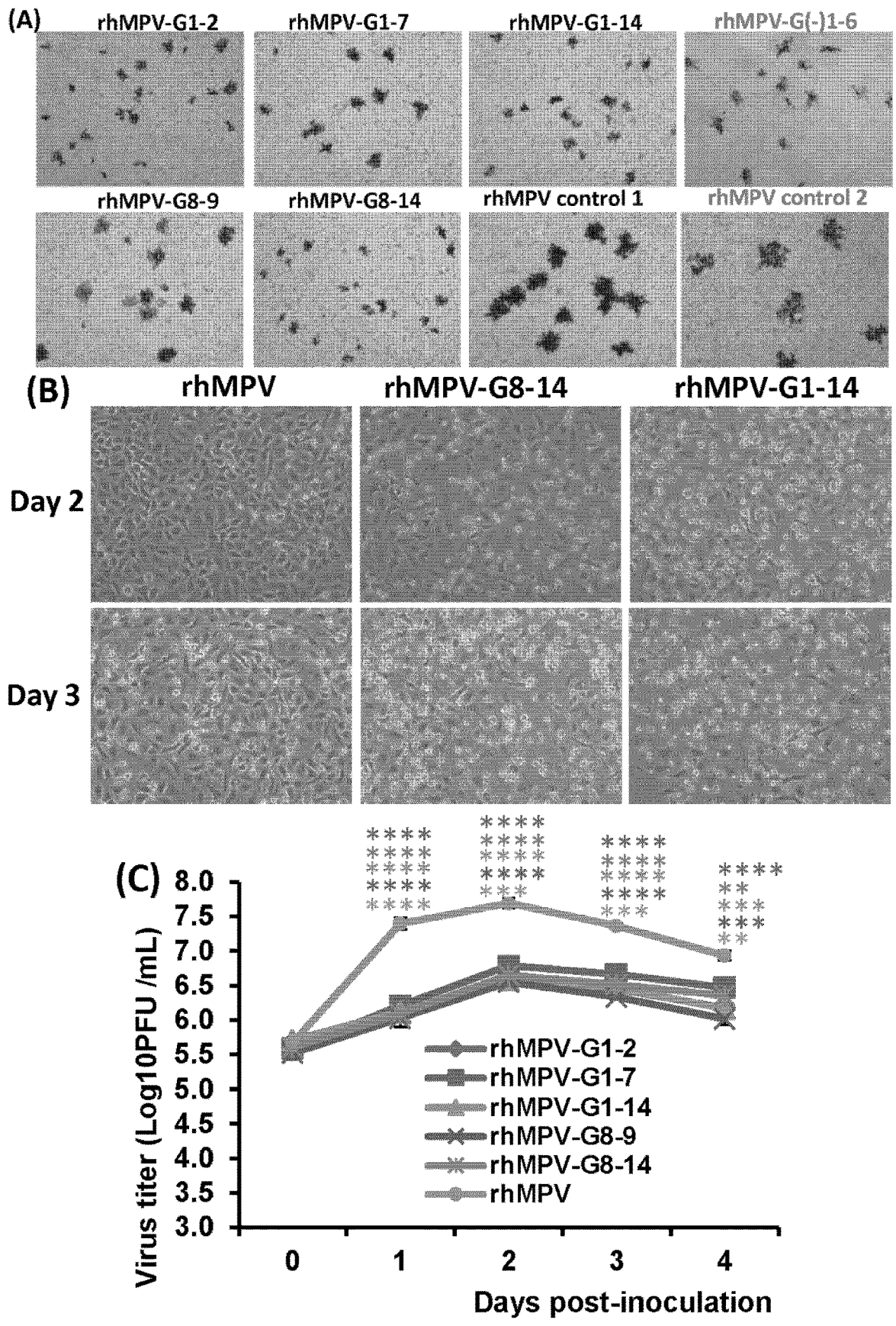
FIG. 32A-C

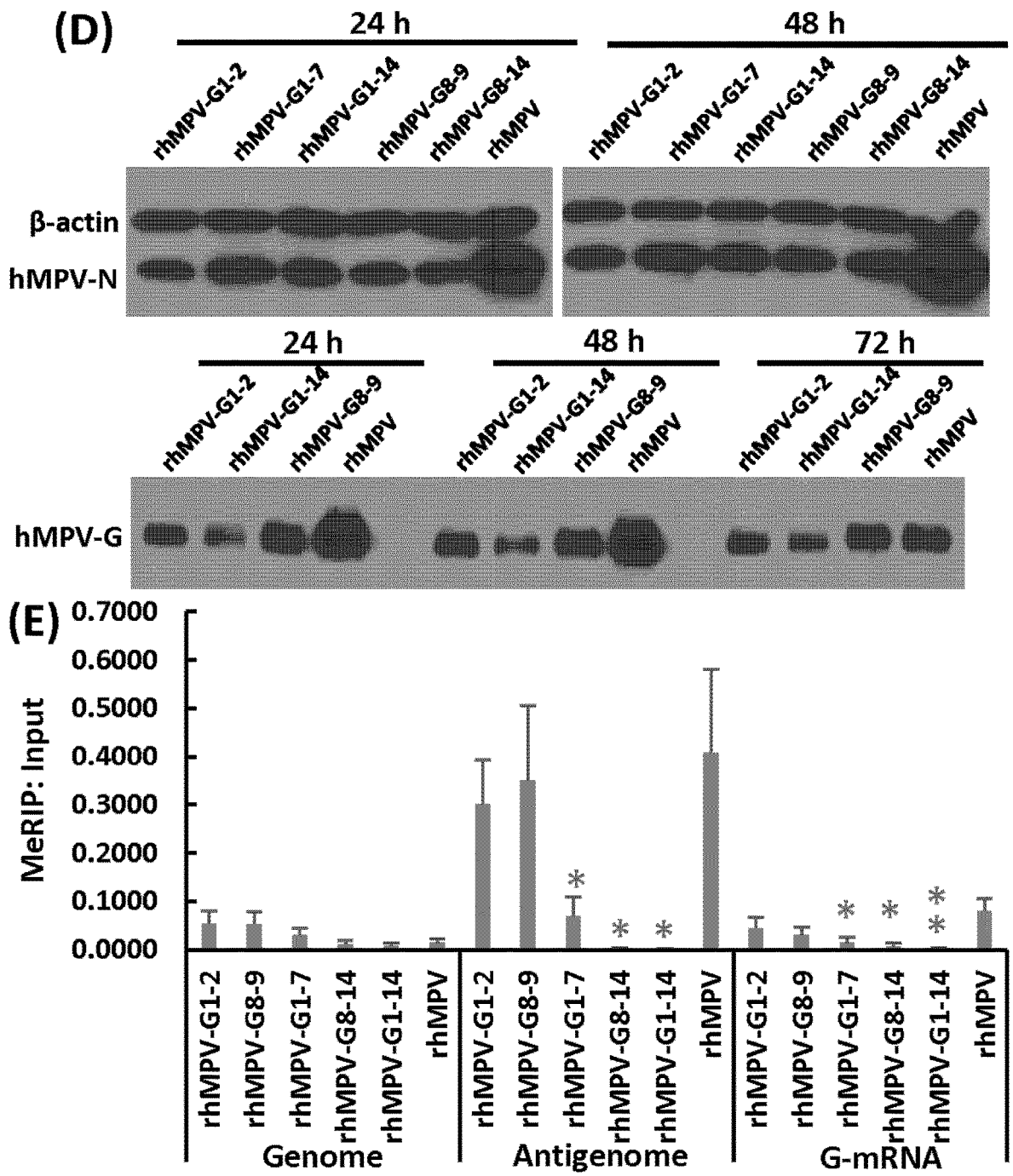
FIG. 32D-E

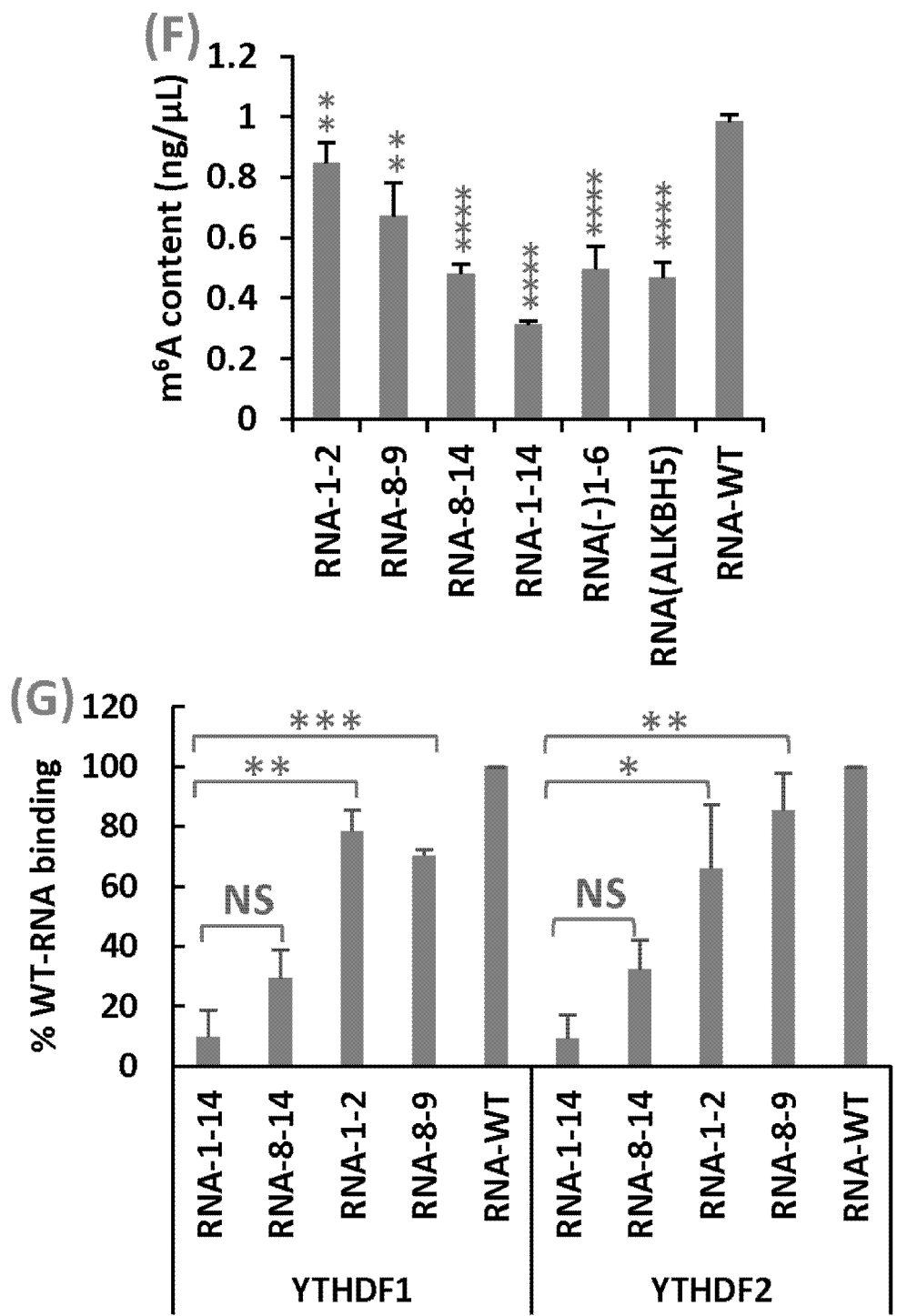
FIG. 32F-G

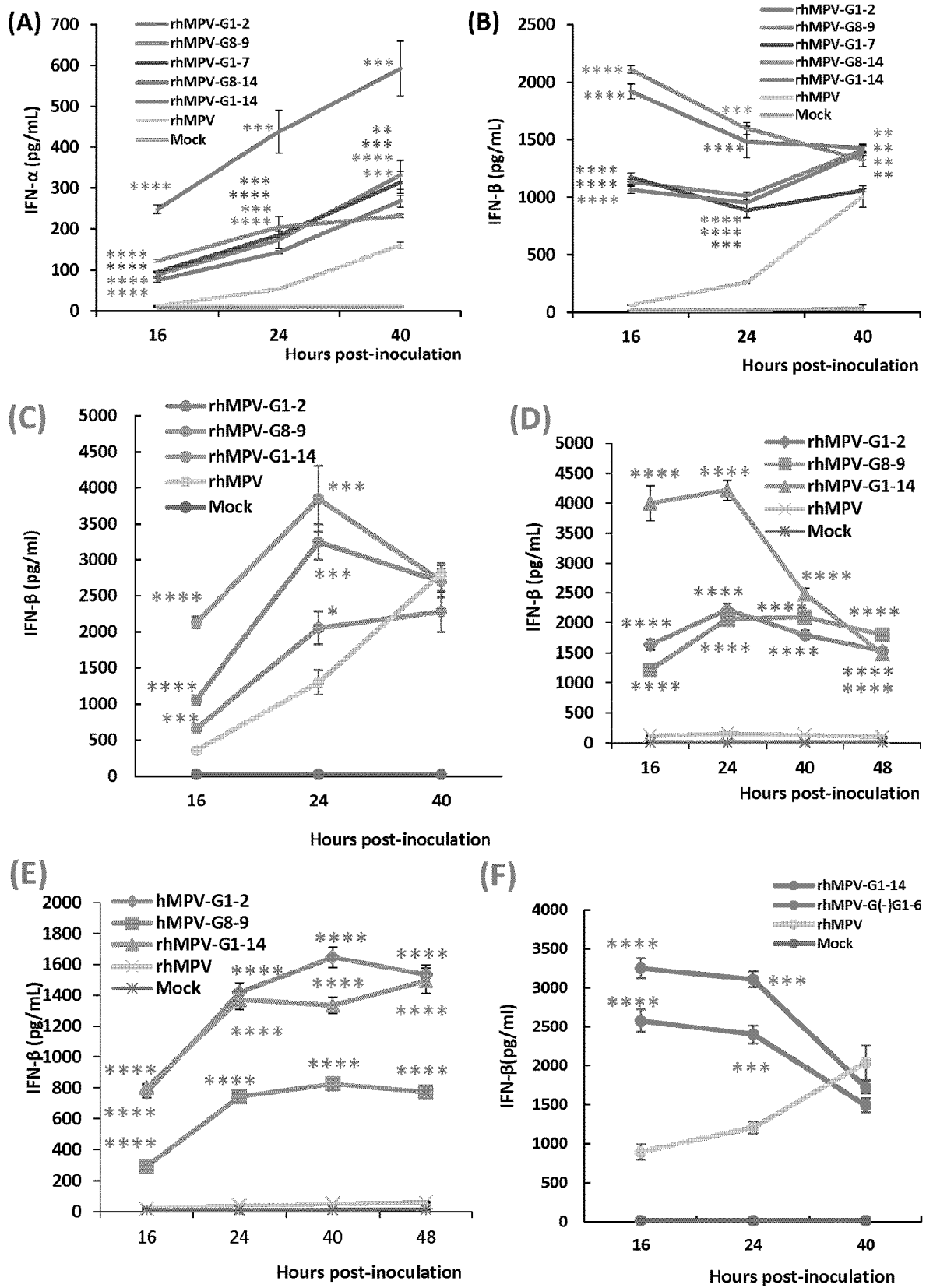
FIG. 33A-F

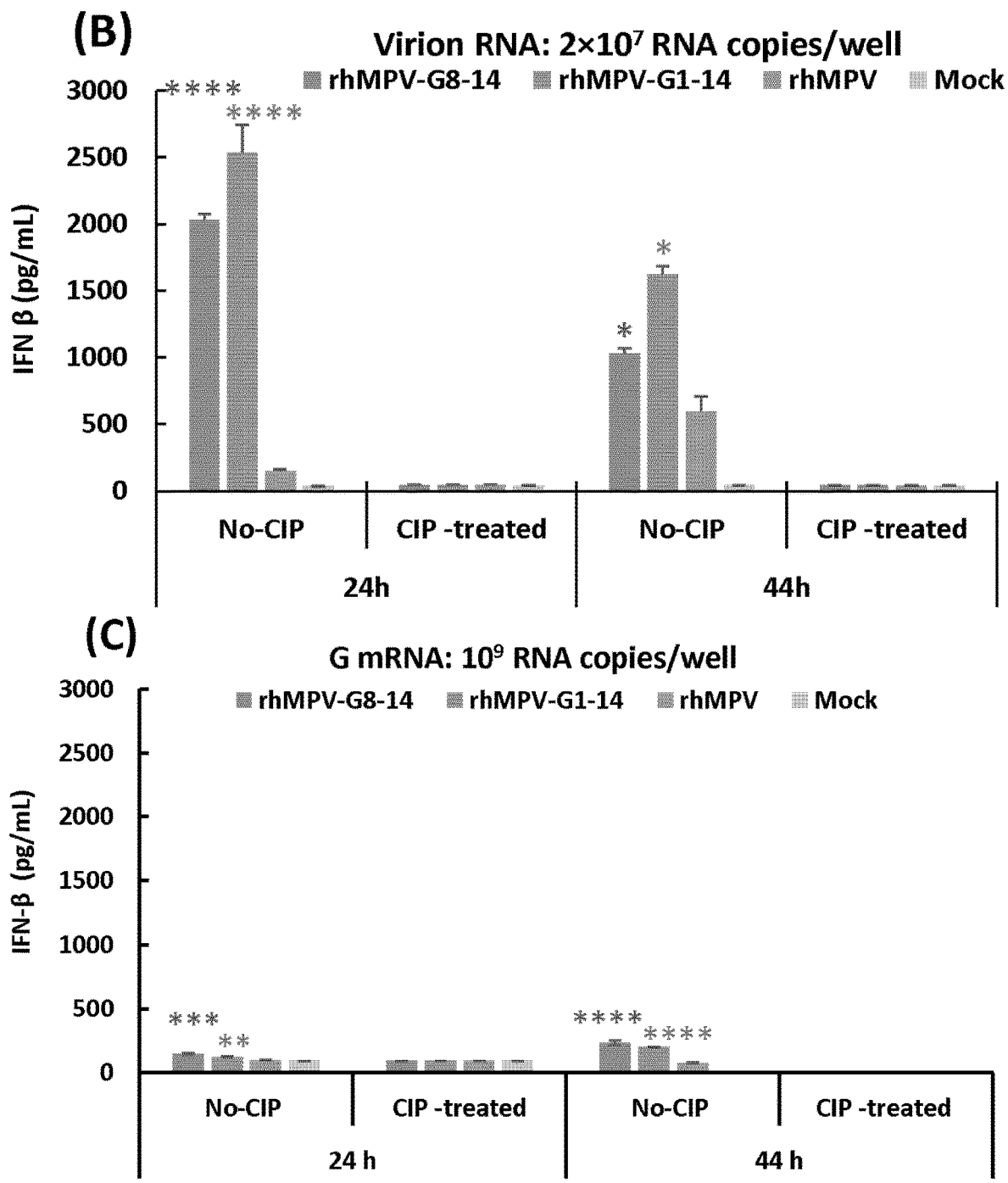
FIG. 34B-C

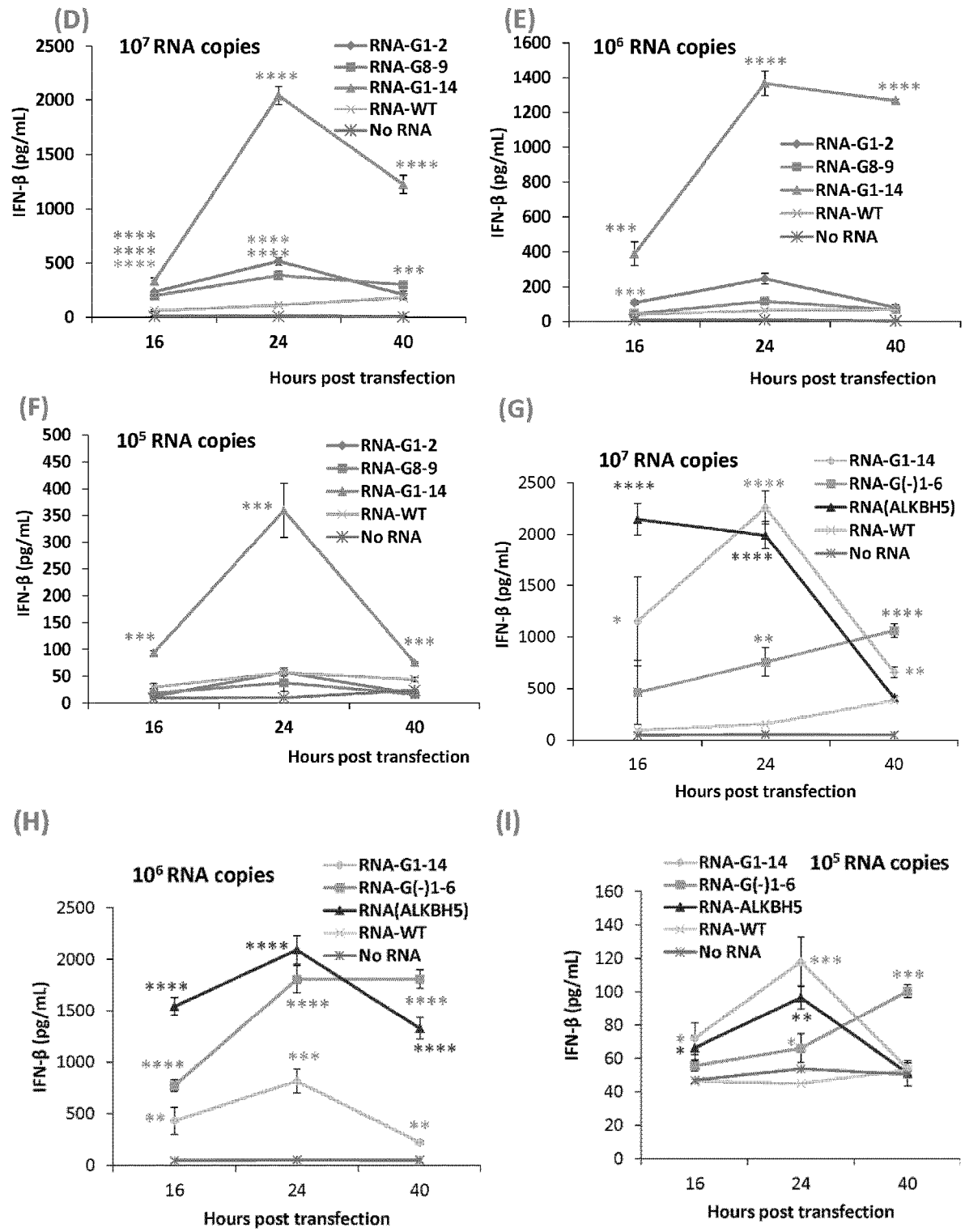
FIG. 34D-I

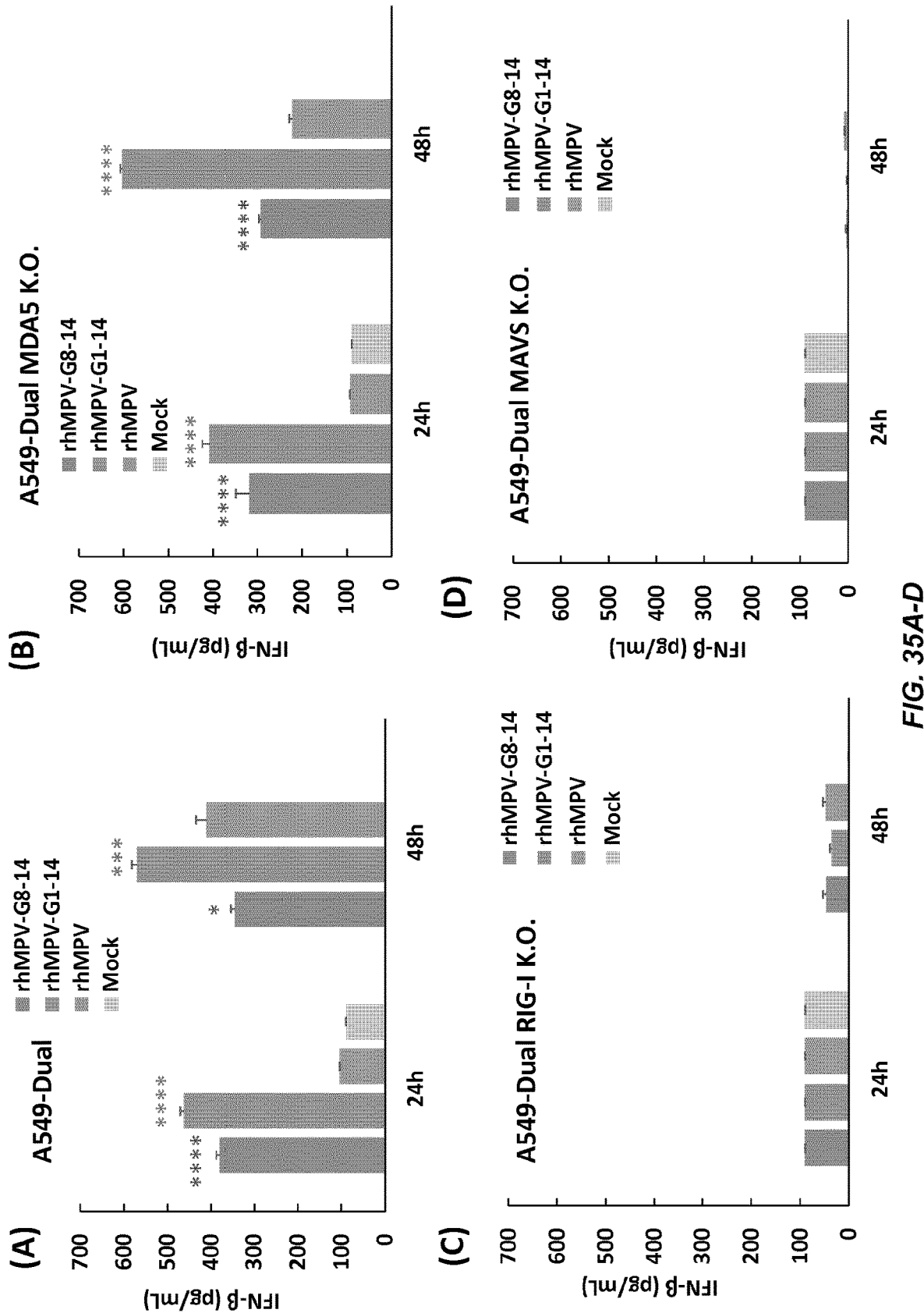
FIG. 35A-D

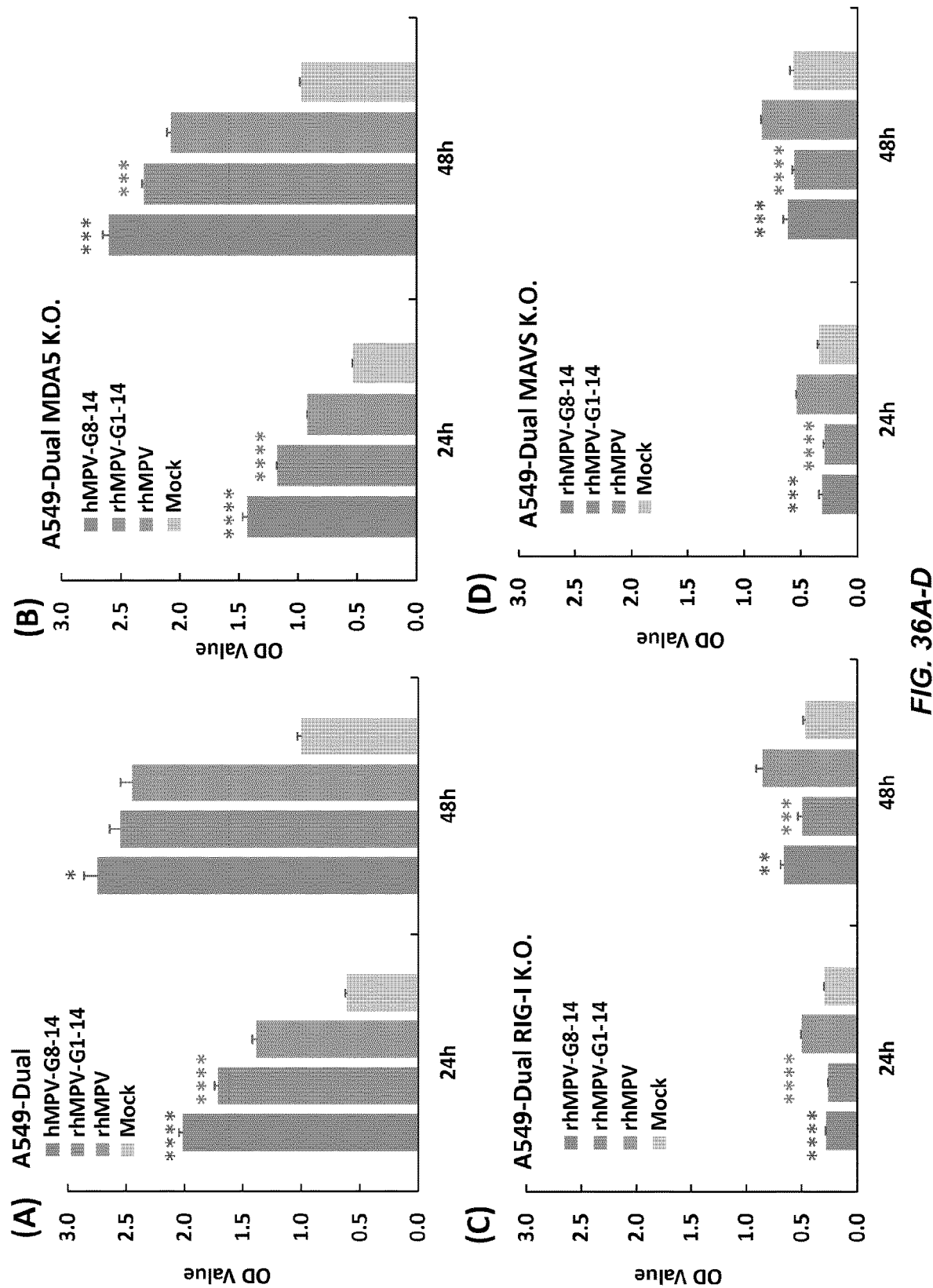
FIG. 36A-D

FIG. 37A-D

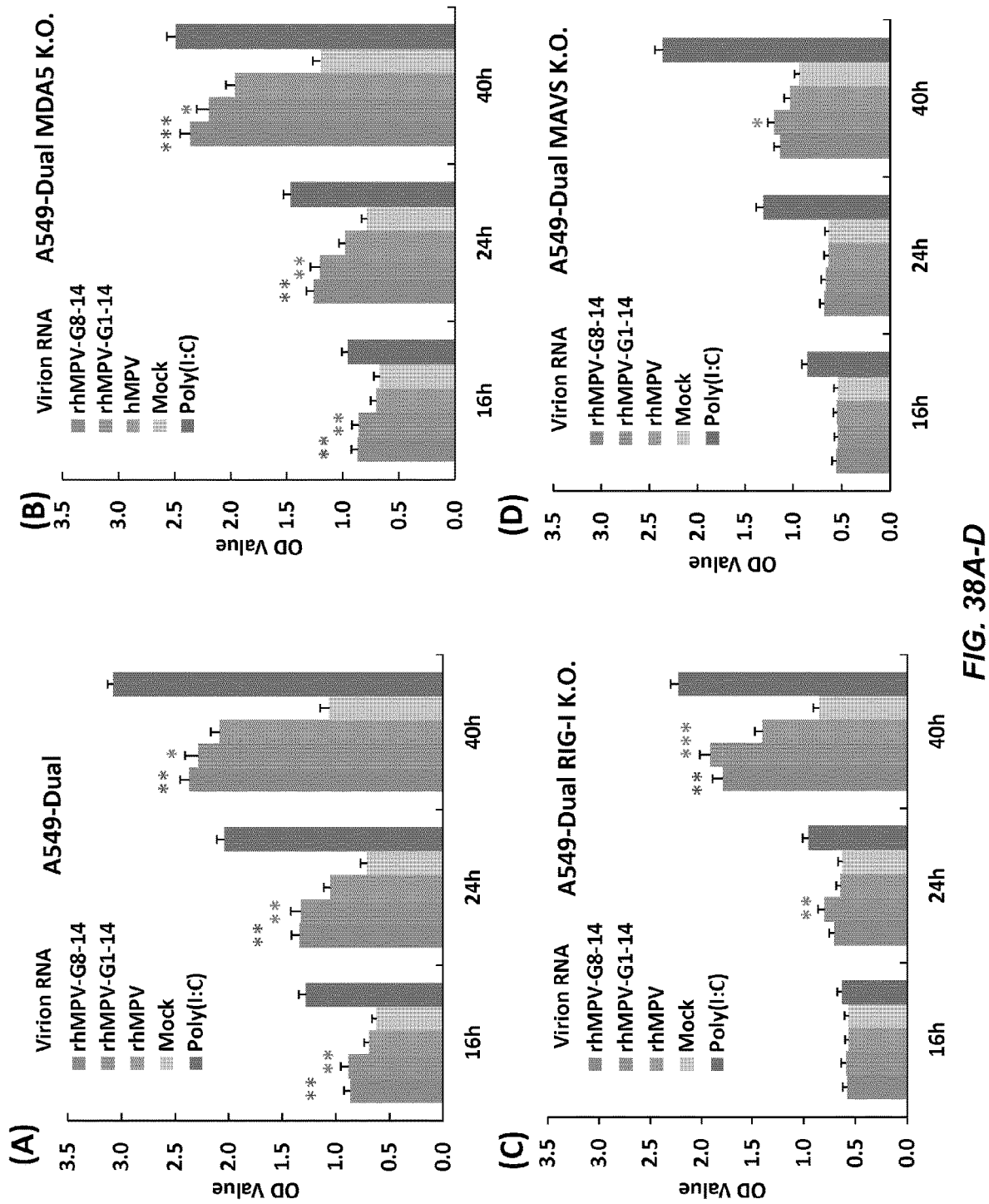
FIG. 38A-D

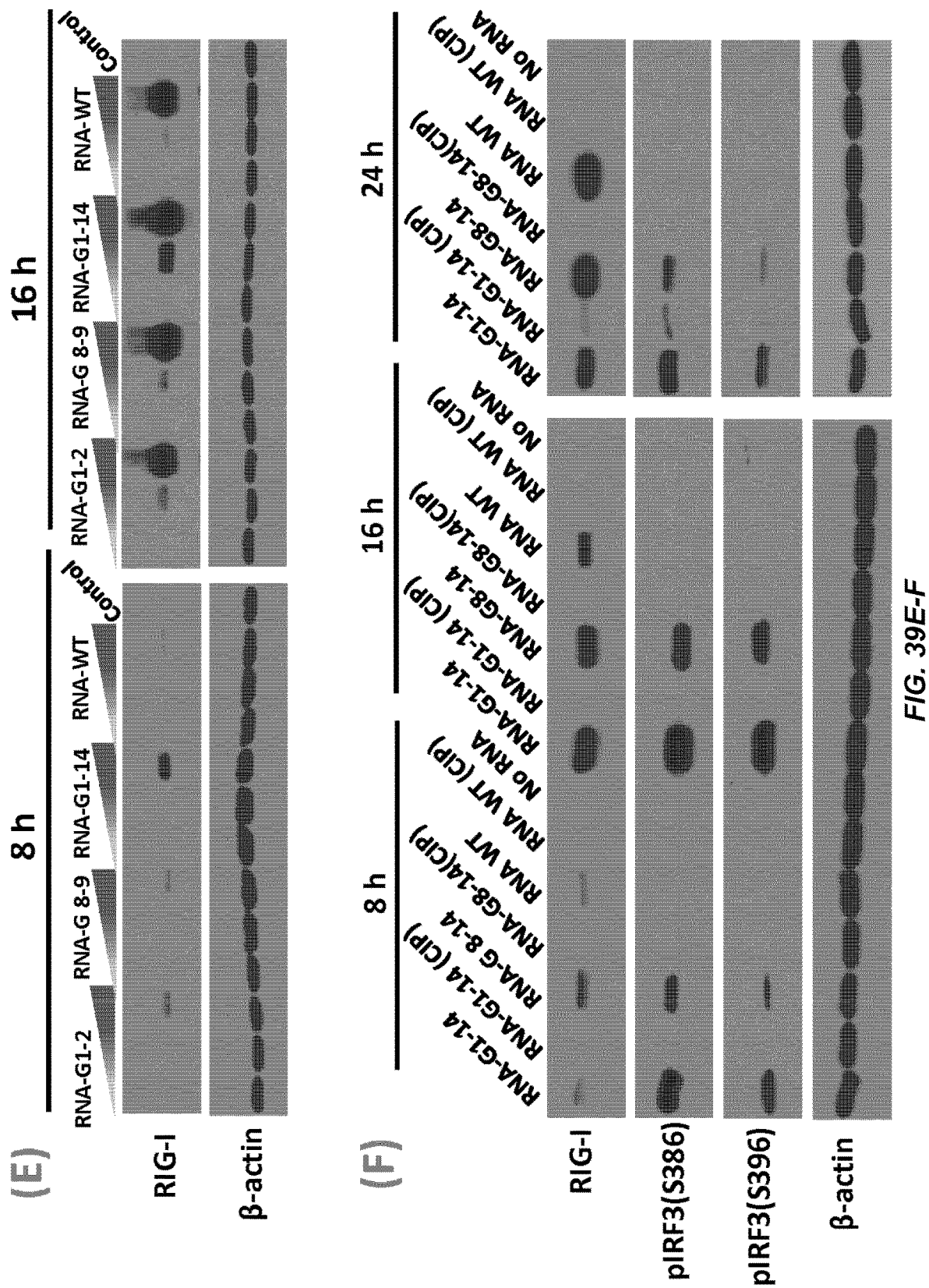
FIG. 39E-F

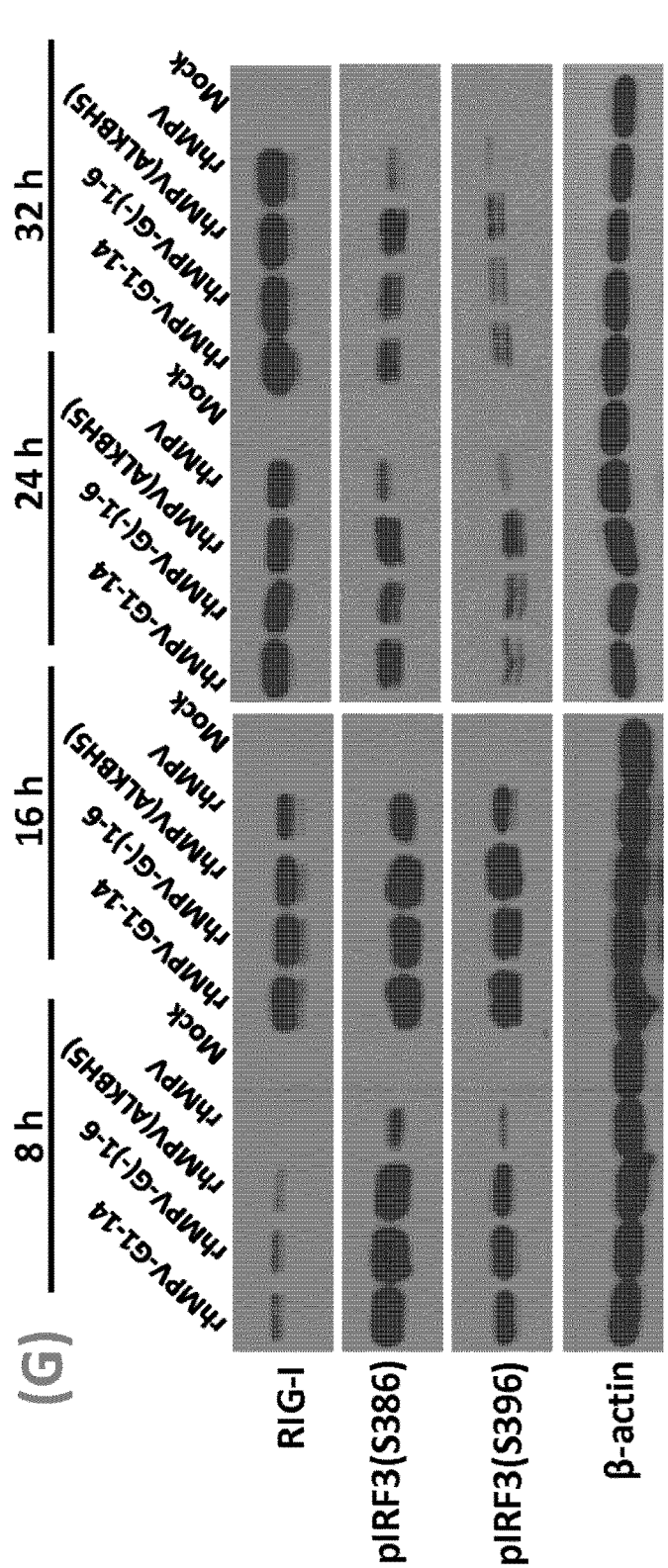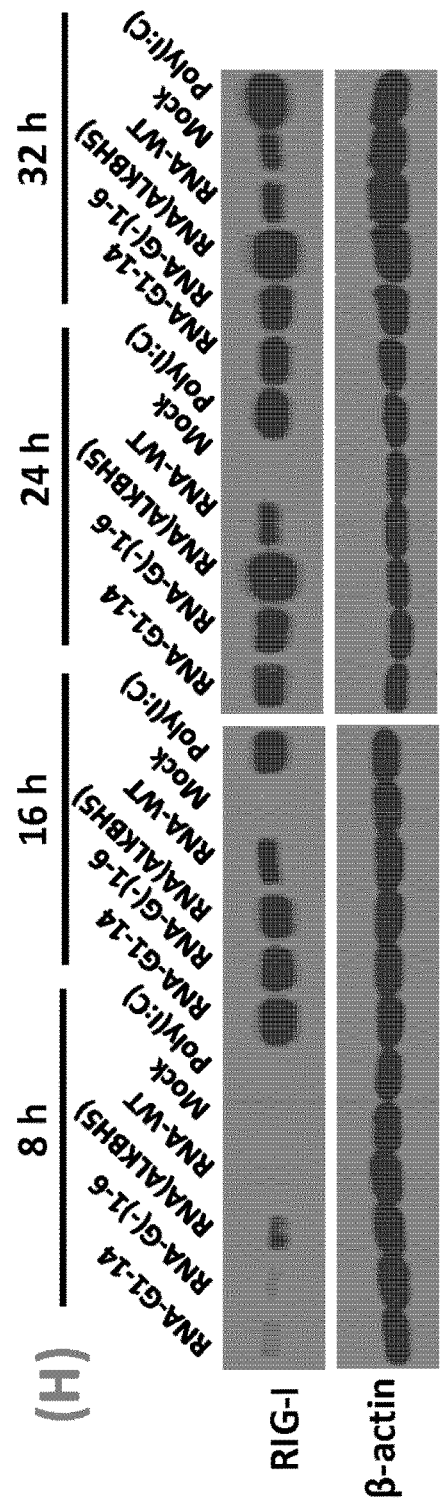
FIG. 39G-H

FIG. 40A-E

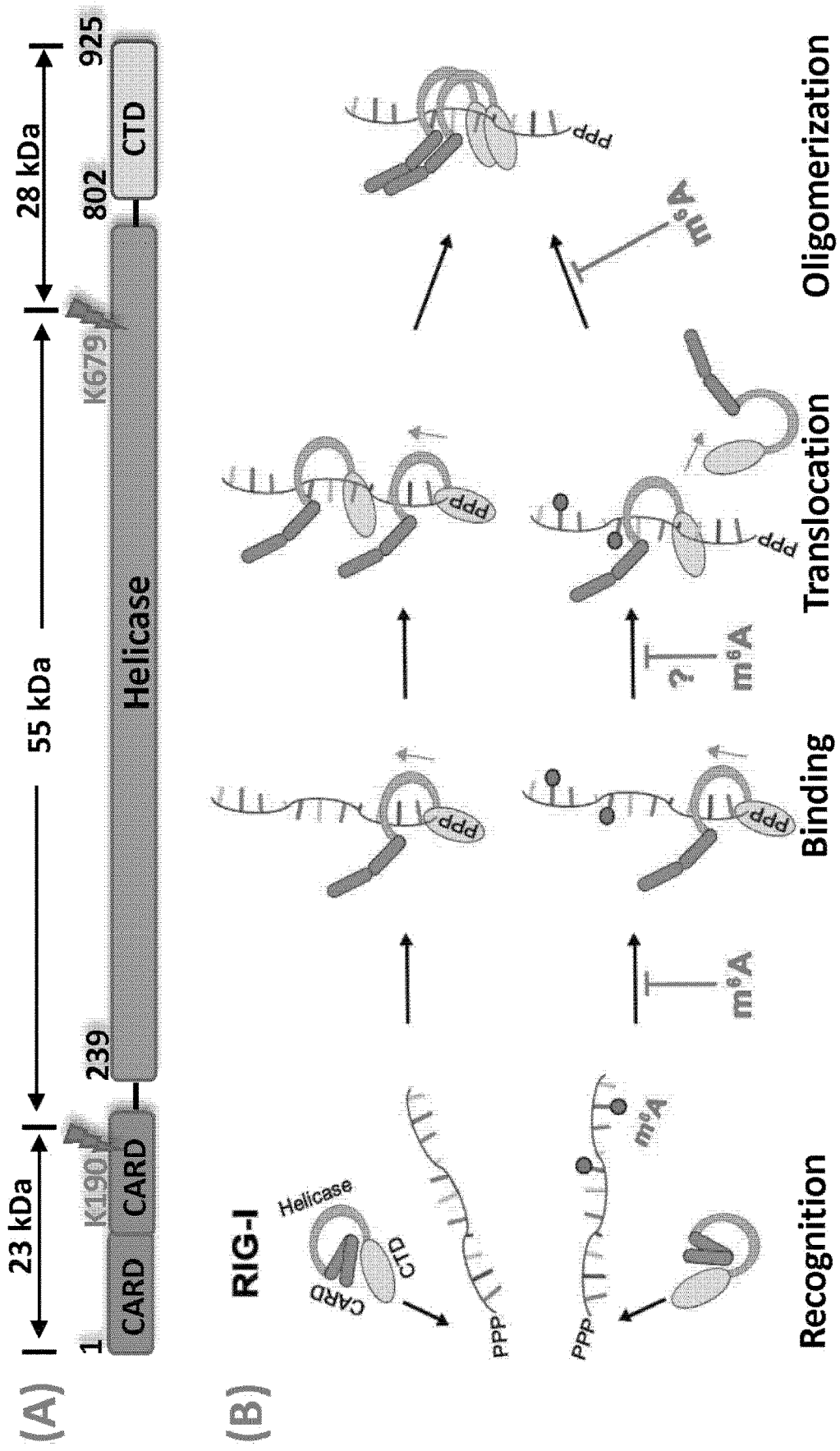
FIG. 41A-B

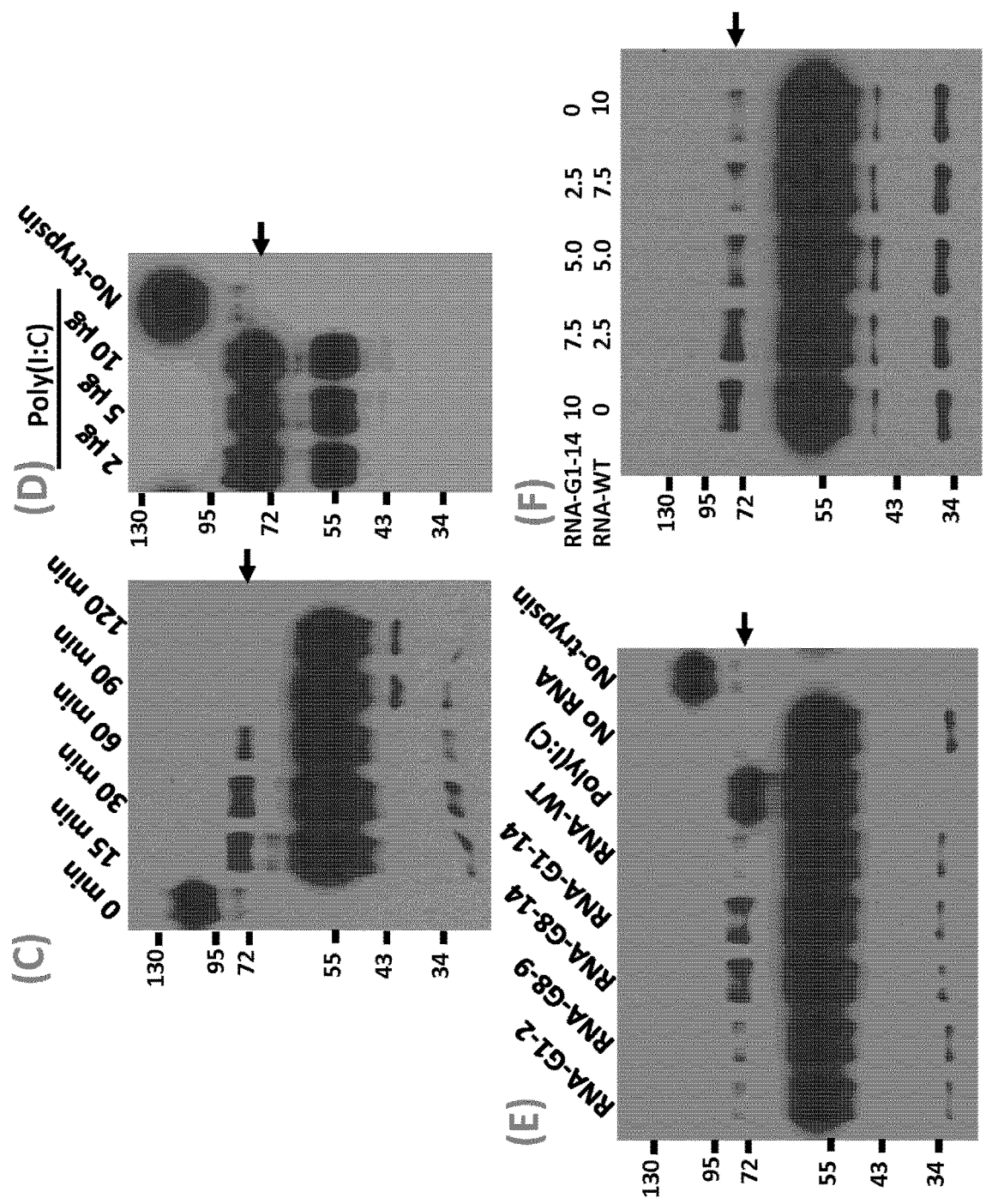
FIG. 41C-F

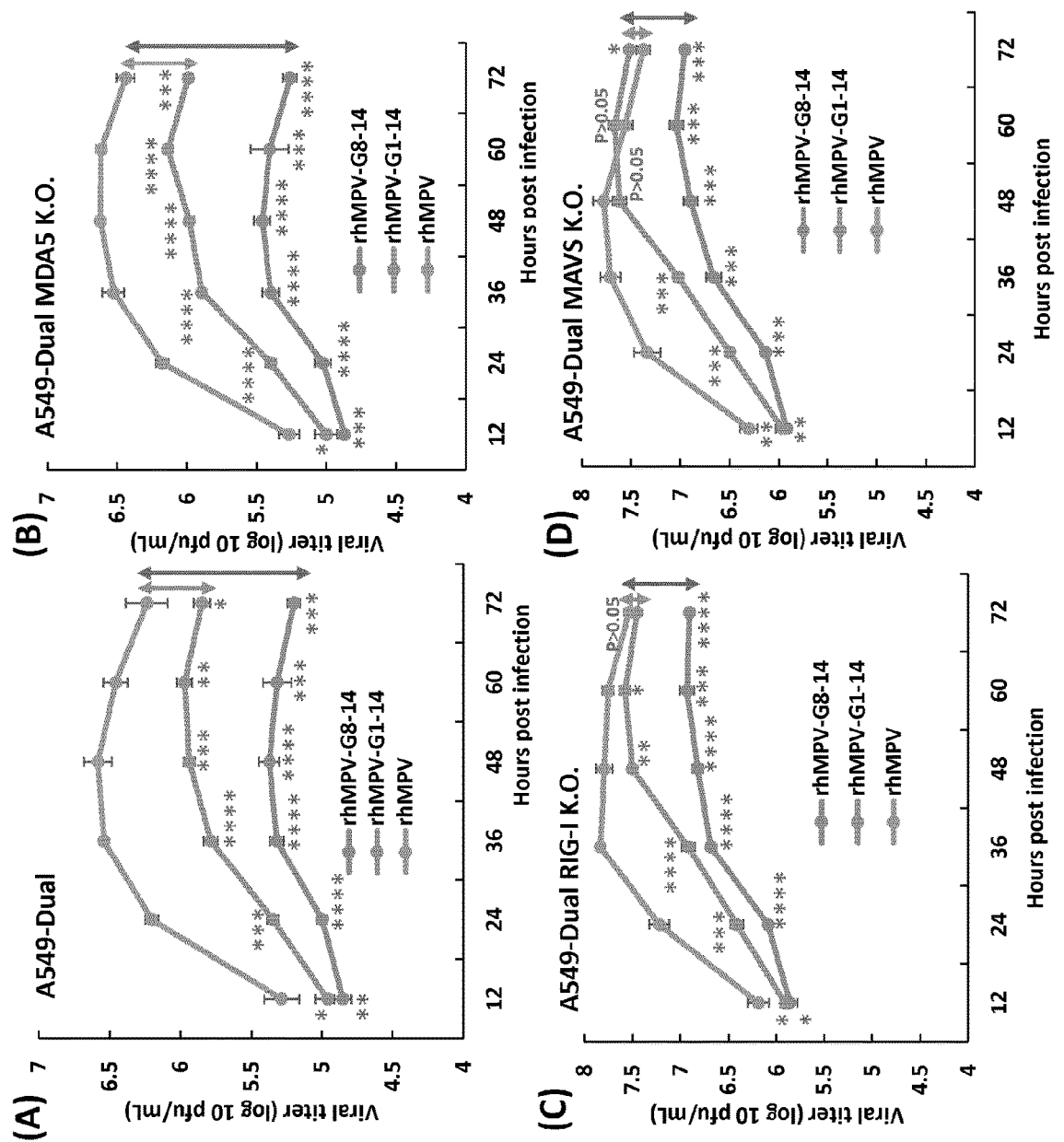
FIG. 42A-D

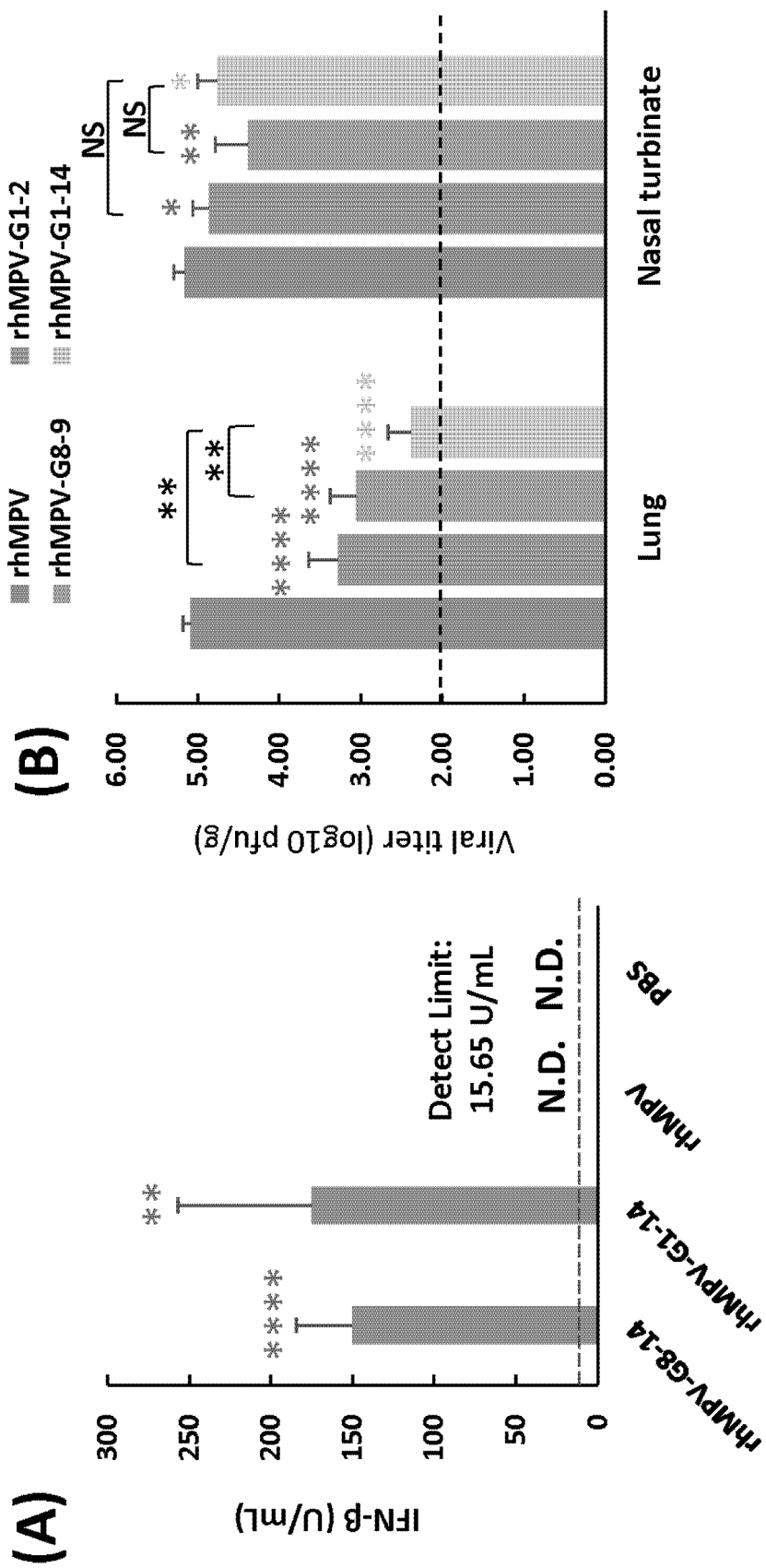
FIG. 43A-B

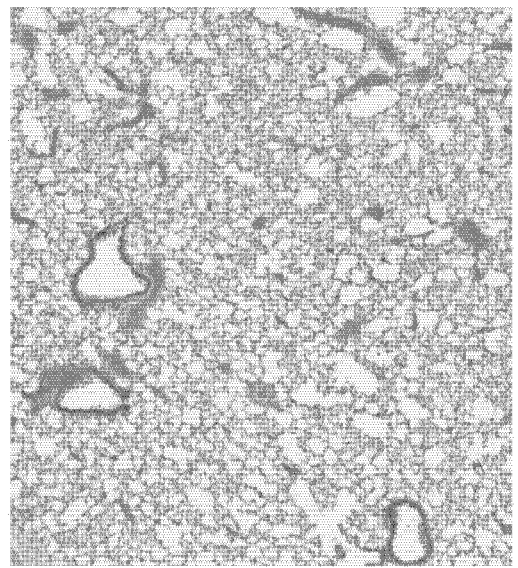
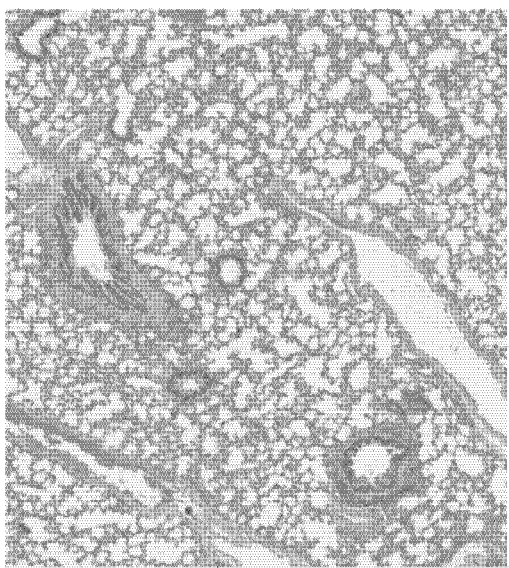
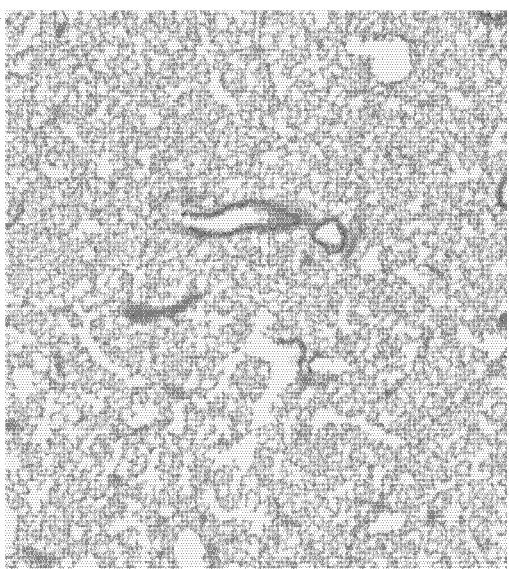
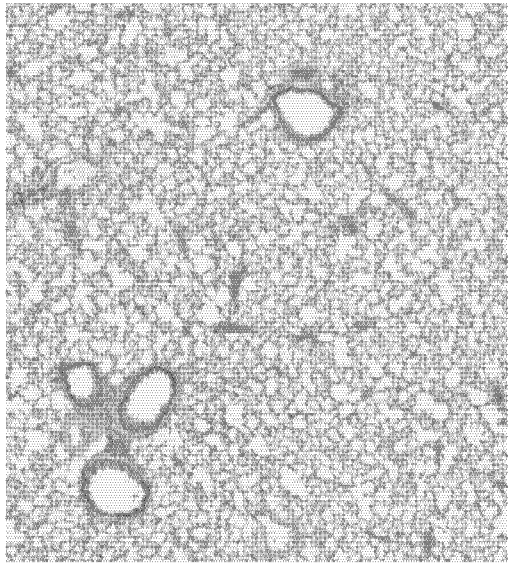
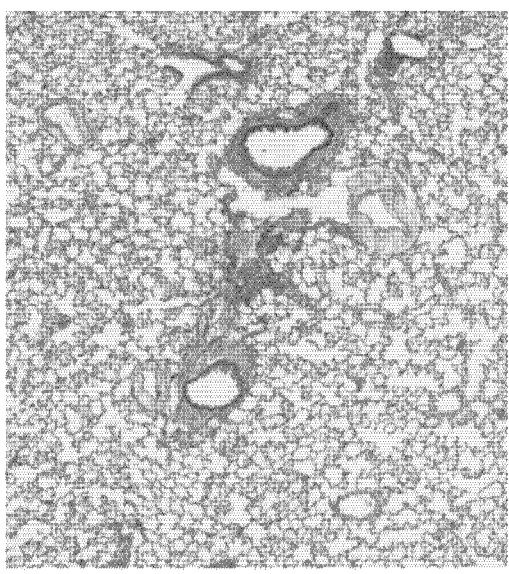
FIG. 43C

FIG. 43D-E

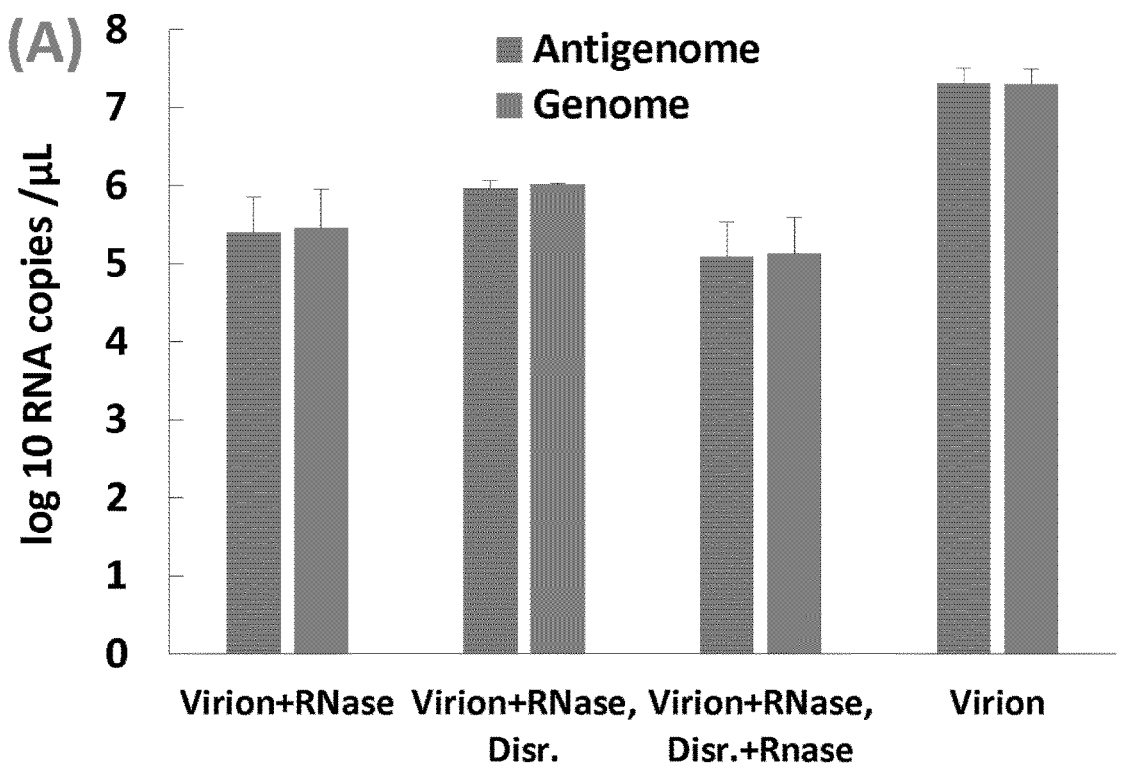
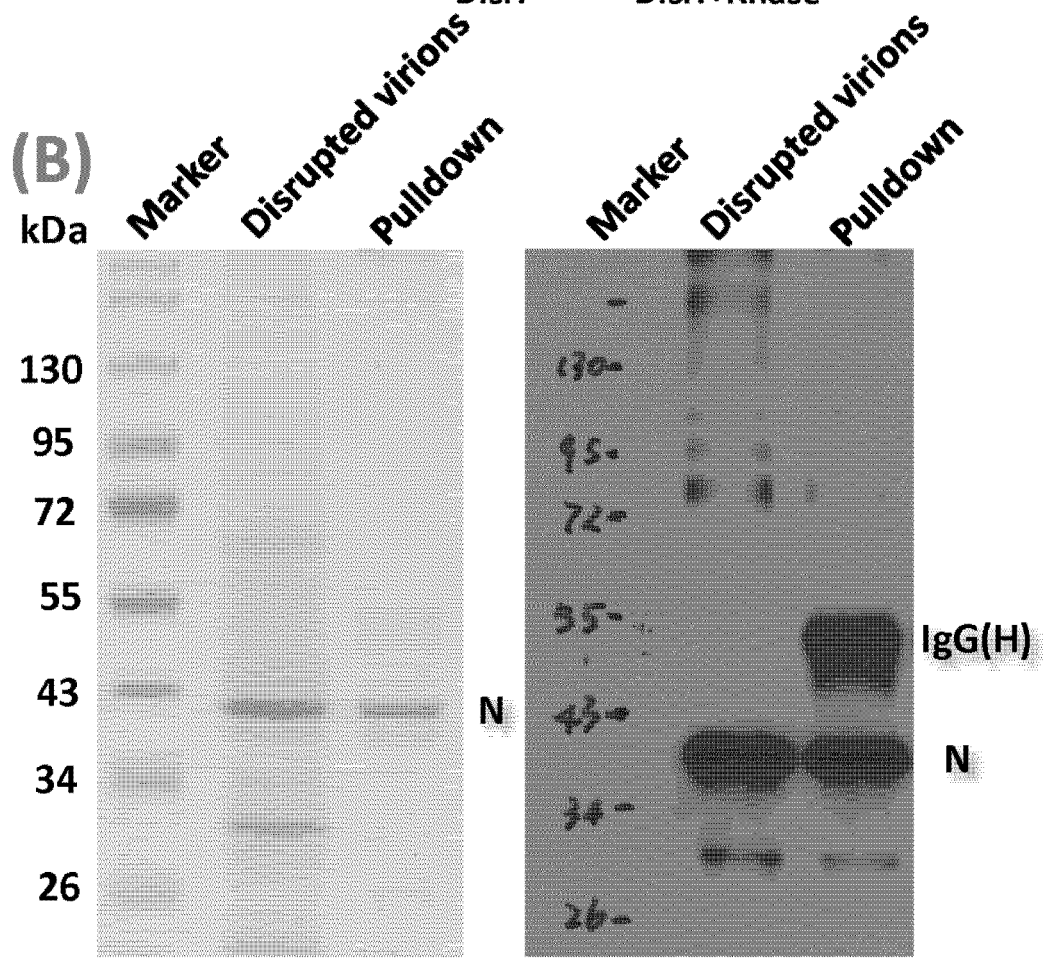
*FIG. 45A-B*

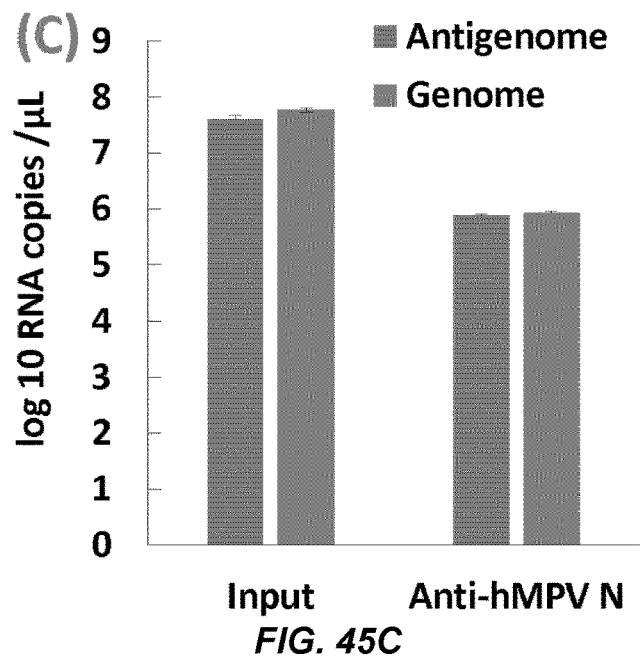
FIG. 45C
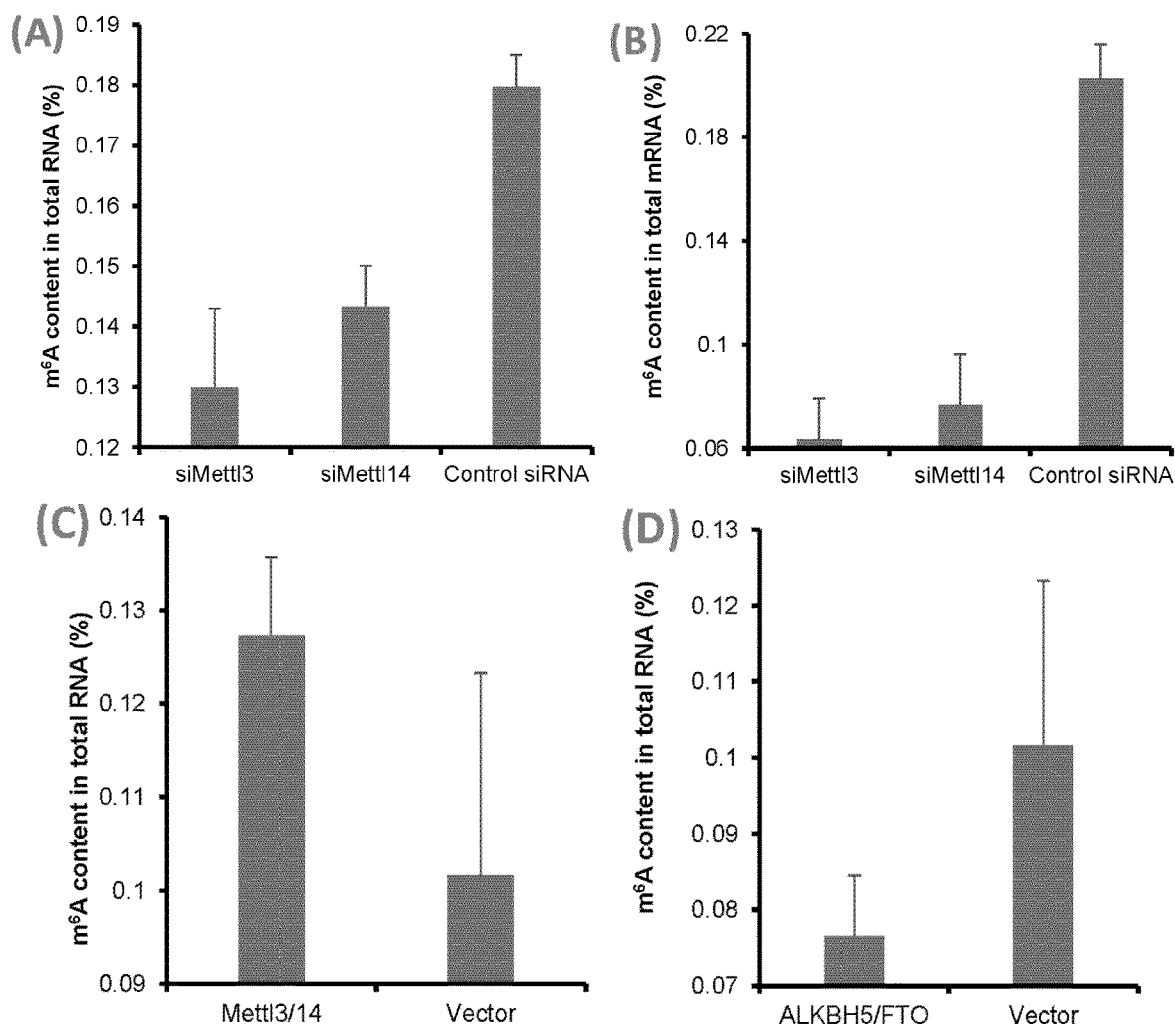
FIG. 46A-D

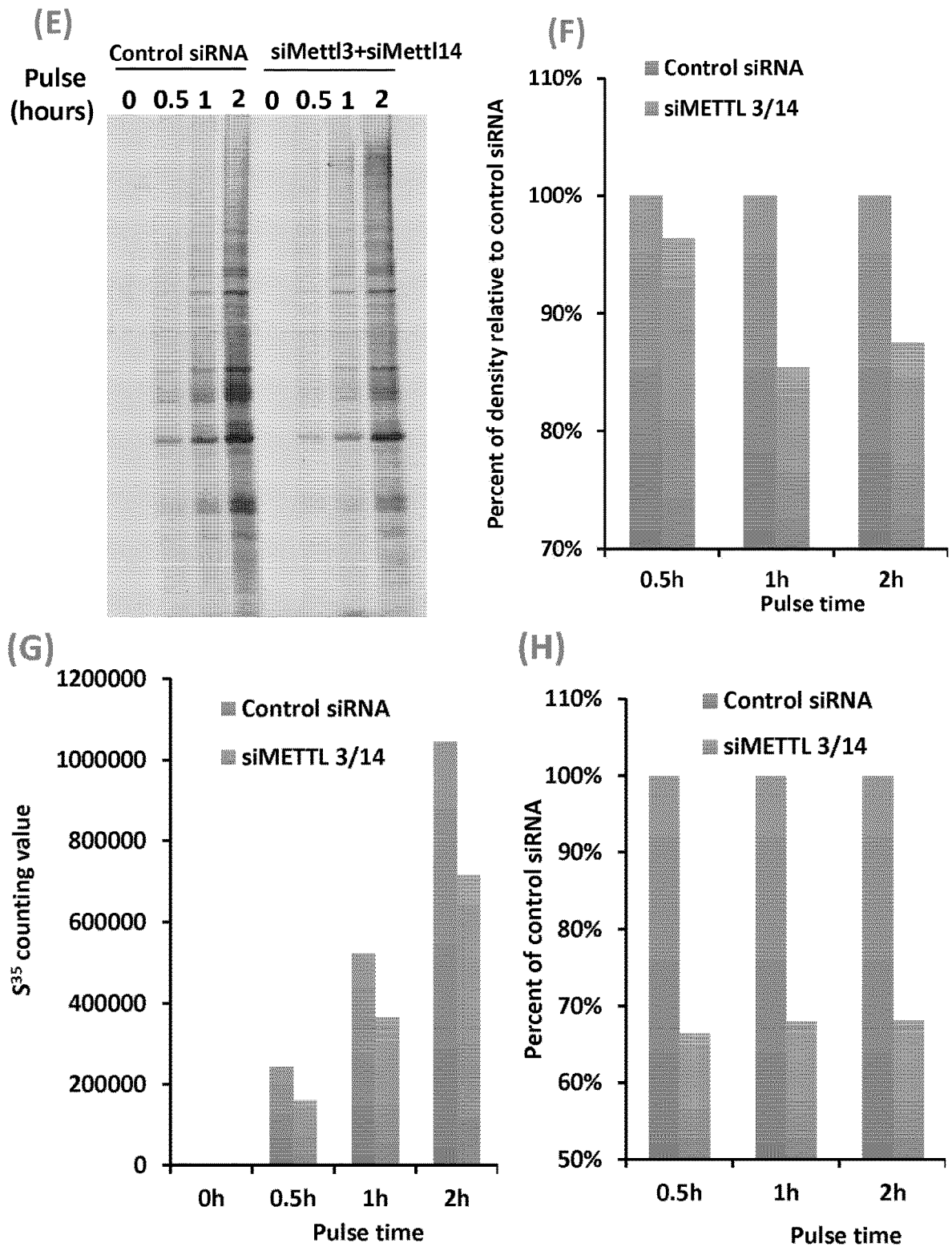
FIG. 46E-H

(A)

| | YTHDF1-HA | YTHDF2-HA |
| --- | --- | --- |
| | I.P. | I.P. |

Input | rhMPV-G8-14 | rhMPV-G1-14 | rhMPV | Input | rhMPV-G8-14 | rhMPV-G1-14 | rhMPV YTHDF-HA — 62 kDa IgG (H Chain) — 50 kDa β-actin — 43 kDa IgG (L Chain) — 22 kDa

(B)

Legend: rhMPV-G8-14, rhMPV-G1-14, rhMPV

Y-axis: %hMPV binding (0.0000–1.2000)

X-axis: YTHDF1, YTHDF2 — Antigenome

*FIG. 53A-B* rhMPV-G1-14 (RNA) | rhMPV-G1-14 (RNA-CIP)

rhMPV-G8-14 (RNA) | rhMPV-G8-14 (RNA-CIP)

rhMPV (RNA) | rhMPV (RNA-CIP)

Lipofectimine 3000 | Normal

*FIG. 55*

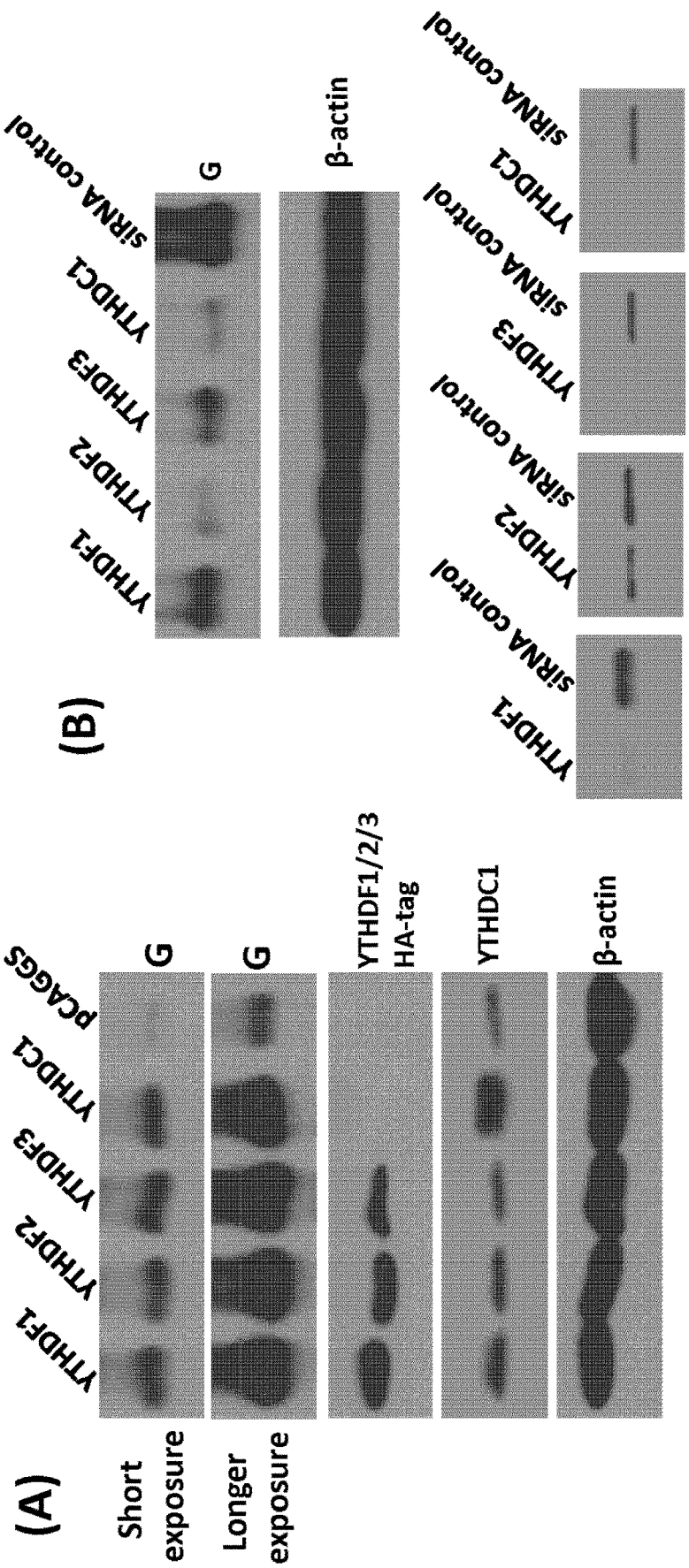
FIG. 57A-B

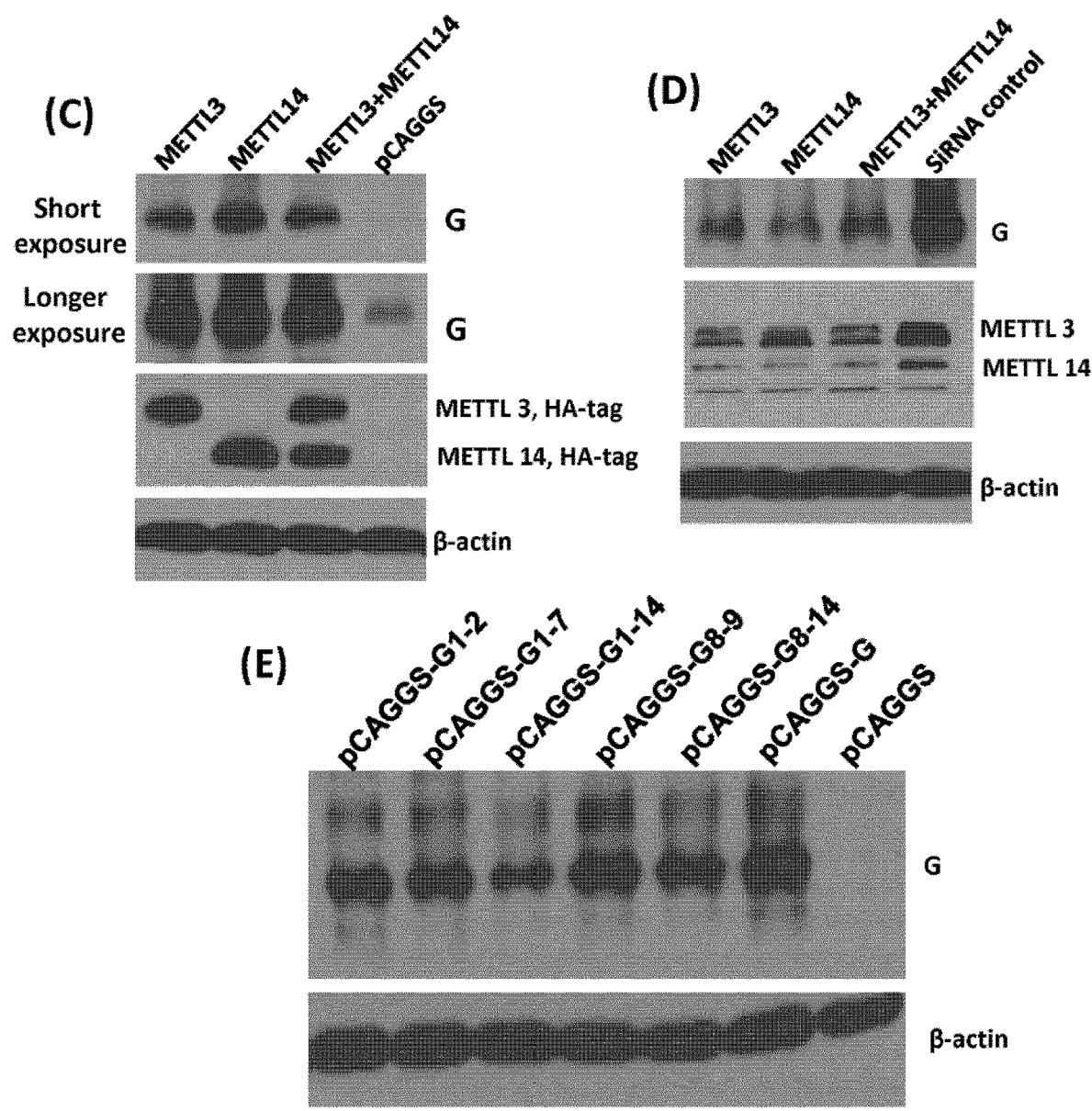
FIG. 57C-E

METHODS AND COMPOSITIONS FOR TREATING NEGATIVE-SENSE SINGLE-STRANDED RNA VIRUS

CROSS-REFERENCE TO RELATED APPLICATIONS

This application is a national phase application under 35 U.S.C. § 371 of International Application No. PCT/US2019/056942 filed Oct. 18, 2019, which claims the benefit of priority of U.S. Provisional Patent Application No. 62/748,175 filed Oct. 19, 2018, all of which are hereby incorporated by reference in their entirety.

STATEMENT OF GOVERNMENT SUPPORT

This invention was made with government support under AI090060 and AI112524 awarded by the National Institutes of Health. The government has certain rights in the invention.

BACKGROUND OF THE INVENTION

I. Field of the Invention

The present invention relates generally to the field of medicine. More particularly, it concerns methods and compositions preventing respiratory syncytial virus infection and the disease it causes.

II. Background

Human respiratory syncytial virus (RSV), a member of the Pneumoviridae [42] and a non-segmented negative-sense (NNS) RNA virus, is the most important cause of upper and lower respiratory tract infection of infants, young children, and immunocompromised individuals and second only to influenza virus for the elderly [43]. Worldwide it is estimated that RSV causes 3.4 million hospitalizations and between 66,000 and 199,000 deaths in children less than 5 years of age [44]. Despite major efforts, no vaccine or antiviral drug is yet available for RSV [43]. The Pneumoviridae family also includes human metapneumovirus (hMPV) which is responsible for 5 to 15% of all respiratory tract infections in infants and young children, a proportion second only to that of RSV [45, 46]. Other important pneumoviruses include avian metapneumovirus (aMPV), pneumonia virus of mice (PVM), and bovine RSV, which cause respiratory tract infections in animals [42]. Together, pneumoviruses are the major causative agents of respiratory tract infection in humans and animals. There is a need in the art for therapeutics that can effectively prevent or treat infections caused by RSV or other viruses in the family Pneumoviridae.

SUMMARY OF THE INVENTION

The inventors found that the genome (negative-sense), antigenome (positive-sense replication intermediate), and mRNAs (transcription products) of negative-sense single-stranded RNA virus of the family Pneumoviridae, such as respiratory syncytial virus (RSV) or metapneumovirus (MPV) are m6A methylated by host cell methyl transferases, which positively regulates viral replication, gene expression, and virus production in human cells. Viral mutants lacking some or all $N^6$-methyladenosine (m6A) modifications provide for attenuated virus with retained immunogenicity.

Thus, the current disclosure fulfills a need in the art by providing methods and viral compositions that can be used to treat and/or prevent viral infections, including those caused specifically by RSV and MPV.

In some embodiments, there is an attenuated negative-sense single-stranded RNA virus of the family Pneumoviridae that is attenuated because the virus has reduced modification of its genome, antigenome, and/or mRNA with methylation, particularly m6A modification, as compared to a non-attenuated or wild-type virus. Additional embodiments concern nucleic acid molecules comprising a nucleic acid sequence having and/or encoding one or more altered m6A consensus sequence sites, host cells containing such nucleic acids, host cells with the ability to yield increased or decreased m6A modifications, including being capable of producing higher yields of viral vaccines that are attenuated by other methods or producing higher or lower yields of one or more proteins or viruses that result from increased methylation, methods of producing attenuated virus, and methods of inducing an immune response using such attenuated RSV.

Embodiments of the disclosure relate to a negative-sense single-stranded RNA virus of the family Pneumoviridae such as syncytial virus (RSV) or metapneumovirus (MPV). Thus, the embodiments described herein are wherein the virus comprises RSV. In other embodiments, the description relates to embodiments in which the virus comprises MPV. The virus may be one that is isolated or relicated in a mammal, such as a human, mouse, rabbit, or rat. In particular embodiments, the virus in one that is isolated from a human and/or is capable of infecting human cells.

Embodiments involve sequence alterations in the viral genome or antigenome encoding $N^6$-methyladenosine (m6A) consensus sites in viral mRNA, antigenome, or genome that disrupt the consensus sequence sites for m6A modification such that these sites in the mRNA, antigenome, and/or genome are no longer modified by m6A. As the genome, antigenome, and mRNA all have m6A modifications, whether the consensus site alteration affects the genome or the antigenome/mRNA depends on whether the alteration is made in a way to result to a change in the consensus sequence in the genome or the antigenome/mRNA. A person of ordinary skill in the art understands the complementary nature of these sequences and can identify in which sequence a change needs to be made in order to effect a change in the genome, antigenome, or mRNA that destroys the consensus sequence, which is understood to be from 5' to 3': Pu [G>A]$m^6$AC[A/C/U] motif (Pu represents purine). The complement from 5' to 3' would be understood to be [U/G/A]GU Py (Py represents pyrimidine). In some embodiments, alterations of a m6A consensus sequence may be 1, 2, 3, or 4 of the following changes: the initial Pu such that it no longer is a purine and is instead a pyrimidine; a U, C, or G substituted for the A that is 3' to the $m^6$-modified Pu; a G, U, A substituted for the C on the 3' side of the A that is 3' to the $m^6$-modified Pu; or, a G substituted for [A/C/U]. Embodiments concern at least 1, 2, 3, or 4 substitutions of nucleic acid residues in a single consensus site.

While some embodiments concern substitution(s) of nucleic acid residue(s), an alteration may include the addition or deletion of nucleotides to alter the sequence such that it no longer functions as an m6A consensus sequence.

In specific embodiments, the sequence alterations change at least two nucleotides of at least one m6A consensus site. In other embodiments, there is at least one sequence alteration that comprises a resulting change of at least an adenine (A) in an m6A consensus site in viral mRNA, genome, and/or the antigenome. In additional embodiments, there is at least one sequence alteration that comprises a resulting change of at least a cytosine in an m6A consensus site in viral mRNA, genome, and/or antigenome. In particular embodiments, there are at least two sequence alterations and the two sequence alterations comprise a change of an adenine and cytosine in the same m6A consensus site in viral mRNA, genome, and/or antigenome. In other embodiments, the sequence alterations changing an m6A consensus site does not alter the amino acid sequence of an encoded polypeptide. In other embodiments, exactly, at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more modified m6A consensus sequence sites (or any range derivable therein) do not result in an altered amino acid at a series of m6A sites in one or multiple genes. In particular embodiments, none of the modified m6A consensus sequence sites results in an altered amino acid being encoded.

In some embodiments, multiple m6A consensus sequence sites may be modified. It is contemplated that exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more m6A consensus sequence sites (or any range derivable therein) in a viral genome, antigenome, and/or mRNA may be altered.

It is contemplated that in certain embodiments the sequence alterations result in reduction of m6A modifications of viral mRNA, genome, and/or antigenome. In some embodiments, there is about, at least about, or at most about a reduction of m6A modification in a virus genome, antigenome, or mRNA (total mRNA or a specific mRNA or a specific subset of mRNA) of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any range derivable therein) compared to the virus lacking the sequence alterations.

In some embodiments, the sequence alterations cause replication of the attenuated virus to be reduced by about, at least about or at most about 5, 10, 15, 20, 25, 30, 35, 40, 45, 50, 60, 70, 80, 90, 100, 110, 120, 130, 140, 150, 160, 170, 180, 190, 200% or more (or any range derivable therein) or by a fold decrease of 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 (or any range derivable therein). The reduction can be measured with respect to any measurement of viral replication, including, but not limited to any measurement set forth in the Examples. In certain embodiments, replication is at least 3-fold, 5-fold, 10-fold, or 20-fold reduced (or any range derivable therein) compared to the virus without mutations in the viral genome encoding one or more $N^6$-methyladenosine (m6A) consensus sites in viral mRNA, genome, or the antigenome.

In some embodiments, the sequence alterations lead to a change in one or more m6A consensus sites in RSV mRNA, genome, and/or RSV antigenome corresponding to the G gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 333, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in regions 392-467 nt, 567-660 nt, and/or 716-795 nt of the G gene. In particular embodiments, there is 1, 2, 3, 4, 5, 6, 7, 8, 9, 10, 11, 12, 13, 14, 15 or more (or any range derivable therein) altered consensus sites in region 392-467 nt of the G gene. In further embodiments, there is 1, 2, 3, 4, 5, 6, 7, 8, 9, 10, 11, 12, 13, 14, 15 or more (or any range derivable therein) altered consensus sites in region 567-660 nt of the G gene. In other embodiments, there is 1, 2, 3, 4, 5, 6, 7, 8, 9, 10, 11, 12, 13, 14, 15 or more (or any range derivable therein) altered consensus sites in region 716-795 nt of the G gene. In specific embodiments, there is 1, 2, 3, 4, 5, 6, 7, 8, 9, 10, 11, 12, 13, 14, 15, 16, 17, 18, 19, 20 or more (or any range derivable therein) consensus sites in regions 392-467 nt and 567-660 nt of the G gene. In specific embodiments, there is 1, 2, 3, 4, 5, 6, 7, 8, 9, 10, 11, 12, 13, 14, 15, 16, 17, 18, 19, 20 or more (or any range derivable therein) in regions 392-467 nt and 716-795 nt of the G gene. In specific embodiments, there is 1, 2, 3, 4, 5, 6, 7, 8, 9, 10, 11, 12, 13, 14, 15, 16, 17, 18, 19, 20 or more (or any range derivable therein) in regions 567-660 nt and 716-795 nt of the G gene. In specific embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more (or any range derivable therein) in regions 392-467 nt, 567-660 nt, and 716-795 nt of the G gene.

In some embodiments, the sequence alterations lead to a change in one or more m6A consensus sites in MPV mRNA, genome, and/or MPV antigenome corresponding to the G gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 333, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein). In some embodiments, the consensus sequence sites comprise one or more of the sites corresponding to sites 1-14 of FIG. 50 of the MPV antigenome or one or more of the following m6A sites in the antigenome: site 1, 171-AAm$^6$AC»TA-175; site 2, 187-GAm$^6$A»GCA-191; site 3, 227-AAm$^6$ACT»G-231; site 4, 246-AGm$^6$AC»TA-250; site 5, 255-AGm$^6$AC»TA-259; site 6, 341-AGm$^6$ACA»G-345; site 7, 346-GAm$^6$A»GCC-351; site 8, 422-GAm$^6$ACA»G-426; site 9, 428-AGm$^6$ACA»G-432; site 10, 453-AAm$^6$AC»TA-457; site 11, 464-GGm$^6$ACA»G-468; site 12, 476-GAm$^6$ACA»G-480; site 13, 518-GAm$^6$ACC»G-522; and site 14, 553-AGm$^6$A»GCC-557. Thus, in particular embodiments, at least 1 of sites 1-14 is mutated. In some embodiments, at least or at most 2 sites of sites 1-14 is mutated. In some embodiments, at least or at most 3 sites of sites 1-14 is mutated. In some embodiments, at least or at most 4 sites of sites 1-14 is mutated. In some embodiments, at least or at most 5 sites of sites 1-14 is mutated. In some embodiments, at least or at most 6 sites of sites 1-14 is mutated. In some embodiments, at least or at most 7 sites of sites 1-14 is mutated. In some embodiments, at least or at most 8 sites of sites 1-14 is mutated. In some embodiments, at least or at most 9 sites of sites 1-14 is mutated. In some embodiments, at least or at most 10 sites of sites 1-14 is mutated. In some embodiments, at least or at most 11 sites of sites 1-14 is mutated. In some embodiments, at least or at most 12 sites of sites 1-14 is mutated. In some embodiments, at least or at most 13 sites of sites 1-14 is mutated. In some embodiments, at least 14 sites of sites 1-14 is mutated. In some embodiments, at least site 1 is mutated. In some embodiments, at least site 2 is mutated. In some embodiments, at least site 3 is mutated. In some embodiments, at least site 4 is mutated. In some embodiments, at least site 5 is mutated. In some embodiments, at least site 6 is mutated. In some embodiments, at least site 7 is mutated. In some embodiments, at least site 8 is mutated. In some embodiments, at least site 9 is mutated. In some embodiments, at least site 10 is mutated. In some embodiments, at least site 11 is mutated. In some embodiments, at least site 12 is mutated. In some embodiments, at least site 13 is mutated. In some embodiments, at least site 14 is mutated. In some embodiments, the genome is mutated. In some embodiments, mutated m6A consensus sites comprise one or more consensus sites corresponding to sites 1-6 of FIG. 51 in the MPV genome or one or more of the following m6A sites in the genome: site 1, 237-G»CG$\underline{m^6}$TC»GC-241; site 2, 290-AG»A$\underline{m^6}$TCC»A-294; site 3, 433-AG$\underline{m^6}$T»C CC-437; site 4, 441-A»C G$\underline{m^6}$TC»GC-445; site 5, 570-AG$\underline{m^6}$ T»C CC-574; and site 6, 616-AG»A$\underline{m^6}$TCC»G-620. Thus, in particular embodiments, at least 1 of sites 1-6 is mutated. In some embodiments, at least or at most 2 sites of sites 1-6 is mutated. In some embodiments, at least or at most 3 sites of sites 1-6 is mutated. In some embodiments, at least or at most 4 sites of sites 1-6 is mutated. In some embodiments, at least or at most 5 sites of sites 1-14 is mutated. In some embodiments, at least 6 sites of sites 1-6 is mutated. In some embodiments, at least site 1 is mutated. In some embodiments, at least site 2 is mutated. In some embodiments, at least site 3 is mutated. In some embodiments, at least site 4 is mutated. In some embodiments, at least site 5 is mutated. In some embodiments, at least site 6 is mutated.

In additional embodiments, there may be sequence alterations affecting an m6A consensus sequence in the genome, antigenome, or mRNA corresponding to the N, P, M, NS1, NS2, F, SH, M2-1, M2-2, and/or L genes. These may be instead of or in addition to sequence alterations affecting the G gene. In some embodiments, the sequence alterations lead to a change in one or more m6A consensus sites in viral mRNA, genome, and antigenome and/or the genome corresponding to the N gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 333, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the N gene. In some embodiments, the sequence alterations lead to a change in one or more m6A consensus sites in RSV mRNA and antigenome and/or the genome corresponding to the P gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 333, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the P gene. In some embodiments, the sequence alterations lead to a change in one or more m6A consensus sites in viral mRNA and antigenome and/or the genome corresponding to the M gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 333, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the M gene. In some embodiments, the sequence alterations lead to a change in one or more m6A consensus sites in mRNA and antigenome and/or the genome corresponding to the L gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 333, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the L gene. In some embodiments, the sequence alterations lead to a change in one or more m6A consensus sites in mRNA and antigenome and/or the genome corresponding to the NS1 gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the NS1 gene. In some embodiments, the sequence alterations lead to a change in one or more m6A consensus sites in mRNA and antigenome and/or the genome corresponding to the NS2 gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the NS2 gene. In some embodiments, the sequence alterations lead to a change in one or more m6A consensus sites in mRNA and antigenome and/or the genome corresponding to the F gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the F gene. In some embodiments, the sequence alterations lead to a change in one or more m6A consensus sites in mRNA and antigenome and/or the genome corresponding to the SH gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the SH gene. In some embodiments, the sequence alterations lead to a change in one or more m6A consensus sites in mRNA and antigenome and/or the genome corresponding to the M2-1 gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the M2-1 gene. In some embodiments, the sequence alterations lead to a change in one or more m6A consensus sites in mRNA and antigenome and/or the genome corresponding to the M2-2 gene. In certain embodiments, there is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more sequence alterations (or any range derivable therein) in 1, 2, 3, 4, 5, 6, 7, 8, 9, 10, 11, 12, 13, 14, 15, 16, 17, 18, 19, 20, 21, 22, 23, 24, 25 m6A consensus sequence sites (or any range derivable therein) in the genome, antigenome, or mRNA corresponding to the M2-2 gene. Moreover, it is specifically contemplated that A or B strains can be used, as well as any of genotypes GA1, GA2, GA3, GA4, GA5, GA6, GA7, SAA1, NA1, NA2, GB1, GB2, GB3, GB4, SAB1, SAB2, SAB3, BA1, BA2, BA3, BA4, BA5, or BA6.

The genome of human RSV was fully sequenced in 1997. Strain include, but not limited to, the following: A/A2, A/1998/12-21 A/RSV-12. A/Riyadh/2009 B/9320, B/NH1276, B/TX11-56, A/GN435/11, A/ON1. It is contemplated that sequence alterations described herein will affect m6A modifications in multiple strains.

In some embodiments, the MPV strain includes. NL/1/00. In some embodiments, the MPV strain includes HMPV subtype A and B lineages (A1, A2, B1, or B2), HMPV NL/1/00, HMPV CA/83/97, HMPV JP/240/03, HMPV CN/gz01/08, HMPV NL/1/99, HMPV CA/75/98.

In some embodiments, nucleic acid molecules having sequence alterations that lead to altered m6A modification in the viral genome or antigenome and mRNA are specifically contemplated. The nucleic acid molecules may be DNA or RNA. In some embodiments, there is an infectious cDNA viral clone containing sequence alterations; an infectious cDNA clone may contain a full-length antigenome of the virus in some embodiments. In other embodiments, there may be one or more genes or other genomic regions with altered m6A consensus sites in a DNA or RNA. In some embodiments, there is also a host cell that is cultured under conditions that accommodate virus replication.

Some embodiments concern methods for inhibiting a negative-sense single-stranded RNA virus of the family Pneumoviridae in a patient, for vaccinating a patient against a negative-sense single-stranded RNA virus of the family Pneumoviridae, for increasing immunity against a negative-sense single-stranded RNA virus of the family Pneumoviridae in a patient, for providing protective immunity against a negative-sense single-stranded RNA virus of the family Pneumoviridae in a patient, for inducing antibodies directed against a negative-sense single-stranded RNA virus of the family Pneumoviridae in a patient, for reducing the severity of an infection from a negative-sense single-stranded RNA virus of the family Pneumoviridae in a patient, for reducing mortality from infection by respiratory syncytial virus in a patient, as well as methods for producing an attenuated respiratory syncytial virus, for producing a vaccine against respiratory syncytial virus, and for producing a respiratory syncytial virus with reduced amount of m6A modification. It is specifically contemplated that any embodiment discussed in the context of a virus of the family Pneumoviridae can be specifically applied or implemented with respect to RSV, MSV, or both. Similarly, any embodiment discussed in the context of RSV can be applied to MSV or another virus of the family Pneumoviridae. It is also specifically contemplated that a specific virus virus of the family Pneumoviridae may be excluded in an embodiment.

In some embodiments methods comprise administering to the patient a composition comprising attenuated virus, such as attenuated negative-sense single-stranded RNA virus of the family Pneumoviridae, including attenuated RSV or MPV discussed in the above paragraphs and in other parts of this disclosure. In specific embodiments, methods comprise administering an effective amount of a composition comprising attenuated RSV. It is contemplated that a patient is administered 1, 2, 3, 4, 5 or more compositions comprising attenuated virus, which may be given at different intervals, with weeks, months, and/or years between an administration. It is contemplated that a patient may receive one or more boosters following an initial vaccination or set of vaccinations. It is contemplated that the amount of viral particles in a composition is $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ viral particles (vp) or plaque forming units (pfu or any range derivable therein). In certain embodiments, there are $10^4$-$10^8$ viral particles or pfu, in the composition.

In some embodiments, the methods, compositions or viruses of the disclosure are ones that are capable of inducing a higher expression of type I interferon in vivo. In some embodiments, the the methods, compositions or viruses of the disclosure are ones that are capable of attenuation in the respiratory tract, such as the lower respiratory track while retaining high immunogenicity. In some embodiments, the methods, compositions or viruses of the disclosure are ones that are capable of While any human patient may be administered attenuated virus, in some embodiments the patient is a pediatric patient, meaning the patient is under the age of 18 years old. A patient under the age of 18 may be termed a pediatric patient. In additional embodiments, the patient is an infant, meaning less than 1 year old at the time of being administered a first and/or a last administration of a composition comprising attenuated virus. In other embodiments, the patient is 5 or younger, is 3 or younger, or is 2 or younger. In some embodiments, the patient is a premature infant. In other embodiments, the patient is a geriatric patient, such 50 or older, 55 or older, 60 or older, 65 or older, or 70 or older. In particular embodiments, the patient is at risk for a viral infection, such as an RSV or MPV infection, which includes but is not limited to medical clinicians, healthcare providers, teachers, hospital workers, or others in areas of higher than average infection rates. It is contemplated that the patient is a subject who is otherwise healthy and/or does not exhibit symptoms of a viral infection, such as an RSV or MPV infection. In specific embodiments, the patient does not exhibit one or more of nasal congestion, runny nose, mild cough, low-grade or high fever, barking cough, difficulty breathing, wheezing, difficulty drinking, lethargy, irritability, bluish color around mouth, lips and/or fingernails, or sleep apnea. In other embodiments, the patient is immunocompromised.

In some embodiments, there are methods for creating an attenuated virus comprising transfecting a cell line with a nucleic acid encoding an attenuated virus; culturing the cell line under conditions to promote viral replication; and collecting viral particles. In certain embodiments, the cell line used to grow the attenuated virus is VERO, MRC-5, HEp-2, A549, or HeLa. In particular embodiments, the cell line is cultured under serum-free conditions. In other embodiments, there are methods for producing an attenuated virus comprising infecting a cell line with an attenuated RSV; culturing the cell line under conditions to promote virus replication; and collecting viral particles. Other steps such as isolating the virus, purifying the virus, freezing the virus, testing the virus, and/or quantitating the virus are included in some embodiments.

In some embodiments, the cell line comprises cells that are reduced in endogenous expression of one or more m6A writer proteins. For example, the cells may comprise an inhibitor of a writer protein or mRNA or may comprise a genetic alteration of the endogenous writer gene. In some embodiments, the writer gene has been disrupted to that no function writer protein is produced in the viral particle or in the host cell. For example, the disruption may be through genetic alteration of the genomic or antigenomic DNA or through inhibition by, for example, siRNA, shRNA, morpholino, antisense nucleic acids, and other ways of inhibiting the production of a protein. In some embodiments, the gene encoding for the writer protein has been mutated by gene editing. In some embodiments, the writer protein comprises one or both of METTL3 and METTL14.

Other methods concern inhibiting a negative-sense single-stranded RNA virus of the family Pneumoviridae in a patient comprising administering to the patient an effective amount of a composition comprising an inhibitor of $N^6$-methyladenosine (m6A) methylation. In some embodiments, the inhibitor is a S-adenosylhomocysteine (SAH) hydrolase inhibitor such as sinefungin. In particular embodiments, the SAH hydrolase inhibitor is 3-deazaadenosine (DAA) or carbocyclic 3-deazaadenosine. In particular embodiments, the patient may be a pediatric patient, meaning the patient is under the age of 18 years old. In additional embodiments, the patient is an infant, meaning less than 1 year old at the time of being administered a first or a last administration of a composition comprising an m6A inhibitor. In other embodiments, the patient is 5 or younger, is 3 or younger, or is 2 or younger. In some embodiments, the patient is a premature infant. In other embodiments, the patient is a geriatric patient, such 50 or older, 55 or older, 60 or older, 65 or older, or 70 or older. In particular embodiments, the patient is at risk for a viral infection, such as an RSV or MPV infection, which includes but is not limited to medical clinicians, healthcare providers, teachers, hospital workers, or others in areas of higher than average infection rates. It is contemplated that the patient is a subject who is otherwise healthy and/or does not exhibit symptoms of a viral infection, such as an RSV or MPV infection. In specific embodiments, the patient does not exhibit one or more of nasal congestion, runny nose, mild cough, low-grade or high fever, barking cough, difficulty breathing, wheezing, difficulty drinking, lethargy, irritability, bluish color around mouth, lips and/or fingernails, or sleep apnea. In other embodiments, the patient is immunocompromised. It is specifically contemplated that any embodiment may be implemented with respect to a pediatric patient, including or excluding a patient who is an infant.

Embodiments also concern a host cell comprising a heterologous nucleic acid encoding exactly or at least or at most 1, 2, 3, 4, or 5 $N^6$-methyladenosine (m6A) reader, eraser, or writer proteins. The host cell may include the writer proteins METTL3 and/or METTL14. In other embodiments, the host cell may include the reader protein YTHDF1, YTHDF2, YTHDF3 and/or YTHDC1. In other embodiments, the cells may include one or more eraser proteins. In some embodiments, the eraser proteins comprise one or both of FTO and ALKBH5. In some embodiments, the cells comprise an inhibitor of an eraser proteins or the cells may be ones that are reduced in their expression of eraser proteins. For example, the cells may comprise a nucleic acid inhibitor of one or more eraser proteins, such as an siRNA, shRNA, antisense, or morpholino, or the cells may have a disruption of one or more eraser genes such that they gene does not produce a functional protein. In some embodiments, the reader, eraser, and/or writer proteins may be overexpressed relative to endogenous levels of expression or at least 1, 2, 3, 4, 5, 6, 7, 8, 9, 10, 20, 40, 50, or 100 times the expression levels of endogenous expression levels (or any range derivable therein). Such a host cell can be used to produce an attenuated virus whose replication is positively affected by m6A modification but that has not been attenuated through loss of m6A consensus sequence sites. Such viruses include RSV, poliovirus, measles virus, mumps virus, rubella virus, yellow fever virus, influenza virus, parainfluenza viruses, metapneumoviruses, Zika virus, dengue viruses, or rhinoviruses. Any embodiment may be implement with or specifically without any of these viruses. It is contemplated that any nonsegmented negative sense RNA virus may be produced in such a cell line, including but not limited to those non-segmented negative-sense (NNS) RNA viruses encompassing a wide range of significant human, animal, and plant pathogens in five families: Paramyxoviridae, Pneumoviridae, Rhabdoviridae, Filoviridae, and Bornaviridae. RSV belongs to the family Pneumoviridae. Other viruses in family Pneumoviridae. also include human metapneumovirus (hMPV). Methods of producing any of these viruses comprise in some embodiments culturing the above-described host cell that also contains an infectious virus or infectious virus clone under conditions to promote viral replication. Other steps may include collecting the replicated virus particles, isolating and/or purifying the virus.

In further embodiments, the cell line can be employed to enhance production of vaccine vectors that deliver various other virus antigens. Such vectors include, but are not limited to, adenovirus, Sendai virus, vesicular stomatitis virus, parainfluenza viruses, measles virus and Newcastle disease virus n some embodiments, the host cell further comprises a heterologous nucleic acid encoding the attenuated virus or a gene or genes whose expression is enhanced by m6A methylation.

The use of the word "a" or "an" when used in conjunction with the term "comprising" in the claims and/or the specification may mean "one," but it is also consistent with the meaning of "one or more," "at least one," and "one or more than one." Any embodiment discussed in the context of comprising may be substituted with the phrase consisting of or consisting essentially of.

It is contemplated that any embodiment discussed herein can be implemented with respect to any method or composition of the invention, and vice versa. Furthermore, compositions can be used to achieve any method embodiments. Any embodiment discussed in the Examples, Figures, or Description of the Drawings can be implemented in the context of any embodiment discussed elsewhere in this disclosure.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, non-recited elements or method steps. The term consisting essentially of, when referring to a therapeutic composition is intended to include all the recited active ingredients and excludes non-recited active ingredients, but also includes any other ingredients, such as excipients, that are not therapeutically active.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D. The RSV genome and antigenome/mRNAs are $m^6A$ methylated. (A) Distribution of $m^6A$ peaks in the RSV antigenome and genome of virions grown in HeLa cells. Confluent HeLa cells were infected by rgRSV at an MOI of 1.0, supernatant was harvested at 36 h post-infection. RSV virions were purified by sucrose gradient ultracentrifugation. Total RNAs were extracted from purified virions and were subjected to $m^6A$-specific antibody immunoprecipitation followed by high throughput sequencing ($m^6A$-seq). A schematic diagram of the RSV antigenome encoding 10 genes is shown. The normalized coverage from $m^6A$-seq of RSV RNA showing the distribution of $m^6A$-immunoprecipitated (IP) reads mapped to the RSV antigenome and genome. The baseline distributions for antigenome and genome from input sample are shown as a blue and pink line respectively. Data presented are the averages from two independent virion samples (n=2). (B) Distribution of $m^6A$ peaks in the RSV mRNAs from RSV-infected HeLa cells. Confluent HeLa cells were infected by rgRSV at an MOI of 1.0, cell lysates were harvested at 36 h post-infection. Total RNAs were extracted from cell lysates, and were enriched for mRNA by binding to oligo dT, and subjected to $m^6A$-seq. The distribution of $m^6A$-immunoprecipitated (IP) reads were mapped to the RSV mRNAs. The baseline distributions for mRNAs from input sample are shown as a pink line. Data presented are the averages from two independent virus-infected HeLa cell samples (n=2). (C) Distribution of $m^6A$ peaks in the RSV antigenome and genome of virions grown in A549 cells. Data presented are the averages from two independent virion samples (n=2). (D) Distribution of $m^6A$ peaks in the RSV mRNAs from RSV-infected A549 cells. Data presented are the averages from two independent virus-infected A549 cell samples (n=2).

FIGS. 2A-K. YTHDF1, 2, 3 (reader) proteins promote RSV replication, gene expression, and progeny virus production. (A) Detection of YTHDF1, 2 3 in HeLa cells stably overexpressing YTHDF1-3. Western blot confirmed the overexpression of YTHDF1-3 proteins in HeLa cells using anti-Flag antibody. (B) YTHDF1, 2, 3 enhance GFP expression in rgRSV-infected cells. HeLa cells stably overexpressing these YTHDF proteins were infected with rgRSV at an MOI of 0.1, and GFP expression was monitored at the indicated times by fluorescence microscopy. (C) YTHDF1, 2, 3 increase the number of GFP-positive cells quantified by flow cytometry. (D) YTHDF1, 2, 3 enhance RSV protein expression. Total cell extracts were harvested from rgRSV-infected HeLa cells at the indicated times and subjected to Western blot using antibody against RSV N, F, or G protein. Western blots shown are the representatives of three independent experiments. RSV F (F0+F1) (E), G (F), and N (G) proteins were quantified by Image J Software. Data are expressed as mean of three independent experiments±standard deviation. (H) YTHDF1, 2, 3 increases RSV progeny virus production. The release of infectious RSV particles was monitored by a single-step growth curve. Virus titer was measured by TCID50. (I) YTHDF1, 2, 3 enhances RSV genomic RNA replication. Total RNA was purified from rgRSV-infected cells using TRizol, and genomic RNA was quantified by real-time RT-PCR using specific primers annealing to the RSV leader sequence and GFP gene. (J) YTHDF1, 2, 3 enhance mRNA transcription. Viral mRNA was separated from total RNA using the Dynabeads mRNA isolation kit and quantified by real-time PCR using primers annealing to the NS1 gene. (K) Ratio between mRNA and genomic RNA. The ratio between NS1 mRNA and genomic RNA was calculated for each cell line. All results are from three independent experiments. Flow cytometry data are expressed as mean±standard deviation. RNA copy and viral titer are the geometric mean titer (GMT) of three independent experiments±standard deviation.

FIGS. 3A-D. Knockdown of endogenous YTHDF1, 2, 3 (reader) proteins diminishes RSV gene expression. HeLa cells were transfected with 150 pmole of siRNA targeting YTHDF1, 2 3 or control siRNA. At 36 h post-transfection, cells were infected with rgRSV at an MOI of 0.5. (A) Immunoblot analysis of YTHDF1, 2, 3 in HeLa cells transfected with siRNA. (B) Immunoblot analysis of RSV G and F proteins. (C) Dynamics of GFP expression in YTHDF1, 2, 3 protein-depleted HeLa cells. (D) Quantification of GFP-positive cells by flow cytometry at 18 h post-inoculation. Fold of GFP signal compared to the control is shown. Western blots and GFP images shown are the representatives of three independent experiments. Flow cytometry data are expressed as mean±standard deviation. The P value (Student's t-test) for YTHDF1, 2, and 3 is $1.098 \times 10^{-6}$, 0.00170, and 0.000972, respectively.

FIGS. 4A-F. Effects of $m^6A$ writer proteins on RSV gene expression. (A) Overexpression of $m^6A$ writer proteins enhances RSV gene expression. HeLa cells were transfected with plasmids encoding METTLE3 and/or METTL14. At 36 h post-transfection, cells were infected with rgRSV at an MOI of 0.5. At 18 h post-infection, cell lysates were harvested for Western blot analysis. (B) Overexpression of $m^6A$ writer proteins enhances RSV expression of GFP. The GFP expression in $m^6A$ writer protein-overexpressed HeLa cells following rgRSV infection was monitored by fluorescence microscopy. Representative images at 18 h post-infection were shown. (C) Quantification of GFP-positive cells by flow cytometry at 18 h post-infection. Fold of GFP signal compared to the control is shown. The P value (Student's t-test) for METTL3, METTL14, and METTL3 &METTL14 is 0.000276, 0.000873, and 0.00228, respectively. (D) Knockdown of $m^6A$ writer proteins diminishes RSV gene expression. HeLa cells were transfected with siRNA targeting METTL3 and/or METTL14. At 36 h post-transfection, cells were infected with rgRSV at an MOI of 0.5. At 18 h post-infection, cell lysates were harvested for Western blot analysis. (D) Knockdown of $m^6A$ writer proteins diminishes GFP expression. The GFP expression in $m^6A$ writer protein-depleted cells following rgRSV infection was monitored by fluorescence microscopy. (E) Quantification of GFP-positive cells by flow cytometry. Western blots and GFP images shown are the representatives of three independent experiments. Fold of GFP signal compared to the control is shown. Flow cytometry data are expressed as mean±standard deviation. The P value (Student's t-test) for METTL3, METTL14, and METTL3 &METTL14 is 0.00441, 0.00458, and 0.000134, respectively.

FIGS. 5A-F. Effects of $m^6A$ eraser proteins on RSV gene expression. (A) Overexpression of $m^6A$ eraser proteins diminishes RSV gene expression. HeLa cells were transfected with plasmids encoding ALKHB5 and/or FTO. At 36 h post-transfection, cells were infected with rgRSV at an MOI of 0.5. At 18 h post-infection, cell lysates were harvested for Western blot analysis. (B) Overexpression of $m^6A$ eraser proteins reduces GFP expression. The GFP expression in $m^6A$ eraser protein-overexpressed HeLa cells following rgRSV infection was monitored by fluorescence microscopy. Representative images at 18 h post-infection are shown. (C) Quantification of GFP-positive cells by flow cytometry at 18 h post-infection. The P value for ALKBH5, FTO, and ALKBH5&FTO is $1.913 \times 10^{-6}$, $1.338 \times 10^{-5}$, and $3.613 \times 10^{-6}$, respectively. (D) Knockdown of $m^6A$ eraser proteins enhances RSV gene expression. HeLa cells were transfected with siRNA targeting ALKHB5 and/or FTO. At 36 h post-transfection, cells were infected with rgRSV at an MOI of 0.5. At 18 h post-infection, cell lysates were harvested for Western blot analysis. (D) Knockdown of $m^6A$ eraser proteins enhances GFP expression. The GFP expression in $m^6A$ eraser protein-depleted cells following rgRSV infection was monitored by fluorescence microscopy. (E) Quantification of GFP-positive cells by flow cytometry. Fold of GFP signal compared to the control is shown. Western blots and GFP images shown are representatives of three independent experiments. Flow cytometry data are expressed as mean±standard deviation. The P value for ALKBH5, FTO, and ALKBH5&FTO is $2.056 \times 10^{-4}$, $3.382 \times 10^{-5}$, and $6.499 \times 10^{-6}$, respectively.

FIGS. 6A-E. RSV infection does not alter the $m^6A$ reader, writer, or eraser protein distribution in cells. HeLa cells were infected by rgRSV at an MOI of 10.0. At 24 h post-infection, mock- or rgRSV-infected cells were stained with anti-reader, writer, or eraser protein antibody and anti-RSV N protein antibody, and were analyzed by confocal microscope. Nuclei were labeled with DAPI. (A) $m^6A$ reader protein YTHDF 1; (B) $m^6A$ writer protein METTL3; and (C) $m^6A$ eraser protein FTO. (D) Detection of $m^6A$ reader, writer, and eraser proteins by Western blot. Nuclear and cytoplasmic fractions were separated from mock- or rgRSV-infected HeLa cells, and were subjected to Western blot. Nuclear and cytoplasmic markers were indicated by Lamin A and $\alpha$-Tubulin, respectively. Representative results from three independent experiments are shown.

FIGS. 7A-G. $m^6A$-abrogating RSV mutants have defects in replication in immortalized cells. (A) Immunoblot analysis of RSV proteins. Confluent A549 cells were infected with each rgRSV at an MOI of 0.1, cell lysates were harvested at 18, 24, and 48 h post-infection, and RSV proteins were detected by specific antibodies against F and G protein. (B) GFP expression of $m^6A$-deficient rgRSV mutants. (C) Quantification of GFP-positive cells by flow cytometry. The P value for rgRSV-G1, G2, G3, G12, and G123 at 18 h post-inoculation is $5.868 \times 10^{-6}$, $7.130 \times 10^{-5}$, $1.646 \times 10^{-5}$, $6.489 \times 10^{-5}$, and $6.983 \times 10^{-6}$, respectively; at 24 h post-inoculation is 0.00261, 0.0418, 0.00766, 0.0138, and 0.0230 respectively; at 48 h post-inoculation is $3.545 \times 10^{-6}$, $1.822 \times 10^{-4}$, $9.828 \times 10^{-6}$, $7.782 \times 10^{-5}$, and $2.475 \times 10^{-5}$, respectively. (D) Single step growth curve of $m^6A$-deficient rgRSV mutants in HeLa cells. Confluent HeLa cells were infected with each rgRSV at an MOI of 1.0, supernatants were harvested at the indicated time, and viral titer was determined by $TCID_{50}$ assay. (E) RSV genomic RNA replication. Total RNA was purified from rgRSV-infected cells using TRizol, and genomic RNA was quantified by real-time RT-PCR using specific primers annealing to the RSV leader sequence and GFP gene. The P value for rgRSV-G1 at 18, 24, and 48 h is 0.000653, $8.658 \times 10^{-5}$, and $1.330 \times 10^{-5}$ respectively. The P value for rgRSV-G12 at 48 h is 0.000141. (F) RSV NS1 mRNA transcription. Viral mRNA was separated from total RNA using the Dynabeads mRNA isolation kit and quantified by real-time PCR using primers annealing to the NS1. The P value for rgRSV-G1 at 18, 24, and 48 h is $1.797 \times 10^{-5}$, $1.112 \times 10^{-4}$, and 0.00119, respectively. (G) RSV G mRNA transcription. The P value for rgRSV-G1 at 18, 24, and 48 h is $7.128 \times 10^{-5}$, $5.019 \times 10^{-6}$, and $1.222 \times 10^{-6}$, respectively. The P value for rgRSV-G12 at 18, 24, and 48 h is 0.00942, 0.000199, and $1.347 \times 10^{-5}$, respectively. Results are from three independent experiments. Flow cytometry data are expressed as mean±standard deviation. RNA copy and viral titer are the geometric mean titer (GMT) of three independent experiments±standard deviation. Western blots shown are the representatives of three independent experiments.

FIGS. 8A-C. $m^6A$-abrogating RSV mutants have defects in replication in HAE culture. (A) Spreading of $m^6A$ deficient rgRSVs in HAE culture. HAE cultures were infected by 800 $TCID_{50}$ of each rgRSV. At the indicated time, virus spreading was monitored by fluorescence microscopy. Representative images at each time point were shown. (B) Quantification of GFP signal in HAE culture. GFP signal was quantified by Image J software, and data are expressed as mean±standard deviation. (C) Virus release from $m^6A$ deficient rgRSV-infected HAE culture. HAE cultures were infected by 800 $TCID_{50}$ of each rgRSV. After virus inoculation, supernatants were collected every 2 days until day 14 post-inoculation. Infectious virus in supernatants was determined by $TCID_{50}$ assay. Viral titers are the geometric mean titer (GMT) of three independent experiments±standard deviation.

FIGS. 9A-E. Pathogenicity and immunogenicity of $m^6A$-deficient rgRSVs in cotton rats. (A) RSV titer in lungs. Four-week-old SPF cotton rats were inoculated intranasally with $2.0 \times 10^5$ $TCID_{50}$ of each rgRSV. At day 4 post-infection, the cotton rats were sacrificed, and lungs and nasal turbinates were collected for virus titration by $TCID_{50}$ assay. Viral titers are the geometric mean titer (GMT) of 5 animals±standard deviation. Detection limit is 2.0 log $TCID_{50}$/g tissue. (B) RSV titer in nasal turbinates. (C) $m^6A$ deficient rgRSVs had less lung histopathological changes compared to rgRSV. Representative pathological changes from each group are shown. Right lung lobe of each cotton rat was fixed in 4% neutral buffered formaldehyde, embedded in paraffin, sectioned at 5 μm, and stained with hematoxylin-eosin (HE) for the examination of histological changes by light microscopy. Micrographs with 20× magnification are shown. (D) $m^6A$ deficient rgRSV provides complete protection against RSV challenge. Four-week-old SPF cotton rats were inoculated intranasally with $2.0 \times 10^5$ $TCID_{50}$ of each rgRSV. At week 4 post-immunization, cotton rats were challenged with $2.0 \times 10^5$ $TCID_{50}$ rgRSV. At day 4 post-challenge, the cotton rats were sacrificed, and lungs and nasal turbinates were collected for virus titration by $TCID_{50}$ assay. Viral titers are the geometric mean titer (GMT) of 5 animals±standard deviation. The detection limit is 2.0 log $TCID_{50}$/g tissue. (E) rgRSV induced a high level of neutralizing antibody. Blood samples were collected from each rat weekly by retro-orbital bleeding. The RSV-neutralizing antibody titer was determined using a plaque reduction neutralization assay, as described in Materials and Methods. The P value for rgRSV-G1 at week 3 and 4 is 0.0166 and 0.0490, respectively.

FIGS. 10A-C. The attenuated phenotype of $m^6A$ deficient rgRSVs is $m^6A$-related. (A) rgRSV-G1 and -G12 were less dependent on the $m^6A$ eraser protein. A549 cells were transfected with a plasmid encoding ALKHB5. At 36 h post-transfection, cells were infected with each rgRSV at an MOI of 0.5. At 18 h post-infection, cell lysates were harvested for Western blot analysis. (B) rgRSV-G1, 2, 3 expression was less dependent on $m^6A$ writer protein. A549 cells were transfected with control siRNA or siRNA targeting METTL4 and METTL13. At 36 h post-transfection, cells were infected with each rgRSV at an MOI of 0.5. At 18 h post-infection, cell lysates were harvested for Western blot analysis. The density of Western blot was quantified by Image J software, and the ratio of the protein bands was calculated. (C) Distribution of $m^6A$ peaks on the RSV mRNAs from A549 cells infected by rgRSV and rgRSV-G12. Confluent A549 cells were infected by each $m^6A$-deficient rgRSV at an MOI of 1.0, cell lysates were harvested at 36 h post-infection. Total RNAs were extracted from cell lysates, and were enriched for mRNA by binding to oligo dT, and subjected to $m^6A$-seq. The distribution of $m^6A$-immunoprecipitated (IP) reads were mapped to the RSV mRNAs (pink block). The baseline distributions for mRNAs from input sample are shown as a pink line. Data presented are the mean coverage from two independent virus-infected A549 cell samples (n=2). Red arrow indicates the $m^6A$ enrichment in G mRNA.

FIGS. 11A-B. A methyltransferase inhibitor Cc3Ado inhibits RSV replication in HEp-2 cells and HAE cultures. (A) HEp-2 cells were infected with 1,000 $TCID_{50}$ of rgRSV or rgRSV-G1857A-G1853A in the presence or absence of 15 μg/ml of Cc3Ado, and GFP expression was photographed at day 3 post-infection. (B) HAE cultures were infected with 1,000 $TCID_{50}$ of rgRSV or rgRSV-G1857A-G1853A in the presence or absence of 50 μg/ml of Cc3Ado, and GFP expression recorded at day 3 post-infection. Data are representative of three independent experiments.

FIGS. 12A-E. RSV infection alters the methylome of host transcripts in HeLa cells. Total RNAs were isolated from mock-infected and rgRSV-infected HeLa cells. Poly(A) enriched mRNAs were purified and subjected to $m^6A$-seq. (A) Metagene analysis of $m^6A$ peaks distribution along the human mRNA in control and infected HeLa cells. (B) Metagene analysis of $m^6A$ peak distribution on lncRNA. (C and D) Distribution of $m^6A$ peaks in the 5' UTR, CDS, and 3' UTR of host cell mRNA transcripts. Charts show the proportion of $m^6A$ peaks in the indicated regions in uninfected (C) and rgRSV-infected HeLa cells (D). (E) GO graphs showing pathway clusters from differential expressed genes in rgRSV-infected HeLa cells. Data presented are the averages from duplicate samples (n=2).

FIGS. 13A-E. RSV infection alters the methylome of host transcripts in A549 cells. Total RNAs were isolated from mock-infected and rgRSV-infected A549 cells. Poly(A) enriched mRNAs were purified and subjected to $m^6A$-seq. (A) Metagene analysis of $m^6A$ peak distribution along the human mRNA in control and infected A549 cells. (B) Metagene analysis of $m^6A$ peak distribution in lncRNA. (C and D) Distribution of $m^6A$ peaks in the 5' UTR, CDS, and 3' UTR of host cell RNA transcripts. Charts show the proportion of $m^6A$ peaks in the indicated regions in uninfected (C) and rgRSV-infected A549 cells (D). (E) GO graphs showing pathway clusters from differential expressed genes in rgRSV-infected A549 cells. Data presented are the average results from duplicate samples (n=2).

FIGS. 14A-C. Transient expression of YTHDF1, 2, 3 proteins enhances RSV gene expression in HeLa cells. HeLa cells were transfected with 1 μg of plasmids encoding YTHDF1, 2, 3 or pCAGGS. At 36 h post-transfection, cells were infected with rgRSV at an MOI of 0.5. (A) Immunoblot analysis of YTHDF1, 2, 3 protein expression. (B) Immunoblot analysis of RSV G and F protein expression. (C) GFP expression. Data are from three independent experiments. Western blots shown are representative of three independent experiments. Flow cytometry data are expressed as mean±standard deviation.

FIGS. 15A-C. Transient expression of YTHDF1, 2, or 3 proteins enhances RSV gene expression in A549 and Vero cells. A549 or Vero cells were transfected with 1 μg of plasmid. At 36 h post-transfection, cells were infected with rgRSV at an MOI of 0.5. (A) Immunoblot analysis of RSV F, G, N, and HA-tagged reader proteins in A549 cells. (B) Dynamics of GFP expression in YTHDF1, 2 or 3 transfected A549 cells at 24 h post-infection. (C) Immunoblot analysis of RSV G and F proteins in Vero cells. Data are from three independent experiments. Western blots shown are the representatives of three independent experiments.

FIGS. 16A-D. HeLa cells stably expressing $m^6A$-related proteins did not significantly affect cell growth or metabolism. (A) The effect of overexpression of $m^6A$-related protein on cell growth. A549 cells were transfected with 1 μg of plasmids encoding $m^6A$-related genes. At 24 and 48 h post-transfection, cells were trypsinized and counted by flow cytometry. Flow cytometry data are plotted as mean of 3 independent experiments±standard deviation. (B) Raw flow cytometry plot at 48 h. (C) The effect of knockdown of $m^6A$-related protein on cell growth. A549 cells were transfected with control siRNA or siRNA targeting $m^6A$-related genes. Cell count from flow cytometry at 24 and 48 h. (D) Raw flow cytometry cell counts at 48 h post transfection.

FIGS. 17A-B. Distribution of m⁶A reader proteins YTHDF2 and 3 in mock and RSV-infected HeLa cells. HeLa cells were infected with rgRSV at an MOI of 10. At 24 h post-infection, mock- or rgRSV-infected cells were stained with anti-reader antibody and anti-RSV N protein antibody, and analyzed by confocal microscopy. Nuclei were labeled with DAPI. (A) Reader protein YTHDF; and (B) Reader protein YTHDF3.

FIG. 18. Distribution of m⁶A writer protein METTL14 in mock and RSV-infected HeLa cells. HeLa cells were infected with rgRSV at an MOI of 10. At 24 h post-infection, mock- or rgRSV-infected cells were stained with anti-writer antibody and anti-RSV N protein antibody and analyzed by confocal microscopy. Nuclei were labeled with DAPI.

FIG. 19. Distribution of m⁶A eraser protein ALKBH5 in mock and RSV-infected HeLa cells. HeLa cells were infected with rgRSV at an MOI of 10. At 24 h post-infection, mock- or rgRSV-infected cells were stained with anti-eraser antibody and anti-RSV N protein antibody and analyzed by confocal microscopy. Nuclei were labeled with DAPI.

FIGS. 20A-D. m⁶A reader protein binds to RSV genomic RNA and mRNA. HeLa cells stably expressing YTHDF2 and vector control HeLa cells were infected with rgRSV at an MOI of 1.0. At 24 h post-infection, cells were lysed and cytoplasmic extracts were immunoprecipitated with an antibody against YTHDF2 (A) or an equivalent amount of HA-tag (non-specific IgG control) (C). The amount of vgRNA and mRNA captured by the YTHDF2 antibody (B) or the HA-tag antibody (D) was quantified by real-time RT-PCR, as was the input RNA, and graphed as the percentage of input. Data are representative of two experiments.

FIGS. 24A-D. Distribution of m⁶A peaks on the RSV mRNAs from A549 cells infected by m⁶A-deficient rgRSVs. Confluent A549 cells were infected by each m⁶A-deficient rgRSV at an MOI of 1.0, cell lysates were harvested at 36 h post-infection. Total RNAs were extracted from cell lysates, and were enriched for mRNA by binding to oligo dT, and subjected to m6A-seq. The distribution of m⁶A-immunoprecipitated (IP) reads were mapped to the RSV mRNAs. The baseline distributions for mRNAs from input sample are shown as a line. Data presented are the mean coverage from two independent virus-infected A549 cell samples (n=2). Arrow indicates the m⁶A enrichment in G mRNA.

FIG. 25. Conserved m⁶A sites in different RSV strains. Based on the m⁶A-seq data from rgRSV-infected A549 cells, the G mRNA has a total of 25 putative m⁶A sites. 100 RSV strains with full-length G mRNA available in GeneBank were selected for sequence alignment. Conserved m⁶A sites in these 100 RSV strains were identified. X axis indicates the 25 putative m⁶A sites. Y axis indicates the numbers of RSV strains containing this specific m⁶A site in X axis.

FIG. 26A-C. The hMPV genome and antigenome are m⁶A methylated. A schematic diagram of the hMPV antigenome encoding 8 genes is shown. Total RNAs were extracted from sucrose gradient purified rhMPV virions grown in A549 cells and were subjected to m⁶A-specific antibody immunoprecipitation followed by high throughput sequencing (m⁶A-seq). (A) Distribution of m⁶A peaks in the hMPV antigenome and genome. Top panel: The m⁶A-seq of hMPV RNA showing the distribution of m⁶A reads mapped to the hMPV antigenome. The baseline signal from input samples is shown as a blue line. Lower panel: The distribution of m⁶A reads from m⁶A-seq was mapped to the hMPV genome. The baseline signal from input samples is shown as a light grey line. The arrow indicates the m⁶A peak. (B) Distribution of m⁶A peaks in the hMPV mRNAs. Data presented are the average results from duplicate samples (n=2). The arrow indicates the m⁶A peak. (C) List of m⁶A peaks in hMPV genome, antigenome, and mRNAs. a. Nucleotide sequence is referred to subtype A strain NL/1/00 (GenBank accession number AF371337). Nucleotide ranges are indicated. b. The hMPV genes are covered by m⁶A peaks. These regions may contain m⁶A sites. c. log 2 enrichment of the m⁶A peaks identified in hMPV antigenome, genome, and mRNA. The P value for each peak is indicated.

FIG. 27A-D. hMPV infection alters the transcriptome of host transcripts. Total RNAs were isolated from mock-infected and hMPV-infected A549 cells. Poly(A) enriched mRNAs were purified and subjected to m⁶A-seq. (A) Motif analysis to identify consensus sequences for m⁶A methylation sites in uninfected and hMPV-infected A549 cells. Frequency of nucleotides at the three positions flanking the central m⁶A sites is shown. (B) Metagene analysis of normalized m⁶A peak distribution along the human reference mRNA in control and infected cells. (C and D) GO graphs showing functional clusters from upregulated genes (C) or downregulated genes (D) identified in hMPV-infected cells.

FIG. 28A-G. m⁶A reader proteins promote hMPV replication, gene expression, and progeny virus production in A549 cells. (A) Overexpression of m⁶A reader proteins. A549 cells were transfected with plasmids encoding YTHDF1, 2, 3, or YTHDC1. At 24 h post-transfection, cells were lysed and subjected to Western blot. YTHDF1-3 proteins were detected by anti-HA tag antibody and YTHDC1 was detected by anti-YTHDC1 antibody. (B) m⁶A reader proteins enhance hMPV protein expression in A549 cells. A549 cells were transfected with plasmids encoding YTHDF1, 2, 3, or YTHDC1. At 24 h post-transfection, cells were infected with rhMPV at an MOI of 5.0. At 12, 18, 24, and 48 h post-infection, total cell extracts were harvested and subjected to Western blot using antibody against hMPV N or G protein. (C) m⁶A increases hMPV progeny virus production. The release of infectious hMPV particles was monitored by a single-step growth curve. Virus titer was measured by an immunostaining plaque assay. *P<0.05, P<0.01, *P<0.001, and ****P<0.0001. Exact P values of YTHDF1, 2, 3, or YTHDC1 compared to pCAGGS are as follows: 12 h, P=0.00124, P=0.00025, P=0.00305, P=0.00003; 18 h, P=0.00871, P=0.00277, P=0.00264, P=0.00207; 24 h, P=0.00115, P=0.00182, P=0.00305, P=0.00993; 48 h, P=0.00170, P=0.00379, P=0.00055, P=0.00165. (D) hMPV genome replication. Total RNA was purified from rhMPV-infected cells using TRizol, and genomic RNA was quantified by real-time RT-PCR using specific primers annealing to the hMPV leader sequence and N gene. (E) hMPV antigenome replication. hMPV antigenome was quantified with specific primers annealing to the hMPV trailer sequence and L gene. Exact P value: P=0.04937, P=0.04752, P=0.00925. (F) G mRNA transcription. N- and G-mRNA and GAPDH mRNA copies were quantified from cDNA pool generated from total RNA and Oligo (dT)$_{23}$. RNA and mRNA copies were normalized by GAPDH. Exact P value: 12 h, P=0.00191, 18 h, P=0.00878, P=0.01498, P=0.01973; 24 h, P=0.00263, P=0.02688, P=0.01444; 48 h, P=0.03959, P=0.01511, P=0.03071. (G) N mRNA transcription. P=0.00364, P=0.00350. All results are from three independent experiments. Western blots shown are the representatives of three independent experiments. RNA copy and viral titer are the geometric mean titer (GM7) of three independent experiments±standard deviation.

FIG. 29A-J. YTHDF1, 2, 3 (reader) proteins promote hMPV replication, gene expression, and progeny virus production in HeLa cells. (A) Detection of YTHDF1, 2 3 in HeLa cells stably overexpressing YTHDF1-3. Western blot confirmed the overexpression of YTHDF1-3 proteins in HeLa cells using anti-Flag antibody. (B) YTHDF1, 2, 3 enhance hMPV protein expression in HeLa cells. HeLa cells stably overexpressing these YTHDF proteins were infected with rhMPV-GFP at an MOI of 0.5. Total cell extracts were harvested from hMPV-infected HeLa cells at the indicated times and subjected to Western blot using antibody against hMPV N, F, or G protein. Western blots shown are the representatives of three independent experiments. (C) YTHDF1, 2, 3 enhance GFP expression in hMPV-GFP-infected cells. HeLa cells stably overexpressing these YTHDF proteins were infected with rhMPV at an MOI of 1.0, and GFP expression was monitored at the indicated times by fluorescence microscopy. (D) YTHDF1, 2, 3 increase the number of GFP-positive cells quantified by flow cytometry. Flow cytometry data are expressed as mean±standard deviation. P values of YTHDF1, 2, and 3 compared to vector control are as follows: 12 h, P=0.00004, P=0.00219, P=0.01188; 18 h, P=0.00005, P=0.00714, P=0.00607; 24 h, P=0.00018, P=0.00507, P=0.00414; 48 h, P=0.0000004, P=0.000003, P=0.000002. (E) YTHDF1, 2, 3 enhance GFP intensity. P values of YTHDF1, 2, 3 compared to vector are as follows: 12 h, P=0.003802, P=0.004390, P=0.003389; 18 h, P=0.000003, P=0.000214, P=0.000004; 24 h, P=0.000003, P=0.000208, P=0.000023; 48 h, P=0.001032, P=0.000045, P=0.000033. (F) YTHDF1, 2, 3 increases hMPV progeny virus production. The release of infectious hMPV particles was monitored by a single-step growth curve. Virus titer was measured by an immunostaining plaque assay. Viral titers are the geometric mean titer (GM7) of three independent experiments±standard deviation. P values of YTHDF1, 2, 3 compared to vector are as follows: 12 h, P=0.02307, P=0.01020, P=0.00953; 18 h, P=0.00151, P=0.01140, P=0.00013; 24 h, P=0.00017, P=0.00178, P=0.00003; 48 h, P=0.00023, P=0.00018, P=0.00205. (G) hMPV genome RNA replication. Exact P values of YTHDF1, 2, 3 compared to vector are as follows: 12 h, P=0.05484, P=0.02933, P=0.02828; 18 h, P=0.00288, P=0.00122, P=0.00204; 24 h, P=0.02298, P=0.02186, P=0.00931; 48 h, P=0.26595, P=0.03483, P=0.03191. (H) hMPV antigenome RNA replication. Exact P values of YTHDF1, 2, 3 compared to vector are as follows: 12 h, P=0.10020, P=0.05994, P=0.02614; 18 h, P=0.00562, P=0.00251, P=0.00429; 24 h, P=0.09292, P=0.03506, P=0.00948; 48 h, P=0.01837, P=0.00887, P=0.01310. (I) G mRNA synthesis. Exact P values of YTHDF1, 2, 3 compared to vector are as follows: 12 h, P=0.00019, P=0.00031, P=0.00171; 18 h, P=0.00204, P=0.00081, P=0.00024; 24 h, P=0.00157, P=0.00037, P=0.00057; 48 h, P=0.01650, P=0.00304, P=0.00075. (J) N mRNA synthesis. Exact P values of YTHDF1, 2, 3 compared to vector are as follows: 12 h, P=0.01482, P=0.00724, P=0.00762; 18 h, P=0.03820, P=0.01051, P=0.01266; 24 h, P=0.13296, P=0.03210, P=0.01762; 48 h, P=0.24640, P=0.02671, P=0.01364. All RNA data were quantified by real-time RT-PCR.

FIG. 30A-G. Effects of m⁶A writer proteins on hMPV gene expression. (A) Overexpression of m⁶A writer proteins enhances hMPV gene expression. A549 cells were transfected with plasmids encoding HA-tagged METTLE3 and/or METTL14. At 24 h post-transfection, cells were infected with rhMPV at an MOI of 5.0. At 12, 18, and 24 h post-infection, cell lysates were harvested for Western blot analysis using antibody against hMPV G and N proteins. Overexpression of METTLE3 and METTL14 was confirmed by Western blot using anti-HA tag antibody. (B) m⁶A writer proteins increase hMPV progeny virus production. The release of infectious hMPV particles was monitored by a single-step growth curve. Virus titer was measured by an immunostaining plaque assay. P values of METTL3, METTL14 or METTL3 plus METTL14 compared to vector are as follows: 12 h, P=0.04474, P=0.00451, P=0.00192; 18 h, P=0.00386, P=0.00036, P=0.00130; 24 h, P=0.01348, P=0.00213, P=0.00842; 48 h, P=0.01133, P=0.00196, P=0.00355. (C) hMPV genome RNA replication. Exact P values of METTL3, METTL14, METTL3+METTL14 compared to pCAGGS are as follows: 12 h, P=0.00196, P=0.68663, P=0.01834; 18 h, P=0.09680, P=0.41626, P=0.02352; 24 h, P=0.36402, P=0.04403, P=0.00728; 48 h, P=0.01571, P=0.00400, P=0.15722. (D) hMPV antigenome RNA replication. Exact P values of METTL3, METTL14, METTL3+METTL14 compared to pCAGGS are as follows: 12 h, P=0.01062, P=0.00013, P=0.00011; 18 h, P=0.00061, P=0.00105, P=0.00004; 24 h, P=0.07619, P=0.01308, P=0.00171; 48 h, P=0.00036, P=0.00026, P=0.00092. (E) G mRNA synthesis. Exact P values of METTL3, METTL14, METTL3+METTL14 compared to pCAGGS are as follows: 12 h, P=0.83915, P=0.01768, P=0.01202; 18 h, P=0.00893, P=0.00688, P=0.00095; 24 h, P=0.42109, P=0.02079, P=0.00506; 48 h, P=0.07359, P=0.16698, P=0.01625. (F) N mRNA synthesis. All RNA data were quantified by real-time RT-PCR. Exact P values of METTL3, METTL14, METTL3+METTL14 compared to pCAGGS are as follows: 12 h, P=0.04018, P=0.17880, P=0.74770; 18 h, P=0.34251, P=0.14461, P=0.01772; 24 h, P=0.92864, P=0.60017, P=0.67147; 48 h, P=0.36368, P=0.86170, P=0.80096. (G) Co-localization of hMPV N and METTL14. A549 cells were infected by rhMPV at an MOI of 5.0. At 24 h post-infection, rhMPV-infected cells were stained with anti-METTL14 antibody and anti-hMPV N protein antibody, and were analyzed by confocal microscope. Nuclei were labeled with DAPI. Mock-infected controls were shown in FIG. 47A. Representative results from three independent experiments are shown.

FIG. 31A-H. Knockdown of $m^6A$ eraser proteins enhances hMPV gene expression. (A) Western blot of hMPV proteins. A549 cells were transfected with siRNA targeting FTO and/or ALKBH5. At 24 h post-transfection, cells were infected with rhMPV at an MOI of 0.5. At 12, 18, and 24 h post-infection, cell lysates were harvested for Western blot analysis using hMPV antibody. Knockdown was confirmed by Western blot using anti-FTO and anti-ALKBH5 antibody. (B) Quantification of hMPV G protein. The density of G protein in Western blot was quantified by Image J. Data are average of three independent experiments. Exact P values of ALKBH5, FTO, ALKBH5+FTO compared to SiRNA control are as follows: 12 h, P=0.37569, P=0.37406, P=0.30388; 18 h, P=2.2879E-6, P=1.2823E-5, P=0.00897; 24 h, P=0.00801, P=0.00099, P=0.12411. (C) Quantification of hMPV N protein. The density of N protein in Western blot was quantified by Image J. Data are average of three independent experiments. Exact P values of ALKBH5, FTO, ALKBH5+FTO compared to SiRNA control are as follows: 12 h, P=0.37201, P=0.51066, P=0.88151; 18 h, P=0.00576, P=0.05129, P=0.00048; 24 h, P=0.86571, P=6.2279E-6, P=0.57172. (D) Knockdown $m^6A$ eraser proteins increases hMPV progeny virus production. Exact P values of ALKBH5, FTO, ALKBH5+FTO compared to siRNA control are as follows: 12 h, P=0.1814, P=0.0660, P=0.0401; 18 h, P=0.0413, P=0.0362, P=0.0083; 24 h, P=0.0232, P=0.0338, P=0.0104; 48 h, P=0.0281, P=0.1210, P=0.0885. (E) hMPV genome RNA replication. Exact P values of ALKBH5, FTO, ALKBH5+FTO compared to SiRNA control are as follows: 12 h, P=0.02901, P=0.41757, P=0.00972; 18 h, P=0.00456, P=0.03716, P=0.00268; 24 h, P=0.02335, P=0.00699, P=0.00416; 48 h, P=0.04565, P=0.74169, P=0.18750. (F) hMPV antigenome RNA replication. Exact P values of ALKBH5, FTO, ALKBH5+FTO compared to SiRNA control are as follows: 12 h, P=0.00028, P=0.00097, P=0.00092; 18 h, P=0.00110, P=0.00059, P=0.00021; 24 h, P=0.00124, P=0.00120, P=0.00043; 48 h, P=0.00875, P=0.00382, P=0.00621. (G) G mRNA synthesis. Exact P values of ALKBH5, FTO, ALKBH5+FTO compared to SiRNA control are as follows: 12 h, P=0.00222, P=0.00131, P=0.00109; 18 h, P=0.00390, P=0.00174, P=0.00024; 24 h, P=0.00346, P=0.00052, P=0.00043; 48 h, P=0.00734, P=0.00129, P=0.00554. (H) N mRNA synthesis. Exact P values of ALKBH5, FTO, ALKBH5+FTO compared to SiRNA control are as follows: 12 h, P=0.00053, P=0.00020, P=0.00020; 18 h, P=0.01025, P=0.00365, P=0.00337; 24 h, P=0.03322, P=0.02088, P=0.01801; 48 h, P=0.05411, P=0.00441, P=0.01979. All RNA data were quantified by real-time RT-PCR.

FIG. 32A-G. $m^6A$-abrogating hMPV mutants are attenuated in replication in cell culture and are defective in $m^6A$ methylation. (A) Immunostaining spots formed by recombinant hMPVs. Vero E6 cells were infected with recombinant hMPV mutants and incubated at 37° C. for 5 days. The cells were stained with an anti-hMPV N protein monoclonal antibody. The left 6 viruses were done as the same time. The right 2 viruses were done at the same time. (B) CPE caused by $m^6A$-deficient rhMPV mutants in A549 cells. Confluent A549 cells were infected with each rhMPV at an MOI of 1.0, CPE was imaged at days 2 and 3. All $m^6A$-deficient rhMPV mutants had an earlier cytopathic effect compared to rhMPV. (C) Growth curve of $m^6A$-deficient rhMPV mutants in A549 cells. Confluent A549 cells were infected with each rhMPV at an MOI of 1.0, total virus in supernatant and cell lysate was harvested at the indicated time, and viral titer was determined by an immunostaining plaque assay. P values of rhMPV-G1-2, G1-7, G1-14, G8-9, or G8-14 compared to rhMPV are as follows: D1, P=0.000053, P=0.000022, P=0.000049, P=0.000097, P=0.000013; D2, P=0.000028, P=0.000081, P=0.000066, P=0.000023, P=0.000342; D3, P=0.000020, P=0.000021, P=0.000203, P=0.000004, P=0.000315; D4, P=0.000079, P=0.001343, P=0.000322, P=0.000122, P=0.005649. (D) Immunoblot analysis of hMPV proteins. Confluent A549 cells were infected with each rhMPV at an MOI of 1.0, cell lysates were harvested at 24, 48, and 72 h post-infection, and hMPV proteins were detected by specific antibodies against N and G protein by Western blot. (E) $m^6A$-mutated hMPV RNA is defective in binding to $m^6A$ antibody by MeRIP assay. An MeRIP assay was carried out to determine the binding of RNA to $m^6A$ antibody using Magna MeRIP™ $m^6A$ kit. Anti-$m^6A$ antibody was first conjugated to magnetic beads. Total RNA (15 μg) was extracted from rhMPV or $m^6A$ deficient rhMPV-infected A549 cells, and incubated with $m^6A$ antibody-associated beads at 4° C. for 2 h with rotation. The RNA-associated magnetic beads were then washed for 3 times. Total RNA was extracted from beads by TRizol reagent and was quantified by real-time RT-PCR using primers annealing to hMPV antigenome, genome, and G mRNA. Exact P values of rhMPV-G1-2, G8-9, G1-7, G8-14 and G1-14 compared to rhMPV are as follows: Genome, P=0.06806, P=0.07424, P=0.18391, P=0.51012, P=0.22587; Antigenome, P=0.39634, P=0.69168, P=0.03009, P=0.01541, P=0.01527; G-mRNA, P=0.16337, P=0.05549, P=0.01933, P=0.01138, P=0.00785. (F) Quantification of $m^6A$ content by $m^6A$ RNA Methylation Assay Kit. Virion RNA was extracted from highly purified wild type and mutant rhMPVs. Total $m^6A$ content of each virion RNA was quantified by $m^6A$ RNA Methylation Assay Kit (Abcam, ab185912) as described in Materials and Methods. Exact P values of rhMPV-G1-2, G8-9, G8-14, G1-14, G(−)1-6 and rhMPV-WT(ALKBH5) compared to rhMPV-WT are as follows: P=0.00900, P=0.00149, P=1.7761E-5, P=2.6994E-7, P=3.6151E-9, P=1.425E-6. (G) $m^6A$-deficient rhMPV RNA has reduced binding efficiency to reader proteins. A549 cells in T25 flasks were transfected with plasmid pYTHDF1-HA or pYTHDF2-HA, and were lysed in 650 μL 1× lysis buffer (abcam, ab152163) at 24 h post transfection. Cell lysate was divided into 3 tube (200 μL/tube) and incubated with $2\times10^8$ copies of virion RNA (rhMPV-G1-14, G8-14, G1-2, G8-9, or rhMPV) and then incubated with 50 μL Pierce anti-HA Magnetic beads at room temperature for 30 min. The amount of virion RNA captured by the YTHDF1 or YTHDF2 was quantified by real-time RT-PCR. Percent of bound RNA of hMPV mutants relative to rhMPV was calculated. Results are from three independent experiments. Exact P values of rhMPV-G8-14, G1-2 and G8-9 compared to rhMPV-G1-14 are as follows: YTHDF1, P=0.47021, P=0.00138, P=0.00004; YTHDF2, P=0.48721, P=0.02531, P=0.00407.

FIG. 33A-G. $m^6A$ deficient rhMPV trigger a higher type I IFN secretion. Dynamics of IFN-α (A) and IFN-β (B) secretion in A549 cells infected by hMPV at MOI of 4.0. A549 cells were infected with rhMPV or each rhMPV mutant at an MOI of 4.0, cell culture supernatants were harvested at 16, 24, and 40 h post-inoculation, and IFN-α and IFN-β in cell supernatants were measured by ELISA. A standard curve was generated using human IFN-α or IFN-β. Data shown are average of three independent experiments. IFN-α: P values of rhMPV-G1-2, G1-7, G1-14, G8-9, or G8-14 compared to rhMPV are as follows: 16 h, P=0.000002, P=0.000008, P=0.0000002, P=0.000001, P=0.000037; 24 h, P=0.000233, P=0.000651, P=0.000024, P=0.000473, P=0.000004; 40 h, P=0.000363, P=0.001191, P=0.000643, P=0.000098, P=0.000315. IFN-0, 16 h, P=0.000001, P=0.0000001, P=0.000001, P=0.000002, P=0.000001; 24 h, P=0.000109, P=0.000003, P=0.000089, P=0.000276, P=0.000027; 40 h, P=0.001712, P=0.002491, P=0.380890, P=0.007107, P=0.003963. (C) Dynamic of IFN-β secretion in A549 cells at MOI of 1.0. A549 cells were infected by rhMPV, rhMPV-G8-9, G1-2, or G1-14 at an MOI of 1.0, IFN-β in cell culture supernatants at 16, 24, and 40 h post-infection was measured by ELISA. Exact P values of rhMPV-G1-2, G8-9 and G1-14 compared to rhMPV are as follows: 16 h, P=8.209E-5, P=0.00096, P=3.341E-6; 24 h, P=0.00035, P=0.01008, P=0.00081; 40 h, P=0.52283, P=0.04606, P=0.49405. (D) Dynamics of IFN-β secretion in TPH-1 cells infected by hMPV at MOI of 4.0. TPH-1 cells were infected each hMPV at an MOI of 4.0, and IFN-β in cell culture supernatants was detected by ELISA kit. Exact P values of rhMPV-G1-2, G8-9 and G1-14 compared to rhMPV are as follows: 16 h, P=9.9466E-6, P=6.8232E-6, P=2.0562E-5; 24 h, P=5.2285E-6, P=1.8678E-6, P=1.9641E-6; 40 h, P=2.6328E-6, P=2.3568E-6, P=1.7651E-6; 48 h, P=1.3019E-6, P=2.4507E-6, P=9.6617E-7. (E) Dynamics of IFN-β secretion in TPH-1 cells infected by hMPV at MOI of 1.0. Exact P values of rhMPV-G1-2, G8-9 and G1-14 compared to rhMPV are as follows: 16 h, P=4.895E-6, P=2.3084E-6, P=9.1479E-7; 24 h, P=2.6423E-6, P=1.89E-6, P=4.3914E-6; 40 h, P=1.823E-6, P=2.9168E-6, P=2.005E-6; 48 h, P=1.9192E-6, P=1.0143E-6, P=6.8216E-6. (F and G) Dynamics of IFN-β secretion at MOI of 4.0. A549 cells (F) or TPH-1 cells (G) were infected with rhMPV-G1-14, G(-)1-6, or rhMPV at an MOI of 4.0, and IFN-β in cell culture supernatants was detected by ELISA kit. Panel F: Exact P values of rhMPV-G1-14 and G(-)1-6 compared to rhMPV are as follows: 16 h, P=1.4327E-5, P=7.3582E-5; 24 h, P=1.1248E-5, P=0.00011; 40 h, P=0.07540, P=0.01606. Panel G: Exact P values of rhMPV-G1-14 and G(-)1-6 compared to rhMPV are as follows: 16 h, P=2.0562E-5, P=1.1296E-6; 24 h, P=1.9641E-6, P=6.1132E-6; 40 h, P=1.7651E-6, P=2.1782E-6; 48 h, P=9.6617E-7, P=2.6455E-6.

FIG. 34A-I. Virion RNA of $m^6A$ deficient rhMPVs trigger a higher type I IFN secretion. (A) IFN-β response in A549 cells transfected with total RNA. Total RNA was extracted from rhMPV, rhMPV-G8-14, or rhMPV-G1-14-infected A549 cells at 24 h post-inoculation, and the antigenome was quantified by real-time RT-PCR. A549 cells in 24-well plates were transfected with $10^8$ antigenome RNA copies of total RNA with or without treatment of calf intestinal phosphatase (CIP). At 24 and 44 h post-transfection, IFN-β in culture medium was measured by ELISA. P values of rhMPV-G8-14 or G1-14 compared to rhMPV are as follows: 24 h, P=0.0000002, P=0.000039; 44 h, P=0.003365, P=0.000165. (B) IFN-β response in A549 cells transfected with virion RNA. Virion RNA was extracted from purified hMPV virions, the level of antigenome was quantified by real-time RT-PCR. A549 cells in 24-well plates were transfected with $2\times10^7$ antigenome copies of virion RNA either with or without CIP treatment. At 24 and 44 h post-transfection, IFN-β in culture medium was measured by ELISA. P values of rhMPV-G8-14 or G1-14 compared to rhMPV are as follows: 24 h, P=0.000004, P=0.000004; 44 h, P=0.022736, P=0.012281. (C) IFN-β response in A549 cells transfected with viral G mRNA. Poly(A)-containing viral mRNA was isolated from total RNA purified from virus-infected cells using a Dynabeads mRNA isolation kit (Life Technologies). The hMPV G mRNA was further isolated by Dynabeads MyOne™ Streptavidin C1 conjugated with poly T-tailed G gene specific primer. The G mRNA copies were quantified by real-time RT-PCR. A549 cells were transfected with 109 RNA copies of G mRNA either with or without CIP treatment. At 24 and 44 h post-transfection, IFN-β in culture medium was measured by ELISA. P values of rhMPV-G8-14 or G1-14 compared to rhMPV are as follows: 24 h, P=0.000371, P=0.002255; 44 h, P=0.000099, P=0.000001. (D, E and F) Comparison of IFN response of virion RNA of hMPV mutants. A549 cells were transfected with $10^7$ (D), $10^6$ (E) and $10^5$ (F) RNA copies of virion RNA of rhMPV-G1-14, G1-2, G8-9, and rhMPV, and dynamics of IFN response was detected by ELISA kit. (G, H, and I) Natural $m^6A$-deficient virion RNA induces IFN response. A549 cells were transfected with $10^7$ (G), $10^6$ (H) and 105 (I) RNA copies of virion RNA of rhMPV-G1-14, G(-)1-6, ALKBH5, and rhMPV, and dynamics of IFN response was detected by ELISA kit. P values for panels D-I are: (D) Exact P values of rhMPV-G1-2, G8-9 and G1-14 compared to rhMPV are as follows: 16 h, P=2.6989E-6, P=9.4265E-5, P=6.1728E-5; 24 h, P=3.6322E-5, P=0.00028 P=2.4336E-6; 40 h, P=0.25414, P=0.00044, P=0.00003. (E) Exact P values of rhMPV-G1-2, G8-9 and G1-14 compared to rhMPV are as follows: 16 h, P=0.00073, P=0.51720, P=0.00091; 24 h, P=0.00045, P=0.01806 P=5.7204E-6; 40 h, P=0.32383, P=0.87823, P=4.3492E-9. (F) Exact P values of rhMPV-G1-2, G8-9 and G1-14 compared to rhMPV are as follows: 16 h, P=0.02384, P=0.16134, P=0.00013; 24 h, P=0.93090, P=0.12806 P=00050; 40 h, P=0.00332, P=0.00029, P=0.00022. (G) Exact P values of rhMPV-G1-14, G(-)1-6 and hMPV(ALKBH5) compared to rhMPV are as follows: 16 h, P=0.01312, P=0.11129, P=2.0409E-5 24 h, P=2.13E-5, P=0.00166, P=1.9338E-5; 40 h, P=0.00128, P=6.9171E-5, P=0.29460. (H) Exact P values of rhMPV-G1-14, G(-)1-6 and hMPV(ALKBH5) compared to rhMPV are as follows: 16 h, P=0.00712, P=2.5255E-5, P=7.3829E-6; 24 h, P=0.00036, P=2.1905E-5, P=1.3462E-5; 40 h, P=0.00015, P=4.5883E-6, P=2.8804E-5. (I) Exact P values of rhMPV-G1-14, G(-)1-6 and hMPV(ALKBH5) compared to rhMPV are as follows: 16 h, P=0.01798, P=0.08709, P=0.02274; 24 h, P=0.00151, P=0.02996, P=0.00081; 40 h, P=0.88326, P=0.00073, P=0.77901.

FIG. 35A-D. IFN response in wild-type, RIG-I, MAVS, or MDA5-knockout A549-Dual™ cells infected by $m^6A$ deficient hMPVs. Confluent wild-type (A), MDA5 (B), RIG-I (C), or MAVS (D)-knockout A549 cells were infected by rhMPV, rhMPV-G8-14, or rhMPV-G1-14 at an MOI of 1.0, cell culture supernatants were harvested at 24 and 48 h post-inoculation. IFN-β in cell supernatants was measured by ELISA. Data shown are average of three independent experiments±standard deviation. P values of rhMPV-G8-14 or G1-14 compared to rhMPV are as follows: A549-Dual, 24 h, P=0.0000006, P=0.0000003; 48 h, P=0.011023, P=0.000516. A549-Dual MDA5 K.O., 24 h, P=0.000004, P=0.000004; 48 h, P=0.000074, P=0.00000002.

FIG. 36A-D. SEAP secretion in wild-type, RIG-I, MAVs, or MDA5-knockout A549-Dual™ cells infected by $m^6A$ deficient hMPV. Confluent wild-type (A), MDA5 (B), RIG-I (C), or MAVs (D)-knockout A549 cells were infected by rhMPV, rhMPV-G8-14, or rhMPV-G1-14 at an MOI of 1.0, cell culture supernatants were harvested at 24 and 48 h post-inoculation. SEAP secreted in cell supernatants was measured by colorimetric enzyme assay with substrate Quanti-Blue™ and read by microplate reader on OD value at 620 nm. Data shown are average of three independent experiments±standard deviation. P values of rhMPV-G8-14 or G1-14 compared to rhMPV are as follows: A549-Dual, 24, P=0.000022, P=0.000365; 48 h, P=0.028380. A549-Dual MDA5 K.O., 24 h, P=0.000036, P=0.000001; 48 h, P=0.000135, P=0.000556. A549-Dual RIG-I K.O., 24 h, P=0.000003, P=0.000001; 48 h, P=0.007404, P=0.000925. A549-Dual MAVS K.O., 24 h, P=0.000211, P=0.000016; 48 h, P=0.000656, P=0.000028.

Figure 37A:
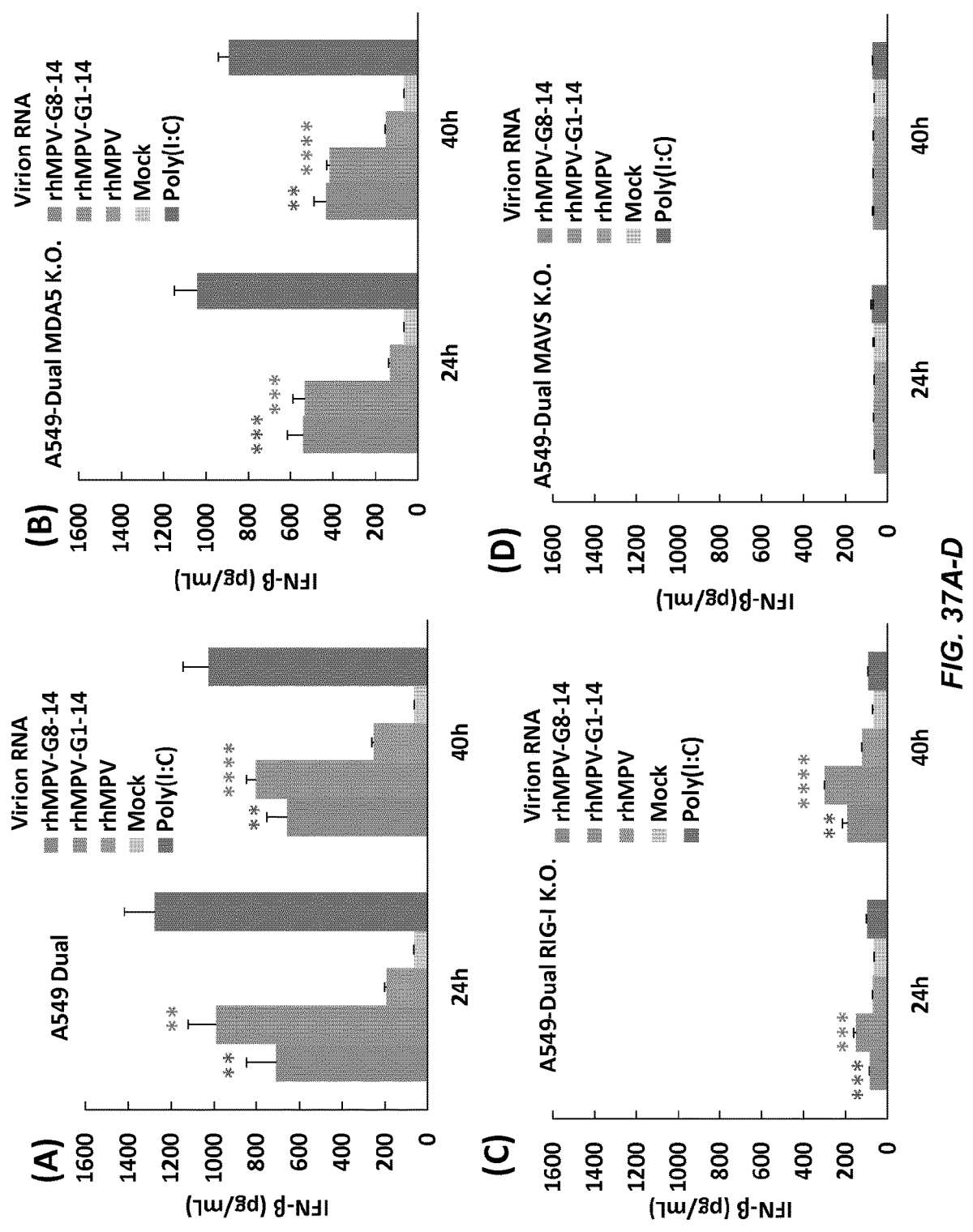

FIG. 37A-D. IFN response in wild-type, RIG-I, MAVS, or MDA5-knockout A549-Dual™ cells transfected by virion RNA. Confluent wild-type (A), MDA5 (B), RIG-I (C), or MAVs (D)-knockout A549 cells were transfected with $10^7$ antigenomic RNA copies of virion RNA of rhMPV, rhMPV-G8-14, or rhMPV-G1-14, cell culture supernatants were harvested at 24 and 40 h post-inoculation. IFN-β in cell supernatants was measured by ELISA. Data shown are average of three independent experiments±standard deviation. P values of rhMPV-G8-14 or G1-14 compared to rhMPV are as follows: A549-Dual, 24 h, P=0.003259, P=0.000450; 48 h, P=0.001945, P=0.000037. A549-Dual MDA5 K.O., 24 h, P=0.000755, P=0.000263; 48 h, P=0.001200, P=0.000008. A549-Dual RIG-I K.O., 24 h, P=0.000593, P=0.000524; 48 h, P=0.007623P=0.00000007.

FIG. 38A-D. SEAP secretion in wild-type, RIG-I, MAVS, or MDA5-knockout A549-Dual™ cells transfected by virion RNA. Confluent wild-type (A), MDA5 (B), RIG-I (C), or MAVs (D)-knockout A549 cells were transfected with $10^7$ antigenomic RNA copies of virion RNA of rhMPV, rhMPV-G8-14, or rhMPV-G1-14 with or without CIP treatment, cell culture supernatants were harvested at 16, 24, and 40 h post-inoculation. SEAP secretion in cell supernatants was measured by colorimetric enzyme assay with substrate Quanti-Blue™ and read by microplate reader on OD value at 620 nm. Data shown are average of three independent experiments. P values of rhMPV-G8-14 or G1-14 compared to rhMPV are as follows: A549-Dual, 16 h, P=0.00283, P=0.00408; 24 h, P=0.00103, P=0.00288; 40 h, P=0.00332, P=0.03540. A549-Dual MDA5 K.O., 16 h, P=0.00565, P=0.00826; 24 h, P=0.00062, P=0.00366; 40 h, P=0.00083, P=0.01011. A549-Dual RIG-I K.O., 24 h, P=0.00421; 40 h, P=0.00102, P=0.00021. A549-Dual MAVS K.O., 40 h, P=0.01194.

FIG. 39A-H. $m^6$A-deficient hMPVs and virion RNA induce a higher expression of RIG-I. (A) $m^6$A-deficient rhMPVs stimulate a higher expression of RIG-I. Confluent A549 cells in 12-well plates were infected by of rhMPV, rhMPV-G8-14, or rhMPV-G1-14 at an MOI of 0.2, 1.0, and 5.0. At 8, 16, 24, and 32 h post-transfection, cells were lysed and 20 μl of cell lysates were subjected to SDS-PAGE and Western blot analysis using antibody specific to RIG-I, hMPV N, or β-actin. (B) $m^6$A-deficient virion RNA induces a higher expression of RIG-I. Confluent A549 cells in 12-well plates were transfected with an increasing amount of poly (I:C) (Sigma-Aldrich, 0.5 and 2.0 μg/well) or virion RNAs ($2\times10^5$, $2\times10^6$, or $2\times10^7$ copies/well) of rhMPV, rhMPV-G8-14, or rhMPV-G1-14. At 8, 16, 24, and 32 h post-transfection, cells were lysed and 20 μl of cell lysates were subjected to SDS-PAGE, and Western blot analysis using antibody against RIG-I or β-actin. (C) $m^6$A-deficient rhMPVs induce higher phosphorylation of IRF3. Confluent A549 cells were infected by of each hMPV at an MOI of 5.0. At 8, 16, 24, and 32 h post-transfection, cells were lysed and 20 μl of cell lysates were subjected to Western blot using antibody specific to IRF3 or phosphorylated IRF3 on site S386 or S396. (D) $m^6$A-deficient virion RNA induce higher phosphorylation of IRF3. Confluent A549 cells were transfected with poly (I:C) or virion RNA from rhMPV, rhMPV-G8-14, and rhMPV-G1-14. At 8, 16, 24, and 32 h post-transfection, 20 μl of cell lysates were subjected to Western blot using antibody specific to IRF3 or phosphorylated IRF3 on site S386 or S396. (E) Comparison of RIG-I expression triggered by virion RNA of rhMPV mutants. Confluent A549 cells were transfected with increasing amounts ($10^5$, $10^6$, and $10^7$ RNA copies) of virion RNA of rhMPV-G1-14, G1-2, G8-9, and rhMPV. At 8 and 16 h post-transfection, RIG-I was detected by Western blot. (F) Removal of 5' triphosphate abolished RIG-I expression. A549 cells were transfected with virion RNA of rhMPV-G1-14, G8-14, and rhMPV with or without CIP treatment. At 8, 16, and 24 h post-transfection, RIG-I was detected by Western blot. (G) $m^6$A-deficient rhMPVs induce higher RIG-I expression and IRF3 phosphorylation. A549 cells were infected by each hMPV at an MOI of 5.0. At indicated time points, RIG-I expression and IRF3 phosphorylation at sites S386 and S396 were detected by Western blot. (H) $m^6$A-deficient virion RNA induces higher RIG-I expression. A549 cells were transfected with $10^7$ copies of each virion RNA. At indicated time points, RIG-I expression were detected by Western blot.

Figure 40A:
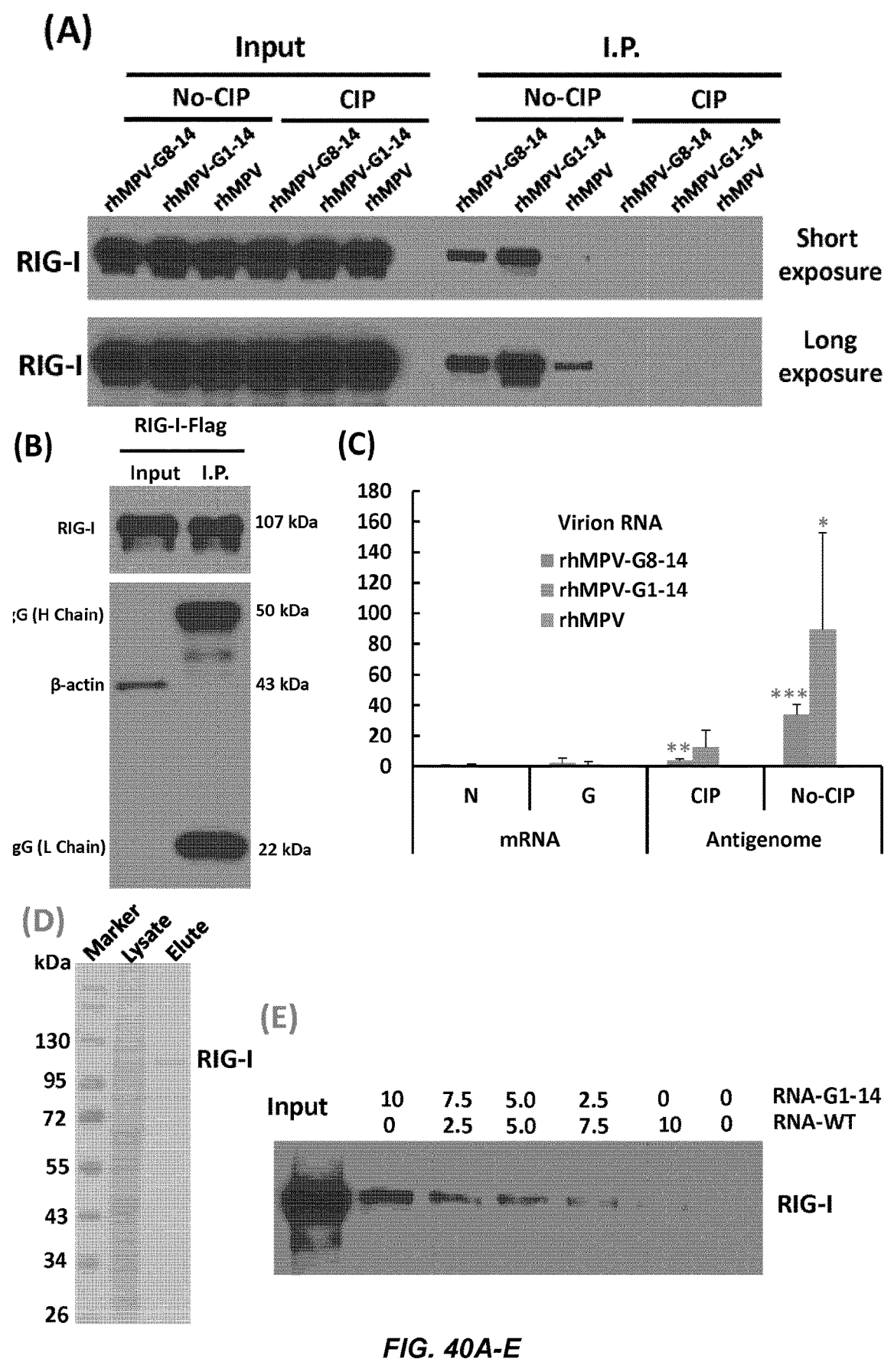

FIG. 40A-E. $m^6$A-deficient antigenome increases binding affinity to RIG-I. (A) Biotinylated virion RNA pulldown RIG-I. $10^9$ copies of virion RNA with or without CIP treatment was biotinylated and incubated with MyOne™ Streptavidin C1 beads in the presence of RNase inhibitor. RNA-associated beads were then washed three times and incubated with 50 μl of A549 cell lysate containing overexpressed RIG-I. Beads were then washed for 3 times and subjected to SDS-PAGE. The pull-down RIG-I protein on Streptavidin beads was detected by Western blot using anti-RIG-I antibody. 5 μl of cell lysate from each sample was loaded as input. (B and C) RIG-I pulldown hMPV RNA. A549 cells in T75 flasks were transfected with 18 μg of pEF-BOS-RIG-I-Flag. At 22 h post-transfection, cell lysates were prepared and 10 incubated with 450 μl of anti-Flag M2 Magnetic beads for 80 min. The mixture was then divided into 13 aliquots, 12 aliquots were incubated with $2\times10^8$ copies of virion RNA (with or without CIP treatment) or $2\times10^9$ copies of N or G mRNA respectively at 37° C. for 1 h, and the $13^{th}$ aliquot was washed and subjected for Western blot for RIG-I and β-actin (B). The magnetic beads were washed with TBS for three times. The bound RNA was extracted by Trizol, and quantified by real-time RT-PCR (C). P value for antigenome of rhMV-G8-14 and G1-14 compared torhMPV: CIP, P=0.0083, P=0.07438; No-CIP, P=0.000909, P=0.0366. (D) Purification of RIG-I protein. HEK-293T cells in T150 flask were transfected with 30 μg of plasmid encoding Flag-tagged RIG-I (pEF-BOS-RIG-I-Flag), and RIG-I protein was purified. (E) Competitive binding of wt virion RNA and $m^6$A-deficient virion RNA to RIG-I. Purified RIG-I protein was incubated with RNA mixtures consisted of different ratios of rhMPV-G1-14 and rhMPV RNA, which are biotinylated and conjugated to Dynabeads® MyOne™ Streptavidin C1 beads in the presence of AMP-PNP. The beads were washed three times with PBS and subjected to Western blot against RIG-I.

FIG. 41A-F. Analysis of RIG-I:RNA conformation by limited trypsin digestion. (A) Domain structure of RIG-I protein. CARD, caspase activation and recruitment domains; Helicase, helicase domain; CTD, C-terminal domain. (B) Model for mechanisms of enhanced RIG-I-mediated IFN signaling by $m^6$A-deficient hMPV RNA. RIG-I is in an autorepressed conformation in the absence of ligand. RIG-I CTD recognizes and binds to 5'ppp of RNA. 5'-ppp-RNA without $m^6$A has a higher binding affinity to helicase domain of RIG-I. RIG-I is an RNA translocase, moving from 5'-ppp to RNA chain. Internal $m^6$A may serve as a "brake" to prevent RIG-I translocation. The RIG-I helicase domain binds the RNA, triggering RIG-I conformational change and subsequent oligomerization. RNAs without $m^6A$ more easily induce RIG-I conformational change. The released CARDs of the activated RIG-I:RNA complex are ubiquitinated for downstream signaling. (C-F) RIG-I fragments were detected by Western blotting with a monoclonal antibody to the helicase domain. (C) Limited trypsin digestion of RIG-I protein in the absence of RNA ligand. RIG-I was incubated with trypsin in the absence of RNA ligands. Aliquots were removed from the reaction at various time points 5 and analyzed by Western blot. (D) Limited trypsin digestion of RIG-I protein with poly (I:C). RIG-I was incubated with 2-10 μg of poly (I:C) and 2 mM AMP-PNP. After 2 h of digestion by trypsin, samples were analyzed by Western blot. (E) Limited trypsin digestion of RIG-I protein with virion RNA. RIG-I was incubated with $10^7$ RNA copies of each virion RNA and 2 mM AMP-PNP. After 2 h of digestion by trypsin, samples were analyzed by Western blot. (F) Competition assay. RIG-I was incubated with a mixture containing different amount of RNA of rhMPV-G1-14 and rhMPV, and 2 mM AMP-PNP. After 2 h of digestion by trypsin, samples were analyzed by Western blot.

FIG. 42A-D. Kinetics of the replication of $m^6A$ deficient rhMPVs in wild-type, RIG-I, MAVS, or MDA5-knockout A549 cells. Confluent wild-type (A), MDA5 (B), RIG-I (C), or MAVS (D)-knockout A549 cells in 24-well plates were infected by rhMPV, rhMPV-G8-14, or rhMPV-G1-14 at an MOI of 1.0, total virus in cell culture supernatants and cell lysate was harvested at the indicated time, and viral titer was determined by an immunostaining plaque assay. Data represent two independent experiments (mean and standard deviation of six samples). The arrow indicates the degree of titer difference compared to rhMPV. P values of rhMPV-G8-14 or G1-14 compared to rhMPV are as follows: A549-Dual, 12 h, P=0.005677, P=0.020272; 24 h, P=0.000003, P=0.000018; 36 h, P=0.000002, P=0.000017; 48 h, P=0.000067, P=0.000450; 60 h, P=0.000120, P=0.001064; 72 h, P=0.000296, P=0.012931. A549-Dual MDA5-K.O., 12 h, P=0.000872, P=0.013116; 24 h, P=0.000010, P=0.000022; 36 h, P=0.000042, P=0.000195; 48 h, P=0.000007, P=0.000014; 60 h, P=0.000127, P=0.000062; 72 h, P=0.000014, P=0.000403. A549-Dual RIG-I-K.O., 12 h, P=0.013642, P=0.016926; 24 h, P=0.000057, P=0.000359; 36 h, P=0.000002, P=0.000023; 48 h, P=0.000085; P=0.004960, 60 h, P=0.000113, P=0.017314; 72 h, P=0.000019. A549-Dual MAVS-K.O., 12 h, P=0.001973, P=0.005915; 24 h, P=0.000107, P=0.000418; 36 h, P=0.000139, P=0.000366; 48 h, P=0.000318; 60 h, P=0.000937; 72 h, P=0.000566, P=0.026082.

FIG. 43A-E. Interferon response, pathogenicity, and immunogenicity of $m^6A$-deficient rhMPVs in cotton rats. (A) Interferon response of rhMPV in cotton rats. Six-week-old specific-pathogen-free (SPF) female cotton rats (5 per group) were inoculated intranasally with 100 μl of PBS or PBS containing $2.0 \times 10^5$ PFU of rhMPV-G8-14, rhMPV-G1-14 or rhMPV. At 48 h post-inoculation, cotton rats were sacrificed and bronchoalveolar lavage (BAL) from the right lung was collected for IFN-β bioactivity assay on CCRT cells as described in Materials and Methods. The IFN-β concentration of each BAL sample was calculated according to the highest dilution of samples and the lowest concentration of standard human IFN-β which inhibited rVSV-GFP replication therefore GFP expression. P value of rhMPV-G8-14 and G1-14 compared to rhMPV is P=0.000022 and P=0.00237 respectively. (B) hMPV titer in lungs and nasal turbinates. Four-week-old SPF cotton rats were inoculated intranasally with $2.0 \times 10^5$ PFU of each rhMPV. At day 4 post-infection, the cotton rats were sacrificed, and lungs and nasal turbinates were collected for virus titration by an immunostaining plaque assay. Viral titers are the geometric mean titer (GMT) of 5 animals±standard deviation. Detection limit is 2.0 log PFU/g tissue. P values of rhMPV-G1-2, G8-9 or G1-14 compared to rhMPV are as follows: Lung, P=4.81×10⁻⁶, P=8.67×10⁻⁷, P=4.38×10⁻⁸; Nasal turbinate, P=0.02583, P=0.00331, P=0.01101. (C) $m^6A$ deficient rhMPVs had less lung histopathological changes compared to rhMPV. Representative pathological changes from each group are shown. Right lung lobe of each cotton rat was fixed in 4% neutral buffered formaldehyde, embedded in paraffin, sectioned at 5 μm, and stained with hematoxylin-eosin (HE) for the examination of histological changes by light microscopy. Micrographs with 20× magnification are shown. (D) $m^6A$ deficient rhMPV provides complete protection against hMPV challenge. Four-week-old SPF cotton rats were inoculated intranasally with $2.0 \times 10^5$ PFU of each rhMPV. At week 4 post-immunization, cotton rats were challenged with $2.0 \times 10^5$ PFU of hMPV. At day 4 post-challenge, the cotton rats were sacrificed, and lungs and nasal turbinates were collected for virus titration by an immunostaining plaque assay. Viral titers are the geometric mean titer (GM7) of 5 animals±standard deviation. The detection limit is 2.0 log PFU/g tissue. (E) $m^6A$ deficient rhMPV induced a high level of neutralizing antibody. Blood samples were collected from each rat weekly by retro-orbital bleeding. The hMPV-neutralizing antibody titer was determined using a plaque reduction neutralization assay, as described in Materials and Methods.

FIG. 45A-C. hMPV genome and antigenome are packaged into virion. (A) Quantification of genome and antigenome in hMPV virions by real-time RT-PCR. Wild type hMPV was grown in T150 flasks of A549 cells and cell culture supernatant was collected at 40 h. hMPV was purified by 20% sucrose cushion, the virion pellet was resuspended in 100 μL NTE buffer, treated with RNase at room temperature for 30 min. The reaction system was diluted in 5 ml NTE buffer and the virion was pelleted down in SW55 Ti ultracentrifugation tube on 10% sucrose cushion and resuspended in 100 μL NTE buffer. (B) Pulldown of N-RNA complex by N antibody. RNase-treated virion was disrupted by 10× Disruption Buffer, mixed with Protein A/G Magnetic beads (MilliPore, LSKMAGAG02) bound with mouse anti-hMPV N antibody (MiiliPore, MAB80138) or mouse IgG (Sigma Aldrich, #I5381) and incubated at room temperature for 2 h and washed with TBS buffer for 3 times. The beads were then subjected for Western blot. (C) Quantification of genome and antigenome in N-RNA complex by real-time RT-PCR. Total RNA was extracted from N-complex pulled down by magnetic beads and subjected to real-time RT-PCR.

FIG. 46A-H. The effects of writer and eraser proteins on host RNA m$^6$A methylation and host mRNA translation. (A) The effects of knockdown of writer proteins on total host RNA. A549 cells were transfected with siRNA targeting METTL3 and METTL14 or control siRNA. At 24 h post-transfection, total RNA was extracted from these cells. The m$^6$A content was quantified by m$^6$A RNA Methylation Assay Kit. Data are the average of three independent experiments±standard deviation. (B) The effects of knockdown of writer proteins on host mRNA. Polyadenylated mRNA from panel A was isolated using poly-A beads, and m$^6$A content was quantified by m$^6$A RNA Methylation Assay Kit. Data are the average of three independent experiments±standard deviation. (C) The effects of overexpression of writer proteins on host RNA. A549 cells were transfected with plasmids encoding METTL3 and METTL14 or control vector. At 24 h post-transfection, total RNA was extracted from these cells. The m$^6$A content was quantified by m$^6$A RNA Methylation Assay Kit. Data are the average of three independent experiments±standard deviation. (D) The effects of overexpression of eraser proteins on host RNA. A549 cells were transfected with plasmids encoding FTO and ALKBH5 or control vector. At 24 h post-transfection, total RNA was extracted from these cells. The m$^6$A content was quantified by m$^6$A RNA Methylation Assay Kit. Data are the average of three independent experiments±standard deviation. (E) The effects of knockdown of writer proteins on host protein translation. A549 cells were transfected with siRNA against METTL3 and METTL14 or control siRNA. After 24 h, cells were incubated in methionine- and cysteine-free media for 1 h, and 50 µCi of [$^{35}$S]-methionine was added. At 0.5, 1, 2 h, cells were washed with PBS, lysed in lysis buffer, analyzed by SDS-PAGE and exposed to film. The gel is the representative of two independent experiments. (F) Quantification of protein bands. Quantification of protein bands in panel E was done using ImageJ software. Data were the average of two independent experiments. (G) [$^{35}$S]incorporation by scintillation counting. 5 µl of each sample from panel E was used for measuring [$^{35}$S] incorporation by scintillation counting. Data were the average of two independent experiments. (F) Percent of [$^{35}$S] incorporation relative to control siRNA. Percentage was calculated from panel G. Data were the average of two independent experiments.

Figure 8A:
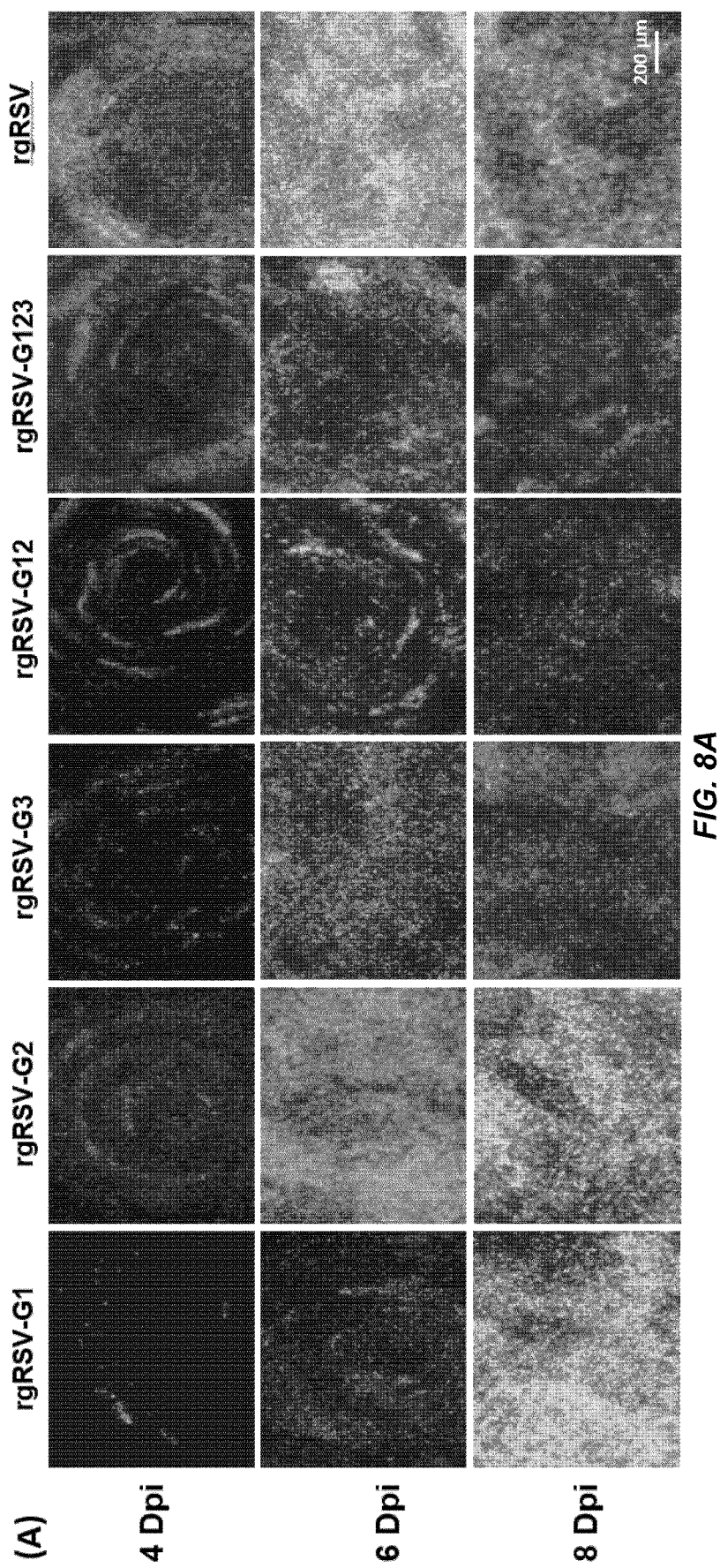

DETAILED DESCRIPTION OF THE INVENTION $N^6$-methyladenosine (m6A or $m^6A$, which are interchangeable) is the most prevalent internal modification of mRNAs in most eukaryotes. RNAs produced in these cells during virus replication may also acquire m6A methylation. The Examples demonstrate that RNAs of human respiratory syncytial virus (RSV), a medically important non-segmented negative-sense (NNS) RNA virus, are modified by m6A within discreet regions and that these modifications enhance viral replication and pathogenesis. Described herein are recombinant RSV variants that are highly attenuated yet retain high immunogenicity. Therefore, the RSV variants described herein can be used for rational design of live attenuated vaccine candidates and for novel antiviral therapeutic agents for RSV.

I. NUCLEIC ACIDS

In certain embodiments, the disclosure concerns recombinant polynucleotides containing or encoding the m6A consensus sites.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene", "polynucleotide", or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges therebetween, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode all or segments of a gene from RSV, such as the G gene. The term "recombinant" may be used in conjunction with a polynucleotide or polypeptide and generally refers to a polypeptide or polynucleotide produced and/or manipulated in vitro or that is a replication product of such a molecule.

In other embodiments, the disclosure concerns isolated nucleic acid segments and recombinant vectors incorporating nucleic acid sequences that RSV genes or variants thereof to generate an immune response in a subject or to generate attenuated virus useful in the compositions and methods described herein.

The nucleic acid segments of the disclosure can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain other embodiments, the disclosure concerns isolated nucleic acid segments that include within their sequence a contiguous nucleic acid sequence from SEQ ID NO:1 (G gene RSV mRNA) or the complement thereof:

(SEQ ID NO: 1)
ATGTCCAAAAACAAGGACCAACGCACCGCTAAGACATTAGAAAGGACCTG

GGACACTCTCAATCATTTATTATTCATATCATCGTGCTTATATAAGTTAA

ATCTTAAATCTGTAGCACAAATCACATTATCCATTCTGGCAATGATAATC

TCAACTTCACTTATAATTGCAGCCATCATATTCATAGCCTCGGCAAACCA

CAAAGTCACACCAACAACTGCAATCATACAAGATGCAACAAGCCAGATCA

AGAACACAACCCCAACATACCTCACCCAGAATCCTCAGCTTGGAATCAGT

CCCTCTAATCCGTCTGAAATTACATCACAAATCACCACCATACTAGCTTC

AACAACACCAGGAGTCAAGTCAACCCTGCAATCCACAACAGTCAAGACCA

AAAACACAACAACAACTCAAACACAACCCAGCAAGCCCACCACAAAACAA

CGCCAAAACAAACCACCAAGCAAACCCAATAATGATTTTCACTTTGAAGT

GTTCAACTTTGTACCCTGCAGCATATGCAGCAACAATCCAACCTGCTGGG

CTATCTGCAAAAGAATACCAAACAAAAAACCAGGAAAGAAAACCACTACC

AAGCCCACAAAAAAACCAACCCTCAAGACAACCAAAAAAGATCCCAAACC

TCAAACCACTAAATCAAAGGAAGTACCCACCACCAAGCCCACAGAAGAGC

CAACCATCAACACCACCAAAACAAACATCATAACTACACTACTCACCTCC

AACACCACAGGAAATCCAGAACTCACAAGTCAAATGGAAACCTTCCACTC

AACTTCCTCCGAAGGCAATCCAAGCCCTTCTCAAGTCTCTACAACATCCG

AGTACCCATCACAACCTTCATCTCCACCCAACACACCACGCCAGTAG

In certain other embodiments, the disclosure concerns isolated nucleic acid segments and recombinant vectors, as RNA or DNA, that include within their sequence a contiguous nucleic acid sequence from SEQ ID NO:2 (RSV antigenome shown with thymine (T) instead of uracil (U)) or the RNA complement thereof (RSV genome):

(SEQ ID NO: 2)
TTGCATAAACCAAAAAAATGGGGCAAATAAGAATTTGATAAGTACCACTTAAAT

TTAACTCCCTTGGTTAGAGATGGGCAGCAATTCATTGAGTATGATAAAAGTTAGA

TTACAAAATTTGTTTGACAATGATGAAGTAGCATTGTTAAAAATAACATGCTATA

CTGATAAATTAATACATTTAACTAATGCTTTGGCTAAGGCAGTGATACATACAAT

CAAATTGAATGGCATTGTGTTTGTGCATGTTATTACAAGTAGTGATATTTGCCCTA

ATAATAATATTGTAGTAAAATCCAATTTCACAACAATGCCAGTACTACAAAATGG

AGGTTATATATGGGAAATGATGGAATTAACACATTGCTCTCAACCTAATGGTCTA

CTAGATGACAATTGTGAAATTAAATTCTCCAAAAAACTAAGTGATTCAACAATGA

CCAATTATATGAATCAATTATCTGAATTACTTGGATTTGATCTTAATCCATAAATT

ATAATTAATATCAACTAGCAAATCAATGTCACTAACACCATTAGTTAATATAAAA

CTTAACAGAAGACAAAAATGGGGCAAATAAATCAATTCAGCCAACCCAACCATG

GACACAACCCACAATGATAATACACCACAAAGACTGATGATCACAGACATGAGA

CCGTTGTCACTTGAGACCATAATAACATCACTAACCAGAGACATCATAACACACA

AATTTATATACTTGATAAATCATGAATGCATAGTGAGAAAACTTGATGAAAGAC

AGGCCACATTTACATTCCTGGTCAACTATGAAATGAAACTATTACACAAAGTAGG

AAGCACTAAATATAAAAATATACTGAATACAACACAAAATATGGCACTTTCCC

TATGCCAATATTCATCAATCATGATGGGTTCTTAGAATGCATTGGCATTAAGCCT

ACAAAGCATACTCCCATAATATACAAGTATGATCTCAATCCATAAATTTCAACAC

AATATTCACACAATCTAAAACAACAACTCTATGCATAACTATACTCCATAGTCCA

GATGGAGCCTGAAAATTATAGTAATTTAAAACTTAAGGAGAGATATAAGATAGA

AGATGGGGCAAATACAACCATGGCTCTTAGCAAAGTCAAGTTGAATGATACACT

CAACAAAGATCAACTTCTGTCATCCAGCAAATACACCATCCAACGGAGCACAGG

AGATAGTATTGATACTCCTAATTATGATGTGCAGAAACACATCAATAAGTTATGT

GGCATGTTATTAATCACAGAAGATGCTAATCATAAATTCACTGGGTTAATAGGTA

TGTTATATGCGATGTCTAGGTTAGGAAGAGAAGACACCATAAAAATACTCAGAG

ATGCGGGATATCATGTAAAAGCAAATGGAGTAGATGTAACAACACATCGTCAAG

ACATTAATGGAAAAGAAATGAAATTTGAAGTGTTAACATTGGCAAGCTTAACAA

-continued

```
CTGAAATTCAAATCAACATTGAGATAGAATCTAGAAAATCCTACAAAAAAATGC

TAAAAGAAATGGGAGAGGTAGCTCCAGAATACAGGCATGACTCTCCTGATTGTG

GGATGATAATATTATGTATAGCAGCATTAGTAATAACTAAATTAGCAGCAGGGG

ACAGATCTGGTCTTACAGCCGTGATTAGGAGAGCTAATAATGTCCTAAAAAATG

AAATGAAACGTTACAAAGGCTTACTACCCAAGGACATAGCCAACAGCTTCTATG

AAGTGTTTGAAAAACATCCCCACTTTATAGATGTTTTTGTTCATTTTGGTATAGCA

CAATCTTCTACCAGAGGTGGCAGTAGAGTTGAAGGGATTTTTGCAGGATTGTTTA

TGAATGCCTATGGTGCAGGGCAAGTGATGTTACGGTGGGGAGTCTTAGCAAAAT

CAGTTAAAAATATTATGTTAGGACATGCTAGTGTGCAAGCAGAAATGGAACAAG

TTGTTGAGGTTTATGAATATGCCCAAAAATTGGGTGGTGAAGCAGGATTCTACCA

TATATTGAACAACCCAAAAGCATCATTATTATCTTTGACTCAATTTCCTCACTTCT

CCAGTGTAGTATTAGGCAATGCTGCTGGCCTAGGCATAATGGGAGAGTACAGAG

GTACACCGAGGAATCAAGATCTATATGATGCAGCAAAGGCATATGCTGAACAAC

TCAAAGAAAATGGTGTGATTAACTACAGTGTACTAGACTTGACAGCAGAAGAAC

TAGAGGCTATCAAACATCAGCTTAATCCAAAAGATAATGATGTAGAGCTTTGAGT

TAATAAAAAATGGGGCAAATAAATCATCATGGAAAAGTTTGCTCCTGAATTCCAT

GGAGAAGATGCAAACAACAGGGCTACTAAATTCCTAGAATCAATAAAGGGCAAA

TTCACATCACCCAAAGATCCCAAGAAAAAAGATAGTATCATATCTGTCAACTCAA

TAGATATAGAAGTAACCAAAGAAAGCCCTATAACATCAAATTCAACTATTATCA

ACCCAACAAATGAGACAGATGATACTGCAGGGAACAAGCCCAATTATCAAAGAA

AACCTCTAGTAAGTTTCAAAGAAGACCCTACACCAAGTGATAATCCCTTTTCTAA

ACTATACAAAGAAACCATAGAAACATTTGATAACAATGAAGAAGAATCCAGCTA

TTCATACGAAGAAATAAATGATCAGACAAACGATAATATAACAGCAAGATTAGA

TAGGATTGATGAAAAATTAAGTGAAATACTAGGAATGCTTCACACATTAGTAGT

GGCAAGTGCAGGACCTACATCTGCTCGGGATGGTATAAGAGATGCCATGGTTGG

TTTAAGAGAAGAAATGATAGAAAAAATCAGAACTGAAGCATTAATGACCAATGA

CAGATTAGAAGCTATGGCAAGACTCAGGAATGAGGAAAGTGAAAAGATGGCAA

AAGACACATCAGATGAAGTGTCTCTCAATCCAACATCAGAGAAATTGAACAACC

TATTGGAAGGGAATGATAGTGACAATGATCTATCACTTGAAGATTTCTGATTAGT

TACCAATCTTCACATCAACACACAATACCAACAGAAGACCAACAAACTAACCAA

CCCAATCATCCAACCAAACATCCATCCGCCAATCAGCCAAACAGCCAACAAAAC

AACCAGCCAATCCAAAACTAACCACCCGGAAAAAATCTATAATATAGTTACAAA

AAAAGGAAAGGGTGCGCGCTGGGGCAAATATGGAAACATACGTGAACAAGCTTC

ACGAAGGCTCCACATACACAGCTGCTGTTCAATACAATGTCTTAGAAAAAGACG

ATGACCCTGCATCACTTACAATATGGGTGCCCATGTTCCAATCATCTATGCCAGC

AGATTTACTTATAAAAGAACTAGCTAATGTCAACATACTAGTGAAACAAATATCC

ACACCCAAGGGACCTTCACTAAGAGTCATGATAAACTCAAGAAGTGCAGTGCTA

GCACAAATGCCCAGCAAATTTACCATATGCGCTAATGTGTCCTTGGATGAAAGAA

GCAAACTAGCATATGATGTAACCACACCCTGTGAAATCAAGGCATGTAGTCTAA

CATGCCTAAAATCAAAAAATATGTTGACTACAGTTAAAGATCTCACTATGAAGAC

ACTCAACCCTACACATGATATTATTGCTTTATGTGAATTTGAAAACATAGTAACA
```

-continued

```
TCAAAAAAAGTCATAATACCAACATACCTAAGATCCATCAGTGTCAGAAATAAA

GATCTGAACACACTTGAAAATATAACAACCACTGAATTCAAAAATGCTATCACA

AATGCAAAAATCATCCCTTACTCAGGATTACTATTAGTCATCACAGTGACTGACA

ACAAAGGAGCATTCAAATACATAAAGCCACAAAGTCAATTCATAGTAGATCTTG

GAGCTTACCTAGAAAAAGAAAGTATATATTATGTTACCACAAATTGGAAGCACA

CAGCTACACGATTTGCAATCAAACCCATGGAAGATTAACCTTTTTCCTCTACATC

AGTGTGTTAATTCATACAAACTTTCTACCTACATTCTTCACTTCACCATCACAATC

ACAAACACTCTGTGGTTCAACCAATCAAACAAAACTTATCTGAAGTCCCAGATCA

TCCCAAGTCATTGTTTATCAGATCTAGTACTCAAATAAGTTAATAAAAAATATAC

ACATGGCGATCGACATGGGGCAAATAATCATTGGAGGAAATCCAACTAATCACA

ATATCTGTTAACATAGACAAGTCCACACACCATACAGAATCAACCAATGGAAAA

TACATCCATAACAATAGAATTCTCAAGCAAATTCTGGCCTTACTTTACACTAATA

CACATGATCACAACAATAATCTCTTTGCTAATCATAATCTCCATCATGATTGCAA

TACTAAACAAACTTTGTGAATATAACGTATTCCATAACAAAACCTTTGAGTTACC

AAGAGCTCGCGTCAACACATAGCATTAGTTAATTAAAAATTAGGGCCCAACAAT

GAACTAGGATATCAAGACTAACAATAACATTGGGGCAAATGCAAACATGTCCAA

AAACAAGGACCAACGCACCGCTAAGACATTAGAAAGGACCTGGGACACTCTCAA

TCATTTATTATTCATATCATCGTGCTTATATAAGTTAAATCTTAAATCTGTAGCAC

AAATCACATTATCCATTCTGGCAATGATAATCTCAACTTCACTTATAATTGCAGC

CATCATATTCATAGCCTCGGCAAACCACAAAGTCACACCAACAACTGCAATCAT

ACAAGATGCAACAAGCCAGATCAAGAACACAACCCCAACATACCTCACCCAGAA

TCCTCAGCTTGGAATCAGTCCCTCTAATCCGTCTGAAATTACATCACAAATCACC

ACCATACTAGCTTCAACAACACCAGGAGTCAAGTCAACCCTGCAATCCACAACA

GTCAAGACCAAAAACACAACAACAACTCAAACACAACCCAGCAAGCCCACCAC

AAAACAACGCCAAAACAAACCACCAAGCAAACCCAATAATGATTTTCACTTTGA

AGTGTTCAACTTTGTACCCTGCAGCATATGCAGCAACAATCCAACCTGCTGGGCT

ATCTGCAAAAGAATACCAAACAAAAAACCAGGAAAGAAAACCACTACCAAGCC

CACAAAAAAACCAACCCTCAAGACAACCAAAAAAGATCCCAAACCTCAAACCAC

TAAATCAAAGGAAGTACCCACCACCAAGCCCACAGAAGAGCCAACCATCAACAC

CACCAAAACAAACATCATAACTACACTACTCACCTCCAACACCACAGGAAATCC

AGAACTCACAAGTCAAATGGAAACCTTCCACTCAACTTCCTCCGAAGGCAATCC

AAGCCCTTCTCAAGTCTCTACAACATCCGAGTACCCATCACAACCTTCATCTCCA

CCCAACACACCACGCCAGTAGTTACTTAAAAACATATTATCACAAAAGGCCTTGA

CCAACCGCGGAGAATCAAAATAAACTCTGGGGCAAATAACAATGGAGTTGCTAA

TCCTCAAAGCAAATGCAATTACCACAATCCTCACTGCAGTCACATTTTGTTTTGCT

TCTGGTCAAAACATCACTGAAGAATTTTATCAATCAACATGCAGTGCAGTTAGCA

AAGGCTATCTTAGTGCTCTGAGAACTGGTTGGTATACCAGTGTTATAACTATAGA

ATTAAGTAATATCAAGAAAAATAAGTGTAATGGAACAGATGCTAAGGTAAAATT

GATAAAACAAGAATTAGATAAAATATAAAAATGCTGTAACAGAATTGCAGTTGCT

CATGCAAAGCACACAAGCAACAAACAATCGAGCCAGAAGAGAACTACCAAGGT
```

-continued

```
TTATGAATTATACACTCAACAATGCCAAAAAAACCAATGTAACATTAAGCAAGA
AAAGGAAAAGAAGATTTCTTGGTTTTTTGTTAGGTGTTGGATCTGCAATCGCCAG
TGGCGTTGCTGTATCTAAGGTCCTGCACCTAGAAGGGGAAGTGAACAAGATCAA
AAGTGCTCTACTATCCACAAACAAGGCTGTAGTCAGCTTATCAAATGGAGTTAGT
GTTTTAACCAGCAAAGTGTTAGACCTCAAAAACTATATAGATAAACAATTGTTAC
CTATTGTGAACAAGCAAAGCTGCAGCATATCAAATATAGAAACTGTGATAGAGT
TCCAACAAAAGAACAACAGACTACTAGAGATTACCAGGGAATTTAGTGTTAATG
CAGGCGTAACTACACCTGTAAGCACTTACATGTTAACTAATAGTGAATTATTGTC
ATTAATCAATGATATGCCTATAACAAATGATCAGAAAAAGTTAATGTCCAACAAT
GTTCAAATAGTTAGACAGCAAAGTTACTCTATCATGTCCATAATAAAAGAGGAA
GTCTTAGCATATGTAGTACAATTACCACTATATGGTGTTATAGATACACCCTGTT
GGAAACTACACACATCCCCTCTATGTACAACCAACACAAAAGAAGGGTCCAACA
TCTGTTTAACAAGAACTGACAGAGGATGGTACTGTGACAATGCAGGATCAGTAT
CTTTCTTCCCACAAGCTGAAACATGTAAAGTTCAATCAAATCGAGTATTTTGTGA
CACAATGAACAGTTTAACATTACCAAGTGAAGTAAATCTCTGCAATGTTGACATA
TTCAACCCCAAATATGATTGTAAAATTATGACTTCAAAAACAGATGTAAGCAGCT
CCGTTATCACATCTCTAGGAGCCATTGTGTCATGCTATGGCAAAACTAAATGTAC
AGCATCCAATAAAAATCGTGGAATCATAAAGACATTTTCTAACGGGTGCGATTAT
GTATCAAATAAAGGGGTGGACACTGTGTCTGTAGGTAACACATTATATTATGTAA
ATAAGCAAGAAGGTAAAAGTCTCTATGTAAAAGGTGAACCAATAATAAATTTCT
ATGACCCATTAGTATTCCCCTCTGATGAATTTGATGCATCAATATCTCAAGTCAA
CGAGAAGATTAACCAGAGCCTAGCATTTATTCGTAAATCCGATGAATTATTACAT
AATGTAAATGCTGGTAAATCCACCACAAATATCATGATAACTACTATAATTATAG
TGATTATAGTAATATTGTTATCATTAATTGCTGTTGGACTGCTCTTATACTGTAAG
GCCAGAAGCACACCAGTCACACTAAGCAAAGATCAACTGAGTGGTATAAATAAT
ATTGCATTTAGTAACTAAATAAAAATAGCACCTAATCATGTTCTTACAATGGTTT
ACTATCTGCTCATAGACAACCCATCTGTCATTGGATTTTCTTAAAATCTGAACTTC
ATCGAAACTCTCATCTATAAACCATCTCACTTACACTATTTAAGTAGATTCCTAGT
TTATAGTTATATAAAACACAATTGCATGCCACTCGAGCTTACCATCTGTAAAAAT
GAAAACTGGGGCAAATATGTCACGAAGGAATCCTTGCAAATTTGAAATTCGAGG
TCATTGCTTAAATGGTAAGAGGTGTCATTTTAGTCATAATTATTTTGAATGGCCAC
CCCATGCACTGCTTGTAAGACAAAACTTTATGTTAAACAGAATACTTAAGTCTAT
GGATAAAAGTATAGATACCTTATCAGAAATAAGTGGAGCTGCAGAGTTGGACAG
AACAGAAGAGTATGCTCTTGGTGTAGTTGGAGTGCTAGAGAGTTATATAGGATC
AATAAACAATATAACTAAACAATCAGCATGTGTTGCCATGAGCAAACTCCTCACT
GAACTCAATAGTGATGATATCAAAAAGCTGAGGGACAATGAAGAGCTAAATTCA
CCCAAGATAAGAGTGTACAATACTGTCATATCATATATTGAAAGCAACAGGAAA
AACAATAAACAAACTATCCATCTGTTAAAAAGATTGCCAGCAGACGTATTGAAG
AAAACCATCAAAAACACATTGGATATCCATAAGAGCATAACCATCAACAACCCA
AAAGAATCAACTGTTAGTGATACAAATGACCATGCCAAAAATAATGATACTACC
TGACAAATATCCTTGTAGTATAACTTCCATACTAATAACAAGTAGATGTAGAGTT
```

-continued

```
ACTATGTATAATCAAAAGAACACACTATATTTCAATCAAAACAACCCAAATAAC

CATATGTACTCACCGAATCAAACATTCAATGAAATCCATTGGACCTCTCAAGAAT

TGATTGACACAATTCAAAATTTTCTACAACATCTAGGTATTATTGAGGATATATA

TACAATATATATATTAGTGTCATAACACTCAATTCTAACACTCACCACATCGTTA

CATTATTAATTCAAACAATTCAAGTTGTGGGACAAAATGGATCCCATTATTAATG

GAAATTCTGCTAATGTTTATCTAACCGATAGTTATTTAAAAGGTGTTATCTCTTTC

TCAGAGTGTAATGCTTTAGGAAGTTACATATTCAATGGTCCTTATCTCAAAAATG

ATTATACCAACTTAATTAGTAGACAAAATCCATTAATAGAACACATGAATCTAAA

GAAACTAAATATAACACAGTCCTTAATATCTAAGTATCATAAAGGTGAAATAAA

ATTAGAAGAACCTACTTATTTTCAGTCATTACTTATGACATACAAGAGTATGACC

TCGTCAGAACAGATTGCTACCACTAATTTACTTAAAAAGATAATAAGAAGAGCT

ATAGAAATAAGTGATGTCAAAGTCTATGCTATATTGAATAAACTAGGGCTTAAA

GAAAAGGACAAGATTAAATCCAACAATGGACAAGATGAAGACAACTCAGTTATT

ACGACCATAATCAAAGATGATATACTTTCAGCTGTTAAAGATAATCAATCTCATC

TTAAAGCAGACAAAAATCACTCTACAAAACAAAAAGACACAATCAAAACAACAC

TCTTGAAGAAATTGATGTGTTCAATGCAACATCCTCCATCATGGTTAATACATTG

GTTTAACTTATACACAAAATTAAACAACATATTAACACAGTATCGATCAAATGAG

GTAAAAAACCATGGGTTTACATTGATAGATAATCAAACTCTTAGTGGATTTCAAT

TTATTTTGAACCAATATGGTTGTATAGTTTATCATAAGGAACTCAAAAGAATTAC

TGTGACAACCTATAATCAATTCTTGACATGGAAAGATATTAGCCTTAGTAGATTA

AATGTTTGTTTAATTACATGGATTAGTAACTGCTTGAACACATTAAATAAAAGCT

TAGGCTTAAGATGCGGATTCAATAATGTTATCTTGACACAACTATTCCTTTATGG

AGATTGTATACTAAAGCTATTTCACAATGAGGGGTTCTACATAATAAAAGAGGTA

GAGGGATTTATTATGTCTCTAATTTTAAATATAACAGAAGAAGATCAATTCAGAA

AACGATTTTATAATAGTATGCTCAACAACATCACAGATGCTGCTAATAAAGCTCA

GAAAAATCTGCTATCAAGAGTATGTCATACATTATTAGATAAGACAGTGTCCGAT

AATATAATAAATGGCAGATGGATAATTCTATTAAGTAAGTTCCTTAAATTAATTA

AGCTTGCAGGTGACAATAACCTTAACAATCTGAGTGAACTATATTTTTTGTTCAG

AATATTTGGACACCCAATGGTAGATGAAAGACAAGCCATGGATGCTGTTAAAAT

TAATTGCAATGAGACCAAATTTTACTTGTTAAGCAGTCTGAGTATGTTAAGAGGT

GCCTTTATATATAGAATTATAAAAGGGTTTGTAAATAATTACAACAGATGGCCTA

CTTTAAGAAATGCTATTGTTTTACCCTTAAGATGGTTAACTTACTATAAACTAAAC

ACTTATCCTTCTTTGTTGGAACTTACAGAAAGAGATTTGATTGTGTTATCAGGACT

ACGTTTCTATCGTGAGTTTCGGTTGCCTAAAAAAGTGGATCTTGAAATGATTATA

AATGATAAAGCTATATCACCTCCTAAAAATTTGATATGGACTAGTTTCCCTAGAA

ATTACATGCCATCACACATACAAAACTATATAGAACATGAAAAATTAAAATTTTC

CGAGAGTGATAAATCAAGAAGAGTATTAGAGTATTATTTAAGAGATAACAAATT

CAATGAATGTGATTTATACAACTGTGTAGTTAATCAAAGTTATCTCAACAACCCT

AATCATGTGGTATCATTGACAGGCAAAGAAAGAGAACTCAGTGTAGGTAGAATG

TTTGCAATGCAACCGGGAATGTTCAGACAGGTTCAAATATTGGCAGAGAAAATG
```

-continued

```
ATAGCTGAAAACATTTTACAATTCTTTCCTGAAAGTCTTACAAGATATGGTGATC

TAGAACTACAAAAAATATTAGAACTGAAAGCAGGAATAAGTAACAAATCAAATC

GCTACAATGATAATTACAACAATTACATTAGTAAGTGCTCTATCATCACAGATCT

CAGCAAATTCAATCAAGCATTTCGATATGAAACGTCATGTATTTGTAGTGATGTG

CTGGATGAACTGCATGGTGTACAATCTCTATTTTCCTGGTTACATTTAACTATTCC

TCATGTCACAATAATATGCACATATAGGCATGCACCCCCCTATATAGGAGATCAT

ATTGTAGATCTTAACAATGTAGATGAACAAAGTGGATTATATAGATATCACATGG

GTGGCATCGAAGGGTGGTGTCAAAAACTATGGACCATAGAAGCTATATCACTAT

TGGATCTAATATCTCTCAAAGGGAAATTCTCAATTACTGCTTTAATTAATGGTGA

CAATCAATCAATAGATATAAGCAAACCAATCAGACTCATGGAAGGTCAAACTCA

TGCTCAAGCAGATTATTTGCTAGCATTAAATAGCCTTAAATTACTGTATAAAGAG

TATGCAGGCATAGGCCACAAATTAAAAGGAACTGAGACTTATATATCACGAGAT

ATGCAATTTATGAGTAAAACAATTCAACATAACGGTGTATATTACCCAGCTAGTA

TAAAGAAAGTCCTAAGAGTGGGACCGTGGATAAACACTATACTTGATGATTTCA

AAGTGAGTCTAGAATCTATAGGTAGTTTGACACAAGAATTAGAATATAGAGGTG

AAAGTCTATTATGCAGTTTAATATTTAGAAATGTATGGTTATATAATCAGATTGC

TCTACAATTAAAAAATCATGCATTATGTAACAATAAACTATATTTGGACATATTA

AAGGTTCTGAAACACTTAAAAACCTTTTTTAATCTTGATAATATTGATACAGCAT

TAACATTGTATATGAATTTACCCATGTTATTTGGTGGTGGTGATCCCAACTTGTTA

TATCGAAGTTTCTATAGAAGAACTCCTGACTTCCTCACAGAGGCTATAGTTCACT

CTGTGTTCATACTTAGTTATTATACAAACCATGACTTAAAAGATAAACTTCAAGA

TCTGTCAGATGATAGATTGAATAAGTTCTTAACATGCATAATCACGTTTGACAAA

AACCCTAATGCTGAATTCGTAACATTGATGAGAGATCCTCAAGCTTTAGGGTCTG

AGAGACAAGCTAAAATTACTAGCGAAATCAATAGACTGGCAGTTACAGAGGTTT

TGAGTACAGCTCCAAACAAAATATTCTCCAAAAGTGCACAACATTATACTACTAC

AGAGATAGATCTAAATGATATTATGCAAAATATAGAACCTACATATCCTCATGGG

CTAAGAGTTGTTTATGAAAGTTTACCCTTTTATAAAGCAGAGAAAATAGTAAATC

TTATATCAGGTACAAAATCTATAACTAACATACTGGAAAAAACTTCTGCCATAGA

CTTAACAGATATTGATAGAGCCACTGAGATGATGAGGAAAAACATAACTTTGCTT

ATAAGGATACTTCCATTGGATTGTAACAGAGATAAAAGAGAGATATTGAGTATG

GAAAACCTAAGTATTACTGAATTAAGCAAATATGTTAGGGAAAGATCTTGGTCTT

TATCCAATATAGTTGGTGTTACATCACCCAGTATCATGTATACAATGGACATCAA

ATATACTACAAGCACTATATCTAGTGGCATAATTATAGAGAAATATAATGTTAAC

AGTTTAACACGTGGTGAGAGAGGACCCACTAAACCATGGGTTGGTTCATCTACAC

AAGAGAAAAAAACAATGCCAGTTTATAATAGACAAGTCTTAACCAAAAAACAGA

GAGATCAAATAGATCTATTAGCAAAATTGGATTGGGTGTATGCATCTATAGATAA

CAAGGATGAATTCATGGAAGAACTCAGCATAGGAACCCTTGGGTTAACATATGA

AAAGGCCAAGAAATTATTTCCACAATATTTAAGTGTCAATTATTTGCATCGCCTT

ACAGTCAGTAGTAGACCATGTGAATTCCCTGCATCAATACCAGCTTATAGAACAA

CAAATTATCACTTTGACACTAGCCCTATTAATCGCATATTAACAGAAAAGTATGG

TGATGAAGATATTGACATAGTATTCCAAAACTGTATAAGCTTTGGCCTTAGTTTA
```

-continued

```
ATGTCAGTAGTAGAACAATTTACTAATGTATGTCCTAACAGAATTATTCTCATAC
CTAAGCTTAATGAGATACATTTGATGAAACCTCCCATATTCACAGGTGATGTTGA
TATTCACAAGTTAAAACAAGTGATACAAAAACAGCATATGTTTTTACCAGACAA
AATAAGTTTGACTCAATATGTGGAATTATTCTTAAGTAATAAAACACTCAAATCT
GGATCTCATGTTAATTCTAATTTAATATTGGCACATAAAATATCTGACTATTTTCA
TAATACTTACATTTTAAGTACTAATTTAGCTGGACATTGGATTCTGATTATACAAC
TTATGAAAGATTCTAAAGGTATTTTTGAAAAAGATTGGGGAGAGGGATATATAA
CTGATCATATGTTTATTAATTTGAAAGTTTTCTTCAATGCTTATAAGACCTATCTC
TTGTGTTTTCATAAAGGTTATGGCAAAGCAAAGCTGGAGTGTGATATGAACACTT
CAGATCTTCTATGTGTATTGGAATTAATAGACAGTAGTTATTGGAAGTCTATGTC
TAAGGTATTTTTAGAACAAAAAGTTATCAAATACATTCTTAGCCAAGATGCAAGT
TTACATAGAGTAAAAGGATGTCATAGCTTCAAATTATGGTTTCTTAAACGTCTTA
ATGTAGCAGAATTCACAGTTTGCCCTTGGGTTGTTAACATAGATTATCATCCAAC
ACATATGAAAGCAATATTAACTTATATAGATCTTGTTAGAATGGGATTGATAAAT
ATAGATAGAATACACATTAAAAATAAACACAAATTCAATGATGAATTTTATACTT
CTAATCTCTTCTACATTAATTATAACTTCTCAGATAATACTCATCTATTAACTAAA
CATATAAGGATTGCTAATTCTGAATTAGAAAATAATTACAACAAATTATATCATC
CTACACCAGAAACCCTAGAGAATATACTAGCCAATCCGATTAAAAGTAATGACA
AAAAGACACTGAATGACTATTGTATAGGTAAAAATGTTGACTCAATAATGTTACC
ATTGTTATCTAATAAGAAGCTTATTAAATCGTCTGCAATGATTAGAACCAATTAC
AGCAAACAAGATTTGTATAATTTATTCCCTATGGTTGTGATTGATAGAATTATAG
ATCATTCAGGCAATACAGCCAAATCCAACCAACTTTACACTACTACTTCCCACCA
AATATCCTTAGTGCACAATAGCACATCACTTTACTGCATGCTTCCTTGGCATCATA
TTAATAGATTCAATTTTGTATTTAGTTCTACAGGTTGTAAAATTAGTATAGAGTAT
ATTTTAAAAGATCTTAAAATTAAAGATCCCAATTGTATAGCATTCATAGGTGAAG
GAGCAGGGAATTTATTATTGCGTACAGTAGTGGAACTTCATCCTGACATAAGATA
TATTTACAGAAGTCTGAAAGATTGCAATGATCATAGTTTACCTATTGAGTTTTTA
AGGCTGTACAATGGACATATCAACATTGATTATGGTGAAAATTTGACCATTCCTG
CTACAGATGCAACCAACAACATTCATTGGTCTTATTTACATATAAAGTTTGCTGA
ACCTATCAGTCTTTTTGTCTGTGATGCCGAATTGTCTGTAACAGTCAACTGGAGTA
AAATTATAATAGAATGGAGCAAGCATGTAAGAAAGTGCAAGTACTGTTCCTCAG
TTAATAAATGTATGTTAATAGTAAAATATCATGCTCAAGATGATATTGATTTCAA
ATTAGACAATATAACTATATTAAAAACTTATGTATGCTTAGGCAGTAAGTTAAAG
GGATCGGAGGTTTACTTAGTCCTTACAATAGGTCCTGCGAATATATTCCCAGTAT
TTAATGTAGTACAAAATGCTAAATTGATACTATCAAGAACCAAAAATTTCATCAT
GCCTAAGAAAGCTGATAAAGAGTCTATTGATGCAAATATTAAAGTTTGATACCC
TTTCTTTGTTACCCTATAACAAAAAAAGGAATTAATACTGCATTGTCAAAACTAA
AGAGTGTTGTTAGTGGAGATATACTATCATATTCTATAGCTGGACGTAATGAAGT
TTTCAGCAATAAACTTATAAATCATAAGCATATGAACATCTTAAAATGGTTCAAT
CATGTTTTAAATTTCAGATCAACAGAACTAAACTATAACCATTTATATATGGTAG
```

-continued

AATCTACATATCCTTACCTAAGTGAATTGTTAAACAGCTTGACAACCAATGAACT

TAAAAAACTGATTAAAATCACAGGTAGTCTGTTATACAACTTTCATAATGAATAA

TGAATAAAGATCTTATAATAAAAATTCCCATAGCTATACACTAACACTGTATTCA

ATTATAGTTATTAAAAATTAAAAATCGTACGATTTTTTAAATAACTTTTAGTGAA

CTAATCCTAAAGTTATCATTTTAATCTTGGAGGAATAAATTTAAACCCTAATCTA

ATTGGTTTATATGTGTATTAACTAAATTACGAGATATTAGTTTTTGACACTTTTTT

TCTCGT.

In certain other embodiments, the disclosure concerns isolated nucleic acid segments that include within their sequence a contiguous nucleic acid sequence from SEQ ID NO:3 (G gene antigenome of hMPV) or the complement thereof (G gene genome sequence):

(SEQ ID NO: 3)

ATGGAGGTGAAAGTGGAGAACATTCGAACAATAGATATGCTCAAAGCAAG

AGTAAAAAATCGTGTGGCACGCAGCAAATGCTTTAAAAATGCCTCTTTGG

TCCTCATAGGAATAACTACATTGAGTATTGCCCTCAATATCTATCTGATC

ATAAACTATAAAATGCAAAAAAACACATCTGAATCAGAACATCACACCAG

CTCATCACCCATGGAATCCAGCAGAGAAACTCCAACGGTCCCCACAGACA

ACTCAGACACCAACTCAAGCCCACAGCATCCAACTCAACAGTCCACAGAA

GGCTCCACACTCTACTTTGCAGCCTCAGCAAGCTCACCAGAGACAGAACC

-continued

AACATCAACACCAGATACAACAAACCGCCCGCCCTTCGTCGACACACACA

CAACACCACCAAGCGCAAGCAGAACAAAGACAAGTCCGGCAGTCCACACA

AAAAACAACCCAAGGACAAGCTCTAGAACACATTCTCCACCACGGGCAAC

GACAAGGACGGCACGCAGAACCACCACTCTCCGCACAAGCAGCACAAGAA

AGAGACCGTCCACAGCATCAGTCCAACCTGACATCAGCGCAACAACCCAC

AAAAACGAAGAAGCAAGTCCAGCGAGCCCACAAACATCTGCAAGCACAAC

AAGAATACAAAGGAAAAGCGTGGAGGCCAACACATCAACAACATACAACC

AAACTAGTTAA

In certain other embodiments, the disclosure concerns isolated nucleic acid segments and recombinant vectors, as RNA or DNA, that include within their sequence a contiguous nucleic acid sequence from SEQ ID NO:4 (hMPV antigenome shown with thymine (T) instead of uracil (U)) or the RNA complement thereof (hMPV genome):

(SEQ ID NO: 4)

GTATAAATTAGATTCCAAAAAAATATGGGACAAGTGAAAATGTCTCTTCAAGGG

ATTCACCTGAGTGATTTATCATACAAGCATGCTATATTAAAAGAGTCTCAGTACA

CAATAAAAAGAGATGTGGGTACAACAACTGCAGTGACACCCTCATCATTGCAAC

AAGAAATAACACTGTTGTGTGGAGAAATTCTGTATGCTAAACATGCTGACTACAA

ATATGCTGCAGAAATAGGAATACAATATATTAGCACAGCTTTAGGATCAGAGAG

AGTGCAGCAGATTCTGAGGAACTCAGGCAGTGAAGTCCAAGTGGTCTTAACCAG

AACGTACTCTCTGGGGAAAATTAAAAACAATAAAGGAGAAGATTTACAGATGTT

AGACATACACGGGGTAGAGAAGAGCTGGGTAGAAGAGATAGACAAAGAAGCAA

GGAAAACAATGGCAACCTTGCTTAAGGAATCATCAGGTAATATCCCACAAAATC

AGAGGCCCTCAGCACCAGACACACCCATAATCTTATTATGTGTAGGTGCCTTAAT

ATTCACTAAACTAGCATCAACCATAGAAGTGGGACTAGAGACCACAGTCAGAAG

GGCTAACCGTGTACTAAGTGATGCACTCAAGAGATACCCTAGAATGGACATACC

AAAGATTGCCAGATCCTTCTATGACTTATTTGAACAAAAAGTGTATCACAGAAGT

TTGTTCATTGAGTATGGCAAAGCATTAGGCTCATCATCTACAGGCAGCAAAGCAG

AAAGTCTATTTGTTAATATATTCATGCAAGCTTATGGGGCCGGTCAAACAATGCT

AAGGTGGGGGGTCATTGCCAGGTCATCCAACAATATAATGTTAGGACATGTATCC

GTCCAAGCTGAGTTAAAACAGGTCACAGAAGTCTATGACTTGGTGCGAGAAATG

GGCCCTGAATCTGGACTTCTACATTTAAGGCAAAGCCCAAAAGCTGGACTGTTAT

CACTAGCCAACTGTCCCAACTTTGCAAGTGTTGTTCTCGGAAATGCCTCAGGCTT

-continued
```
AGGCATAATCGGTATGTATCGAGGGAGAGTACCAAACACAGAATTATTTTCAGC

AGCTGAAAGTTATGCCAAAAGTTTGAAAGAAAGCAATAAAATAAATTTCTCTTC

ATTAGGACTTACAGATGAAGAGAAAGAGGCTGCAGAACATTTCTTAAATGTGAG

TGACGACAGTCAAAATGATTATGAGTAATTAAAAAAGTGGGACAAGTCAAAATG

TCATTCCCTGAAGGAAAAGATATTCTTTTCATGGGTAATGAAGCAGCAAAATTAG

CAGAAGCTTTCCAGAAATCATTAAGAAAACCAGGTCATAAAAGATCTCAATCTA

TTATAGGAGAAAAAGTGAATACTGTATCAGAAACATTGGAATTACCTACTATCA

GTAGACCTGCAAAACCAACCATACCGTCAGAACCAAAGTTAGCATGGACAGATA

AAGGTGGGGCAACCAAAACTGAAATAAAGCAAGCAATCAAAGTCATGGATCCCA

TTGAAGAAGAAGAGTCTACCGAGAAGAAGGTGCTACCCTCCAGTGATGGGAAAA

CCCCTGCAGAAAAGAAACTGAAACCATCAACTAACACCAAAAAGAAGGTTTCAT

TTACACCAAATGAACCAGGGAAATATACAAAGTTGGAAAAAGATGCTCTAGATT

TGCTCTCAGATAATGAAGAAGAAGATGCAGAATCTTCAATCTTAACCTTTGAAGA

AAGAGATACTTCATCATTAAGCATTGAGGCCAGATTGGAATCAATAGAGGAGAA

ATTAAGCATGATATTAGGGCTATTAAGAACACTCAACATTGCTACAGCAGGACCC

ACAGCAGCAAGAGATGGGATCAGAGATGCAATGATTGGCGTAAGAGAGGAATT

AATAGCAGACATAATAAAGGAAGCTAAAGGGAAAGCAGCAGAAATGATGGAAG

AGGAAATGAGTCAACGATCAAAAATAGGAAATGGTAGTGTAAAATTAACAGAA

AAAGCAAAAGAGCTCAACAAAATTGTTGAAGATGAAAGCACAAGTGGAGAATC

CGAAGAAGAAGAAGAACCAAAAGACACACAAGACAATAGTCAAGAAGATGACA

TTTACCAGTTAATTATGTAGTTTAATAAAAATAAACAATGGGACAAGTAAAAATG

GAGTCCTACCTAGTAGACACCTATCAAGGCATTCCTTACACAGCAGCTGTTCAAG

TTGATCTAATAGAAAAGGACCTGTTACCTGCAAGCCTAACAATATGGTTCCCTTT

GTTTCAGGCCAACACACCACCAGCAGTGCTGCTCGATCAGCTAAAAACCCTGAC

AATAACCACTCTGTATGCTGCATCACAAAATGGTCCAATACTCAAAGTGAATGCA

TCAGCCCAAGGTGCAGCAATGTCTGTACTTCCCAAAAAATTTGAAGTCAATGCGA

CTGTAGCACTCGATGAATATAGCAAACTGGAATTTGACAAACTCACAGTCTGTGA

AGTAAAAACAGTTTACTTAACAACCATGAAACCATACGGGATGGTATCAAAATT

TGTGAGCTCAGCCAAATCAGTTGGCAAAAAAACACATGATCTAATCGCACTATGT

GATTTTATGGATCTAGAAAAGAACACACCTGTTACAATACCAGCATTCATCAAAT

CAGTTTCAATCAAAGAGAGTGAGTCAGCTACTGTTGAAGCTGCTATAAGCAGTG

AAGCAGACCAAGCTCTAACACAGGCCAAAATTGCACCTTATGCGGGATTAATTA

TGATCATGACTATGAACAATCCCAAAGGCATATTCAAAAAGCTTGGAGCTGGGA

CTCAAGTCATAGTAGAACTAGGAGCATATGTCCAGGCTGAAAGCATAAGCAAAA

TATGCAAGACTTGGAGCCATCAAGGGACAAGATATGTCTTGAAGTCCAGATAAC

AACCAAGCACCTTGGCCAAGAGCTACTAACCCTATCTCATAGATCATAAAGTCAC

CATTCTAGTTATATAAAAATCAAGTTAGAACAAGAATTAAATCAATCAAGAACG

GGACAAATAAAAATGTCTTGGAAAGTGGTGATCATTTTTTCATTGTTAATAACAC

CTCAACACGGTCTTAAAGAGAGCTACTTAGAAGAGTCATGTAGCACTATAACTG

AAGGATATCTCAGTGTTCTGAGGACAGGTTGGTACACCAATGTTTTTACACTGGA

GGTAGGCGATGTAGAGAACCTTACATGTGCCGATGGACCCAGCTTAATAAAAAC
```

-continued

```
AGAATTAGACCTGACCAAAAGTGCACTAAGAGAGCTCAGAACAGTTTCTGCTGA

TCAACTGGCAAGAGAGGAGCAAATTGAAAATCCCAGACAATCTAGATTCGTTCT

AGGAGCAATAGCACTCGGTGTTGCAACTGCAGCTGCAGTTACAGCAGGTGTTGC

AATTGCCAAAACCATCCGGCTTGAAAGTGAAGTAACAGCAATTAAGAATGCCCT

CAAAAAGACCAATGAAGCAGTATCTACATTGGGGAATGGAGTTCGTGTGTTGGC

AACTGCAGTGAGAGAGCTGAAAGATTTTGTGAGCAAGAATCTAACACGTGCAAT

CAACAAAAACAAGTGCGACATTGCTGACCTGAAAATGGCCGTTAGCTTCAGTCA

ATTCAACAGAAGGTTCCTAAATGTTGTGCGGCAATTTTCAGACAACGCTGGAATA

ACACCAGCAATATCTTTGGACTTAATGACAGATGCTGAACTAGCCAGAGCTGTTT

CCAACATGCCAACATCTGCAGGACAAATAAAACTGATGTTGGAGAACCGTGCAA

TGGTAAGAAGAAAGGGTTCGGATTCCTGATAGGAGTTTACGGAAGCTCCGTAA

TTTACATGGTGCAACTGCCAATCTTTGGGGTTATAGACACGCCTTGCTGGATAGT

AAAAGCAGCCCCTTCTTGTTCAGGAAAAAAGGGAAACTATGCTTGCCTCTTAAGA

GAAGACCAAGGATGGTATTGTCAAAATGCAGGGTCAACTGTTTACTACCCAAAT

GAAAAGACTGTGAAACAAGAGGAGACCATGTCTTTTGCGACACAGCAGCAGGA

ATCAATGTTGCTGAGCAGTCAAAGGAGTGCAACATAAACATATCTACTACTAATT

ACCCATGCAAAGTTAGCACAGGAAGACATCCTATCAGTATGGTTGCACTATCTCC

TCTTGGGGCTTTGGTTGCTTGCTACAAGGGAGTGAGCTGTTCCATTGGCAGCAAC

AGAGTAGGGATCATCAAGCAACTGAACAAAGGCTGCTCTTATATAACCAACCAA

GACGCAGACACAGTGACAATAGACAACACTGTATACCAGCTAAGCAAAGTTGAA

GGCGAACAGCATGTTATAAAAGGAAGGCCAGTGTCAAGCAGCTTTGACCCAGTC

AAGTTTCCTGAAGATCAATTCAATGTTGCACTTGACCAAGTTTTCGAGAGCATTG

AGAACAGTCAGGCCTTGGTGGATCAATCAAACAGAATCCTAAGCAGTGCAGAGA

AAGGAAACACTGGCTTCATCATTGTAATAATTCTAATTGCTGTCCTTGGCTCTACC

ATGATCCTAGTGAGTGTTTTTATCATAATAAAGAAAACAAAGAAACCCACAGGA

GCACCTCCAGAGCTGAGTGGTGTCACAAACAATGGCTTCATACCACATAATTAGT

TAATTAAAAATAAAGTAAATTAAAATAAATTAAAATTAAAAATAAAAATTTGGG

ACAAATCATAATGTCTCGCAAGGCTCCGTGCAAATATGAAGTGCGGGCAAATG

CAATAGAGGAAGTGAGTGCAAGTTTAACCACAATTACTGGAGTTGGCCAGATAG

ATACTTATTAATAAGATCAAATTATTTATTAAATCAACTTTTAAGGAACACTGAT

AGAGCTGATGGCTTATCAATAATATCAGGAGCAGGCAGAGAAGATAGGACACAA

GATTTTGTCCTAGGTTCCACCAATGTGGTTCAAGGTTATATTGATGATAACCAAA

GCATAACAAAAGCTGCAGCCTGTTACAGTCTACATAATATAATCAAACAACTAC

AAGAAGTTGAAGTTAGGCAGGCTAGAGATAACAAACTATCTGACAGCAAACATG

TAGCACTTCACAACTTAGTCCTATCTTATATGGAGATGAGCAAAACTCCTGCATC

TTTAATCAACAATCTCAAGAGACTGCCGAGAGAGAAACTGAAAAAATTAGCAAA

GCTCATAATTGACTTATCAGCAGGTGCTGAAAATGACTCTTCATATGCCTTGCAA

GACAGTGAAAGCACTAATCAAGTGCAGTGAGCATGGTCCAGTTTTCATTACTATA

GAGGTTGATGACATGATATGGACTCACAAGGACTTAAAAGAAGCTTTATCTGAT

GGGATAGTGAAGTCTCATACTAACATTTACAATTGTTATTTAGAAAACATAGAAA
```

-continued
```
TTATATATGTCAAGGCTTACTTAAGTTAGTAAAAACACATCAGAGTGGGATAAAT

GACAATGATAACATTAGATGTCATTAAAAGTGATGGGTCTTCAAAAACATGTACT

CACCTCAAAAAAATAATTAAAGACCACTCTGGTAAAGTGCTTATTGTACTTAAGT

TAATATTAGCTTTACTAACATTTCTCACAGTAACAATCACCATCAATTATATAAA

AGTGGAAAACAATCTGCAAATATGCCAGTCAAAAACTGAATCAGACAAAAAGGA

CTCATCATCAAATACCACATCAGTCACAACCAAGACTACTCTAAATCATGATATC

ACACAGTATTTTAAAAGTTTGATTCAAAGGTATACAAACTCTGCAATAAACAGTG

ACACATGCTGGAAAATAAACAGAAATCAATGCACAAATATAACAACATACAAAT

TTTTATGTTTTAAATCTGAAGACACAAAAACCAACAATTGTGATAAACTGACAGA

TTTATGCAGAAACAAACCAAAACCAGCAGTTGGAGTGTATCACATAGTAGAATG

CCATTGTATATACACAGTTAAATGGAAGTGCTATCATTACCCAACCGATGAAACC

CAATCCTAAATGTTAACACCAGATTAGGATCCATCCAAGTCTGTTAGTTCAACAA

TTTAGTTATTTAAAAATATTTTGAAAACAAGTAAGTTTCTATGATACTTCATAATA

ATAAGTAATAATTAATTGCTTAATCATCATCACAACATTATTCGAAACCATAACT

ATTCAATTTAAAAAGTAAAAAACAATAACATGGGACAAGTAGTTATGGAGGTGA

AAGTGGAGAACATTCGAACAATAGATATGCTCAAAGCAAGAGTAAAAAATCGTG

TGGCACGCAGCAAATGCTTTAAAAATGCCTCTTTGGTCCTCATAGGAATAACTAC

ATTGAGTATTGCCCTCAATATCTATCTGATCATAAACTATAAAATGCAAAAAAAC

ACATCTGAATCAGAACATCACACCAGCTCATCACCCATGGAATCCAGCAGAGAA

ACTCCAACGGTCCCCACAGACAACTCAGACACCAACTCAAGCCCACAGCATCCA

ACTCAACAGTCCACAGAAGGCTCCACACTCTACTTTGCAGCCTCAGCAAGCTCAC

CAGAGACAGAACCAACATCAACACCAGATACAACAAACCGCCCGCCCTTCGTCG

ACACACACACAACACCACCAAGCGCAAGCAGAACAAAGACAAGTCCGGCAGTC

CACACAAAAAACAACCCAAGGACAAGCTCTAGAACACATTCTCCACCACGGGCA

ACGACAAGGACGGCACGCAGAACCACCACTCTCCGCACAAGCAGCACAAGAAA

GAGACCGTCCACAGCATCAGTCCAACCTGACATCAGCGCAACAACCCACAAAAA

CGAAGAAGCAAGTCCAGCGAGCCCACAAACATCTGCAAGCACAACAAGAATAC

AAAGGAAAAGCGTGGAGGCCAACACATCAACAACATACAACCAAACTAGTTAAC

AAAAAATACAAAATAACTCTAAGATAAACCATGCAGACACCAACAATGGAGAA

GCCAAAAGACAATTCACAATCTCCCCAAAAAGGCAACAACACCATATTAGCTCT

GCCCAAATCTCCCTGGAAAAAACACTCGCCCATATACCAAAAATACCACAACCA

CCCCAAGAAAAAAACTGGGCAAAACAACACCCAAGAGACAAATAACAATGGAT

CCTCTCAATGAATCCACTGTTAATGTCTATCTTCCTGACTCATATCTTAAAGGAGT

GATTTCCTTTAGTGAGACTAATGCAATTGGTTCATGTCTCTTAAAAAGACCTTACC

TAAAAAATGACAACACTGCAAAAGTTGCCATAGAGAATCCTGTTATCGAGCATG

TTAGACTCAAAAATGCAGTCAATTCTAAGATGAAAATATCAGATTACAAGATAG

TAGAGCCAGTAAACATGCAACATGAAATTATGAAGAATGTACACAGTTGTGAGC

TCACATTATTAAAACAGTTTTTAACAAGGAGTAAAAATATTAGCACTCTCAAATT

AAATATGATATGTGATTGGCTGCAGTTAAAGTCTACATCAGATGATACCTCAATC

CTAAGTTTTATAGATGTAGAATTTATACCTAGCTGGGTAAGCAATTGGTTTAGTA

ATTGGTACAATCTCAACAAGTTGATTCTGGAATTCAGGAAAGAAGAAGTAATAA
```

-continued

```
GAACTGGTTCAATCTTGTGTAGGTCATTGGGTAAATTAGTTTTTGTTGTATCATCA

TATGGATGTATAGTCAAGAGCAACAAAAGCAAAAGAGTGAGCTTCTTCACATAC

AATCAACTGTTAACATGGAAAGATGTGATGTTAAGTAGATTCAATGCAAATTTTT

GTATATGGGTAAGCAACAGTCTGAATGAAATCAAGAAGGGCTAGGGTTGAGAA

GTAATCTGCAAGGCATATTAACTAATAAGCTATATGAAACTGTAGATTATATGCT

TAGTTTATGTTGCAATGAAGGTTTCTCACTTGTGAAAGAGTTCGAAGGCTTTATT

ATGAGTGAAATTCTTAGGATTACTGAACATGCTCAATTCAGTACTAGATTTAGAA

ATACTTTATTAAATGGATTAACTGATCAATTAACAAAATTAAAAAATAAAAACA

GACTCAGAGTTCATGGTACCGTGTTAGAAAATAATGATTATCCAATGTACGAAGT

TGTACTTAAGTTATTAGGAGATACTTTGAGATGTATTAAATTATTAATCAATAAA

AACTTAGAGAATGCTGCTGAATTATACTATATATTTAGAATATTCGGTCACCCAA

TGGTAGATGAAAGAGATGCAATGGATGCTGTCAAATTAAACAATGAAATCACAA

AAATCCTTAGGTGGGAGAGCTTGACAGAACTAAGAGGGGCATTCATATTAAGGA

TTATCAAAGGATTTGTAGACAACAACAAAAGATGGCCCAAAATTAAAAACTTAA

AAGTGCTTAGTAAGAGATGGACTATGTACTTCAAAGCAAAAAGTTACCCCAGTC

AACTTGAATTAAGCGAACAAGATTTTTTAGAGCTTGCTGCAATACAGTTTGAACA

AGAGTTTTCTGTCCCTGAAAAAACCAACCTTGAGATGGTATTAAATGATAAAGCT

ATATCACCTCCTAAAAGATTAATATGGTCTGTGTATCCAAAAAATTACTTACCTG

AGAAAATAAAAAATCGATATCTAGAAGAGACTTTCAATGCAAGTGATAGTCTCA

AAACAAGAAGAGTACTAGAGTACTATTTGAAAGATAATAAATTCGACCAAAAAG

AACTTAAAAGTTATGTTGTTAAACAAGAATATTTAAATGATAAGGATCATATTGT

CTCGCTAACTGGAAAAGAAAGAGAATTAAGTGTAGGTAGAATGTTTGCTATGCA

ACCAGGAAAACAGCGACAAATACAAATATTGGCTGAAAAATTGTTAGCTGATAA

TATTGTACCTTTTTTCCCAGAAACCTTAACAAAGTATGGTGATCTAGATCTTCAGA

GAATAATGGAAATCAAATCGGAACTTTCTTCTATTAAAACTAGAAGAAATGATA

GTTATAATAATTACATTGCAAGAGCATCCATAGTAACAGATTTAAGTAAGTTCAA

CCAAGCCTTTAGGTATGAAACTACAGCGATCTGTGCGGATGTAGCAGATGAACT

ACATGGAACACAAAGCCTATTCTGTTGGTTACATCTTATCGTCCCTATGACAACA

ATGATATGTGCCTATAGACATGCACCACCAGAAACAAAAGGTGAATATGATATA

GATAAGATAGAAGAGCAAAGTGGTTTATATAGATATCATATGGGTGGTATTGAA

GGATGGTGTCAAAAACTCTGGACAATGGAAGCTATATCTCTATTAGATGTTGTAT

CTGTAAAAACACGATGTCAAATGACATCTTTATTAAACGGTGACAACCAATCAAT

AGATGTAAGTAAACCAGTTAAGTTATCTGAGGGTTTAGATGAAGTGAAAGCAGA

TTATAGCTTGGCTGTAAAAATGTTAAAAGAAATAAGAGATGCATACAGAAATAT

AGGCCATAAACTTAAAGAAGGGGAAACATATATATCAAGAGATCTTCAGTTTAT

AAGTAAGGTGATTCAATCTGAAGGAGTAATGCATCCTACCCCTATAAAAAAGAT

CTTAAGAGTGGGACCATGGATAAACACAATATTAGATGACATTAAAACCAGTGC

AGAGTCAATAGGGAGTCTATGTCAGGAATTAGAATTTAGGGGGGAAAGCATAAT

AGTTAGTCTGATATTAAGGAATTTTTGGCTGTATAATTTATACATGCATGAATCA

AAGCAACACCCCCTAGCAGGGAAGCAGTTATTCAAACAACTAAATAAAACATTA
```

-continued

```
ACATCAGTGCAGAGATTTTTTGAAATAAAAAAGGAAAATGAAGTAGTAGATCTA

TGGATGAACATACCAATGCAGTTTGGAGGAGGAGATCCAGTAGTCTTCTATAGAT

CTTTCTATAGAAGGACCCCTGATTTTTTAACTGAAGCAATCAGTCATGTGGATAT

TCTGTTAAGAATATCAGCCAACATAAGAAATGAAGCGAAAATAAGTTTCTTCAA

AGCCTTACTGTCAATAGAAAAAAATGAACGTGCTACACTGACAACACTAATGAG

AGATCCTCAAGCTGTTGGCTCAGAGCGACAAGCAAAAGTAACAAGTGATATCAA

TAGAACAGCAGTTACCAGCATCTTAAGTCTTTCTCCAAATCAACTTTTCAGCGAT

AGTGCTATACACTACAGTAGAAATGAAGAAGAGGTCGGAATCATTGCTGACAAC

ATAACACCTGTTTATCCTCATGGACTGAGAGTTTTGTATGAATCATTACCTTTTCA

TAAAGCTGAAAAGTTGTGAATATGATATCAGGAACGAAATCCATAACCAACTT

ATTACAGAGAACATCTGCTATTAATGGTGAAGATATTGACAGAGCTGTATCCATG

ATGCTGGAGAACCTAGGATTATTATCTAGAATATTGTCAGTAGTTGTTGATAGTA

TAGAAATTCCAACCAAATCTAATGGTAGGCTGATATGTTGTCAGATATCTAGAAC

CCTAAGGGAGACATCATGGAATAATATGGAAATAGTTGGAGTAACATCCCCTAG

CATCACTACATGCATGGATGTCATATATGCAACTAGCTCTCATTTGAAAGGGATA

ATCATTGAAAAGTTCAGCACTGACAGAACTACAAGAGGTCAAAGAGGTCCAAAG

AGCCCTTGGGTAGGGTCGAGCACTCAAGAGAAAAAATTAGTTCCTGTTTATAACA

GACAAATTCTTTCAAAACAACAAAGAGAACAGCTAGAAGCAATTGGAAAAATGA

GATGGGTATATAAAGGGACACCAGGTTTAAGACGATTACTCAATAAGATTTGTCT

TGGAAGTTTAGGCATTAGTTACAAATGTGTAAAACCTTTATTACCTAGGTTTATG

AGTGTAAATTTCCTACACAGGTTATCTGTCAGTAGTAGACCTATGGAATTCCCAG

CATCAGTTCCAGCTTATAGAACAACAAATTACCATTTTGACACTAGTCCTATTAA

TCAAGCACTAAGTGAGAGATTTGGGAATGAAGATATTAATTTGGTCTTCCAAAAT

GCAATCAGCTGTGGAATTAGCATAATGAGTGTAGTAGAACAATTAACTGGTAGG

AGTCCAAAACAGTTAGTTTTAATACCTCAATTAGAAGAAATAGACATTATGCCAC

CACCAGTGTTTCAAGGGAAATTCAATTATAAGCTAGTAGATAAGATAACTTCTGA

TCAACATATCTTCAGTCCAGACAAAATAGATATGTTAACACTGGGGAAAATGCTC

ATGCCCACTATAAAAGGTCAGAAAACAGATCAGTTCCTGAACAAGAGAGAGAAT

TATTTCCATGGGAATAATCTTATTGAGTCTTTGTCAGCAGCGTTAGCATGTCATTG

GTGTGGGATATTAACAGAGCAATGTATAGAAAATAATATTTTCAAGAAAGACTG

GGGTGACGGGTTCATATCGGATCATGCTTTTATGGACTTCAAAATATTCCTATGT

GTCTTTAAAACTAAACTTTTATGTAGTTGGGGGTCCCAAGGGAAAAACATTAAAG

ATGAAGATATAGTAGATGAATCAATAGATAAACTGTTAAGGATTGATAATACTTT

TTGGAGAATGTTCAGCAAGGTTATGTTTGAATCAAAGGTTAAGAAAAGGATAAT

GTTATATGATGTAAAATTTCTATCATTAGTAGGTTATATAGGGTTTAAGAATTGG

TTTATAGAACAGTTGAGATCAGCTGAGTTGCATGAGGTACCTTGGATTGTCAATG

CCGAAGGTGATCTGGTTGAGATCAAGTCAATTAAAATCTATTTGCAACTGATAGA

GCAAAGTTTATTTTTAAGAATAACTGTTTTGAACTATACAGATATGGCACATGCT

CTCACAAGATTAATCAGAAAGAAGTTGATGTGTGATAATGCACTATTAACTCCGA

TTCCATCCCCAATGGTTAATTTAACTCAAGTTATTGATCCTACAGAACAATTAGCT

TATTTCCCTAAGATAACATTTGAAAGGCTAAAAAATTATGACACTAGTTCAAATT
```

-continued

```
ATGCTAAAGGAAAGCTAACAAGGAATTACATGATACTGTTGCCATGGCAACATG

TTAATAGATATAACTTTGTCTTTAGTTCTACTGGATGTAAAGTTAGTCTAAAAAC

ATGCATTGGAAAACTTATGAAAGATCTAAACCCTAAAGTTCTGTACTTTATTGGA

GAAGGGGCAGGAAATTGGATGGCCAGAACAGCATGTGAATATCCTGACATCAAA

TTTGTATACAGAAGTTTAAAAGATGACCTTGATCATCATTATCCTTTGGAATACC

AGAGAGTTATAGGAGAATTAAGCAGGATAATAGATAGCGGTGAAGGGCTTTCAA

TGGAAACAACAGATGCAACTCAAAAAACTCATTGGGATTTGATACACAGAGTAA

GCAAAGATGCTTTATTAATAACTTTATGTGATGCAGAATTTAAGGACAGAGATGA

TTTTTTTAAGATGGTAATTCTATGGAGGAAACATGTATTATCATGCAGAATTTGC

ACTACTTATGGGACAGACCTCTATTTATTCGCAAAGTATCATGCTAAAGACTGCA

ATGTAAAATTACCTTTTTTTGTGAGATCAGTAGCCACCTTTATTATGCAAGGTAGT

AAACTGTCAGGCTCAGAATGCTACATACTCTTAACACTAGGCCACCACAACAATT

TACCCTGCCATGGAGAAATACAAAATTCTAAGATGAAAATAGCAGTGTGTAATG

ATTTTTATGCTGCAAAAAAACTTGACAATAAATCTATTGAAGCCAACTGTAAATC

ACTTTTATCAGGGCTAAGAATACCGATAAATAAGAAAGAATTAAATAGACAGAG

AAGGTTATTAACACTACAAAGCAACCATTCTTCTGTAGCAACAGTTGGAGGTAGC

AAGGTCATAGAGTCTAAATGGTTAACAAACAAGGCAAACACAATAATTGATTGG

TTAGAACATATTTTAAATTCTCCAAAAGGTGAATTAAATTATGATTTTTTTGAAGC

ATTAGAAAATACTTACCCTAATATGATTAAACTAATAGATAATCTAGGGAATGCA

GAGATAAAAAAACTGATCAAAGTAACTGGATATATGCTTGTAAGTAAAAAATGA

AAAATGATAAAAATGATAAAATAGGTGACAACTTCATACTATTCCAAAGTAATC

ATTTGATTATGCAATTATGTAATAGTTAATTAAAAACTAAAAATCAAAAGTTAGA

AACTAACAACTGTCATTAAGTTTATTAAAAATAAGAAATTATAATTGGATGTATA

CG.
```

In certain embodiments, the current disclosure provides polynucleotide variants having substantial identity to the sequences disclosed herein; those comprising at least 50%, 60%, 70%, 75%, 80%, 85%, 90%, 95%, 96%, 97%, 98%, or 99% or higher sequence identity, including all values and ranges there between, compared to a polynucleotide sequence of this disclosure using the methods described herein (e.g., BLAST analysis using standard parameters).

Certain embodiments relate to a nucleotide of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1950, 2000, 2050, 2100, 2150, 2200, 2250, 2300, 2350, 2400, 2450, 2500, 2550, 2600, 2650, 2700, 2750, 2800, 2850, 2900, 2950 contiguous nucleic acids (or any derivable range therein) having at least 10, 20, 30, 40, 50, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% identity (or any derivable range therein) to a nucleic acid of the disclosure or segment thereof, such as to SEQ ID NO:1-4 (RNA or DNA version), or a segment thereof or a complement of SEQ ID NO: 1-4, or a complementing segment thereof. Throughout this disclosure, an RNA molecule may specifically be an mRNA molecule in some embodiments.

Certain embodiments relate to a nucleic acid of the disclosure, such as a nucleic acid (RNA or DNA) of SEQ ID NO:1-4 (or its complement or a complementing segment thereof), wherein the nucleic acid is modified to have at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 (or any derivable range therein) substitutions, such as substitutions of a guanine for a uracil, an adenine for a uracil, a cytosine for a uracil, a cytosine for a guanine, an adenine for a guanine, a uracil for a guanine, or combinations thereof.

In some embodiments, the disclosure relates to a nucleic acid comprising exactly or at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 225, 250, 275, or 300 (or any derivable range therein) contiguous nucleic acids of SEQ ID NO:1-4 (or its complement or an RNA or DNA version thereof), wherein at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 (or any derivable range therein) of the uracils, guanines, or m6A modification sites are substituted.

In some embodiments, the disclosure relates to a nucleic acid comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 225, 250, 275, or 300 (or any derivable range therein) contiguous nucleic acids of SEQ ID NO:1-4 (RNA or DNA, as well as its complement or a complimenting segment thereof), wherein at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) of the m6A consensus sites are modified.

The disclosure also contemplates the use of polynucleotides which are complementary to all the above described polynucleotides.

Nucleic acids of the disclosure may be modified through recombinant DNA technology to include the variants described herein. The DNA is converted to RNA by an RNA polymerase, provided with the RSV nucleocapsid protein, the polymerase protein, phosphoprotein and M2-1 protein to assemble a functional capsid that can replicate and produce complete RSV for use as a modified virus, as further described herein.

A nucleic acid sequence can be "heterologous," which means that it is in a context of a cell or amid a nucleic acid sequence in which it is not found in nature. Instead, the heterologous nucleic acid is foreign to the cell in which the nucleic acid is being introduced or to the nucleic acid in which is incorporated, which includes a sequence homologous to a sequence in the cell or nucleic acid but in a position within the host cell or nucleic acid where it is ordinarily not found.

II. HOST CELLS

As used herein, the terms "cell", "cell line", and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for heterologous nucleic acids or viruses. A host cell may be "infected", "transfected", "transformed", or "transduced," which refers to a process by which exogenous nucleic acid, such as a recombinant protein-encoding sequence, is transferred or introduced into the host cell. A transformed cell includes the primary subject cell and its progeny. A transduced cell has received nucleic acid via a virus vector such as a lentivirus or adeno-associated virus vector. In the case of a lentivirus vector, the transduced gene is integrated into a chromosome of the cell.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

III. IMMUNE RESPONSE AND ASSAYS

The current disclosure concerns evoking or inducing an immune response in a subject against RSV. In one embodiment, the immune response can protect a subject at risk of developing RSV disease.

A. Immunoassays

Embodiments include the implementation of serological assays to evaluate whether and to what extent an immune response is induced or evoked by compositions of the disclosure. There are many types of immunoassays that can be implemented. Immunoassays encompassed by some embodiments include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non-specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non-specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

B. Diagnosis of RSV

In addition to the use of compositions of the disclosure comprising viral particles, proteins, polypeptides, and/or peptides, as well as antibodies binding these polypeptides, proteins, and/or peptides, to treat or prevent infection as described above, the current disclosure contemplates the use of these compositions in a variety of ways, including the detection of the presence of RSV to diagnose an infection in a patient. One method of detecting the presence of infections involves the steps of obtaining a sample suspected of being infected by RSV, such as a sample taken from an individual, for example, from one's nasal discharges, nasal swab/wash, blood, saliva, tissues, bone, muscle, cartilage, or skin. Following isolation of the sample, diagnostic assays utilizing the polypeptides, proteins, peptides, and/or antibodies of the present invention may be carried out to detect the presence of RSV, and such assay techniques for determining such presence in a sample are well known to those skilled in the art and include methods such as radioimmunoassay, western blot analysis and ELISA assays. In general, in accordance with the invention, a method of diagnosing an infection is contemplated wherein a sample suspected of being infected with RSV has added to it the polypeptide, protein, peptide, antibody, or monoclonal antibody in accordance with the present invention, and RSV infection is indicated by antibody binding to the polypeptides, proteins, and/or peptides, or polypeptides, proteins, and/or peptides binding to the antibodies in the sample.

Accordingly, antibodies in accordance with the invention may be used for the prevention of infection from RSV (i.e., passive immunization), for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies, including the products of an Fab immunoglobulin expression library. Accordingly, the invention contemplates the use of single chains such as the variable heavy and light chains of the antibodies. Generation of any of these types of antibodies or antibody fragments is well known to those skilled in the art. Specific examples of the generation of an antibody to a bacterial protein can be found in U.S. Patent Application Pub. No. 20030153022, which is incorporated herein by reference in its entirety.

Any of the above described polypeptides, proteins, peptides, and/or antibodies may be labeled directly with a detectable label for identification and quantification of staphylococcal bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

C. Protective Immunity

In some embodiments of the disclosure, the compositions, particularly those comprising attenuated RSV particles, confer protective immunity to a subject with respect to the disease associated with an RSV infection. Protective immunity refers to a body's ability to mount a specific immune response that protects the subject from developing a particular disease or condition that involves the agent against which there is an immune response. An immunogenically effective amount is capable of conferring protective immunity to the subject. In some embodiments, a patient population may have fewer symptoms, less severe symptoms, less risk of morbidity, reduced duration of symptoms (for example, by days or weeks), and/or reduced complications from an RSV infection. In some embodiments, the reduction may be expressed as a reduction of 10, 20, 30, 40, 50, 60, 70, 80, 90% or more as compared to a patient population not receiving the attenuated RSV.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

Methods may be employed with respect to individuals who have tested positive for previous exposure to RSV or who are deemed to be at high risk for complications related to RSV, including infants of less than one year old, children younger than 12, premature infants of less than one year old, immunocompromised individuals, and the elderly, such as those over 70 years old.

In particular, the disclosure encompasses a method of protection from RSV infection and disease. The immunogenic compositions and vaccines of the disclosure are also advantageous to use to inoculate health care workers.

D. Formulations and Modes of Administration

The present disclosure includes methods for preventing or inhibiting RSV infections. As such, the disclosure contemplates vaccines for use in active immunization embodiments. Immunogenic compositions, proposed to be suitable for use as a vaccine, may be prepared from host cells.

The vaccines of the disclosure may be prepared for delivery as nose drop or aerosols to be delivered intranasally. They may also be delivered as injectables either as liquid solutions or suspensions: solid forms suitable for solution in or suspension in liquid prior to injection may also be prepared. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be administered intra-nasally by drops or aerosol or parenterally, by injection, for example, either subcutaneously or intramuscularly. Oral formulations include such normally employed excipients as, for example, pharmaceutical grades of mannitol, lactose, starch, magnesium stearate, sodium saccharine, cellulose, magnesium carbonate and the like.

The compositions may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

In some embodiments, pharmaceutical compositions are administered to a subject. Different aspects of the current disclosure involve administering an effective amount of a composition to a subject.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present disclosure will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

E. In Vitro, Ex Vivo, or In Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject.

In certain aspects of the present disclosure, the compositions may be administered either in vitro, ex vivo, or in vivo. In certain in vitro embodiments, autologous B-lymphocyte cell lines are incubated with a virus of the instant invention for 24 to 48 hours and/or any other composition described herein for two hours. The transduced cells can then be used for in vitro analysis, or alternatively for ex vivo administration. U.S. Pat. Nos. 4,690,915 and 5,199,942, both incorporated herein by reference, disclose methods for ex vivo manipulation of blood mononuclear cells and bone marrow cells for use in therapeutic applications.

IV. KITS

The disclosure additionally provides kits for detecting modified adenosines in RNA, kits for detecting RSV, and kits comprising compositions of the disclosure. Each kit may also include additional components that are useful for amplifying the nucleic acid, or sequencing the nucleic acid, or other applications of the present invention as described herein. The kit may optionally provide additional components that are useful in the procedure. These optional components include buffers, capture reagents, developing reagents, labels, reacting surfaces, means for detection, control samples, instructions, and interpretive information. The kit may also include reagents for RNA isolation and/or purification.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments, are provided as an example, and are not intended as limitations on the scope of the invention. Changes therein and other uses which are encompassed within the spirit of the invention as defined by the scope of the claims will occur to those skilled in the art.

Example 1: Viral $N^6$-Methyladenosine Upregulates Replication and Pathogenesis of Human Respiratory Syncytial Virus A. Results The RSV genome and antigenome/mRNAs are $m^6A$ methylated in both HeLa and A549 cells. RSV has a non-segmented negative-sense (NNS) RNA genome of 15,222 nucleotides (RSV A2 strain). As is typical for NNS RNA viruses, replication of the viral genomic RNA (vgRNA) produces an exact, positive-sense full-length complementary RNA (cRNA) antigenome [39]. Both the genome and antigenome are encapsidated by the nucleocapsid (N) protein and both nucleocapsids can be packaged into virions, as for many NNS RNA viruses [47]. Using linear sucrose density gradient ultracentrifugation, the inventors first purified RSV virions from supernatants of RSV-infected human cervical carcinoma cells (HeLa), as this cell line is commonly used in RSV research. To investigate whether RSV RNA contains $m^6A$, RNA was extracted from virions grown in HeLa cells and the presence of $m^6A$ in viral RNA from virions was quantified by liquid chromatography-tandem mass spectrometry (LC-MS/MS). It was found that approximately 0.7% of the A bases were $m^6A$ methylated in RSV viral RNAs, a somewhat higher level than the host mRNAs (0.1-0.4%).

To locate the $m^6A$ sites on RSV viral RNA, the inventors sonicated virion RNA and subjected it to $m^6A$-specific antibody immunoprecipitation followed by high throughput sequencing ($m^6A$-seq), then mapped all the reads onto either the genome or antigenome sequence. Several $m^6A$ peaks were identified on both strands of the viral RNA (FIG. 1A). The RSV antigenomic RNA contained major $m^6A$ peaks in the regions complementary to the N, P, G, and F genes and in two regulatory elements, the gene end (ge) sequence of N and the intergenic (ig) sequence between the P and M genes (FIG. 1A and Supplementary Table 1). In the genomic RNA, eleven $m^6A$ peaks were detected in the NS2, N, P, M, G, and L genes and four regulatory elements including the gene start (gs) of NS2, ig between P and M, ge of M, ig between M and G, ge of G, and ig between G and L (FIG. 1A and Supplementary Table 1). The G gene regions from both genome and antigenome have the strongest $m^6A$ enrichment with peak size of 822 nt and 672 nt, respectively. Despite the sequences being reverse complementary, the locations of $m^6A$ peaks identified from both strands largely overlap (FIG. 1A). Together, these results confirm that both RSV genome and antigenome RNAs contain $m^6A$.

The inventors also mapped $m^6A$ peaks in mRNAs purified from RSV-infected cells. To do this, total RNA was isolated from rgRSV-infected HeLa cells, enriched for mRNA by binding to oligo dT, and subjected to $m^6A$-seq. As RSV mRNAs also contain poly(A) and are subsequently detected from poly(dT)-enriched $m^6A$-seq, the inventors identified 16 $m^6A$ peaks from RSV mRNAs (FIG. 1B, Supplementary Table 2) which were largely overlapped with those of antigenome (FIG. 1A, Supplementary Table 1), indicating the cellular $m^6A$ machinery methylates both types of positive-strand viral RNAs similarly. Interestingly, the G gene transcript has the strongest $m^6A$ enrichment with 846 bp peak size.

The inventors next performed $m^6A$-seq of rgRSV grown in tumor-derived human lung alveolar epithelial cells (A549 cells), a relevant cell line for RSV infection. RNAs of virions and RSV-infected A549 cells were prepared as described above and were m⁶A sequenced. Similar to HeLa cells, it was found that genome, antigenome, and mRNAs were m⁶A methylated in A549 cells (FIGS. 1C and D). For virion RNAs, a total of 9 and 15 m⁶A peaks were identified in the genome and antigenome respectively (FIG. 1C and Supplementary Table 3). Similar to virions grown in HeLa cells, the location of m⁶A peaks identified from genome and antigenome largely overlap.

G gene regions from both genome and antigenome have the strongest m⁶A enrichment with 696 and 846 bp peak size, respectively. For the RNAs extracted from virus-infected cells, a total of 18 m⁶A peaks were identified in mRNAs (FIG. 1D and Supplementary Table 4). Again, the G gene transcript has the strongest m⁶A enrichment with 1046 bp peak size.

The inventors next analyzed the overlapping regions based on m⁶A-seq data from HeLa and A549 cells (Supplementary Table 5 and 6). For virion RNA, six and four overlapping regions were identified in the genome (gs of NS2, NS2, N, P, ig between P and M, and G) and antigenome (N, M, G, and F), respectively (Supplementary Table 5). For RNAs purified from RSV-infected cells, 11 overlapping m⁶A peaks were also found in mRNAs, respectively (Supplementary Table 6). Although there are some differences, the majority of m⁶A peaks are highly conserved between the two cell lines suggesting that RSV utilizes the host m⁶A machinery to methylate these specific sites.

Figure 12E:
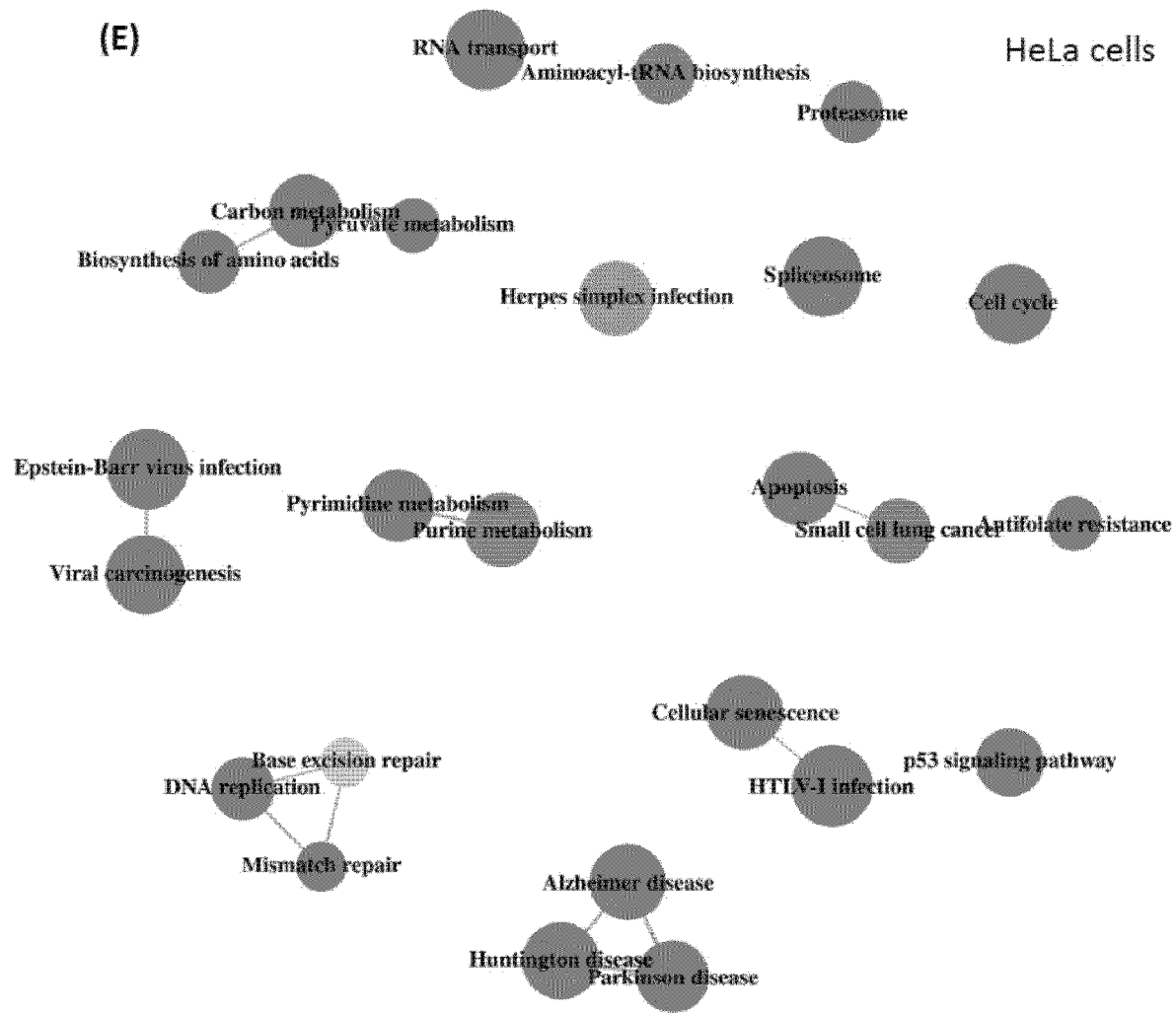
Figure 13E:
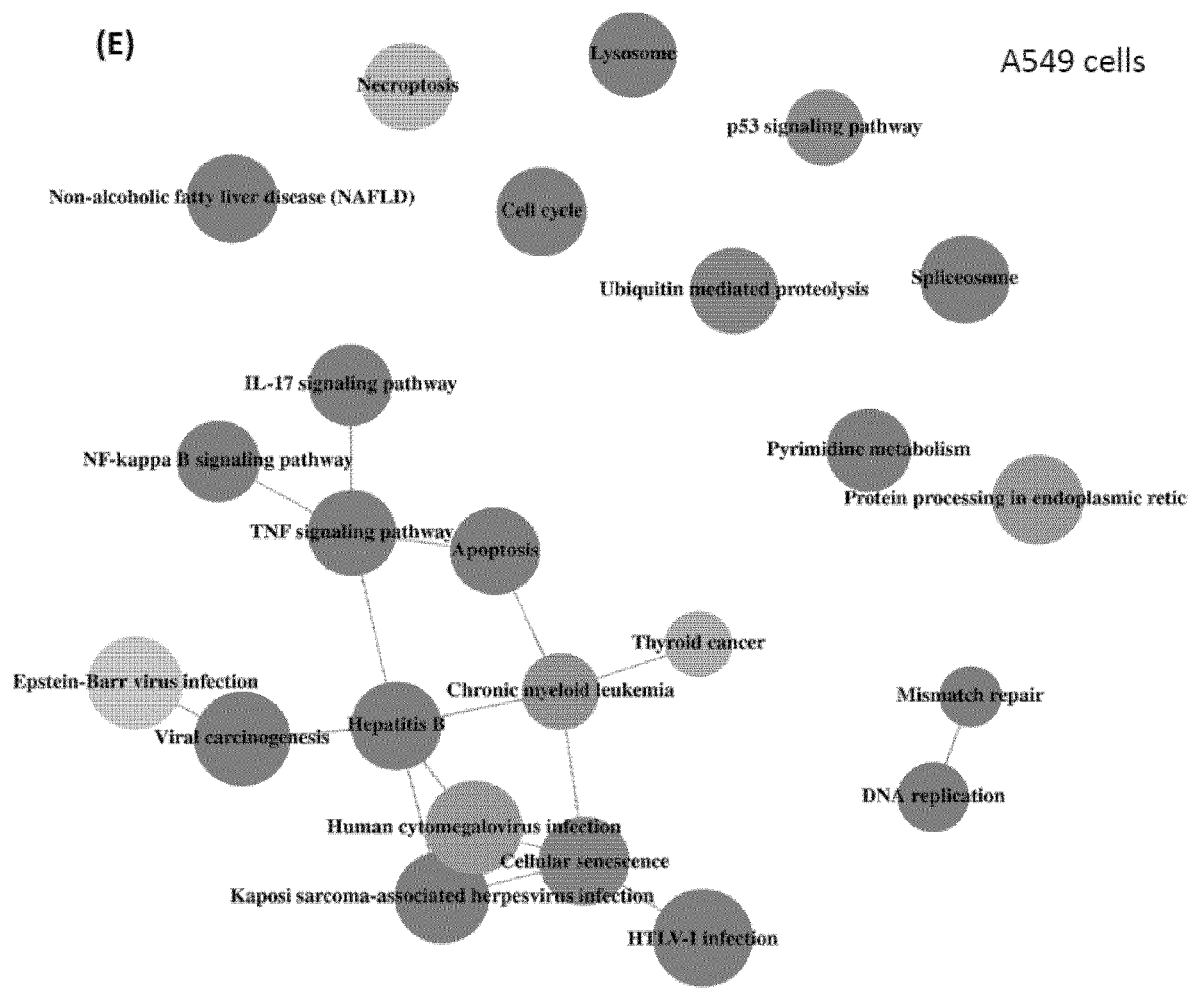

RSV infection alters the m⁶A distribution and gene expression of host cell transcripts. The inventors next determined the effects of RSV infection on the abundance and distribution of m⁶A on cellular transcripts. To do this, total RNA was isolated from mock-infected and rgRSV-infected HeLa cells, enriched for mRNA by binding to oligo dT, and subjected to m⁶A-seq. Metagene analysis showed that RSV-infected and mock-infected HeLa cells have m⁶A peaks enriched near the start and stop codons of open reading frames (FIG. 12A), which is consistent with the known distribution of m⁶A sites on transcripts [9-11]. Unlike the distribution of m⁶A peaks on mRNA, the peaks are mostly uniformly distributed on lncRNA with slightly more enrichment at its 5' end (FIG. 12B). The distribution of m⁶A peaks in each annotation also recapitulate m⁶A site distribution [9-11] with the majority of peaks residing in the CDS and 3' UTR regions (FIGS. 12C and D). Differential peak analysis using the count based QNB test [48] identified 2256 differentially methylated peaks (Supplementary Table 7). Analysis of RNA-seq data from the host cell (HeLa) revealed over 9,000 differentially expressed genes at an adjusted P value cutoff of 0.05 (Supplementary Table 8). These data suggest RSV infection significantly altered both the epitranscriptome and the transcriptome of the host cells. Pathway enrichment analysis shows differentially expressed genes are enriched in pathways including cell cycle, metabolism, RNA synthesis and transport, and response to viral infection (FIG. 12E).

As expected, the distribution of m⁶A sites was highly conserved between cell lines (FIG. 13A-D). RSV infection altered the expression of over 7,000 host cell genes in A549 cells (Supplementary Table 9) involved in a series of signal pathways (FIG. 13E) despite very few m⁶A peaks were found to be differentially methylated (Supplementary Table 10). Therefore, RSV infection may have widespread effects on host gene expression partially attributed to alteration of the deposition of m⁶A. Collectively, RSV infection seems to be sensed and actively responded to by the host m⁶A regulators to trigger broad changes in post-transcriptional methylation profiles of host mRNAs in some cell lines, which in turn may impact the expression of key genes in multiple functional pathways relevant to the host response to viral infection.

m⁶A reader proteins positively regulate RSV replication, gene expression, and virus production. To begin to explore the role of m⁶A modification in RSV replication and gene expression, the inventors first took advantage of HeLa cells that stably overexpress m⁶A "reader" proteins, YTHDF1, YTHDF2, and YTHDF3, which are m⁶A-binding proteins (FIG. 2A). Briefly, HeLa cells were infected with rgRSV at an MOI of 0.1, and viral protein expression, RNA synthesis, and virus production were monitored at 12, 18, and 24 h post-infection. As shown in FIG. 2B, stronger GFP expression (more green cells, brighter cells) was observed in HeLa cells overexpressing YTHDF1-3 compared to the vector control. Quantification by flow cytometry showed that significantly more GFP-positive cells were detected in HeLa cells overexpressing m⁶A reader proteins at 12, 18, and 24 h post-infection than in the vector control (P<0.05) (FIG. 2C).

The inventors next measured the expression of RSV F and G proteins (the two major surface glycoproteins) and N protein (the major component of the nucleocapsid complex). As shown in FIG. 2D, more F, G, and N proteins were detected in all three YTHDF-overexpressing HeLa cell lines at all three time points. Quantitative analysis of the protein bands showed a dramatic increase in viral protein expression during the first 12 h. Later time points were not as large possibly because the virus had already reached maximal levels of replication (FIGS. 2E, F, and G). Next, the inventors measured the release of infectious virus particles in a single step growth curve. The RSV titer was significantly increased in all three YTHDF-overexpressing cell lines at 12, 18, and 24 h post-inoculation (FIG. 2H) (P<0.05 or 0.01). Overexpression of YTHDF2 had the most dramatic impact on virus production, increasing RSV titer by 1-2 logs at all three time points compared to the vector control HeLa cells (P<0.05 or 0.01) (FIG. 2H).

The upregulating role of m⁶A reader proteins on RSV replication was also confirmed in HeLa cells transiently expressing YTHDF1-3 (FIG. 14A). HeLa cells were transfected with plasmids expressing YTHDF1, YTHDF2, or YTHDF3, and were infected by rgRSV. Compared to HeLa cells stably overexpressing YTHDF1-3 (FIG. 2D), transient overexpression of YTHDF1-3 led to a more robust enhancement of F and G protein synthesis (FIG. 14B) and GFP expression (FIG. 14C).

Figure 16A:
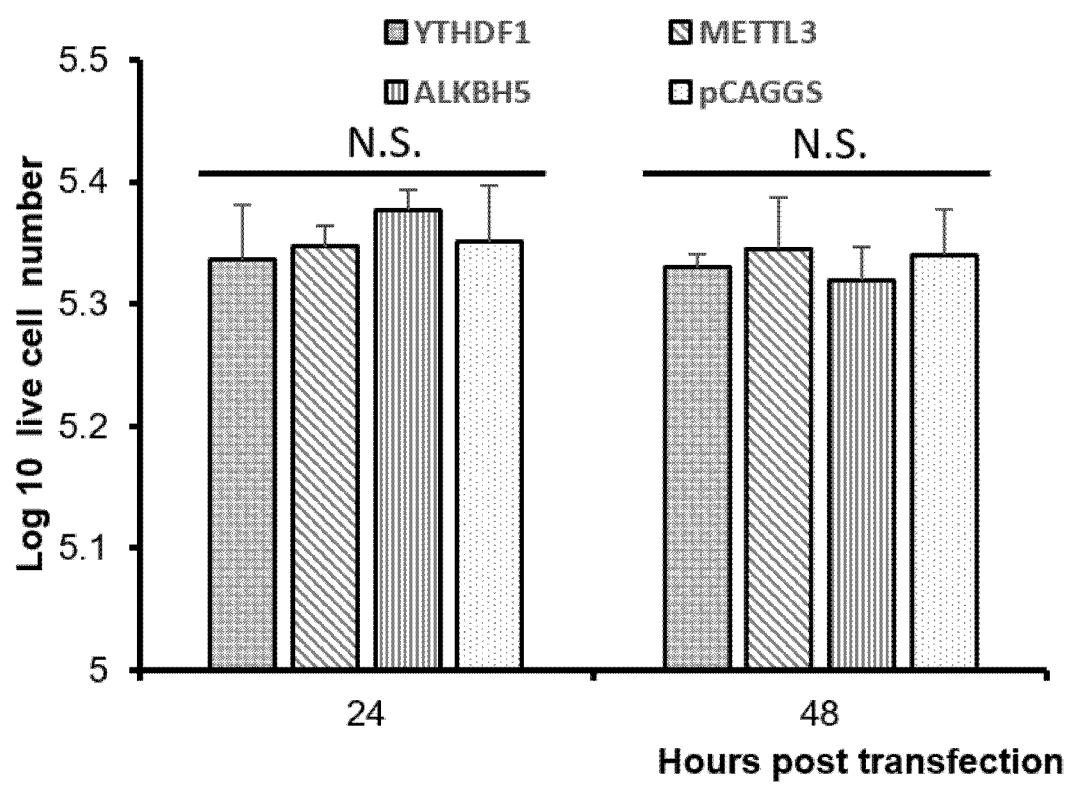
Figure 16B:
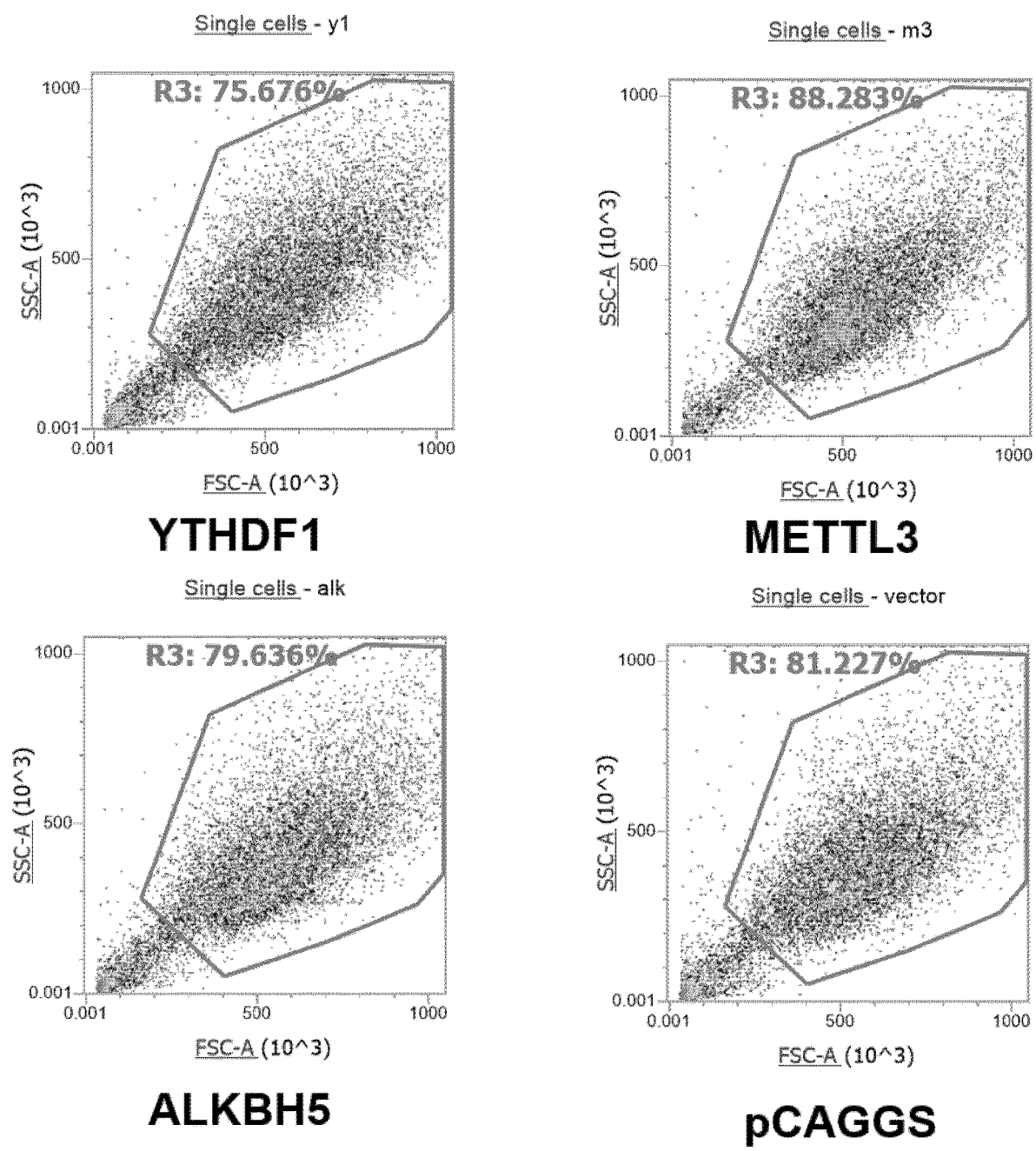

Currently, whether m⁶A machinery plays pro- or anti-viral function is controversial for some viruses (eg. HIV) [30, 31, 49]. In the case of KSHV, m⁶A machinery has a pro- or anti-viral effect depending on the cell line [34-36]. Thus, the inventors further analyzed viral replication and gene expression in A549 cells, a physiologically relevant cell line for RSV. Similar to the observations in HeLa cells, enhanced F, G, and N protein synthesis (FIG. 15A) and GFP expression (FIG. 15B) was detected when YTHDF1-3 proteins were transiently overexpressed in A549 cells. The inventors also tested RSV replication in Vero cells, the WHO-approved cell line for production of RSV live attenuated vaccine candidates. Similarly, m⁶A reader proteins (YTHDF1-3) enhanced RSV protein synthesis in Vero cells (FIG. 15C). Thus, a pro-viral function for m⁶A was observed in all three cell lines. It should be noted that overexpression of YTHDF1-3 proteins in all three cell lines did not significantly affect the growth or survival of the cells (FIGS. 16A and B)

One of the unique features of RSV and other viruses of the Mononegavirales order is that the genome RNA is completely encapsidated by the N protein and this complex serves as the template for two distinct RNA syntheses: genomic/anti-genomic RNA replication and mRNA transcription [50]. Both processes are carried out by a single RNA dependent RNA polymerase (RdRp) complex [50]. Thus, the RSV genomic RNA (the replication product) and mRNAs (the transcription product) were measured by real-time RT-PCR. Overexpression of YTHDF1-3 significantly increased both RSV genomic RNA (FIG. 21) and mRNA synthesis (FIG. 2J) in virus-infected cells. Overexpression of YTHDF1 and 3 did not alter the balance between the synthesis of genomic RNA and mRNA whereas overexpression of YTHDF2 led to a more dramatic increase in replication than transcription (FIG. 2K). It appears that overexpression of YTHDF1-3 enhanced the ability of the RSV RdRp to both replicate and transcribe.

Figure 16C:
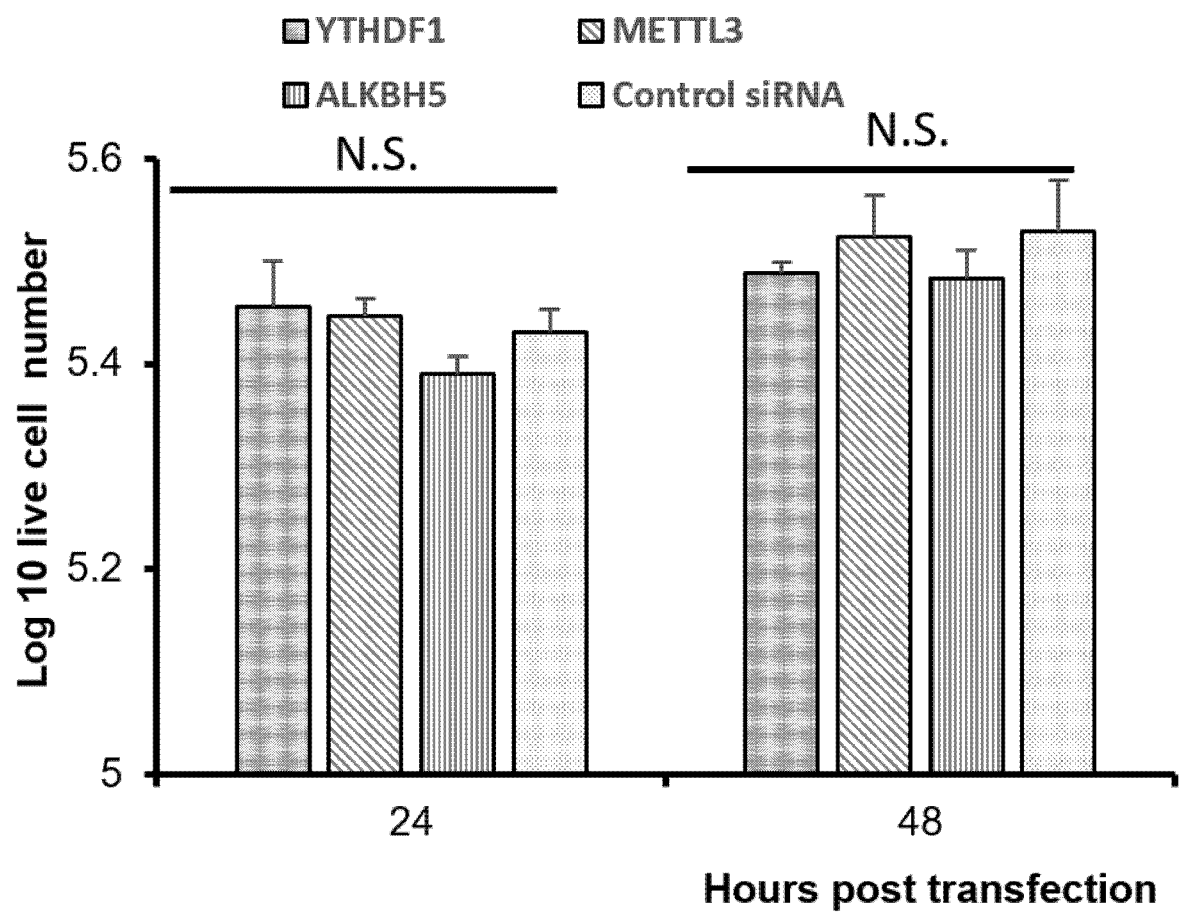
Figure 21:
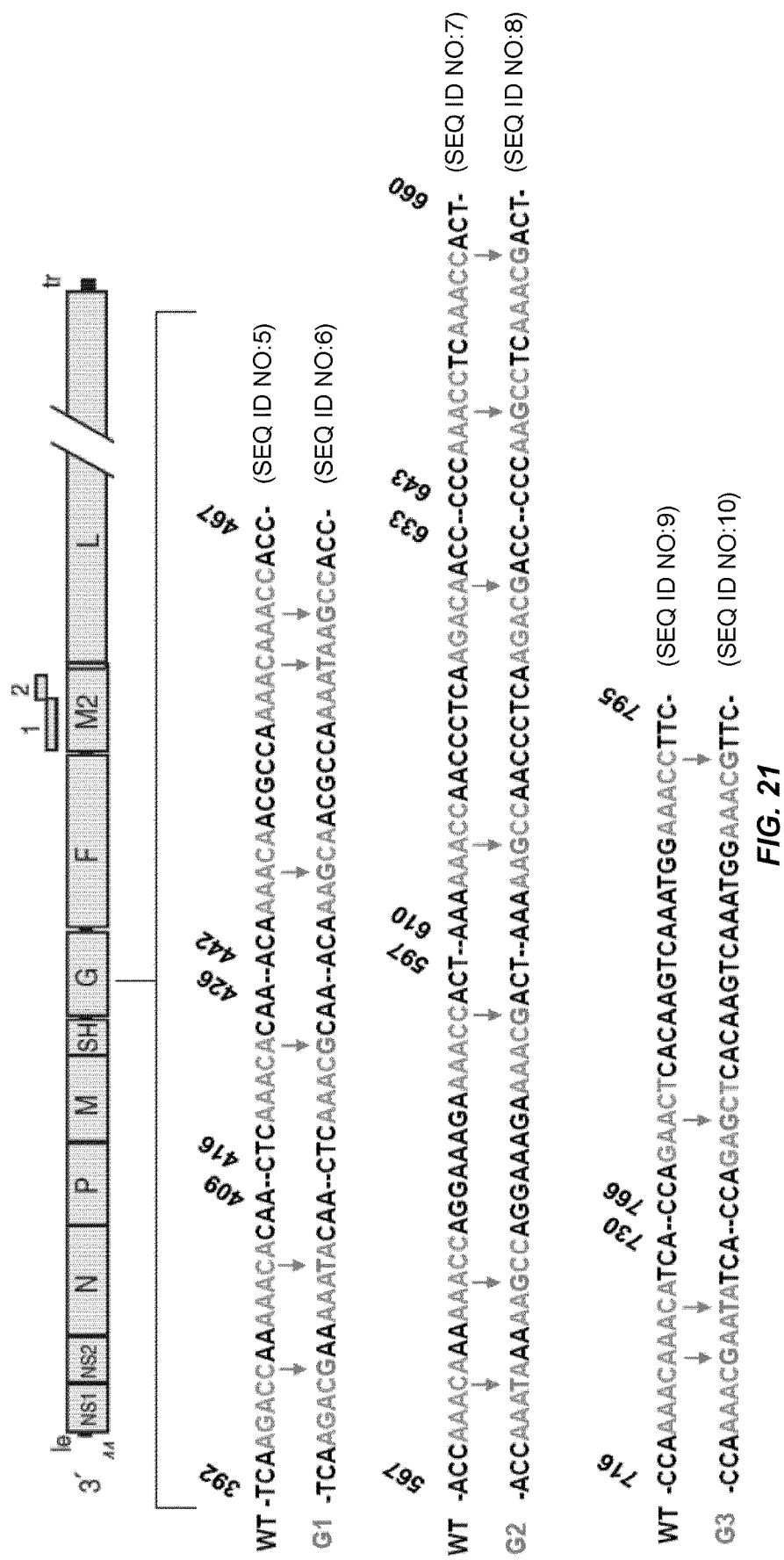
FIG. 21. Mutagenesis strategy in putative m⁶A site in the RSV G mRNA. Schematic diagram of the RSV genome with the mutations for altering the critical A or C residues in the m⁶A motifs to produce rgRSV lacking that putative m⁶A modification site in the G gene. Three m⁶A peaks, G1, G2, and G3, are shown; each containing 6, 7, and 4 m⁶A sites, respectively. Consensus m⁶A motifs and inactivating mutations are shown. Dashes represent nucleotides not shown. G gene sequence of RSV A2 strain (accession number M74568) is shown.

As a complementary approach, the inventors also tested RSV replication and gene expression in HeLa cells when $m^6A$ reader proteins were knocked down by siRNA. The inventors first examined cell survival when they were transfected with control siRNA or YTHDF1-3 siRNA. Counting live cells by flow cytometry showed that siRNA targeting YTHDF1-3 did not significantly alter cell survival (FIGS. 16C and D). Knockdown of individual, endogenous YTHDF1-3 proteins (FIG. 3A) did significantly reduced viral F and G protein synthesis (FIG. 3B) and GFP expression (FIGS. 3C and D) relative to the control siRNA transfected cells. Collectively, these results demonstrate that $m^6A$ binding proteins promote RSV genome replication, mRNA transcription, and as a result, viral protein expression, and progeny virus production.

$m^6A$ writer proteins positively regulate RSV replication and gene expression. The internal $m^6A$ addition is catalyzed by host methyltransferases termed $m^6A$ writer proteins [17]. Next the role of the $m^6A$ writer proteins in RSV replication and protein expression was examined. To do this, HeLa cells were transfected with plasmids encoding the $m^6A$ writer proteins, METTL3 or METTL14, or both, followed by rgRSV infection. More F and G protein synthesis (FIG. 4A) and GFP expression (FIGS. 4B and C) were observed when METTL3 and METTL14 were overexpressed in HeLa cells. In contrast, less F and G proteins were synthesized (FIG. 4D) and less GFP was expressed (FIGS. 4E and F) when endogenous METTL3, METTL14, or both, were knocked down in HeLa cells using siRNA. These results suggest that modification of RSV RNA by $m^6A$ writers facilitates RSV replication and gene expression.

$m^6A$ eraser proteins downregulated RSV replication and gene expression. Internal $m^6A$ modifications are reversible and can be removed by $m^6A$ eraser proteins [7, 8]. Thus, the effects of overexpression of eraser proteins by transfection of HeLa cells with plasmids encoding $m^6A$ eraser proteins AlkBH5 or FTO, or both was examined (FIG. 5). Overexpression of eraser proteins dramatically reduced RSV F and G protein expression by 80- and 20-fold, respectively (FIG. 5A), and GFP expression by 20-50 times (FIGS. 5B and C). Next, AlkBH5 or FTO, or both, was knocked down in HeLa cells, followed by rgRSV infection. Knockdown of AlkBH5 and FTO enhanced the expression of F protein by 3-fold, G protein by 5-fold (FIG. 5D), and GFP expression by 10-fold (FIGS. 5E and F) compared to the cells transfected with control siRNA. Therefore, over-expression of $m^6A$ eraser proteins negatively regulated RSV replication and gene expression.

RSV infection does not alter the translocation of $m^6A$-related proteins. The fact that the RNAs of RSV, a cytoplasmic replicating virus, are $m^6A$ modified suggests that $m^6A$-related proteins are present in the cytoplasm and raises the possibility that they may shuttle from the nucleus into the cytoplasm in response to virus infection. To directly visualize the locations of the $m^6A$ reader, writer, and eraser proteins, mock and rgRSV infected HeLa cells were stained with antibodies specific to each $m^6A$-related protein and analyzed by confocal microscopy. As shown in FIG. 6A and FIG. 17, $m^6A$ reader proteins (YTHDF1-3) were distributed in the cytoplasm in both mock and RSV-infected cells. In contrast, the majority of $m^6A$ writer proteins (METTL3 and METTL14) and eraser protein (AlkBH5) were distributed in the nucleus although a small fraction of these proteins was also found in the cytoplasm (FIG. 6B and FIGS. 18 and 19). Another eraser protein, FTO, was exclusively located in the nucleus (FIG. 6C). To quantify $m^6A$-related proteins, nuclear and cytoplasmic fractions were isolated and analyzed by Western blot. Equal amounts of $m^6A$ related proteins were detected in the cytoplasmic and nuclear fractions (FIGS. 6D and E). Therefore, RSV infection does not significantly alter the distribution pattern of $m^6A$-related proteins in HeLa cells. These results also suggest that the presence of a small fraction of cytoplasmic $m^6A$ writer proteins in the cytoplasm is sufficient for installing $m^6A$ on RSV RNAs.

$m^6A$ reader proteins bind to both RSV genomic RNA and mRNA. Since the biological function of $m^6A$ is mediated by $m^6A$ binding proteins, it was next determined whether YTHDF2 can directly bind to RSV RNAs in virus-infected cells. Briefly, HeLa cells were infected with rgRSV, cell lysates were harvested and a specific antibody against YTHDF2 was used to precipitate YTHDF2, and any bound RSV genomic RNA and N mRNA were detected by real-time RT-PCR. As expected, YTHDF2 was detected by YTHDF2-specific antibody (FIG. 20A). Both RSV genomic RNA and N mRNA were efficiently precipitated as complexes, with YTHDF2 (FIG. 20B). This result was further confirmed by pulling down HA-tagged YTHDF2 from total cell lysates of HeLa cells overexpressing YTHDF2 with HA antibody (FIG. 20C). Similarly, significant amounts of RSV genomic RNA and N mRNA bound to YTHDF2 (FIG. 20D).

Figure 7C:
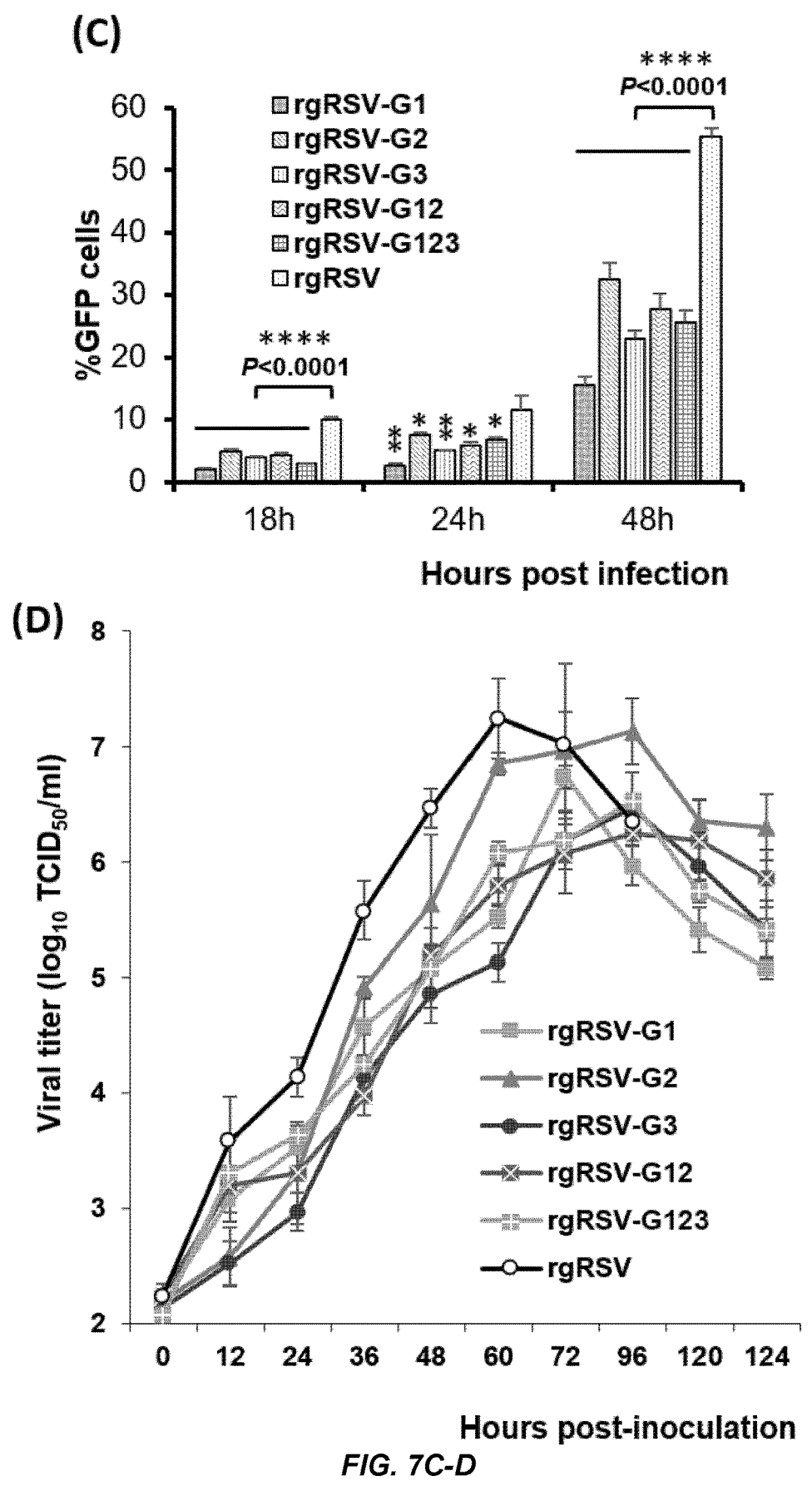
Figure 7E:
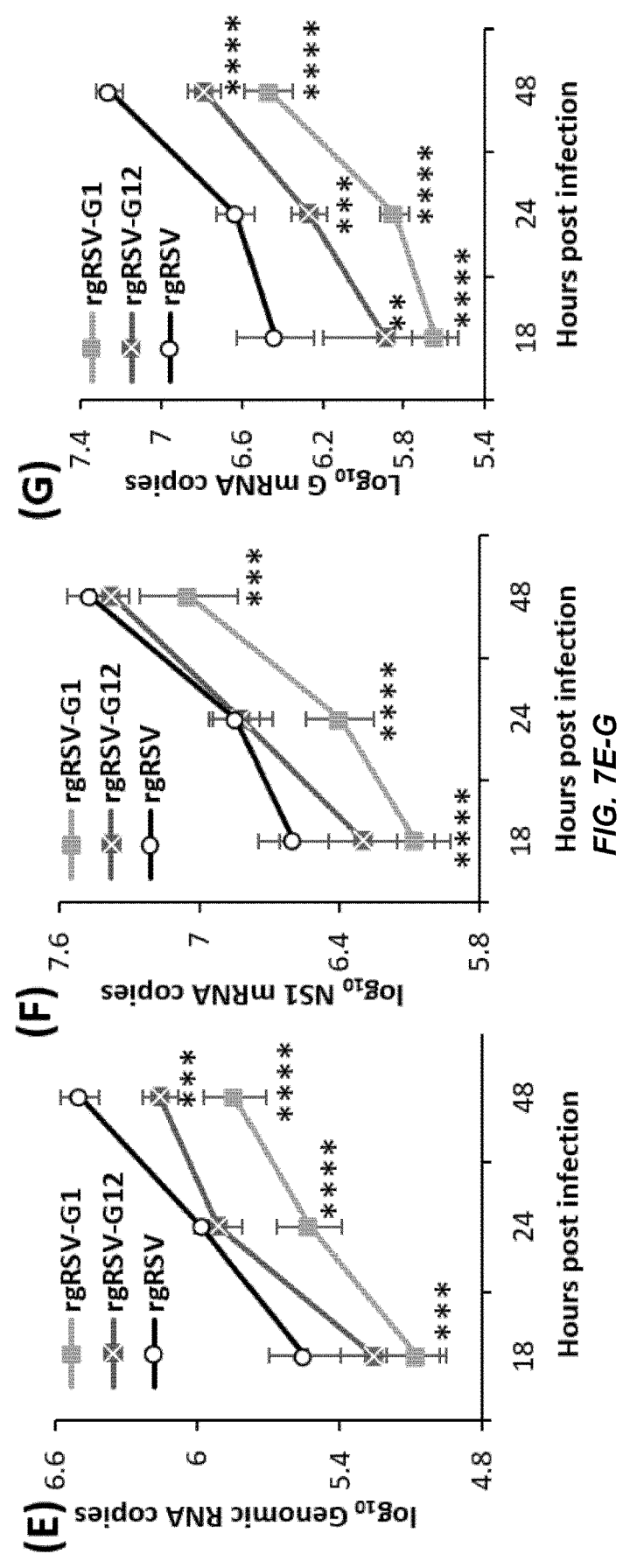
Figure 22:
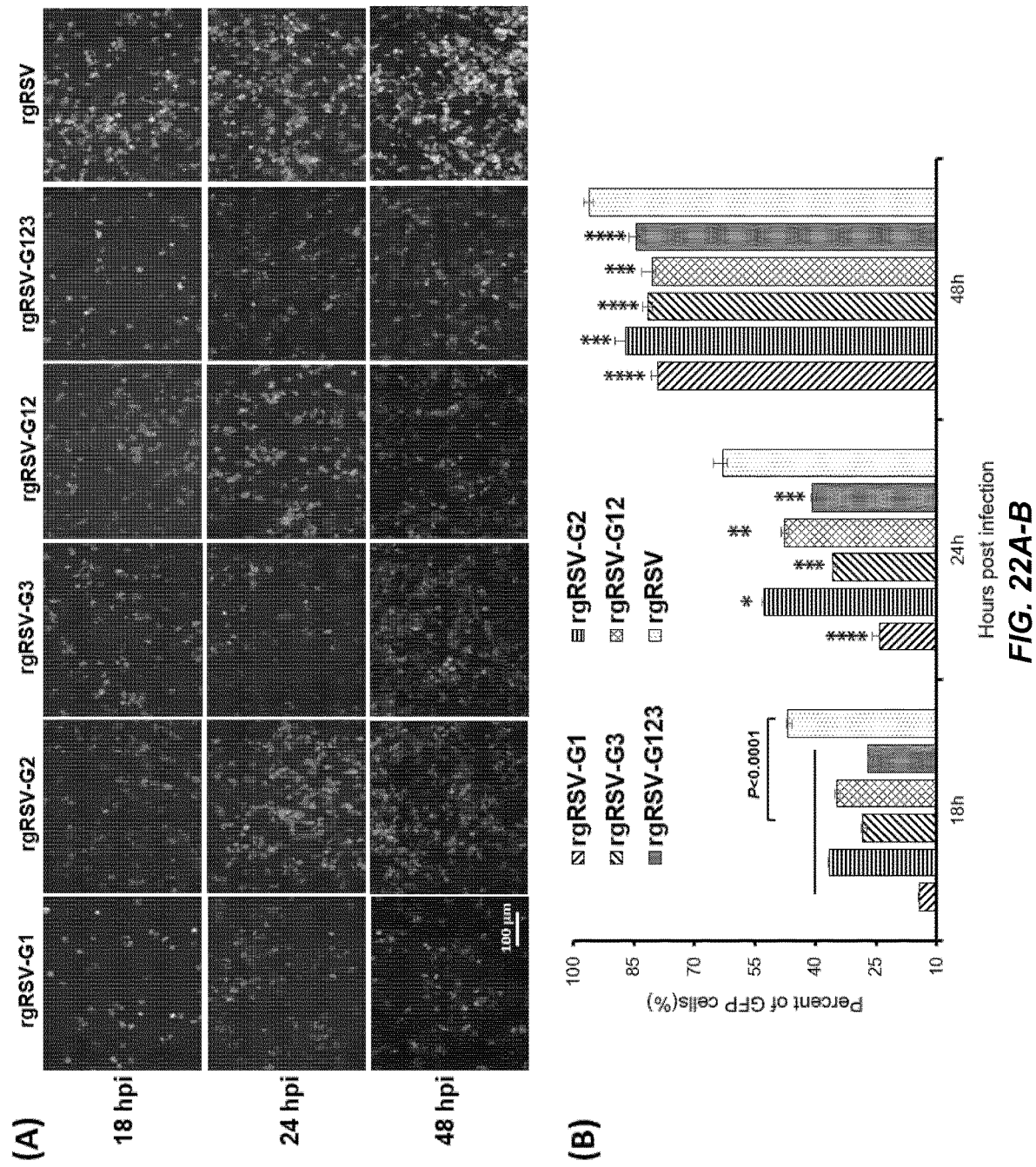
FIGS. 22A-B. Replication of m⁶A deficient rgRSVs in A549 cells. (A) GFP expression of m⁶A deficient rgRSVs. Confluent A549 cells were infected with each m⁶A-deficient rgRSV mutant at an MOI of 1.0, GFP images were photographed at 18, 24, and 48 h post-infection. (B) Quantification of GFP-positive cells by flow cytometry. GFP images shown are representative of three independent experiments. Flow cytometry data are expressed as mean of three independent experiments±standard deviation.

Abrogation of $m^6A$ sites in G mRNA results in attenuation of RSV in cell culture. Based on $m^6A$-seq of mRNA, G mRNA has the most abundant $m^6A$ enrichment among RSV mRNAs in both HeLa and A549 cells (FIG. 1). In addition, the most abundant $m^6A$ enrichments in genome and antigenome are also located in the region covering the G gene. Thus, the inventors decided to mutate the $m^6A$ sites in the G gene which was found to be conserved in the $m^6A$-seq from both HeLa and A549 cells. Those $m^6A$ peaks in the G gene are clustered in three regions, 392-467 nt, 567-660 nt, and 716-795 nt. Since it is known that $m^6A$ modified sites in RNA contain the conserved Pu [G>A]$m^6$AC[A/C/U] motif (Pu represents purine) [1], the inventors searched for this motif in these three regions in G mRNA and identified 6, 7, and 4 potential $m^6A$ sites in regions 1, 2, and 3 respectively (FIG. 21). Subsequently, the inventors mutated the A or C within the consensus site to a T or G in these sites without changing the amino acid they encoded (FIG. 21). In addition, M-fold and Genscript software was used to predict that these mutations did not alter RNA secondary structure or codon usage. These mutations were predicted to remove the $m^6A$ sites in the G mRNA and in the G gene region of the antigenome. To determine the role of G mRNA $m^6A$ sites in the RSV life cycle, these G mutations were introduced into an infectious cDNA clone of the RSV A2 strain and recovered a panel of m⁶A-deficient rgRSV mutants. First, the potential m⁶A sites in regions 1, 2, and 3 were mutated individually to produce rgRSV-G1, G2, and G3, respectively. Second, mutations of m⁶A sites in regions 1 and 2 were combined to produce rgRSV-G12. Third, m⁶A sites in regions 1, 2, and 3 were combined to produce rgRSV-G123. Next, the RSV replication and gene expression in A549 cells infected by each rgRSV mutant was monitored. All m⁶A-deficient rgRSVs had various degrees of reduction in viral N, F, and G protein synthesis in A549 cells compared to the parental rgRSV (FIG. 7A). Significantly less GFP expression was observed in m⁶A-deficient rgRSVs compared to rgRSV at 48 h post-infection (FIGS. 7B and C, and FIG. 22). Single-step growth curves showed that m⁶A-deficient rgRSVs had delayed replication kinetics and had 0.5-1.5 log reductions in peak titer compared to rgRSV (FIG. 7D). Overall, m⁶A-deficient rgRSVs had variable degrees of attenuation in replication in immortalized cell culture. Mutants rgRSV-G1, G3, G12, and G123 had a moderate defect whereas rgRSV-G2 had a mild defect in replication. It was next determined the amount of RSV genome, NS1 mRNA, and G mRNA synthesized by rgRSV-G1 and G12 in A549 cells. Both rgRSV-G1 and G12 had defects in genome (FIG. 7E), NS1 (FIG. 7F), and G (FIG. 7G) mRNA synthesis compared to rgRSV, and rgRSV-G1 had more defects than rgRSV-G12. Next, the percentage of reduction for NS1 and G mRNA was calculated. It was found that NS1 mRNA had significantly less reduction than G mRNA, suggesting that removal of the m⁶A from the G mRNA may accelerate its decay.

m⁶A-deficient rgRSVs are defective in replication and spread in primary well differentiated human airway epithelial (HAE) cultures. The inventors next tested the replication and spread of m⁶A-deficient rgRSVs in HAE cultures, a near in vivo model for lower airway infection. These cultures are pseudostratified and polarized, closely resembling the in vivo airway epithelium morphology and function, including mucus production and ciliary motion. RSV infects the ciliated cells on the apical surface where it attaches to its receptor, CX3CR1, on the cilia [51]. Infection spreads from an infected ciliated cell to neighboring ciliated cells, usually in a counter-clockwise fashion, due to the concerted ciliary beat, likely mimicking RSV infection and spread in human airways [51]. Briefly, HAE cultures were infected with 800 TCID$_{50}$ (equal to 400 pfu) of each recombinant virus, and viral release and spread was monitored. As in A549 cells, m⁶A-deficient rgRSVs had a delay in viral gene expression (GFP production) and spread (FIGS. 8A and B). At day 4 post-inoculation, m⁶A-deficient rgRSVs had fewer green cells compared to rgRSV. Although several rgRSV mutants gradually increased at days 6 and 8, the density of green cells remained less than for rgRSV. rgRSV-G1 was delayed in spreading but eventually spread to most susceptible cells at day 8. rgRSV-G2 had a delay at the early time point (day 4) but had wild type level of spreading at later times. Recombinant rgRSV-G12 was the most defective virus in HAE cultures, displaying a weak GFP signal during the entire experimental period. In addition, m⁶A-deficient rgRSVs had delays in virus release in HAE culture with 1-2 log defects in virus yield (FIG. 8C). These results demonstrate that m⁶A-deficient rgRSVs were defective in replication and spread in this near in vivo lung infection model.

Figure 9C:
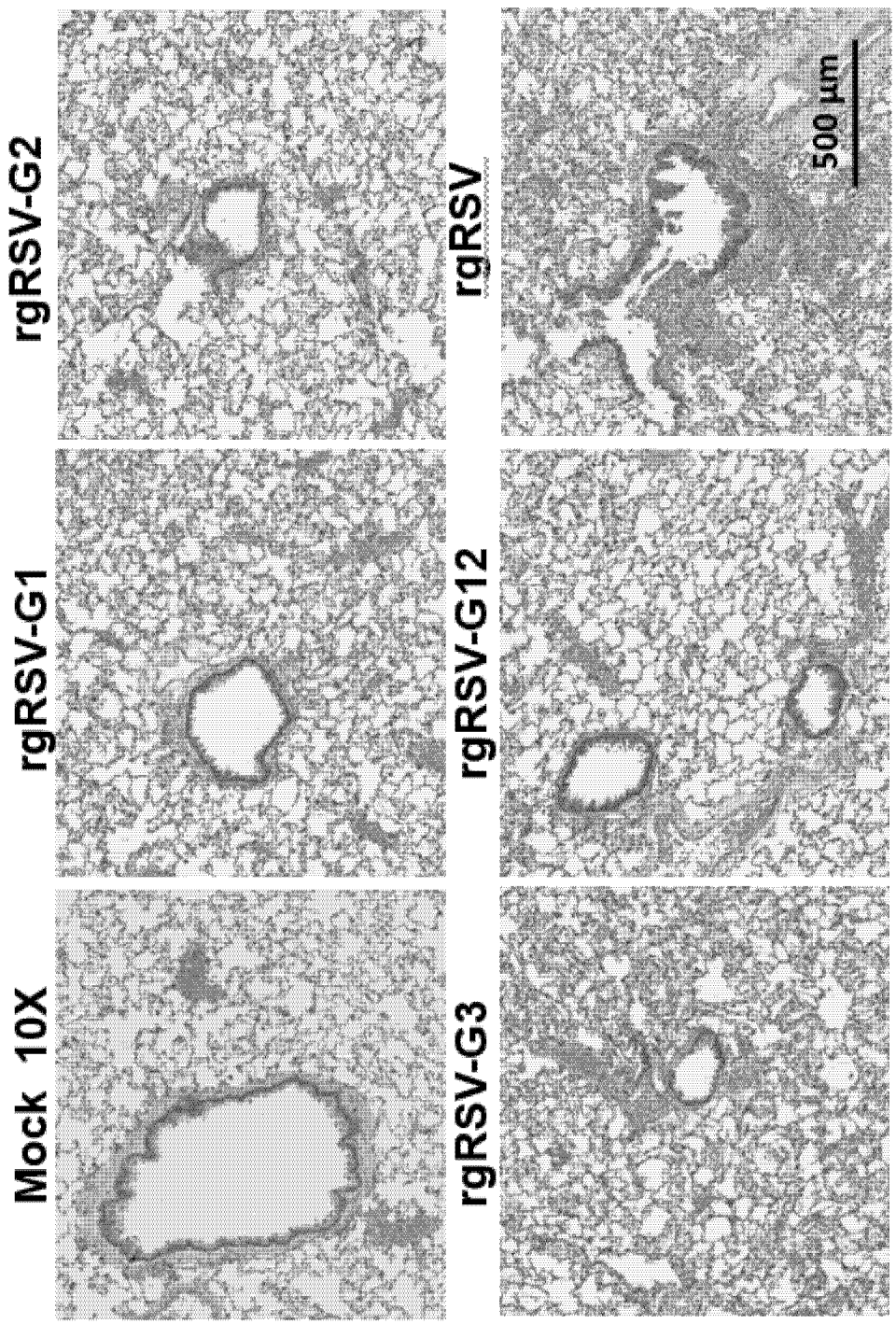
Figure 9D:
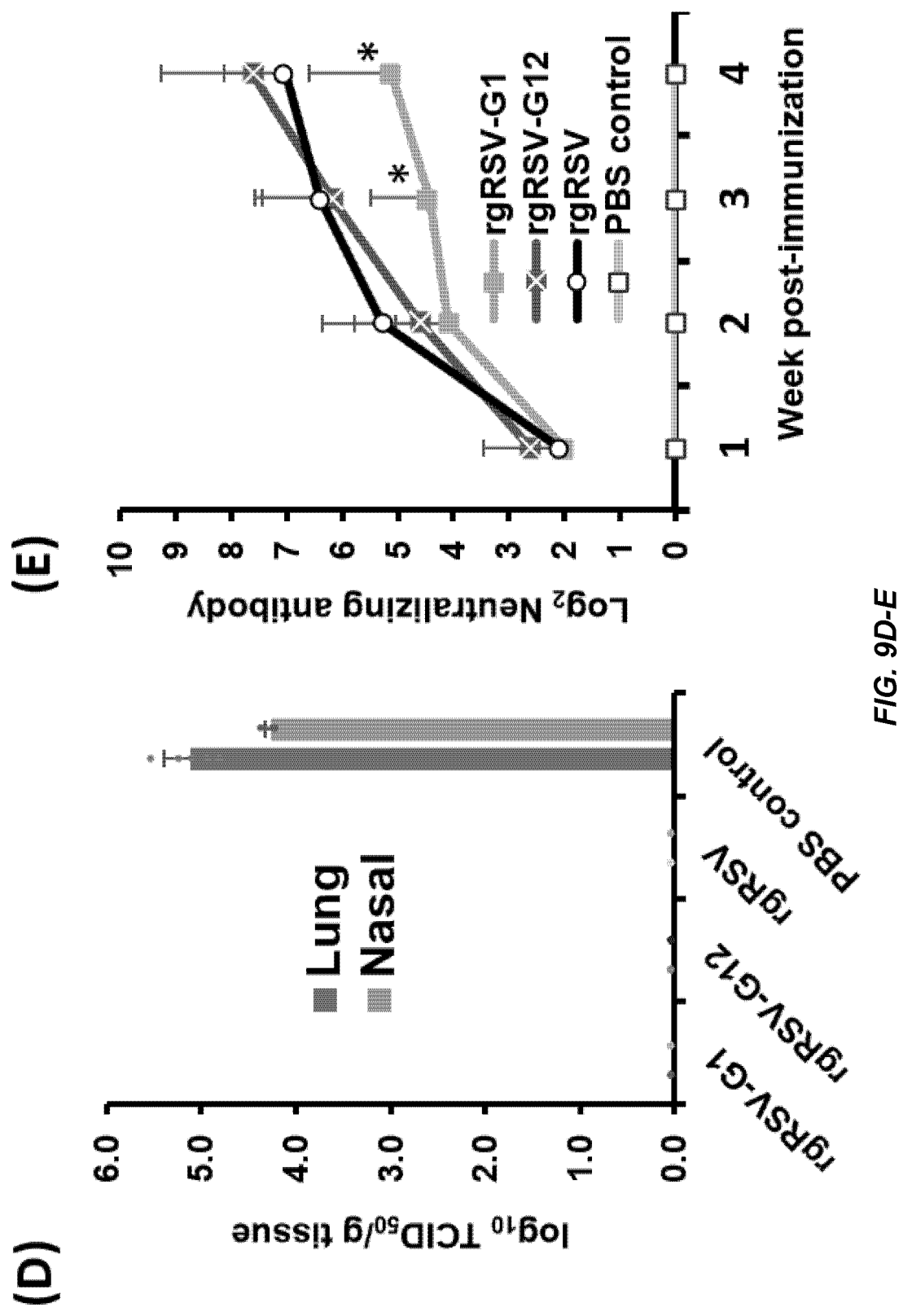
Figure 23:
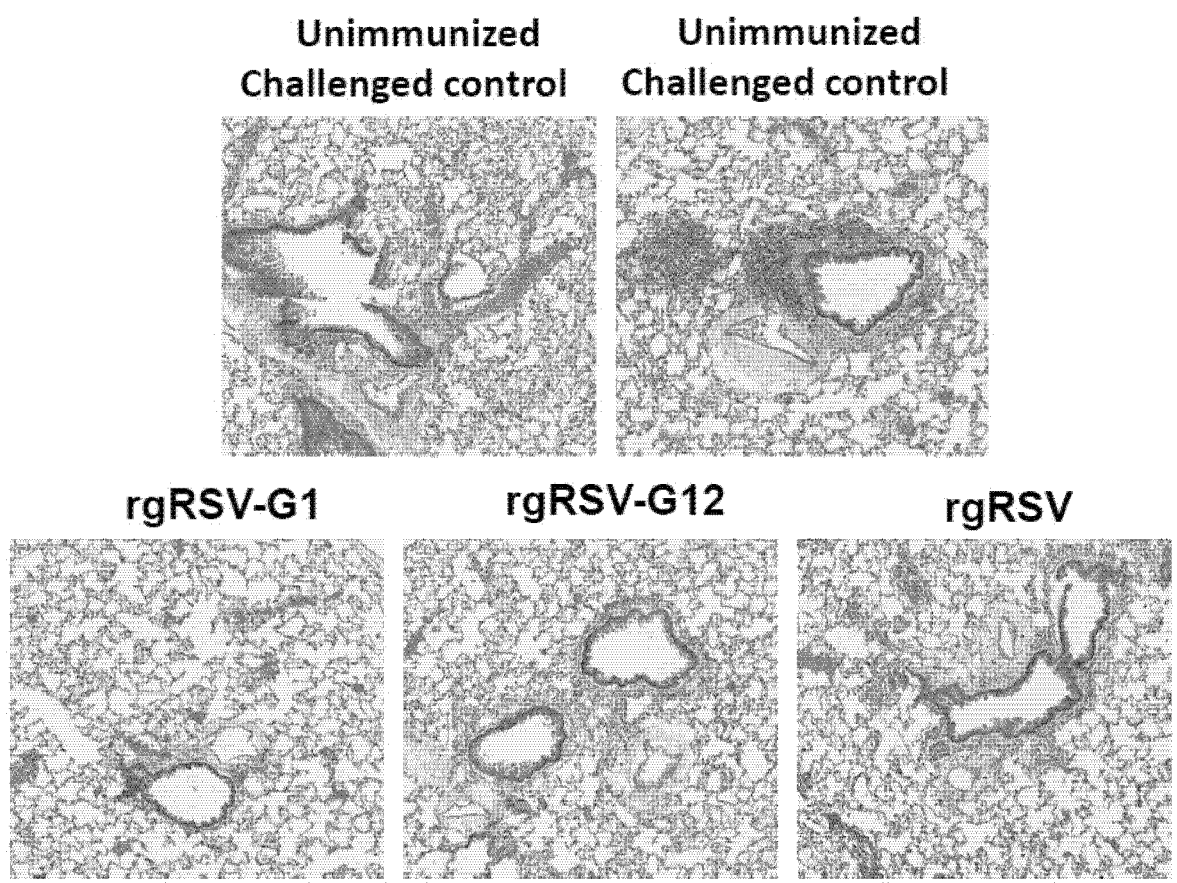
FIG. 23. Immunization with m⁶A deficient rgRSVs protects cotton rats from lung damage after RSV challenge. Four-week-old SPF cotton rats were inoculated intranasally with $2.0\times10^5$ TCID$_{50}$ of each rgRSV. At week 4 post-immunization, cotton rats were challenged with $2.0\times10^5$ TCID$_{50}$ rgRSV. At day 4 post-challenge, the cotton rats were sacrificed, and right lung lobe of each cotton rat was fixed in 4% neutral buffered formaldehyde, embedded in paraffin, sectioned at 5 µm, and stained with hematoxylin-eosin (HE) for the examination of histological changes by light microscopy. Representative pathological changes from each group are shown.

Abrogation of m⁶A sites in G mRNA results in rgRSVs that have defects in replication in cotton rats. The inventors tested replication and pathogenesis of four m⁶A-deficient rgRSV mutants, rgRSV-G1, G2, G3, and G12, in cotton rats, the best available small animal model for RSV infection. Based on replication and spread in immortalized cells and HAE culture, rgRSV-G2 exhibited mild attenuation whereas rgRSV-G1, G3, and G12 represent moderate to high attenuation. Briefly, cotton rats were inoculated intranasally with 2×10⁵ TCID$_{50}$ of each rgRSV mutant. At day 4 postinoculation, cotton rats were sacrificed, and viral replication in the nasal turbinates and lungs, and pulmonary histology, were determined. Parental rgRSV replicated efficiently in the lungs (FIG. 9A) and nasal turbinates (FIG. 9B) with average viral titers of 4.70±0.10 log$_{10}$ TCID$_{50}$/g and 4.10±0.10 log$_{10}$ TCID$_{50}$/g, respectively. Mutant rgRSV-G1 with m⁶A mutations in peak 1 of the G mRNA had a 7-fold reduction in replication in nasal turbinate and lung titers, respectively (P<0.05). Mutant rgRSV-G2 with m⁶A mutations in peak 2 of the G mRNA had no significant reduction in replication in lung (P>0.05) but 3-fold reductions in nasal turbinate (P<0.05). Mutant rgRSV-G12, which is a combination of all mutations in m⁶A peaks 1 and 2 in G mRNA, had the most dramatic defect in replication, with reductions of 100- and 200-fold in viral titer in nasal turbinate and lung, respectively. It should be noted that 4 out of 5 cotton rats had below detection limit level of RSV replication in the nasal turbinate and 3 out of 5 cotton rats had below detection limit level of RSV replication in lungs, suggesting that rgRSV-G12 is highly attenuated in vivo. The rgRSV-G3 with m⁶A mutations in peak 3 of the G mRNA had 5-fold reductions in replication in nasal turbinate and lung (P<0.05). Histologic examination showed that rgRSV caused moderate pulmonary histopathological changes, including interstitial pneumonia and peribronchial lymphoplasmocytic infiltrates (FIG. 9C). In contrast, m⁶A-deficient rgRSV mutants only had mild and less pulmonary histopathological changes compared to rgRSV (FIG. 9C). These results showed that m⁶A-deficient rgRSV mutants had significant reductions in viral replication in both the upper and lower respiratory tracts in cotton rats and were less pathogenic compared to rgRSV. These results indicate that viral m⁶A upregulates viral replication and pathogenesis in vivo.

m⁶A-deficient rgRSVs provide complete protection against challenge with parental RSV. To determine whether defects in viral m⁶A methylation impair the immunogenicity of the virus, the protection efficacy of a partially attenuated (rgRSV-G1) and highly attenuated (rgRSV-G12) virus in cotton rats was evaluated. The parental rgRSV served as a control. An ideal vaccine candidate should retain similar or higher immunogenicity compared to the parental virus. To do this, six-week-old female SPF cotton rats were immunized intranasally with 2×10⁵ TCID$_{50}$ of each recombinant virus. Serum samples were collected weekly for detection of antibody response. At week 4 post-inoculation, animals were challenged with 2×10⁵ TCID$_{50}$ of parental rgRSV. At day 4 post-challenge, all the animals were sacrificed and nasal turbinate and lung tissue samples were collected for virus detection and pathological examination. Cotton rats immunized with parental rgRSV or m⁶A-deficient rgRSVs did not have any detectable infectious virus in either the nasal turbinate or lung tissue after challenge with rgRSV (FIG. 9D). In contrast, unvaccinated challenged controls had average titers of 5.12±0.28 and 4.27±0.07 log$_{10}$ PFU/g in the lung and nasal turbinate, respectively (FIG. 9D). These results demonstrate that immunization with the rgRSV-G1 and G12 provided complete protection from challenge with rgRSV. Lung histology showed that unvaccinated challenged controls had moderate histologic lesions (FIG. 23). However, the vaccinated challenged groups had only mild lesions in lungs. In addition, no enhanced lung damage was observed for m⁶A-deficient rgRSV immunized cotton rats upon reinfection with rgRSV (FIG. 23). The two m⁶A-deficient rgRSV triggered similar levels of neutralizing antibody compared to rgRSV (P>0.05) (FIG. 9E). Antibody was detectable at week 1 postimmunization, and the levels gradually increased during weeks 2 to 4. No RSV-specific antibody was detected in the unvaccinated control. These results demonstrate that m⁶A-deficient rgRSV retained high immunogenicity and provided complete protection against RSV infection in cotton rats.

Figure 10C:
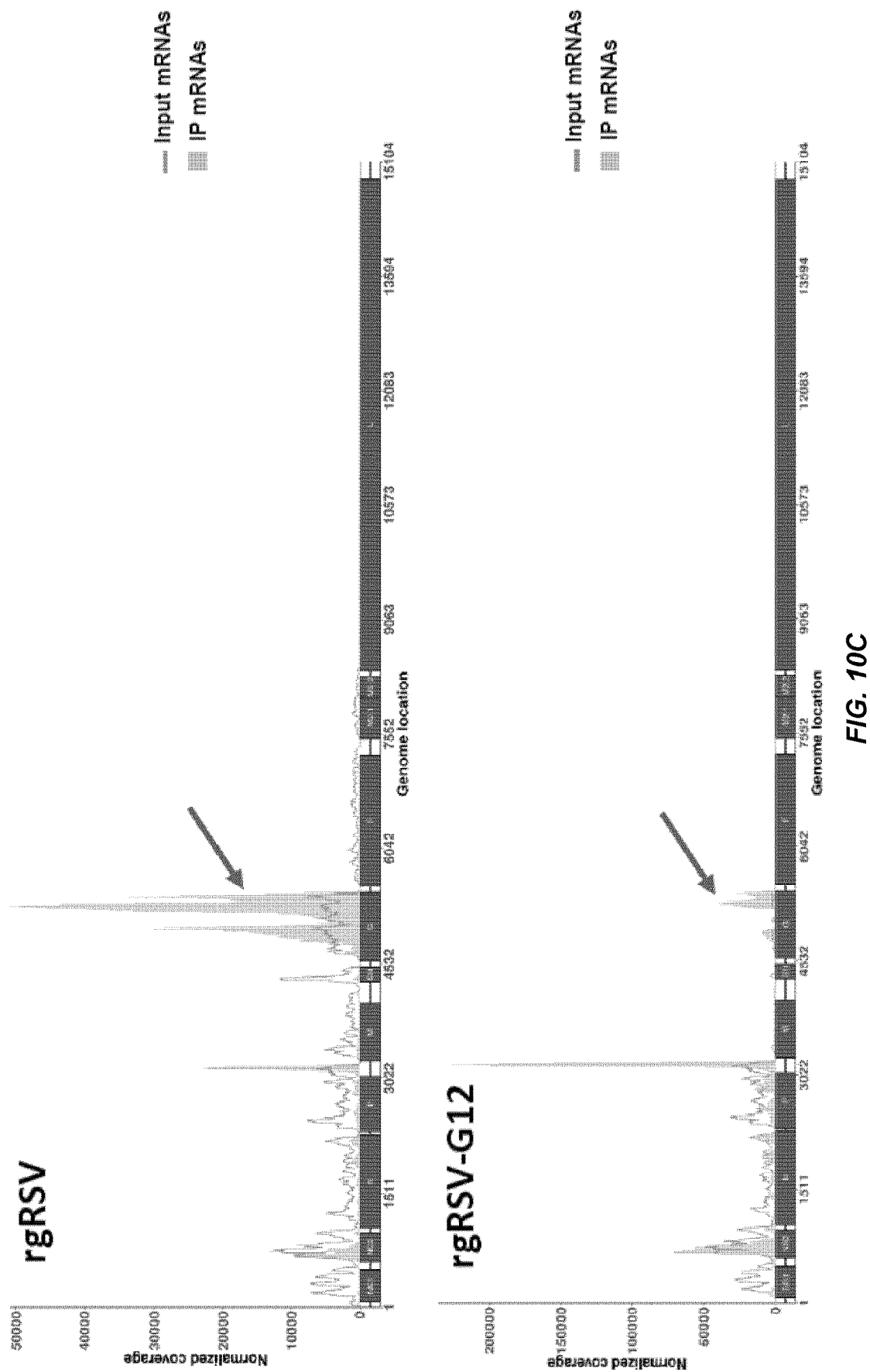

Replication and gene expression of m⁶A-deficient rgRSVs are less dependent on host m⁶A machinery. If the attenuated phenotype of m⁶A-deficient rgRSVs is indeed m⁶A-dependent, alteration of host m⁶A machinery would have no or less of an impact on replication and gene expression since major m⁶A sites have been removed from the G mRNA in these m⁶A-deficient viruses. To address this question, the inventors tested replication of rgRSV-G1 and G12 in A549 cells overexpressing AlkBH5 which is an m⁶A eraser protein. Consistent with previous results, overexpression of AlkBH5 led to 70% and 42% reduction in RSV G and F protein synthesis in rgRSV-infected cells compared to vector control cells (FIG. 10A). The inventors also observed a reduction in replication and protein expression of the m⁶A-deficient rgRSVs in AlkBH5 overexpressing cells, but the level of reduction was much less compared to the parental rgRSV. For example, only 17% and 10% reduction in RSV G and F protein synthesis was observed for rgRSV-G12, and 50% and 20% reduction in G and F protein was observed for rgRSV-G1, respectively. The inventors also tested the replication of rgRSV-G123 in m⁶A writer protein-depleted A549 cells. Knockdown of MELL3 and METTL14 led to 32 and 22% reduction in RSV G and F protein in rgRSV-infected A549 cells whereas only 25% and 8% reduction in G and F in rgRSV-G123-infected A549 cells (FIG. 10B). Thus, these results showed that replication and gene expression of m⁶A-deficient rgRSVs were less dependent on host m⁶A machinery, suggesting that the attenuated phenotype of these mutants is likely due to the deficiency in m⁶A methylation of the viral RNA.

m⁶A-deficient rgRSVs had significant reductions in m⁶A enrichment specifically in G mRNA. To determine whether m⁶A sites are indeed missing from the G gene, A549 cells were infected by each m⁶A-deficient rgRSV, and polyadenylated mRNAs were isolated and subjected to m⁶A-seq. As shown in FIG. 10C and FIG. 24, the enrichment of m⁶A in the G mRNA of each m⁶A-deficient rgRSV significantly decreased compared to the G mRNA from the parental rgRSV, confirming that m⁶A methylation in the G mRNA has indeed been significantly reduced.

Carbocyclic 3-deazaadenosine (Cc3Ado) inhibited viral m⁶A which in turn inhibited RSV replication. Cc3Ado is an inhibitor of S-adenosyl-L-homocysteine (SAH) hydrolase, which catalyzes the reversible hydrolysis of SAH to adenosine and homocysteine [52, 53]. Inhibition of SAH hydrolase leads to an accumulation of SAH in cells, which in turn leads to a perturbation of methylation reactions. Since inhibition of SAH hydrolase will likely inhibit both mRNA cap methylation and m⁶A methylation, the inventors generated a RSV mutant that was completely defective in mRNA cap G-N-7 and ribose 2'-O methylations, which allows one to test the effect of Cc3Ado on m⁶A methylation. To do this, two mutations (G1853A and G1857A) were introduced into the SAM binding site in the L gene, and generated an RSV mutant (rgRSV-G1853A-G1857A) which inactivated the SAM binding site and is completely defective in mRNA cap methylation. As expected, rgRSV-G1853A-G1857A was defective in replication in HEp-2 cells, producing significantly less GFP compared to rgRSV (FIG. 11A). Interestingly, Cc3Ado inhibited rgRSV spread over 3 days in both rgRSV and rgRSV-G1853A-G1857A-infected cells (FIG. 11A), suggesting that inhibition of m⁶A of both cap methylation and m⁶A methylation by Cc3Ado does inhibit RSV replication and gene expression.

Next, the inventors tested the effects of Cc3Ado on RSV spread in HAE cultures, mimicking the testing of an antiviral treatment of RSV infection in human airways. Similar to HEp-2 cells, rgRSV-G1853A-G1857A was significantly attenuated for replication in HAE cells compared to rgRSV (FIG. 11B). After treatment with Cc3Ado, the GFP signal was further reduced in rgRSV-G1853A-G1857A-infected HAE cells (FIG. 11B). These results demonstrate that inhibition of m⁶A by Cc3Ado decreases RSV replication and gene expression, suggesting that compounds that target m⁶A addition may have potential as antiviral drugs for RSV.

The biological function of m⁶A methylation in viral RNAs has remained uncertain since its discovery 40 years ago. Here, it is shown, for the first time, that the genome, antigenome, and mRNAs of RSV, an NNS RNA virus, are m⁶A methylated in both HeLa and A549 cells. The inventors showed that m⁶A modification positively regulates each step in the RSV replication cycle ranging from genome replication, mRNA transcription and viral protein synthesis, to progeny infectious particle production. Consistent with the positive effect of viral m⁶A methylation, m⁶A-deficient rgRSVs were significantly attenuated in viral replication, gene expression, and spread in A549 cells and HAE cultures. The inventors demonstrated for the first time that m⁶A regulates RSV replication and pathogenesis in an animal model. Furthermore, this example demonstrates that m⁶A could be a target for the development of live attenuated vaccine candidates as well as broad-spectrum antiviral drugs. Altogether, this work reveals that viral m⁶A has pro-viral functions in the RSV life cycle, virulence, and pathogenesis.

The m⁶A methylation of RNAs is modulated by writers, erasers, and readers in host cells. It should be noted that m⁶A methylation and its reader proteins may play distinct roles in a virus life cycle. In this study, it shown that overexpression of both m⁶A reader and writer proteins positively regulated RSV replication while knockdown inhibited RSV gene expression and replication. The opposite was true for eraser proteins: overexpression decreased RSV gene expression and replication whereas knockdown increased them. Overall, the biological functions of writers, erasers, and readers in regulating RSV replication and gene expression are consistent with each other.

In contrast, m⁶A writer and m⁶A reader proteins have been found to negatively regulate HCV production [37], opposite to RSV and influenza virus. Depletion of m⁶A writers increased infectious HCV particle production [37]. The m⁶A reader proteins relocalize to lipid droplets, the sites of HCV assembly, and suppress the packaging of HCV RNA into infectious viral particles [37]. Currently, the role of m⁶A reader proteins in the HIV life cycle is controversial [29-31]. One group found that YTHDF overexpression enhanced HIV-1 protein and RNA expression, and virus replication in CD4+ T cells [29], but others found that overexpression of m⁶A reader proteins inhibited HIV-1 infection by decreasing HIV-1 reverse transcription [31]. In a separate study, it was shown that the m⁶A sites within the Rev-response element (RRE) RNA structure alter nuclear export of HIV RNA [30]. Thus, m⁶A readers have distinct effects on the life cycles of different viruses, as they are multifunctional and play many important biological roles ranging from RNA stability, decay, and transport, to protein translation.

The inventors performed $m^6A$ sequencing of viral RNAs from HeLa and A549 cells. Majority of viral $m^6A$ peaks identified in these two cell lines overlap although there are also differences in $m^6A$ peak distributions. This finding suggests that different host cells may modify viral RNAs somewhat differently. These results with RSV indicate that the conserved, high density $m^6A$ sites are the ones that are functionally most important. Overall, the host $m^6A$ machinery promotes RSV replication and gene expression in both HeLa and A549 cells. The $m^6A$-seq also found that the viral G mRNA has the most abundant $m^6A$ peaks among the 10 RSV mRNAs in both HeLa and A549 cells. In addition, the strongest $m^6A$ peaks in both the genome and the antigenome are located in the G gene region. As expected, the $m^6A$ peaks in the two positive strand RNA species, the G mRNA and G gene region of the antigenome, are largely identical. Another interesting finding was that the positions of the $m^6A$ modifications in the genome and antigenome largely overlapped despite the fact that the sequence of the antigenome is complementary to the genome.

Figure 25:
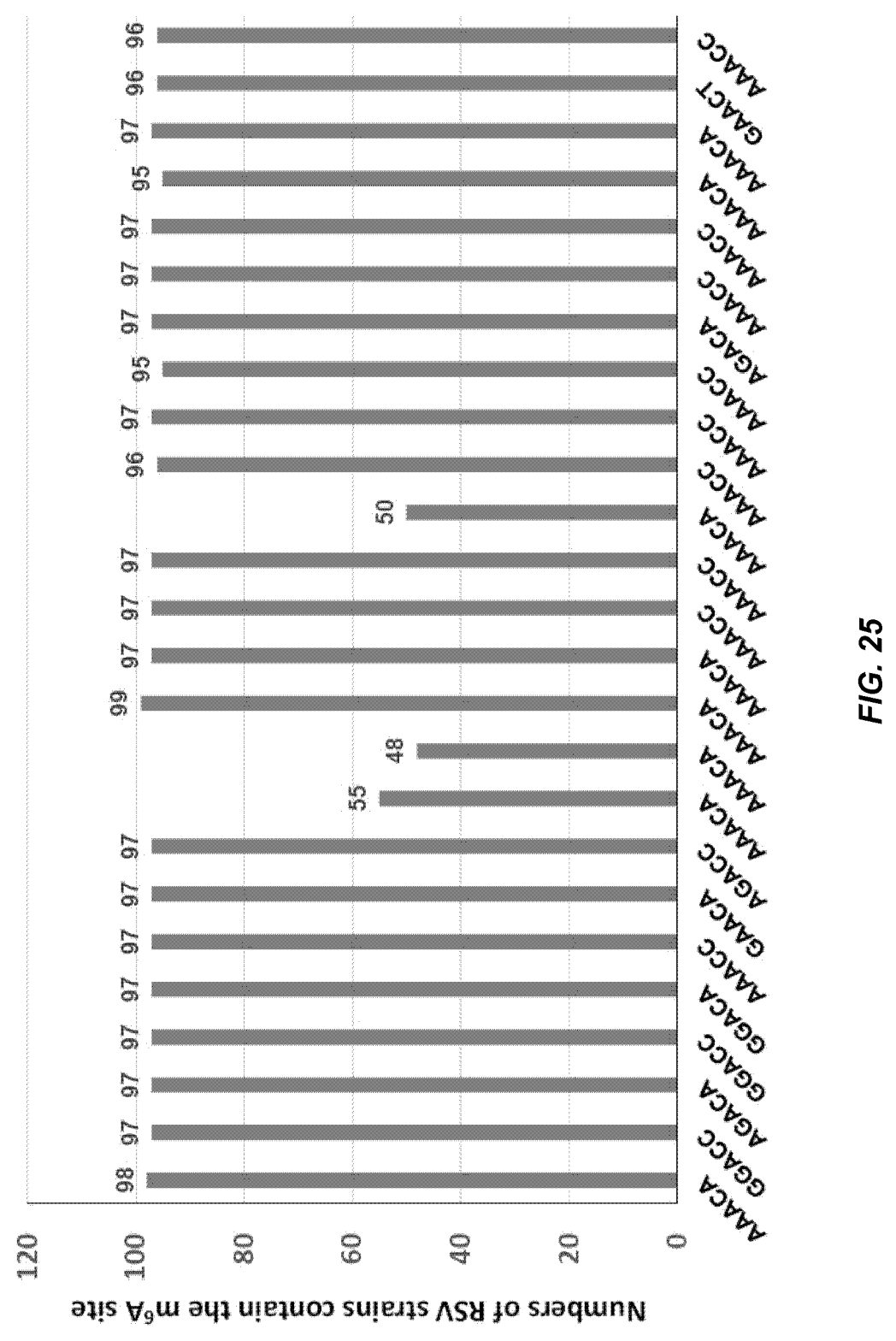

Since G mRNA has the strongest $m^6A$ enrichment, the inventors searched the three peaks in the G sequence for $m^6A$ motifs, identifying a total of 18 putative $m^6A$ sites. It is known that the G gene is the most genetically diverse RSV gene. However, bioinformatics analysis of 100 RSV strains (FIG. 25) found that those 18 $m^6A$ sites are highly conserved in the G gene, suggesting that $m^6A$ sites in the G gene may provide an evolutionary advantage for virus infection, replication, and spreading. Mutations in these three $m^6A$ peaks in the G mRNA showed that peaks 1 and 3 play a major role in regulating RSV replication whereas peak 2 plays a minor role, as recombinant rgRSV mutants in peak 1 and 3 (rgRSV-G1 and G3) had greater deficits in replication compared to mutants in peak 2 (rgRSV-G2).

The G protein is primarily responsible for the attachment of RSV to host cells and plays a role in modulating innate immune responses [51, 54]. Although it is not essential for the production of infectious RSV, RSV G is necessary for full infectivity [55, 56]. The G protein also plays an important role in the assembly of filamentous virions which have been shown to be the equivalent of virions [57]. It is likely that the abundant $m^6A$ modifications of the G mRNA enhances its stability, enabling more translation, insertion into virions and enhanced production of infectious virions. However, a portion of the G protein produced in a cell is released in a soluble form that affects leukocyte migration [64]. Enhanced G protein expression could enhance the production of soluble G protein, thereby affecting the immune response to RSV. It is also possible that $m^6A$ modification of viral RNAs facilitate the virus to escape the surveillance of host innate immunity to allow for efficient gene expression and virus replication.

Accumulating evidence suggests that $m^6A$ modification of cellular RNAs is important for diverse biological processes in vivo, including embryo development, cancer, and disease physiology [1, 16]. Importantly, it was found that viral $m^6A$ also modulates viral replication and pathogenesis in vivo. It was found that abrogating $m^6A$ peaks in the G gene resulted in rgRSV mutants that had significant reductions in viral replication in both the upper and lower respiratory tract of cotton rats and were less pathogenic in cotton rats.

However, the degree of attenuation in cell culture did not always match that in vivo. For example, rgRSV-G1 and G12 had similar levels of attenuation in immortalized cells (A549 and HeLa cells). In cotton rats, rgRSV-G1 replication was 7-fold reduced in the lung and nasal turbinate, respectively, whereas rgRSV-G12 had more than 100-fold reductions. Recombinant rgRSV-G2 was only mildly attenuated in cell culture. This recombinant had similar level of replication in lungs (P>0.05), and only had 3-fold reduction in nasal turbinates (P<0.05). Therefore, it appears that $m^6A$ sites in peaks 1 and 2 contributed synergistically to the highly attenuated phenotype of rgRSV-G12 in vivo. The phenotype of these mutants in primary differentiated HAE culture seems to correlate better with the phenotype in cotton rats than in HeLa and A549 cells. For example, rgRSV-G1 and G2 had delayed spreading in HAE culture but had spread robustly by late time points whereas rgRSV-G12 had much less spread during the entire experimental period. From this perspective, HAE culture may be better system to predict virus replication in vivo. Parental rgRSV caused changes in lung histology ranging from peribronchiolar mononuclear cell infiltrates to interstitial pneumonia. In contrast, $m^6A$-deficient rgRSVs had significantly less histopathology. These results demonstrate that $m^6A$ not only modulates the virus life cycle in vitro but also regulates viral replication and pathogenesis in vivo.

In this study, the inventors designed mutations in predicted $m^6A$ sites to avoid as much as possible alterations to the predicted mRNA secondary structure and to avoid changes in the efficiency of translation of the new codon relative to the original codon. The inventors also confirmed the loss of $m^6A$ in the predicted region of the G mRNA by $m^6A$ sequencing and tested the functional consequences of reducing the $m^6A$ modifications. Functional loss of $m^6A$ modifications was examined by comparing replication of the mutant rgRSV in A549 cells overexpressing or depleted of $m^6A$-related proteins. The $m^6A$-deficient rgRSVs (G1, G12, and G123) were much less dependent on host $m^6A$ enzyme compared to the parental rgRSV, confirming that the attenuated phenotype of $m^6A$-deficient rgRSVs is due to the reduction of $m^6A$ sites in G mRNA. Removal of $m^6A$ sites in the mRNA also removes them from the antigenome, but not from other viral mRNAs, other locations in the antigenome, or sites in the genome. Therefore, rgRSVs lacking particular $m^6A$ peaks in the G gene would be partially but not fully independent of host $m^6A$ enzymes. It is not clear if or how previous studies that mutated putative $m^6A$ sites in the genes of other viruses (HIV, influenza virus, and HCV) [30, 32, 37] confirmed that the phenotypes of the recombinant viruses were indeed due to the lack of $m^6A$ sites in viral genes.

A potentially important application of this study is in the rational design of live attenuated RSV vaccine candidates by inhibiting $m^6A$ addition to the mRNA and antigenome, or perhaps the viral genome. Currently, there is no FDA-approved vaccine for RSV despite the fact that it was first isolated in 1953. For decades, approaches to generate RSV vaccines employing inactivated virus or viral proteins have failed either due to a lack of immunogenicity or the potential for causing enhanced pulmonary disease upon natural infection with the same virus [43]. A live attenuated vaccine, similar to the effective vaccines for the related measles and mumps viruses, would seem to be one of the most promising methods for protection from RSV disease. However, it has been a challenge to strike the right balance between attenuation and immunogenicity [43].

Although mutations in individual $m^6A$ peaks in the G mRNA were not sufficient to achieve complete attenuation of RSV replication in vivo, the combination of $m^6A$ mutations in peaks 1 and 2 resulted in a recombinant virus that was sufficiently attenuated both in vitro and in vivo. Importantly, cotton rats vaccinated with rgRSV-G12 had similar neutralizing antibody response levels compared to parental rgRSV and were completely protected from rgRSV challenge. In addition, no enhanced lung damage was observed. Thus, rgRSV-G12 may be a good live attenuated vaccine candidate for RSV. This study demonstrates that inhibition of $m^6A$ methylation may be a novel method for rationally designing live attenuated vaccines.

Since $m^6A$ methylation occurred in the genome, antigenome, and mRNAs, one approach would be to combine multiple $m^6A$ mutations in selected gene regions (such as G gene, N gene, ig, and ge sequences) to generate a panel of RSV mutants with various degrees of attenuation in vivo. This approach would allow one to identify an RSV mutant that is sufficiently attenuated yet retains optimal immunogenicity. Another distinct advantage is that combinations of multiple $m^6A$ mutations in viral RNAs will enhance the genetic stability of a vaccine strain, because reversion to wild type at any nucleotide should not provide a major fitness gain. In fact, no revertant was found when rgRSV-G12 was blindly passed in A549 cells for 15 passages, suggesting that $m^6A$-deficient rgRSV is genetically stable. These $m^6A$-deficient rgRSVs would also provide invaluable tools to understand the roles of $m^6A$ modification in the innate immune response. In fact, it has been shown that internal $m^6A$ modification of in vitro synthesized RNAs prevents recognition of the RNA by the host pattern recognition receptors TLR3 and RIG-I [58]. From this prospective, $m^6A$ modification may provide an additional molecular signature for the host to discriminate self from non-self RNA by innate immunity, similar to RNA ribose 2'-O methylation of the mRNA cap.

This study also provides a novel approach for enhancing viral titers in cell culture, an important consideration in the production of live attenuated vaccines. Attenuated viruses typically grow to lower titers than wild-type virus. In the case of RSV, a relatively large dose of vaccine candidate is required to induce a protective immune response in humans, making vaccine production expensive. One strategy includes producing live attenuated vaccines in cells overexpressing one or more $m^6A$ reader or writer proteins, since overexpression of these host $m^6A$ machinery components enhance virus yield at least 10-fold. Such a boost in the production of a vaccine should greatly enhance its economic feasibility.

This study also provides an approach for developing novel antiviral drugs by targeting $m^6A$ methylation and $m^6A$-related enzymes. It was found that a small molecule inhibitor of $m^6A$ methylation inhibited RSV replication. Previously, it was shown that an SAH hydrolase inhibitor, 3-deazaadenosine (DAA), is capable of inhibiting the replication of diverse viruses, including Rous sarcoma virus, HIV-1, RSV, parainfluenza virus type 3, VSV, measles virus, and reovirus [52, 53, 59]. Interestingly, mRNAs of all these viruses are capped, G-N-7 and 2'-O methylated, and polyadenylated. Translation of viral proteins likely follows a cap methylation-dependent translation mechanism. Thus, these studies could not discriminate between the antiviral effect of DAA on mRNA cap methylation and internal $m^6A$ methylation. To overcome this obstacle, a recombinant virus (rgRSV-G1853A-G1857A) that was completely defective in mRNA cap methylation was generated, allowing for the independent analysis of the inhibitory effect of $m^6A$ on virus replication. It was found that replication of rgRSV-G1857A-G1853A was further inhibited in the presence of Cc3Ado, suggesting that this drug also inhibits RSV replication by another mechanism, likely the only other known methylation of RNA, that of $m^6A$ methylation. The demonstration of the antiviral effect of SAM-dependent methylase inhibitors suggests that inhibition of mRNA cap methylation and $m^6A$ methylation could collectively contribute to the inhibition of RSV infection. Alternatively, it will be interesting to test the antiviral effect of methylase inhibitors on viruses (such as caliciviruses) which do not require cap-dependent translation machinery. If $m^6A$ positively regulates viral replication for a wide range of viruses, inhibition of $m^6A$ methylation or perturbation of $m^6A$-related enzymes may serve as novel broad-spectrum antiviral drugs.

In summary, the inventors mapped the internal $m^6A$ modifications in RSV RNAs and showed that $m^6A$ enhances RSV replication, gene expression, and virus production. In addition, evidence that $m^6A$ upregulates RSV pathogenesis and virulence in vivo is provided. These findings highlight viral $m^6A$ machinery as a possible novel target for rational design of live attenuated vaccines, for enhanced production of live attenuated vaccines, and for broad-spectrum antiviral drug discovery.

B. Materials and Methods

The animal study was conducted in strict accordance with USDA regulations and the recommendations in the Guide for the Care and Use of Laboratory Animals of the National Research Council and was approved by The Ohio State University Institutional Animal Care and Use Committee (IACUC; animal protocol no. 2009A0221). The animals were housed within the University Laboratory Animal Resources (ULAR) facilities of The Ohio State University according to the guidelines of the Institutional Animal Care and Use Committee (IACUC). The animal care facilities at The Ohio State University are AAALAC accredited. Every effort was made to minimize potential distress, pain, or discomfort to the animals throughout all experiments.

Cell lines. HeLa (ATCC CCL-2), A549 (ATCC CCL-185), Vero (ATCC CRL-CCL81), and HEp-2 (ATCC CCL-23) cell lines were purchased from the American Type Culture Collection (Manassas, VA) and were grown in Dulbecco's modified Eagle's medium (DMEM; Life Technologies) supplemented with 10% FBS. HeLa cells overexpressing the empty vector (pPB-CAG), YTHDF1, YTHDF2, or YTHDF3 were maintained in DMEM, 10% FBS and 1 µg/ml of puromycin every passage to select for YTHDF1-3 overexpressing cells. Primary, well-differentiated human airway epithelial (HAE) cultures were grown on collagen coated Transwell inserts (Corning Incorporated, Corning, NY) at an air-liquid interface, as previously described [51]. Upon reaching confluency and forming tight junctions, the apical medium was removed and cultures were maintained at the air-liquid interface for 4 to 6 weeks to generate well-differentiated, polarized cultures. All cell lines used in this study were free of *mycoplasma*, as confirmed by the LookOut *Mycoplasma* PCR Detection Kit (Sigma).

Virus stocks and purification. Recombinant RSV containing a green fluorescence protein (GFP) gene between the leader sequence and NS1 gene (rgRSV) [51] was propagated and titered in HeLa cells or A549 cells. To prepare purified rgRSV, 20 T150 flasks of HeLa cells or A549 cells were infected by rgRSV at an MOI of 0.1, and cell culture supernatants harvested at 48 or 72 h post-infection were clarified by centrifugation at 10,000×g for 30 min. Virus was concentrated through a 35% (wt/vol) sucrose cushion by centrifugation at 30,000×g for 2 h at 4° C. in a Ty 50.2 rotor (Beckman). The pellet was resuspended in DMEM with 10% trehalose and further purified through a sucrose gradient (20-55%) by centrifugation at 35,000×g for 2 h at 4° C.

in an SW55 rotor (Beckman). The final pellet was resuspended in 0.5 ml of DMEM with 10% trehalose.

$m^6A$-seq. High-throughput sequencing of the RSV and host methylome was carried out using $m^6A$-seq as described previously [19]. For $m^6A$-seq of the rgRSV genome and antigenome, RNAs were extracted from purified rgRSV virions and purified with the RiboMinus Eukaryote System v2 kit (Thermo Fisher). For $m^6A$-seq of host transcripts, total RNAs were extracted from mock or rgRSV-infected HeLa or A549 cells and polyadenylated RNAs were isolated using Dynabeads mRNA DIRECT Purification kit (Thermo Fisher). Purified RNAs were sonicated with Bioruptor Pico (Diagenode) with 30 s ON 30 s OFF for 30 cycles, mixed with 1 µl of affinity purified anti-$m^6A$ monoclonal antibody (NEB) in IPP buffer (150 mM NaCl, 0.1% NP-40, 10 mM Tris-HCl, pH 7.4) and incubated for 2 h at 4° C. Enriched mRNA fragments were purified with RNA Clean & Concentrator kit (Zymo) and used for library generation with TruSeq Stranded mRNA Library Prep kit (Illumina). Sequencing was carried out on Illumina HiSeq 4000 according to the manufacturer's instructions. Two replicates of RNA samples from virions, virus-infected cells, and mock-infected cells were subjected to $m^6A$-seq. For data analysis, after removing the adapter sequences, the reads were mapped to the human genome (hg38) and rgRSV genome and antigenome by using Hisat2 [60] with peak calling as described [61]. Metagene analysis was performed by R package Guitar [62]. Differential methylation analysis was performed with count based negative binomial model implemented in QNB test [48].

Quantification of RSV RNA $m^6A$ level using liquid chromatography-mass spectrometry (LC-MS/MS). RSV RNA (250 mg) was extracted from highly purified rgRSV virions using an RNeasy Mini kit (Qiagen) and purified twice with RiboMinus Eukaryote System v2 kit (Thermo Fisher). Purified RNA was digested and subjected to a quantitative analysis of the $m^6A$ level using LC-MS/MS as previously described [7].

Host Cell Gene Differential Expression analysis. Host cell differential gene expression was analyzed by R package DESeq2 [62] using wald-test. The significantly differentially expressed genes were reported at adjusted P value cutoff of 0.05.

Gene Ontogeny (GO) analysis. GO analysis was performed using the R package cluster Profiler [62]. Specifically, enrichKEGG function was called to analyze for enriched pathway and enrichMap function was called to generate network plot of enriched pathway.

Plasmids and site-directed mutagenesis. The pPB-CAG plasmid vector was used to overexpress the readers (YTHDF1-3), writers (METTL3, METTL14), and erasers (FTO, ALKBH5) as described previously [31]. Plasmid (RW30) encoding the full-length antigenomic cDNA of RSV strain A2 with GFP inserted between the leader and the NS1 gene, and support plasmids expressing RSV A2 strain N protein (pTM1-N), P protein (pTM1-P), L protein (pTM1-L), and M2-1 protein (pTM1-M2-1) were generously provided by Dr. P. L. Collins, NIAID, Bethesda, MD. Mutations to the potential $m^6A$ sites in G gene were introduced into the RW30 plasmids using QuikChange site-directed mutagenesis kit (Stratagene, La Jolla, CA). There are 3 $m^6A$ peaks, G1, G2, and G3 in G gene which has 6, 7, and 4 putative $m^6A$ sites, respectively. The potential $m^6A$ sites mutants in G1 peak include 394-AG$\underline{m^6}$ACC-400; 401-AA$\underline{m^6}$ACA-407; 418-AA$\underline{m^6}$ACA-424; 444-AA$\underline{m^6}$ACA-450; 455-AA$\underline{m^6}$ACA-461; 459-AA$\underline{m^6}$ACC-465; mutants in G2 peak include 569-AA$\underline{m^6}$ACA-575; 576-AA$\underline{m^6}$ACC-582; 589-AA$\underline{m^6}$ACC-595; 612-AA$\underline{m^6}$ACC-618; 625-AG$\underline{m^6}$ACA-631; 645-AA$\underline{m^6}$ACC-651; 652-AA$\underline{m^6}$ACC-658; and mutants in G3 peak include 718-AA$\underline{m^6}$ACA-724; 722-AA$\underline{m^6}$ACA-728; 768-GA$\underline{m^6}$ACT-774; 787-AA$\underline{m^6}$ACC-793 (FIG. 19). The A or C within the consensus $m^6A$ sites was mutated to a T or G in these sites without changing the encoded amino acid. Mutant G12 combined the mutations from G1 and G2. Mutant G123 was a combined the mutations from G1, G2, and G3. To generate an rgRSV mutant lacking cap methylation, residues G1853 and G1857 in the S-adenosyl-L-methionine (SAM) binding site in the L gene were mutated to alanine in the RW30 backbone. All plasmids and mutations were confirmed by DNA sequencing.

siRNA and siRNA transfection. siRNAs against METTL3, METTL14, FTO, ALKBH5, YTHDF1, YTHDF2, YTHDF3 or non-targeting AllStars negative control siRNA were purchased from Qiagen (Valencia, CA, sequences listed in Supplementary Table 11). All siRNA transfections were performed using the Lipofectamine 3000 transfection reagent (Thermo-Fisher) according to the manufacturer's instructions.

Antibodies and Western blotting. The antibodies used in this study were anti-YTHDF1 (Proteintech, Rosemont, IL), anti-YTHDF2 (Abcam, Cambridge, MA), anti-YTHDF3 (Abcam), anti-METTL 3 (Proteintech), anti-METTL 14 (Proteintech), anti-ALKBH5 (Sigma-Aldrich), anti-FTO (Abcam), and anti-RSV serum (Virostat), F (Abcam), G (Abcam), anti-FLAG (Sigma-Aldrich), anti-Actin (Proteintech) and anti-Tubulin (Abcam). Cells were harvested and lysed in RIPA buffer (Abcam) supplemented with protease inhibitor cocktail (Sigma-Aldrich). Western blotting was performed as described. Tubulin or actin was used as a loading control.

Immunofluorescence analysis and confocal microscopy. Mock or rgRSV-infected cells were fixed in acetone and methanol at the ratio of 1:1 for 30 min, and blocked with 5% milk in PBST. Slides were stained with all primary antibodies (1:100), washed 3 times with PBST, and stained with conjugated Alexa Fluor secondary antibodies Alexa Fluor 488/594 (Thermo-Fisher; 1:300), and mounted with Slow-Fade™ Diamond Antifade Mountant with DAPI (Thermo-Fisher). Imaging was performed on an Olympus FV 1000 confocal microscopy system at The Ohio State University Campus Microscopy & Imaging Facility.

Real-time RT-PCR. RSV genomic RNA and mRNA were quantified by real-time RT-PCR. HeLa or A549 cells were infected with rgRSV or an rgRSV mutant at an MOI of 0.1. At 12, 18 and 24 post-infection, total RNA was isolated from cells using TRIzol (Life Technologies). Viral genomic RNA copies were quantified by real-time RT-PCR using two primers specifically targeting the RSV leader sequence and GFP gene. Poly (A)-containing viral mRNAs were isolated from total RNA using a Dynabead mRNA isolation kit (Life Technologies) according to the manufacturer's recommendations. Using the viral mRNAs as the template, the NS1 and G mRNA copies were quantified by real-time RT-PCR using two primers targeting the viral NS1 and G genes, respectively.

RNA-immunoprecipitation (RIP). The RIP assay was performed as described previously [37]. Briefly, HeLa cells were infected with rgRSV at MOI of 1.0 and cell extracts were harvested in polysome lysis buffer after 36 h post-infection. RNP complexes were immunoprecipitated with anti-HA antibody conjugated to magnetic beads (Sigma) or anti-YTHDF2 antibody overnight at 4° C., and washed five times with ice-cold NT2 buffer. For the RIP with anti-YTHDF2 antibody, additional secondary antibody was added. After the final wash, 10% of the beads were used for immunoblotting and the remaining 90% were used for RNA extraction using TRIzol (ThermoFisher).

Recovery of RSV from the full-length cDNA clones. rgRSV mutants were rescued from the full-length cDNA of the RSV A2 strain [63]. HEp-2 cells were infected with MVA-T7 at an MOI of 10, then transfected with 1.2 μg of plasmid RW30 or RW30 mutant, 0.4 μg of pTM1-N, 0.2 μg of pTM1-P, 0.1 μg of pTM1-M2-1, and 0.1 μg of pTM1-L using the Lipofectamine 3000 reagent (Life Technologies). At day 4 post-transfection, the cells were harvested using scrapers and were co-cultured with new flask of HEp-2 cells at 50 to 60% confluence. When an extensive cytopathic effect (CPE) was observed, the cells were subjected to three freeze-thaw cycles, followed by centrifugation at 4,000×g for 10 min. The supernatant was subsequently used to infect new HEp-2 cells. The successful recovery of the rgRSV was confirmed by the presence of green fluorescent cells, followed by RT-PCR and sequencing. Recombinants rgRSV carrying mutations in $m^6A$ sites were designated as rgRSV-G1, G2, G3, G12, and G123. Recombinant rgRSV carrying double mutations in the SAM binding site of L gene was designated as rgRSV-G1853A-G1857A.

RT-PCR and sequencing. All plasmids, viral mutants and stocks, and virus isolates from the nasal turbinates and lungs of cotton rats were sequenced to confirm virus identity. Viral RNA was extracted from 100 μl of each recombinant virus using an RNeasy minikit (Qiagen, Valencia, CA). A 1.5-kb DNA fragment spanning the RSV G gene was amplified by RT-PCR. The PCR products were purified and sequenced using a sequencing primer at The Ohio State University Plant Microbe Genetics Facility to confirm the presence of the designed mutations.

Viral replication kinetics. Confluent HeLa or A549 cells in 6-well-plate were infected with wild-type rgRSV or mutant rgRSV at an MOI of 0.1. After 1 h of adsorption, the inoculum was removed and the cells were washed three times with DMEM. Fresh DMEM (supplemented with 2% FBS) was added, and the infected cells were incubated at 37° C. At different time points post-inoculation, the supernatant and cells were harvested by three freeze-thaw cycles, followed by centrifugation at 1,500×g at room temperature for 15 min. The virus titer was determined by $TCID_{50}$ assay in HEp-2 cells [51].

Genetic stability of rgRSV mutants in cell culture. Confluent Vero cells in T25 flasks were infected with each rgRSV mutant at an MOI of 0.1. At day 3 post-inoculation, the cell culture supernatant was harvested and used for the next passage in Vero cells. Using this method, each rgRSV mutant was repeatedly passaged 15 times in Vero cells. At each passage, the G gene was amplified by RT-PCR and sequenced. At passage 15, the entire genome of each recombinant virus was amplified by RT-PCR and sequenced.

Replication and pathogenesis of rgRSV mutants in cotton rats. Thirty 6-week-old specific-pathogen-free (SPF) male cotton rats (Envigo, Indianapolis, IN) were randomly divided into 6 groups (5 cotton rats per group). Prior to virus inoculation, the cotton rats were anesthetized with isoflurane. The cotton rats in group 1 were inoculated with $2.0 \times 10^5$ $TCID_{50}$ of parental rgRSV and served as positive controls. The cotton rats in groups 2 to 5 were inoculated with $2.0 \times 10^5$ $TCID_{50}$ of four $m^6A$ deficient rgRSV mutants, rgRSV-G1, G2, G3, and G12. Each cotton rat was inoculated intranasally with a volume of 100 μl. At day 4 post-infection, the cotton rats were sacrificed via carbon dioxide inhalation. The left lung and nasal turbinates were collected for virus titration and the right lung was collected for histological analysis.

Immunogenicity of rgRSV in cotton rats. For the immunogenicity study, twenty 6-week-old female cotton rats (Envigo) were randomly divided into five groups (5 cotton rats per group). Cotton rats in groups 1, 2, and 3 were intranasally inoculated with $2.0 \times 10^5$ $TCID_{50}$ of two $m^6A$ deficient rgRSV mutants (rgRSV-G1 and G12) and rgRSV, respectively. Cotton rats in groups 4 were mock-infected with DMEM and served as unvaccinated challenged control. After immunization, the cotton rats were evaluated daily for any possible abnormal reaction and blood samples were collected from each cotton rat weekly by facial vein retro-orbital plexus sampling, and serum was used for detection of neutralizing antibodies. At 4 weeks post-immunization, the cotton rats in groups 2 to 5 were challenged with $2.0 \times 10^5$ $TCID_{50}$ of parental rgRSV via intranasal route, and evaluated twice daily for the presence of any clinical symptoms. At 4 days post-challenge, all cotton rats were euthanized by C02 asphyxiation, and their lungs and nasal turbinates were collected for virus titration. The immunogenicity of rgRSV mutants was assessed based on their ability to trigger neutralizing antibody, the ability to prevent rgRSV replication in lungs and nose, and the ability to protect lung from pathological changes.

Pulmonary histology. After sacrifice, the right lung of each animal was removed, inflated, and fixed with 4% neutral buffered formaldehyde. Fixed tissues were embedded in paraffin and a microtome used to generate 5 m sections. Slides were then stained with hematoxylin-eosin (H&E) for the examination of histological changes by light microscopy. Histopathological changes were evaluated based on the extent of interstitial inflammation, edema, and peribronchiolar inflammation.

Determination of viral titer in lung and nasal turbinate. The nasal turbinate and the left lung from each cotton rat were removed, weighed, and homogenized in either 3 ml or 2 ml of DMEM. The lung was homogenized using a Precellys 24 tissue homogenizer (Bertin, MD) by following the manufacturer's recommendations. The nasal turbinates were homogenized by hand with a 15 mL capacity PYREX® homogenizer (Corning, NY). The presence of infectious virus was determined by TCID50 assay in HEp-2 cells.

Determination of RSV-neutralizing antibody. RSV-specific neutralizing antibody titers were determined using a plaque reduction neutralization assay. Briefly, cotton rat sera were collected by retro-orbital plexus sampling weekly until challenge. The serum samples were heat inactivated at 56° C. for 30 min. Twofold dilutions of the serum samples were mixed with an equal volume of DMEM containing approximately 50 $TCID_{50}$/well rgRSV in a 96-well plate, and the plate was incubated at room temperature for 1 h with constant rotation. The mixtures were then transferred to confluent HEp-2 cells in a 96-well plate in triplicate. After 1 h of incubation at 37° C., the virus-serum mixtures were removed and the cells were overlaid with 0.7500 methylcellulose in overlay media (1×MEM, 2% FBS, Sodium bicarbonate, 25 mM HTEPES, 1% L-Glutamine, 1% Pen Strep) and incubated for another 3 days before counting the fluorescent foci. The numbers of foci at each serum dilution were plotted and the 50% plaque reduction titer was used as the RSV-specific neutralizing antibody titer.

Statistical analysis. Quantitative analysis was performed by either densitometric scanning of autoradiographs or by using a phosphorimager (Typhoon; GE Healthcare, Piscataway, NJ) and ImageQuant TL software (GE Healthcare, Piscataway, NJ). Statistical analysis was performed by one-way multiple comparisons using SPSS (version 8.0) statistical analysis software (SPSS Inc., Chicago, IL). A P value of <0.05 was considered statistically significant.

C. Tables

SUPPLEMENTARY TABLE 1

$m^6A$ peaks in RSV RNAs purified from virions grown in HeLa cells

| RSV RNAs | Peak no. | Peak range (nt)[A] | Gene location[B] | Peak size (nt) | Enrichment Score | Enrichment Fold[C] |
|---|---|---|---|---|---|---|
| Genome | 1 | 599-972 | gs, NS2 | 373 | 5.07 | 2.34 |
| | 2 | 1571-1645 | N | 74 | 3.42 | 1.77 |
| | 3 | 1795-1944 | N | 149 | 2.89 | 1.53 |
| | 4 | 2617-2766 | P | 149 | 3.65 | 1.87 |
| | 5 | 3066-3215 | ig | 149 | 8.81 | 3.13 |
| | 6 | 3963-4262 | M, ge, ig | 299 | 3.22 | 1.68 |
| | 7 | 4711-5533 | G, ge, ig | 822 | 6.68 | 2.74 |
| | 8 | 11291-1365 | L | 74 | 3.39 | 1.76 |
| | 9 | 13459-3533 | L | 74 | 3.29 | 1.71 |
| | 10 | 13758-3832 | L | 74 | 2.70 | 1.43 |
| | 11 | 13908-3982 | L | 74 | 3.44 | 1.78 |
| Antigenome | 1 | 1645-1719 | N | 74 | 2.39 | 1.26 |
| | 2 | 2543-2991 | P | 448 | 3.07 | 1.62 |
| | 3 | 4786-5458 | G | 672 | 5.49 | 2.45 |
| | 4 | 5833-5907 | F | 74 | 4.66 | 2.22 |

[A] Nucleotide sequence is referred to RSV A2 strain. Nucleotide ranges are indicated. $m^6A$ peaks in G gene region are highlighted by yellow color.
[B] The RSV genes and regulatory elements are covered by $m^6A$ peaks. These regions may contain $m^6A$ sites. However, whether these regions indeed contain $m^6A$ sites will require to search the presence of $m^6A$ motif, Pu $[G > A]m^6AC[A/C/U]$ motif (Pu represents purine). RSV gene start, gene end, and intergenic sequence are indicated by gs, ge, and ig, respectively.
[C] log2 enrichment of the $m^6A$ peaks identified in RSV antigenome and genome.

SUPPLEMENTARY TABLE 2

$m^6A$ peaks in RSV mRNAs from rgRSV-infected HeLa cells

| RSV RNAs | Peak no. | Peak range (nt)[A] | Gene location[B] | Peak size (nt) | Enrichment Score | Enrichment Fold[C] |
|---|---|---|---|---|---|---|
| mRNAs | 1 | 1-50 | Leader | 49 | 3.87 | 1.95 |
| | 2 | 450-648 | NS1, ge, ig, gs, NS2 | 198 | 3.45 | 1.78 |
| | 3 | 898-997 | NS2, ge, ig | 99 | 5.45 | 2.44 |
| | 4 | 1895-1944 | N | 49 | 2.79 | 1.48 |
| | 5 | 2194-2243 | N | 49 | 5.73 | 2.52 |
| | 6 | 2444-2542 | P | 98 | 3.24 | 1.69 |
| | 7 | 2743-2792 | P | 49 | 4.04 | 2.01 |
| | 8 | 3042-3190 | P, ge, ig | 148 | 16.05 | 4.01 |
| | 9 | 3740-3789 | M | 49 | 3.70 | 1.88 |
| | 10 | 3989-4138 | M, ge, ig | 149 | 5.95 | 2.57 |
| | 11 | 4288-4337 | gs, SH | 49 | 3.81 | 1.93 |
| | 12 | 4388-4437 | SH | 49 | 7.81 | 2.96 |
| | 13 | 4687-5533 | G, ge, ig | 846 | 15.38 | 3.94 |
| | 14 | 7279-7328 | ge, ig | 49 | 4.48 | 2.16 |
| | 15 | 8326-8375 | ig, $g^s$ | 49 | 8.32 | 3.05 |
| | 16 | 13909-3958 | L | 49 | 5.43 | 2.44 |

[A] Nucleotide sequence is referred to RSV A2 strain. Nucleotide ranges are indicated. $m^6A$ peaks in G gene region are highlighted by yellow color.
[B] The RSV mRNAs and regulatory elements are covered by $m^6A$ peaks. These regions may contain $m^6A$ sites. However, whether these regions indeed contain $m^6A$ sites will require to search the presence of $m^6A$ motif, Pu $[G > A]m^6AC[A/C/U]$ motif (Pu represents purine). RSV gene start, gene end, and intergenic sequence are indicated by gs, ge, and ig, respectively.
[C] log2 enrichment of the $m^6A$ peaks identified in RSV mRNAs.

SUPPLEMENTARY TABLE 3 m⁶A peaks in RSV RNAs purified virions grown in A549 cells

| RSV RNAs | Peak no. | Peak range (nt) | Gene location | Peak size (nt) | Enrichment Score | Enrichment Fold |
|---|---|---|---|---|---|---|
| Genome | 1 | 599-798 | gs, NS2 | 199 | 13.73 | 3.77 |
|  | 2 | 1746-1944 | N | 198 | 21.94 | 4.45 |
|  | 3 | 2194-2243 | N | 49 | 10.15 | 3.34 |
|  | 4 | 2444-2542 | P | 98 | 7.62 | 2.93 |
|  | 5 | 2593-2841 | P | 248 | 9.65 | 3.27 |
|  | 6 | 2992-3240 | P, ge, ig, gs | 248 | 178.31 | 7.47 |
|  | 7 | 4737-5085 | G | 348 | 35.42 | 5.14 |
|  | 8 | 5135-5483 | G | 348 | 90.27 | 6.49 |
|  | 9 | 5883-6082 | F | 199 | 6.30 | 2.65 |
| Antigenome | 1 | 400-848 | NS1, ge, ig, gs, NS2 | 448 | 9.89 | 3.31 |
|  | 2 | 898-997 | NS2, ge, ig | 99 | 6.66 | 2.73 |
|  | 3 | 1347-1446 | N | 99 | 4.57 | 2.19 |
|  | 4 | 1496-1695 | N | 199 | 6.86 | 2.77 |
|  | 5 | 2095-2243 | N | 148 | 14.49 | 3.85 |
|  | 6 | 2344-2393 | P | 49 | 3.07 | 1.62 |
|  | 7 | 2444-3290 | P, ge, ig, gs, M | 846 | 20.56 | 4.36 |
|  | 8 | 4039-4138 | ig | 99 | 8.43 | 3.07 |
|  | 9 | 4537-4686 | ig, gs, G | 149 | 3.64 | 1.86 |
|  | 10 | 4737-5434 | G | 697 | 47.63 | 5.57 |
|  | 11 | 5484-5533 | ig | 49 | 17.78 | 4.15 |
|  | 12 | 5783-6082 | F | 299 | 12.5 | 3.64 |
|  | 13 | 8326-8375 | ig, gs | 49 | 5.55 | 2.47 |
|  | 14 | 12114-2263 | L | 149 | 5.78 | 2.53 |
|  | 15 | 14806-4855 | L | 49 | 13.29 | 3.73 |

SUPPLEMENTARY TABLE 4 m⁶A peaks in RSV mRNAs purified from rgRSV-infected A549 cells

| RSV RNAs | Peak no. | Peak range (nt) | Gene location | Peak size (nt) | Enrichment Score | Enrichment Fold |
|---|---|---|---|---|---|---|
| mRNAs | 1 | 1-50 | leader | 49 | 3.86 | 1.95 |
|  | 2 | 450-798 | NS1, ge, ig, gs, NS2 | 348 | 12.19 | 3.61 |
|  | 3 | 898-997 | NS2, ge, ig | 99 | 3.58 | 1.84 |
|  | 4 | 1048-1246 | N | 198 | 2.58 | 1.37 |
|  | 5 | 1297-1396 | N | 99 | 3.03 | 1.60 |
|  | 6 | 1496-1695 | N | 199 | 5.12 | 2.35 |
|  | 7 | 1796-1994 | N | 198 | 5.87 | 2.55 |
|  | 8 | 2045-2642 | N, ge, ig, gs, P | 597 | 5.21 | 2.38 |
|  | 9 | 2743-3589 | P, ge, ig, gs, M | 846 | 22.23 | 4.47 |
|  | 10 | 3989-4138 | M, ge, ig | 149 | 4.34 | 2.11 |
|  | 11 | 4188-4337 | ig, gs, SH | 149 | 2.46 | 1.30 |
|  | 12 | 4487-5533 | ig, gs, G, ge, ig | 1046 | 85.69 | 6.42 |
|  | 13 | 5783-6082 | F | 299 | 6.61 | 2.72 |
|  | 14 | 6481-6580 | F | 99 | 2.42 | 1.27 |
|  | 15 | 7628-7876 | M2-1 | 248 | 2.86 | 1.51 |
|  | 16 | 7977-8026 | M2-1 | 49 | 2.90 | 1.53 |
|  | 17 | 8326-8424 | ig, gs, L | 98 | 2.54 | 1.34 |
|  | 18 | 12114-12163 | L | 49 | 5.10 | 2.35 |

SUPPLEMENTARY TABLE 5

Overlapping m⁶A peaks in RSV RNAs purified virions grown in HeLa and A549 cells

| RSV RNAs | Overlapping Peak no. | Peak range (nt) | Peak size (nt) | Gene location |
|---|---|---|---|---|
| Genome | 1 | 599-798 | 199 | gs, NS2 |
|  | 2 | 1795-1944 | 149 | N |
|  | 3 | 2617-2766 | 149 | P |
|  | 4 | 3066-3215 | 149 | ig |
|  | 5 | 4737-5085 | 348 | G |
|  | 6 | 5135-5483 | 348 | G |
| Antigenome | 1 | 1645-1695 | 50 | N |
|  | 2 | 2543-2991 | 448 | P |
|  | 3 | 4786-5434 | 648 | G |
|  | 4 | 5833-5907 | 74 | F |

SUPPLEMENTARY TABLE 6

Overlapping m6A peaks in RSV mRNAs purified
from rgRSV-infected HeLa and A549 cells

| RSV RNAs | Overlapping Peak no. | Peak range (nt) | Peak size (nt) | Gene location |
|---|---|---|---|---|
| mRNAs | 1 | 1-50 | 49 | Leader |
| | 2 | 450-648 | 198 | NS1, ge, ig, gs, NS2 |
| | 3 | 898-997 | 99 | NS2, ge, ig |
| | 4 | 1895-1944 | 49 | N |
| | 5 | 2194-2243 | 49 | N |
| | 6 | 2444-2542 | 98 | P |
| | 7 | 2743-2792 | 49 | P |
| | 8 | 3989-4138 | 149 | M, ge, ig |
| | 9 | 4288-4337 | 49 | gs, SH |
| | 10 | 4687-5533 | 846 | G, ge, ig |
| | 11 | 8326-8375 | 49 | ig, gs |

SUPPLEMENTARY TABLE 7 siRNA used for knocking down host m6A machinery

| siRNA | Sequences (5'-3') |
|---|---|
| YTHDF1 | 5'-CCGCGTCTAGTTGTTCATGAA-3' |
| YTHDF2 | 5'-AAGGACGTTCCCAATAGCCAA-3' |
| YTHDF3 | 5'-ATGGATTAAATCAGTATCTAA-3' |
| METTL3 | 5'-CTGCAAGTATGTTCACTATGA-3' |
| METTL14 | 5'-AAGGATGAGTTAATAGCTAAA-3' |
| ALKBH5 | 5'-AAACAAGTACTTCTTCGGCGA-3' |
| FTO | 5'-AAATAGCCGCTGCTTGTGAGA-3' |
| Control siRNA | 5' ACGTGACACGTTCGGAGAA-3' |

Example 2: $N^6$-Methyladenosine is a Molecular Signature for Discrimination of Self and Non-Self RNA by Cytoplasmic RNA Sensor RIG-I Internal $N^6$-methyladenosine ($m^6A$) modification of RNA is one of the most common and abundant modifications in eukaryotic cells as well as in viruses. However, the biological role(s) of RNA $m^6A$ in virus-host interaction remains elusive. Using human metapneumovirus (hMPV), a medically important non-segmented negative-sense RNA virus as a model, the inventors demonstrate that $m^6A$ serves as a molecular marker for innate immune discrimination self and nonself RNAs. The inventors show that hMPV RNAs are $m^6A$ methylated and that viral $m^6A$ methylation promotes hMPV replication and gene expression. HMPV infection leads to differential expression of interferon-related genes involved in innate immune signaling pathways. Inactivating these $m^6A$ sites with synonymous mutations resulted in $m^6A$ deficient recombinant hMPVs that induced significantly higher expression of type I interferon that restricted viral replication. Notably, the induction of type I interferons by $m^6A$-deficient rhMPVs and virion RNA was dependent on the cytoplasmic RNA sensor RIG-I, not MDA5. Mechanistically, $m^6A$-deficient virion RNA induces higher expression of RIG-I, enhances its binding affinity to RIG-I, and facilitates the conformational change of RIG-I, leading to enhanced induction of type I IFN expression. The replication of $m^6A$-deficient rhMPVs was attenuated in wild type A549 cells but was restored in cells knocked out for RIG-I and MAVS. Furthermore, $m^6A$-deficient rhMPVs triggered higher type I interferon in vivo and were significantly attenuated in the lower respiratory tract yet retained high immunogenicity in cotton rats. Collectively, these results highlight that (i) virus acquires $m^6A$ in their RNAs as a means of mimicking cellular RNA to avoid the detection by innate immunity; and (ii) viral $m^6A$ RNA can serve as a novel target to attenuate hMPV for vaccine purposes.

Here, the inventors demonstrate that $m^6A$ modification serves as a molecular marker for innate sensing by cells to discriminate self and nonself RNA and that $m^6A$ regulates viral pathogenesis. The inventors found that the genome, antigenome, and mRNAs of human metapneumovirus (hMPV) are $m^6A$ modified and that $m^6A$ modification in hMPV RNAs positively regulated each step in the hMPV replication cycle, including RNA replication, mRNA transcription, protein synthesis, and progeny virus production. Next, the inventors generated recombinant (r)hMPVs lacking various $m^6A$ sites in the G gene region of the antigenome and the G gene in the genome and found that replication of the $m^6A$-deficient rhMPVs was significantly reduced in cell culture while inducing an elevated type I interferon (IFN-I) response. The inventors showed that the $m^6A$-deficient hMPV antigenome and/or genome, but not the viral mRNA, was responsible for the enhanced IFN response. Mechanistically, $m^6A$-deficient hMPV virion RNA enhances its binding affinity to RIG-I, facilitates the conformational change of RIG-I, and induces higher RIG-I expression. Depletion of RIG-I and the mitochondrial antiviral signaling (MAVS) but not MDA5 completely abrogated the rhMPV-induced type I IFN responses. Furthermore, the inventors demonstrated that in a cotton rat model $m^6A$-deficient rhMPVs were highly attenuated in replication in the lungs and provided complete protection against hMPV reinfection. These results suggest that the $m^6A$ modification serves as a molecular signature for host innate immunity to discriminate self from non-self RNA, and that inactivating the $m^6A$ modification could serve as a means to attenuate hMPV and perhaps other NNS RNA viruses for the vaccine purposes.

A. Materials and Methods

Ethics Statement.

The animal study was conducted in strict accordance with the Guide for the Care and Use of Laboratory Animals of the National Research Council and was approved by The Ohio State University Institutional Animal Care and Use Committee (IACUC; animal protocol no. 2009A0221). The animal care facilities at The Ohio State University are AAALAC accredited. Every effort was made to minimize potential distress, pain, or discomfort to the animals throughout all experiments.

Cell Lines.

Vero E6 cells (ATCC CRL-1586), A549 cells (ATCC CCL-185), and THP-1 (ATCC TIB-202) were purchased from the American Type Culture Collection (Manassas, VA). A549-Dual™, A549-Dual™ KO-RIG-I, A549-Dual™ KO-MDA5, and A549-Dual™ KO-MAVS knockout cells were purchased from InvivoGen (San Diego, CA). BHK-SR19-T7 cells were kindly provided by Apath, LLC, Brooklyn, NY. All cell lines were grown in Dulbecco's modified Eagle's medium (DMEM; Life Technologies) supplemented with 10% FBS. The medium for the BHK-SR19-T7 cells was supplemented with 10 μg/ml puromycin (Life Technologies) during every other passage to select for T7 polymerase-expressing cells. A549-Dual™ and knockout cell lines were supplemented with Normocin™ (100 μg/ml), blasticidin (10 μg/ml) and Zeocin™ (100 μg/ml). HeLa cells overexpressing the empty vector (pPB-CAG), YTHDF1, YTHDF2, or YTHDF3 were maintained in DMEM supplemented with 10% FBS and 1 µg/ml of puromycin every passage to select for YTHDF1-3 overexpressing cells. All cell lines used in this study were free of *mycoplasma*, as confirmed by the LookOut *Mycoplasma* PCR Detection Kit (Sigma).

Plasmids and site-directed mutagenesis. Plasmids encoding the full-length genomic cDNA of hMPV strain NL/1/00 (phMPV), and support plasmids expressing hMPV N protein (pCITE-N), P protein (pCITE-P), L protein (pCITE-L), and M2-1 protein (pCITE-M2-1) were kindly provided by Ron A. M. Fouchier at the Department of Virology, Erasmus Medical Center, Rotterdam, The Netherlands (50). The F cleavage site in the genome of hMPV NL/1/00 was modified to a trypsin-independent F cleavage site, as described previously (51). A GFP gene was cloned into the gene junction between N and P in plasmid phMPV, resulted in the construction of phMPV-GFP. The G gene of hMPV strain NL/1/00 was cloned into pCAGGS resulted in the construction of pCAGGS-G. Mutations to the potential $m^6A$ sites in G gene were introduced into the plasmids pCAGGS-G and phMPV using QuikChange site-directed mutagenesis kit (Stratagene, La Jolla, CA). The pPB-CAG plasmid vector was used to overexpress the readers (YTHDF1-3 and YTHDC1), writers (METTL3, METTL14), and erasers (FTO, ALKBH5) as described previously (29, 31). These $m^6A$ sites mutants in G gene region of the antigenome include: site 1, 171-AA$m^6A$ C»T A-175; site 2, 187-GA$m^6$ A»G CA-191; site 3, 227-AA$m^6$AC T»G -231; site 4, 246-AG$m^6A$ C»T A-250; site 5, 255-AG$m^6A$ C»T A-259; site 6, 341-AG$m^6$AC A»G -345; site 7, 346-GA$m^6$ A»G CC-351; site 8, 422-GA$m^6$AC A»G -426; site 9, 428-AG$m^6$AC A»G 432; site 10, 453-AA$m^6A$ C»T A-457; site 11, 464-GG$m^6$AC A»G -468; site 12, 476-GA$m^6$AC A»G -480; site 13, 518-GA$m^6$AC C»G -522; and site 14, 553-AG$m^6$ A»G CC-557 (FIG. 45). The $m^6A$ mutants in the G gene of the genome include: site 1, 237- G»C G$m^6$T C»G C-241; site 2, 290-A G»A $m^6$TC C»A -294; site 3 433-AG$m^6$ T»C CC-437; site 4, 441- A»C G$m^6$T C»G C-445; site 5, 570-AG$m^6$ T»C CC-574; and site 6, 616-A G»A $m^6$TC C»G -620. The A or C within the consensus $m^6A$ sites was mutated G»A to a T or G in these sites without changing the encoded amino acid. Mutants G1-2, G8-9, G8-14, and G1-14 were a combination of mutations in sites 1 and 2, sites 8 and 9, sites 8 to 14, and sites 1 to 14, respectively. Mutant G(−)1-6 is the combined mutation of all six $m^6A$ sites in the G gene in the genome. All constructs were sequenced at The Ohio State University Plant Microbe Genetics Facility.

Virus Stocks and Purification.

Parental hMPV strain NL/1/00 was propagated and titrated in Vero E6 cells. To prepare highly purified hMPV for $m^6A$ sequencing, 20 T150 flasks of A549 cells were infected by hMPV at an MOI of 0.5, and cell culture supernatants harvested at 72 h post-infection were clarified by centrifugation at 5,000×g for 30 min. Virus was concentrated by centrifugation at 30,000×g for 2 h at 4° C. in a Ty 50.2 rotor (Beckman). The pellet was resuspended in NTE buffer (0.05 M Tris-HCl, 0.15 M NaCl, 15 mM CaCl$_2$) [pH 6.5]) supplemented with 10% trehalose and further purified through a sucrose gradient by centrifugation at 35,000×g for 18 h at 4° C. in an SW55 rotor (Beckman). Solution layer containing virus was extracted with syringe, diluted with NTE buffer and centrifuged at 30,000×g for 2 h at 4° C. in SW55 rotor. The final pellet was resuspended in 0.5 ml of NTE buffer.

$m^6A$-Seq.

High-throughput sequencing of the hMPV and host methylome was carried out using $m^6A$-seq as described previously (38). For $m^6A$-seq of the hMPV genome and antigenome, RNAs were extracted from highly purified hMPV virions and purified with the RiboMinus Eukaryote System v2 kit (Thermo Fisher). For $m^6A$-seq of host transcripts, total RNAs were extracted from mock or hMPV-infected A549 cells and polyadenylated RNAs were isolated using Dynabeads mRNA DIRECT Purification kit (Thermo Fisher). Purified RNAs were sonicated with Bioruptor Pico (Diagenode) with 30 s ON 30 s OFF for 30 cycles, mixed with 2.5 mg of affinity purified anti-$m^6A$ polyclonal antibody (NEB cat. E1610) in IPP buffer (150 mM NaCl, 0.1% NP-40, 10 mM Tris-HCl, pH 7.4) and incubated for 2 h at 4° C. Enriched mRNA fragments were purified with RNA Clean & Concentrator kit (Zymo) and used for library generation with Kapa RNA HyperPrep kit (Roche). Sequencing was carried out on Illumina HiSeq 4000 at SE50 bp mode according to the manufacturer's instructions. Two replicates of RNA samples from virions, virus-infected cells, and mock-infected cells were subjected to $m^6A$-seq. For data analysis, after removing the adapter sequences, the reads were mapped to the human genome (hg38) and hMPV genome by using Hisat2 (52). Peak calling for the viral genome RNA was done by first dividing the hMPV genome into 30 bp consecutive bins where read count was quantified. Then the inventors applied Fisher's exact test to assess enrichment of coverage by $m^6A$-IP in that bin. The odds ratio was computed by (IP/overall IP)/(Input/overall Input) where overall IP/Input were represented by median of read counts of bins across the same strand of the whole virus genome. Note, when calling peaks for mRNAs of the hMPV, the overall IP/Input were represented by the median of bins across the gene instead of the whole virus genome. Finally, the inventors merged all neighboring bins that are significant (at FDR<0.05 cutoff) in all replicates and report them as consistent peaks.

Differential Expression Analysis of Host Cells.

The input of $m^6A$-seq is equivalent to regular RNA-seq, therefore the inventors quantified the gene-level read count of input samples that aligned to hg38 for differential gene expression analysis. DESeq2 was used to make an inferential test where differentially expressed genes were identified at FDR<0.1 cutoff.

Differential Methylation Analysis of Host Cell.

To compare the $m^6A$-methylome of the mock infected and hMPV infected cells, the inventors first called peaks using fisher's exact test on 50 bp consecutive bins as described in previous section. The inventors then used QNB package for differential methylation test with default setting.

Quantification of hMPV RNA $m^6A$ Level Using Liquid Chromatography-Mass Spectrometry (LC-MS/MS).

hMPV RNA (250 mg) was extracted from highly purified rhMPV virions using an RNeasy Mini kit (Qiagen) and purified twice with RiboMinus Eukaryote System v2 kit (Thermo Fisher). To examine the purify of virion RNA, oligo d(T) was used for reverse transcription, followed by qPCR for quantification for j-actin and viral N and G mRNAs. Virion RNA which was free of contamination of host RNA and viral mRNAs was used for LC-MS/MS, $m^6A$ antibody pulldown assay, and $m^6A$-seq. Purified RNA was digested and subjected to quantitative analysis of m⁶A level using LC-MS/MS as previously described.

Colorimetric Quantification of Viral m⁶A Methylation.

Virion RNA was extracted from sucrose gradient ultracentrifugation-purified wild type and mutant rhMPVs. Total m⁶A content on virion RNA was quantified by m⁶A RNA Methylation Assay Kit (Abcam, ab185912). Briefly, m⁶A was detected using a specific capture anti-m⁶A antibody and then quantified colorimetrically by reading the absorbance at 450 nm. A standard curve was generated using known m⁶A methylated RNA (range from 0.02 to 1 ng of m⁶A) as a positive control. The m⁶A content was calculated from each RNA samples based on their OD450 values. The percent change was calculated by dividing m⁶A contents in viral RNA from the treated group by those from the control group.

Gene Ontogeny (GO) Analysis.

GO analysis was performed using the online analysis software metascape www.metascape.org (53).

siRNA and Plasmid Transfection.

siRNAs against METTL3, METTL14, FTO, ALKBH5, YTHDF1, YTHDF2, YTHDF3 or non-targeting AllStars negative control siRNA were purchased from Qiagen. All siRNA and plasmid transfections were performed using the Lipofectamine 3000 transfection reagent (Thermo-Fisher) according to the manufacturer's instructions. Briefly, ninety percent confluent A549 cells in 12-well plates were transfected with 1 µg of plasmid or 30 pmol of siRNA and 24 hours later infected with hMPV. At 12, 18, 24 and 48 hours post infection cells were lysed in RIPA buffer (Abcam) on ice and collected for Western blot.

Antibodies and Western blotting. The antibodies used in this study were anti-YTHDF1 (Proteintech, Rosemont, IL), anti-YTHDF2 (Abcam, Cambridge, MA), anti-YTHDF3 (Abcam), anti-METTL3 (Proteintech), anti-METTL14 (Abcam), anti-ALKBH5 (Sigma-Aldrich), anti-FTO (Abcam), anti-hMPV serum (prepared in cotton rats), anti-hMPV N antibody (US Biological), anti-RIG-I (Abcam, ab180675), anti-MDA5 (Abcam), anti-FLAG (Sigma-Aldrich), anti-Actin (Abcam), and anti-HA antibody(Abcam). Cells were harvested and lysed in RIPA buffer (Abcam) supplemented with protease inhibitor cocktail (Sigma-Aldrich). Western blotting was performed as described. Actin was used as a loading control.

Immunofluorescence Analysis and Confocal Microscopy.

Mock or hMPV-infected cells were fixed in acetone and methanol at the ratio of 1:1 for 30 min, and blocked with goat serum (Sigma-Aldrich, G0923). Slides were stained with all primary antibodies (1:100), washed 3 times with PBS, and stained with conjugated Alexa Fluor secondary antibodies Alexa Fluor 488/594 (Thermo-Fisher; 1:300), and mounted with SlowFade™ Diamond Antifade Mountant with DAPI (Thermo-Fisher). Imaging was performed on an Olympus FV 1000 confocal microscopy system at The Ohio State University Campus Microscopy & Imaging Facility.

Recovery of rhMPVs from the Full-Length cDNA Clones.

rhMPVs or rghMPV (rhMPV expressing GFP) were rescued using a reverse genetics system as described previously (50, 54). Briefly, T25 flasks of BHK-SR19-T7 cells (kindly provided by Apath LLC), which stably express T7 RNA polymerase, were transfected with 3.75 µg of plasmid phMPV, 3.0 µg of pCITE-N, 1.5 µg of pCITE-P, 1.5 µg of pCITE-L, and 1.5 µg of pCITE-M2-1 using Lipofectamine 2000 (Life Technologies). At day 6 post-transfection, the cells were harvested using cell scrapers and were co-cultured with Vero-E6 cells at 50-60% confluence. When extensive cytopathic effects (CPE) were observed, the cells were subjected to three freeze-thaw cycles in the presence of 10% trehalose, followed by centrifugation at 3,000×g for 10 min. The supernatant was subsequently used to infect new Vero E6 cells. The successful recovery of the rhMPVs was confirmed by methylcellulose overlay plaque assay, immunostaining, and reverse transcription (RT)-PCR.

Immunostaining Plaque Assay.

Vero E6 cells were seeded in 24-well plates, infected with serial dilutions of rhMPV, and overlayed with methylcellulose. At day 5 postinfection, cells were fixed with 10% neutral buffered formaldehyde at room temperature for 30 min and then the mixture of overlay and formaldehyde was removed. Cells were permeabilized in phosphate-buffered saline (PBS) containing 0.4% Triton X-100 at room temperature for 10 min and blocked at 37° C. for 1 h using 1% bovine serum albumin (BSA) in PBS. The cells were then incubated with anti-hMPV N-protein primary monoclonal antibody (Millipore, Billerica, MA) at a dilution of 1:2,000 overnight at 4° C., followed by incubation with horseradish peroxidase (HRP)-labeled rabbit anti-mouse secondary antibody (Thermo Scientific, Waltham, MA) at a dilution of 1:5,000. After incubation with 3-amino-9-ethylcarbazole (AEC) chromogen substrate (Sigma, St. Louis, MO), positive cells were visualized under a microscope. The viral titer was calculated as the number of PFU per ml.

Viral Replication Kinetics in A549 Cells.

Confluent A549 cells or knockout cells in 24-well plates were infected with parental rhMPV or rhMPV mutant at an MOI of 1.0 or 5.0. After 1 h of adsorption, the inoculum was removed and the cells were washed three times with PBS. Fresh DMEM (supplemented with 1% FBS) was added and the infected cells were incubated at 37° C. At different time points post-infection, the supernatant and cells were harvested by three freeze-thaw cycles, followed by centrifugation at 1,500×g at room temperature for 15 min. The virus titer was determined by an immunostaining assay in Vero E6 cells.

Quantification of Viral Genome, Antigenome, and mRNA by Real-Time RT-PCR.

Ninety percent confluent A549 cells were infected with each rhMPV mutant at an MOI of 1.0 or 5.0. At indicated time points, total RNA was isolated from virus-infected cells using the TRIzol reagent (Life Technologies). Poly(A)-containing viral mRNA was isolated from total RNA using a Dynabeads mRNA isolation kit (Life Technologies) according to the manufacturer's recommendations. The first strand of DNA was generated from genomic and antigenomic RNA with primers targeting leader and trailer sequence, respectively, and real-time PCR was performed in TB-Green premix Ex Taq™ (TaKaRa, Japan) with the primer pairs located on N and L gene, respectively. A cDNA pool was generated from total RNA with Oligo $(dT)_{23}$ (Sigma-Aldrich), and hMPV N and G-mRNA copies were quantified with the primer pairs located on N and G gene, respectively. RNA and mRNA copies of each sample were normalized by respective mRNA copies of human GAPDH.

RT-PCR and Sequencing.

All plasmids, viral mutants and stocks, and virus isolates from the nasal turbinates and lungs of cotton rats were sequenced. Viral RNA was extracted from 100 µl of each recombinant virus using an RNeasy mini kit (Qiagen, Valencia, CA) and total RNA from infected tissue was extracted with TRIzol reagent. A 1-kb DNA fragment spanning the hMPV G gene was amplified by RT-PCR. The PCR products were purified and sequenced using a sequencing primer at The Ohio State University Plant Microbe Genetics Facility to confirm the presence of the designed mutations.

Isolation of total viral RNA, virion RNA, and G mRNA.

Confluent A549 cells in 150-mm dishes were mock infected or infected with wild-type or mutant rhMPV at an MOI of 0.5. At day 2 postinfection, total RNA was isolated from virus-infected cells using the TRIzol reagent (Life Technologies) and dissolved in RNase-free water. Subsequently, poly(A)-containing RNA was isolated from total RNA using a Dynabeads mRNA Direct™ kit (Life Technologies) according to the manufacturer's recommendations. Finally, hMPV G mRNA was isolated by Dynabeads MyOne™ Streptavidin C1 (ThermoFisher Scientific) conjugated with poly T-tailed G gene specific primer. Virion RNA was extracted from sucrose-gradient purified virions of rhMPV or rhMPV mutant. HMPV genome, antigenome, and G mRNA were quantified by real-time RT-PCR.

[$^{35}$S]-Methionine Metabolic Labeling.

A549 cells were transfected with siRNA against METTL3 and METTL14 or control siRNA. After 24 h, cells were incubated in methionine- and cysteine-free media for 1 h, and 50 μCi of [$^{35}$S]-methionine was added. At indicated time points, cells were washed with PBS and disrupted in lysis buffer. Cell lysates were resolved on SDS-PAGE and exposed to film. Quantification of [$^{35}$S]-labeled proteins was performed using ImageJ software. 5 μl of each protein sample was used for measuring total [$^{35}$S] incorporation by scintillation counting (Beckman).

MeRIP Assay.

MeRIP assay was carried out using a procedure provided by Millipore Magna MeRIP™ m6A kit (Catalog No. 17-10499). Magnetic Beads A/G blend (25 μl) was washed and incubated with anti-m$^6$A antibody (5 μl) at room temperature for 30 min and washed three times to remove any unbound antibody. Total RNA (15 μg) was extracted from rhMPV or m$^6$A deficient rhMPV-infected A549 cells. The RNA samples were treated at 85° C. for 5 min and chilled on ice immediately, and incubated with m$^6$A antibody-associated beads at 4° C. for 2 h with rotation. The RNA-associated magnetic beads were then washed for 3 times. Total RNA was extracted from beads by TRIzol reagent and was quantified by real-time RT-PCR using primers annealing to hMPV antigenome, genome, and G mRNA.

Measurement of Interferon in Virus-Infected or RNA-Transfected Cells.

For virus-infection, A549 cells or THP-1 cells infected by rhMPV or hMPV mutant at MOI of 1.0 or 4.0, cell supernatants were harvested at 16, 24, and 48 h post-infection and IFN-α and -β concentrations were determined by commercial enzyme-linked immunosorbent assays (ELISA) according to the manufacturer's instructions (PBL, Piscataway, NJ). A known concentration of human IFN-α and -β was used to generate the standard curve. Prior to RNA transfection, viral RNA was treated with or without calf intestinal alkaline phosphatase (CIP; Promega) at the dose of 10$^7$ copies/10 U for 30 min at 37° C. After inactivation of CIP at 65° C. for 15 min, viral RNA was further purified by TRIzol reagent and quantified by real-time RT-PCR. A549 cells or A549-Dual cell lines in 24-well plates were transfected with CIP-treated or untreated viral RNA by Lipofectamine 3000. At 24 and 48 hours post-transfection, culture medium was harvested for IFN-β quantification by ELISA.

Immunoprecipitation Assay of RIG-I and Virion RNA.

Confluent six-well-plates of A549 cells were transfected with 2 μg of plasmid pEF-BOS-RIG-I-Flag (kindly provided by Dr. Jacob Yount). At 24 h post-transfection, cells were lysed in lysis buffer (Abcam, ab152163). Cell lysates were harvested after centrifugation at 13,000×g for 10 min and incubated with Anti-FLAG©M2 magnetic beads (Sigma-Aldrich, M8823) at room temperature for 80 min. The mixture was then divided into 13 aliquots (150 μl/tube), and 12 aliquots were incubated with 2×10$^8$ copies of virion RNA (with or without CIP treatment) or 2×10$^9$ copies of hMPV mRNA respectively at 37° C. for 1 h. Beads associated RNA:protein complex were washed in lysis buffer for three times, and total RNA was extracted from beads by TRizol reagent and quantified by real-time RT-PCR. The 13$^{th}$ aliquot was washed and subjected to Western blot.

RIG-I Pull-Down Assay.

10$^9$ copies of virion RNA with or without CIP treatment was biotinylated with Pierce™ RNA 3' End Biotinylation Kit (Thermo Fisher Scientific) according to the product instruction. Purified 3' end biotinylated RNA was incubated with MyOne™ Streptavidin C1 beads (Thermo Fisher Scientific) in the presence of RNase inhibitor at room temperature for 30 min with rotation. RNA-associated beads were then washed three times and incubated with 50 μl of A549 cell lysate containing overexpressed RIG-I and 1 unit of RNase inhibitor at room temperature for 1 h with rotation. Beads were then washed for 3 times and subjected to SDS-PAGE. The pull-down RIG-I protein on Streptavidin beads were detected by Western blot using anti-RIG-I antibody. For control, mixture of cell lysate and RNA-associated beads were loaded as input.

Limited Trypsin Digestion of RIG-I.

Recombinant human RIG-I protein was purified from HEK-293T cells transfected with a plasmid encoding Flag-tagged RIG-I (pEF-BOS-RIG-I-Flag). The concentration of RIG-I protein was measured by Bradford assay. Recombinant RIG-I (50 nM) was incubated with 2×10$^7$ copies of virion RNA of wild type or mutant hMPV in 30 μL MOPS buffered reaction system (10 mM MOPS pH 7.4, 1 mM DTT, 1 mM MgCl$_2$, 0.002% Tween20) in the presence of RNase inhibitor and AMP-PNP (2 mM). The reaction mixtures were incubated at 37° C. for 30 min to permit RIG-I: RNA complex formation and mixed with 10 μL of tosylsulfonyl phenylalanyl chloromethyl ketone (TPCK)-trypsin (2.5 ng/μL) and incubated at room temperature. At indicated time points (0 to 120 min), 10 μL was removed, mixed with 5×SDS-PAGE loading dye, and boiled for Western blot probed with an anti-RIG-I helicase antibody (Abcam). Poly(I:C) (2-10 μg) was used as a positive control. For the competition assay, wild type and rhMPV-G1-14 virion RNA were diluted to 2×10$^6$ copies/μL and different ratios of these two RNAs were mixed (10:0, 7.5:2.5, 5:5, 2.5:7.5, and 0:10), and were incubated with purified RIG-I and AMP-PNP and the conformation of RIG-I was examined by limited trypsin digestion, as described above.

Interferon Response of rhMPV and Mutants in Cotton Rats.

Six-week-old specific-pathogen-free (SPF) female cotton rats (Envigo, Indianapolis, IN) were inoculated intranasally with 100 μl of PBS or PBS containing 2.0×10$^5$ PFU of rhMPV-G8-14, rhMPV-G1-14 or rhMPV. Each group contains 5 cotton rats. Forty-eight hours post-inoculation, cotton rats were sacrificed and 1 ml of PBS was injected into the right lung of each cotton rats. Approximately 1 ml of bronchoalveolar lavage (BAL) was collected for IFN-β bioactivity assay on CCRT cells. Briefly, CCRT cells were cultured in 96-well plates with 100 μl of DMEM medium supplemented with 2% FBS. BAL supernatant (250 1) was mixed with the same volume of DMEM containing 0.1 M HCl, incubated at room temperature for 2 h to destroy type II interferon, and neutralized with 27.8 μl of DMEM containing 7.5% NaHCO$_3$. The treated BAL mixture was 2-fold serially diluted (1:2-1:128) and added to CCRT cell culture medium in duplicate in a volume of 100 μl/well. A known concentration of human IFN-β was 2-fold serially diluted (250 U~7.8 U/ml) and used to generate a standard curve. Cells were incubated at 37° C. in 5% C02 for another 24 h and infected by 104 PFU of recombinant vesicular stomatitis virus expressing GFP reporter (rVSV-GFP) per well. GFP positive cells were observed under UV microscope at 24 h post-infection. The IFN-β concentration of each BAL sample was calculated according to the highest dilution of samples and the lowest concentration of standard human IFN-β which inhibited rVSV-GFP replication therefore GFP expression.

Replication and Pathogenesis of rhMPV in Cotton Rats.

Twenty-five 6-week-old female SPF cotton rats (Envigo, Indianapolis, IN) were randomly divided into 5 groups (5 cotton rats per group). Prior to virus inoculation, the cotton rats were anesthetized with isoflurane. The cotton rats in groups 1-4 were intranasally inoculated with $2.0\times10^5$ PFU of rhMPV, rhMPV-G1-2, rhMPV-G8-9, and rhMPV-G1-14. The cotton rats in group 5 were mock infected with 100 μl of PBS and served as uninfected controls. Each cotton rat was inoculated intranasally with a volume of 100 μl. After inoculation, the animals were evaluated on a daily basis for any clinical signs. At day 4 postinfection, the cotton rats were sacrificed, and lungs and nasal turbinates were collected for both virus isolation and histological analysis.

Immunogenicity of rhMPV in Cotton Rats.

For the immunogenicity study, thirty 4-week-old cotton rats (Envigo) were randomly divided into four groups (5 cotton rats per group). Cotton rats in groups 1 were mock-infected with PBS and served as uninfected unchallenged control. Cotton rats in groups 2-5 were intranasally inoculated with $2.0\times10^5$ PFU of rhMPV, rhMPV-G1-2, rhMPV-G8-9 and rhMPV-G1-14, respectively. Cotton rats in groups 4 were mock-infected with PBS and served as uninfected challenged control. After immunization, the cotton rats were evaluated daily for any possible abnormal reaction and blood samples were collected from each cotton rat weekly by facial vein retro-orbital bleeding, and serum was used for detection of neutralizing antibodies. At 4 weeks post-immunization, the cotton rats in groups 2 to 6 were challenged with $2.0\times10^5$ PFU of parental rhMPV via intranasal route, and evaluated twice daily for the presence of any clinical symptoms. At 4 days post-challenge, all cotton rats were euthanized by $CO_2$ inhalation, and their lungs and nasal turbinates were collected for virus titration. The immunogenicity of rhMPV mutant was assessed based on their ability to trigger neutralizing antibody, the ability to prevent hMPV replication in lungs and nasal turbinates, and the ability to protect lung from pathological changes.

Genetic Stability of rhMPV Mutants in Cell Culture.

Confluent Vero-E6 cells in T25 flasks were infected with each rhMPV mutant at an MOI of 0.1. At day 3 post-inoculation, the cell culture supernatant was harvested and used for the next passage in Vero-E6 cells. Using this method, each rhMPV mutant was repeatedly passaged 15 times in Vero-E6 cells. At each passage, the G gene was amplified by RT-PCR and sequenced. At passage 15, the entire genome of each recombinant virus was amplified by RT-PCR and sequenced.

Pulmonary Histology.

After sacrifice, the right lung of each animal was removed, inflated, and fixed with 4% neutral buffered formaldehyde. Fixed tissues were embedded in paraffin and sectioned at 5 m. Slides were then stained with hematoxylin-eosin (H&E) for the examination of histological changes by light microscopy. Histopathological changes were evaluated based on the extent of interstitial inflammation, edema, and peribronchiolar inflammation.

Determination of Viral Titer in Lung and Nasal Turbinate.

The nasal turbinate and the left lung from each cotton rat were removed, weighed, and homogenized in 1 ml of PBS solution using a Precellys 24 tissue homogenizer (Bertin, MD) following the manufacturer's recommendations. The presence of infectious virus was determined by an immunostaining plaque assay in Vero E6 cells, as described above.

Determination of hMPV-Neutralizing Antibody.

hMPV-specific neutralizing antibody titers were determined using a plaque reduction neutralization assay (55). Briefly, cotton rat sera were collected by retro-orbital bleeding weekly until challenge. The serum samples were heat inactivated at 56° C. for 30 min. Twofold dilutions of the serum samples were mixed with an equal volume of DMEM containing approximately 100 PFU/well rhMPV in a 96-well plate, and the plate was incubated at 37° C. for 1 h with constant rotation. The mixtures were then transferred to confluent Vero-E6 cells in a 24-well plate in triplicate. After 1 h of incubation at 37° C., the virus-serum mixtures were removed and the cells were overlaid with 0.75% methylcellulose in DMEM and incubated for another 5 days before immunostaining plaque titration. The plaques were counted, and 50% plaque reduction titers were calculated as the hMPV-specific neutralizing antibody titers.

Statistical Analysis.

Quantitative analysis was performed by either densitometric scanning of autoradiographs or by using a phosphorimager (Typhoon; GE Healthcare, Piscataway, NJ) and ImageQuant TL software (GE Healthcare, Piscataway, NJ). Statistical analysis was performed by one-way multiple comparisons using SPSS (version 8.0) statistical analysis software (SPSS Inc., Chicago, IL). A P value of <0.05 was considered statistically significant.

B. Results

The hMPV Genome, Antigenome, and mRNAs Contain $m^6A$ Modifications.

Figure 26A:
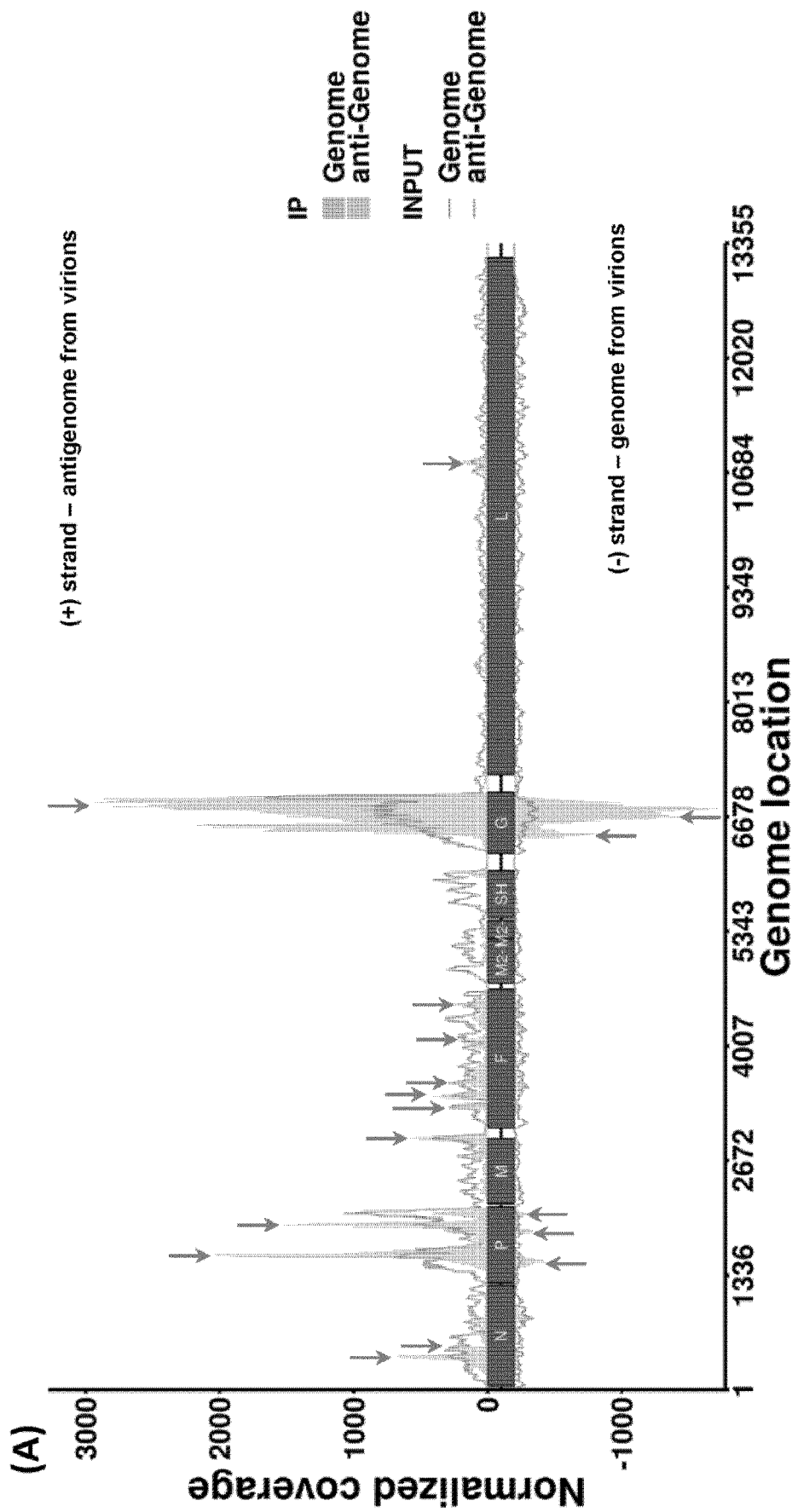

HMPV virions contain its NNS RNA genome of 13,350 nucleotides (subtype A strain NL/1/00, GenBank accession number AF371337). During replication, the viral RNA dependent RNA polymerase copies the negative-sense genomic RNA (vgRNA) to produce an exact, positive-sense full-length complementary RNA (cRNA) antigenome. To determine whether hMPV vgRNA contains $m^6A$, hMPV was grown in A549 cells (a lung epithelial cell line) and viral vgRNA was extracted from purified hMPV virions, sonicated, and subjected to $m^6A$-specific antibody immunoprecipitation followed by high throughput sequencing ($m^6A$-seq). Although it has not been reported for hMPV, previous studies with several other NNS RNA viruses have shown that both the genome and the antigenome can be packaged into virions (56). Interestingly, the inventors found that sequencing reads from $m^6A$-seq aligned to both the genome and antigenome, indicating that hMPV virions contain both the genome and the antigenome. To prove this, purified hMPV virions were disrupted by detergent, digested with RNase, and the RNase-resistant viral nucleocapsid (N-RNA complex) was pulled down by hMPV N antibody. Both genome and antigenome were detected in N-RNA complex by real-time RT-PCR (FIG. 45A-D). This demonstrates that both the genome and the antigenome are indeed encapsidated by N protein and packaged into hMPV virions. The $m^6A$-seq found $m^6A$ peaks on both the genome and antigenome. In the genomic RNA, a total of 5 $m^6A$ peaks were detected spread through the P and G gene regions (FIGS. 26A and C). The largest $m^6A$ peak was found in the G gene with a log 2 enrichment of 3.06, followed by the next largest peak in the P gene with a log 2 enrichment of 2.33. Interestingly, a total of 12 m$^6$A peaks were also found in the antigenome RNA, including regions complementary to the N, P, M, F, G, and L genes (FIGS. 26A and C). Similar to the genome RNA, the strongest m$^6$A peaks were found in the G gene with a log 2 enrichment of 3.12. Interestingly, the regions of m$^6$A peaks identified in both strands are largely overlapping, despite the genome being complementary to the antigenome. Thus, these results show that both the genome and the antigenome of hMPV are m$^6$A modified.

Figure 26B:
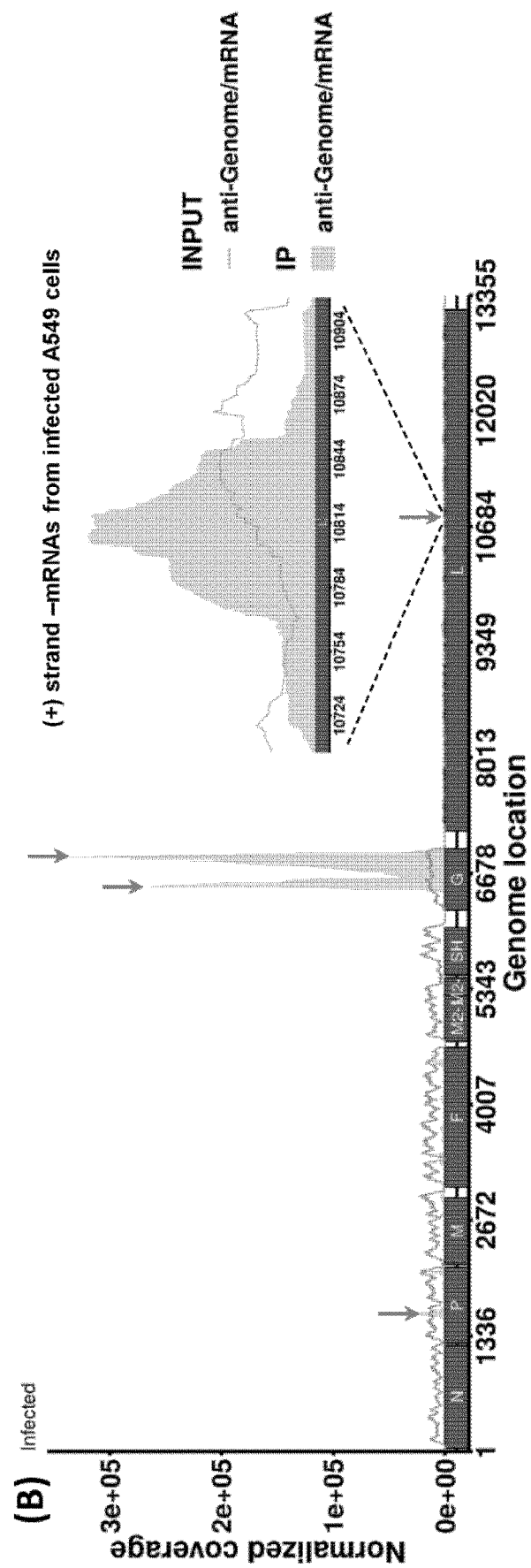

In virus-infected cells, hMPV produces three types of RNAs, genome and antigenome (the replication products) which are neither capped nor polyadenylated, and 8 species of mRNAs (transcription products) which are capped and polyadenylated. The inventors next determined whether hMPV mRNAs were m$^6$A modified by performing m$^6$A-seq of polyadenylated mRNAs from virus-infected cells. This analysis revealed m$^6$A peaks in 3 of the 8 mRNA species, P, G, and L (FIGS. 26B and C). Notably, several m$^6$A-modified regions in hMPV mRNAs largely overlapped with those found in the antigenome. Again, the G mRNA has by far the strongest m$^6$A enrichments among all the hMPV mRNAs. This result suggests that the host m$^6$A machinery methylates positive-strand viral mRNAs and antigenomes similarly.

hMPV Infection Leads to Differential Expression of Interferon-Related Genes Involved in the Innate Immune Response.

Figure 27C:
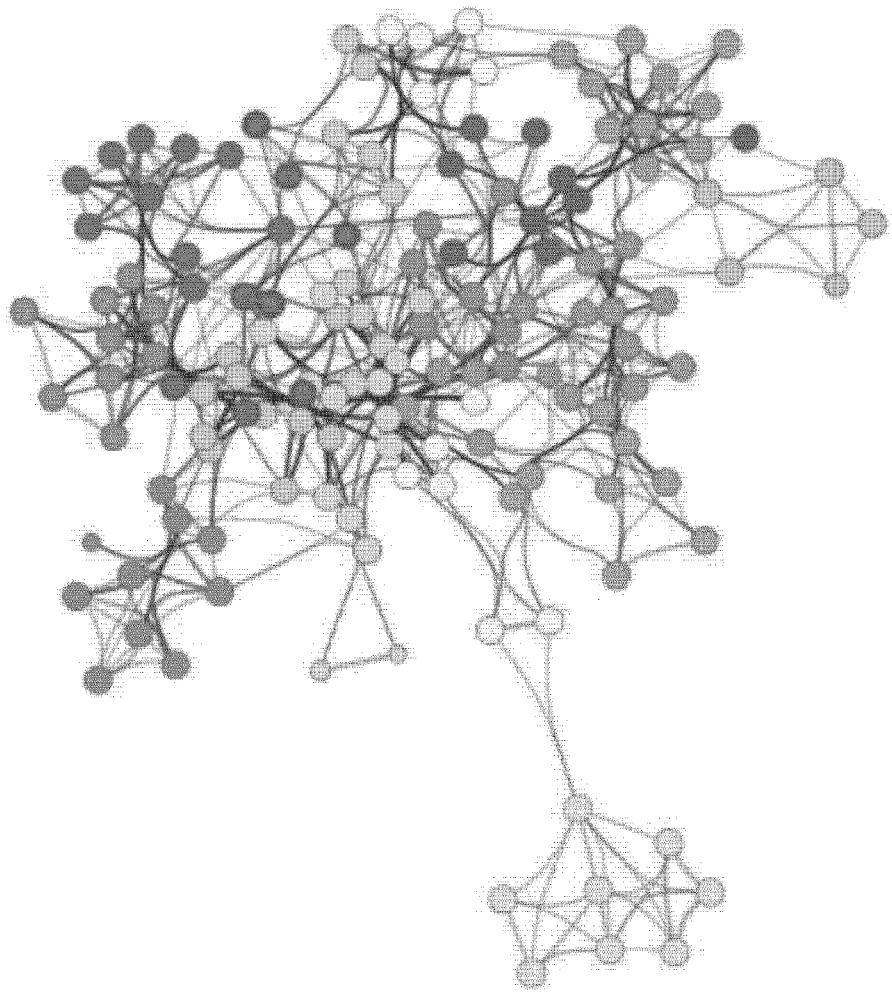
Figure 27D:
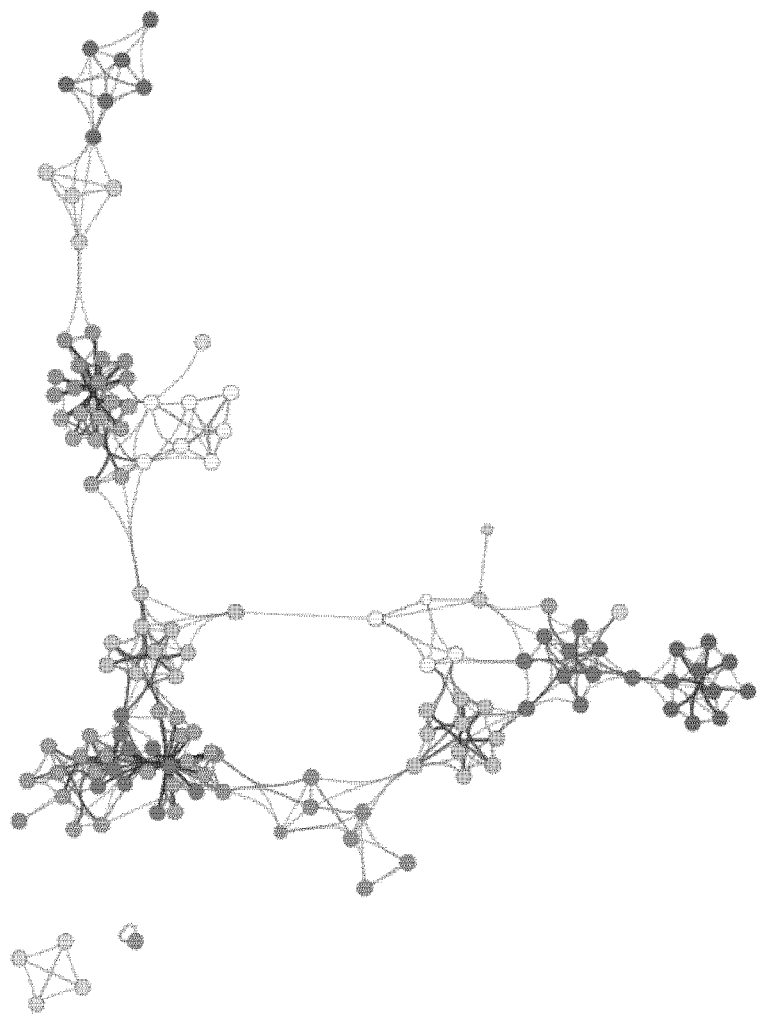

The inventors next determined whether hMPV infection can alter the abundance and distribution of m$^6$A on host transcripts. Total RNA was isolated from hMPV-infected or mock-infected A549 cells, and polyadenylated mRNAs were isolated and subjected to m$^6$A-seq. High quality m$^6$A peaks were detected in both hMPV-infected and mock-infected samples, as demonstrated by finding the m$^6$A consensus sequence GGACU similarly enriched in both sets of samples (FIG. 27A). Metagene analysis showed that hMPV infection slightly increased m$^6$A levels in the 5' and 3' UTR regions of the host transcriptome, but slightly decreased the m$^6$A levels in the coding sequence (CDS) and noncoding sequence (NCS) regions of the host mRNAs (FIG. 27B). Differential methylation analysis using count-based model identified only 21 differentially methylated peaks at FDR<10%, suggesting that hMPV infection leads to little alteration of host epitranscriptome. In contrast, the inventors found a large number of genes differentially expressed in response to hMPV infection. Gene ontology (GO) analysis revealed that the upregulated genes are strikingly enriched in innate host defense transcripts including the cytokine and interferon signaling pathway and inflammatory responses (FIG. 27C). Numerous interferon encoded genes are upregulated including interferon lambda receptor 1, interferon beta 1, interferon lambda 2, interferon lambda 4, and genes involved in Pattern Recognition Receptor (PRR) including RIG-I, MDA5, LPG2, and multiple interferon-stimulated genes (ISGs). In contrast, the downregulated genes are enriched in the cell cycle, metabolism, and translation category (FIG. 27D). These results suggest that hMPV infection significantly alters the host gene expression but has a minimal impact on methylome of cellular mRNAs relevant to host responses to viral infection.

m$^6$A Reader Proteins Positively Regulate hMPV Replication, Gene Expression, and Virus Production.

The biological functions of m$^6$A modification are mediated by m$^6$A-binding proteins with a YTH domain located in cytoplasmic (YTHDF1, YTHDF2, and YTHDF3) and nuclear (YTHDC1) compartments (21). The inventors first examined the effects of overexpression of m$^6$A reader proteins on hMPV replication and gene expression. Briefly, A549 cells were transfected with plasmids expressing YTHDF1, YTHDF2, YTHDF3 or YTHDC1 (FIG. 28A), followed by infection with hMPV, and the expression of the hMPV G protein (one of the two major surface glycoproteins) and the N protein (the major component of the inner nucleocapsid complex) was measured by Western blot. As shown in FIG. 28B, viral G and N protein expression was significantly increased in A549 cells that transiently overexpressed YTHDF1-3 and YTHDC1, particularly at early time points post-inoculation. Next, the inventors measured the release of infectious virus in a single step growth curve. The hMPV titer was significantly increased in all four overexpressing cell lines at all time points (P<0.01, 0.001, or 0.0001) (FIG. 28C). Furthermore, viral replication intermediate (antigenomic RNA) and transcription products (N and G mRNAs) were significantly increased in overexpressing cell lines in some time points (P<0.05 or 0.01), as quantified by real-time RT-PCR (FIG. 28D-G). Thus, transient overexpression of m$^6$A reader proteins promotes hMPV replication and gene expression in A549 cells.

Figure 29J:
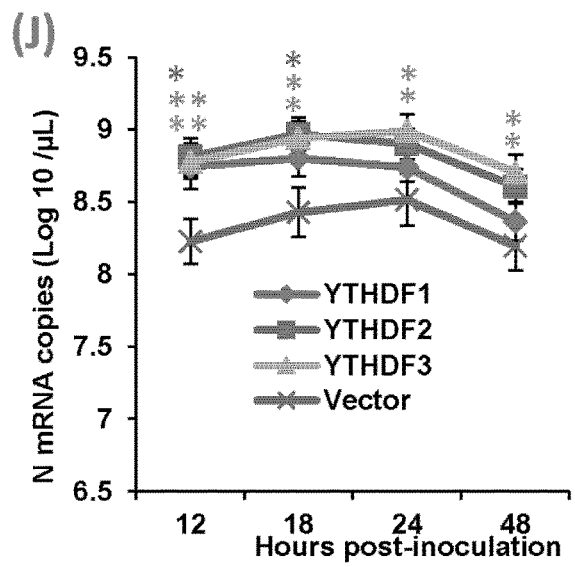

The inventors next examined whether the enhanced hMPV replication and gene expression by m$^6$A reader proteins was cell type-specific. To do this, the inventors constructed HeLa cells stably overexpressing YTHDF1, YTHDF2, or YTHDF3 (FIG. 29A). Briefly, HeLa cells were infected with rghMPV (a recombinant hMPV expressing GFP) at an MOI of 0.5, and viral protein expression, RNA synthesis, and virus production were monitored. Similar to hMPV infection in A549 cells, significantly more hMPV F, G, and N proteins were detected in all three YTHDF-overexpressing HeLa cell lines (P<0.05) (FIG. 29B). In addition, significantly stronger GFP expression was observed in HeLa cells overexpressing YTHDF1-3 compared to the lentivirus vector control HeLa cells at 12, 18, 24, and 48 h post-infection (FIG. 29C). Flow cytometry analysis found significantly more GFP-positive cells (FIG. 29D) with stronger GFP intensity (FIG. 29E) in HeLa cells overexpressing m$^6$A reader proteins (P<0.05). Finally, a single step growth curve assay showed that the rghMPV titer was significantly increased in all three YTHDF-overexpressing cell lines at 12, 18, 24, and 48 h post-inoculation (FIG. 29F). Thus, YTHDF1-3 promotes hMPV replication and gene expression in HeLa cells. Collectively, these results demonstrate that m$^6$A binding proteins promote hMPV genome replication, mRNA transcription, viral protein expression, and progeny virus production in both A549 and HeLa cells.

m$^6$A Writer Proteins Positively Regulate hMPV Replication and Gene Expression.

Figure 30A:
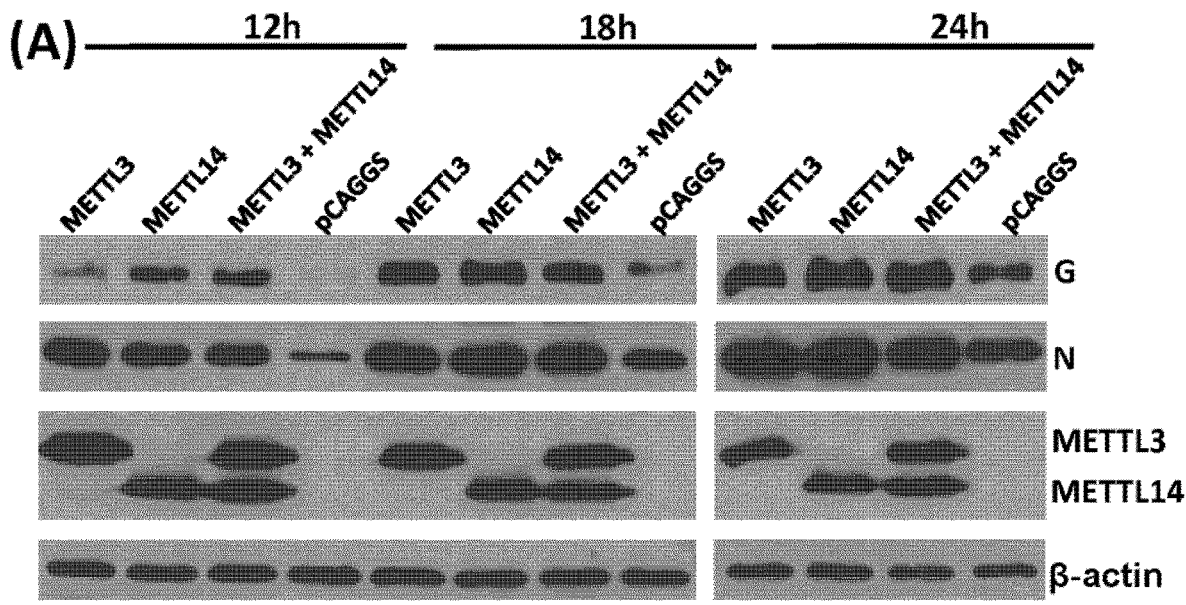

The addition of internal m$^6$A on RNA is catalyzed by m$^6$A writer proteins composed of two host RNA methyltransferases, METTL3 and METTL14 (25). Thus, the role of the m$^6$A writer proteins in hMPV replication and protein expression was examined. A549 cells were transfected with plasmids encoding HA-tagged METTL3, METTL14, or both, followed by rhMPV infection. Western blotting showed that METTL3, METTL14, or both were overexpressed in transfected A549 cells. Interestingly, the expression of hMPV G and N proteins was significantly increased in METTL3 and METTL14 overexpressing A549 cells (FIG. 30A). Consistent with this, the hMPV titer was significantly increased in METTL3 and METTL14 overexpressing A549 cells compared to the vector-transfected cells (FIG. 30B). Quantification of viral RNA in virus-infected cells showed that antigenome synthesis was significantly increased in METTL3 and METTL14 overexpressing A549 cells (FIG. 30D) although genome synthesis did not have a significant increase (FIG. 30C). In addition, G (FIG. 30E) and N (FIG. 30F) mRNA synthesis was significantly increased at some time points.

Internal m$^6$A modifications are reversible and can be removed by m$^6$A eraser proteins, AlkBH5 and FTO (27, 28). The inventors thus examined the effects of knockdown of eraser proteins by transfecting A549 cells with siRNA against AlkBH5 or FTO, or both (FIG. 31A). Knockdown of AlkBH5 and FTO increased viral G and N protein expression, most obviously at 18 hours post-infection. Quantification of Western blot gels from three independent experiment showed that G and N protein expression was significantly increased at 18 h post-infection (FIG. 31B). Viral protein expression was also increased but did not display a significant difference compared to the control siRNA-transfected cells (FIG. 31B) at some time points. In addition, genome (FIG. 31E), antigenome (FIG. 31F), N (FIG. 31H), and G (FIG. 31G) mRNA synthesis was significantly increased in eraser knockdown cells compared to the control siRNA-transfected cells. Taken together, these results demonstrated that modification of hMPV RNA by m$^6$A writers enhances hMPV replication and gene expression.

The inventors next examined whether manipulation of m$^6$A eraser and writer proteins affect host RNA m$^6$A methylation. As shown in FIG. 46A, siRNA knockdown of Mettl3 and Mettl14 led to 27.7% and 20.3% reduction in m$^6$A contents in total RNA compared to the RNA from control siRNA-transfected cells. Next, polyadenylated mRNAs were isolated from total RNA. It was found that siRNA knockdown of Mettl3 and Mettl14 led to 68.7% and 62.2% reduction in m$^6$A contents in host mRNA (FIG. 46B). Consistent with this finding, overexpression of Mettl3 and Mettl14 led to a 24.3% increase in host RNA m$^6$A methylation (FIG. 46C). In addition, overexpression of eraser proteins (FTO and ALKBH5) led to a significant reduction (24.6%) in m$^6$A content of host RNA (FIG. 46D). The inventors also found that siRNA knockdown of Mettl3 and Mettl14 reduced host protein translation relative to control siRNA (FIG. 46E-H). Quantification of protein density showed that knockdown of writer protein led to 4%, 14.6%, and 12.5% reduction in host protein translation at 0.5, 1, and 2 h after [S$^{35}$] labeling (FIG. 46F). Scintillation counting showed that 30-33% reduction in [S$^{35}$] incorporation (FIG. 46I1). These results suggest that the altered viral replication and gene expression is likely due to the changes of both viral and host RNA m$^6$A methylation.

Localization of m$^6$A Writer, Eraser, and Reader Proteins in hMPV-Infected Cells.

Figure 30G:
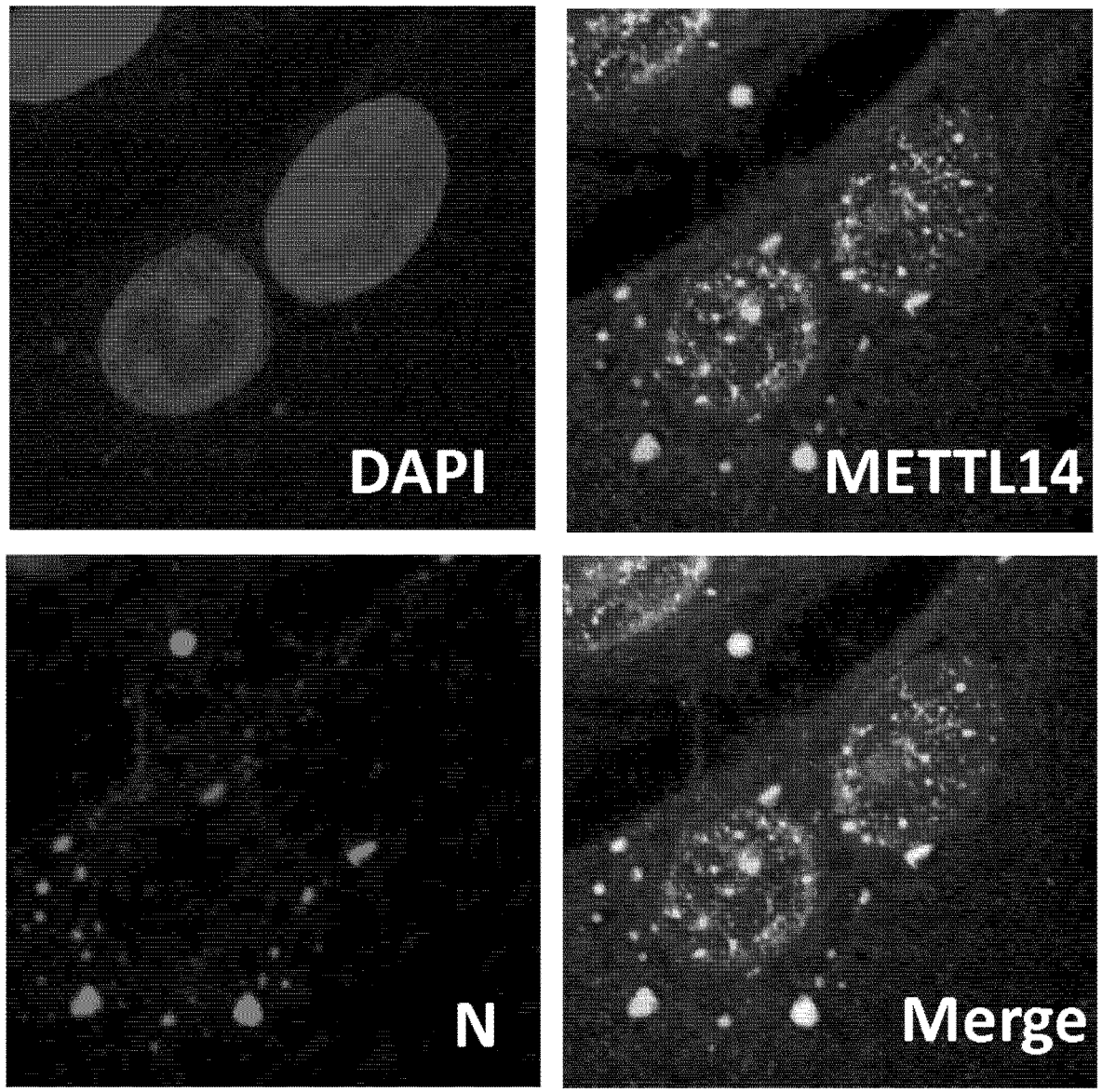
Figure 33G:
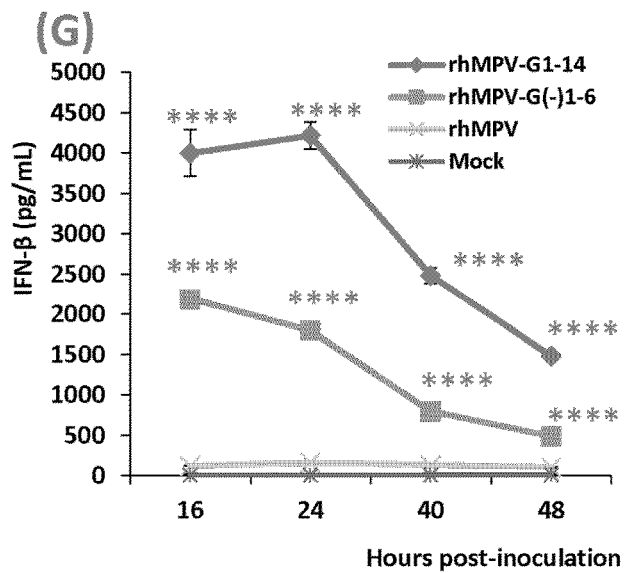
Figure 47A:
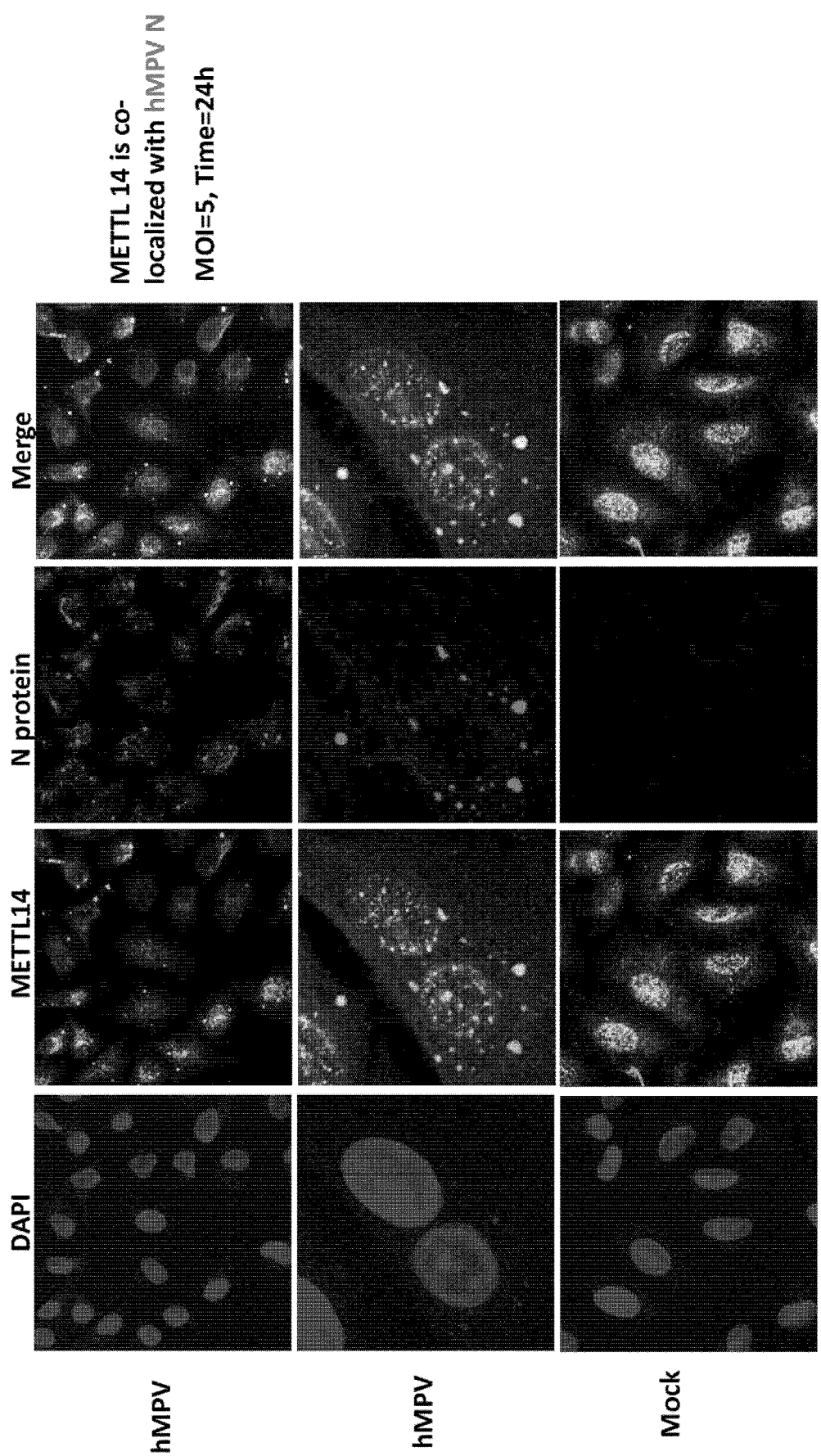
FIG. 47A-B. The effects of hMPV infection on distribution of m$^6$A writer proteins in cells. A549 cells were infected by rhMPV at an MOI of 5.0. At 24 h post-infection, mock- or rhMPV-infected cells were stained with anti-reader or writer protein antibody and anti-hMPV N protein antibody, and were analyzed by confocal microscope. Nuclei were labeled with DAPI. (A) METTL14; (B) METTL3. Representative results from three independent experiments are shown.
Figure 47B:
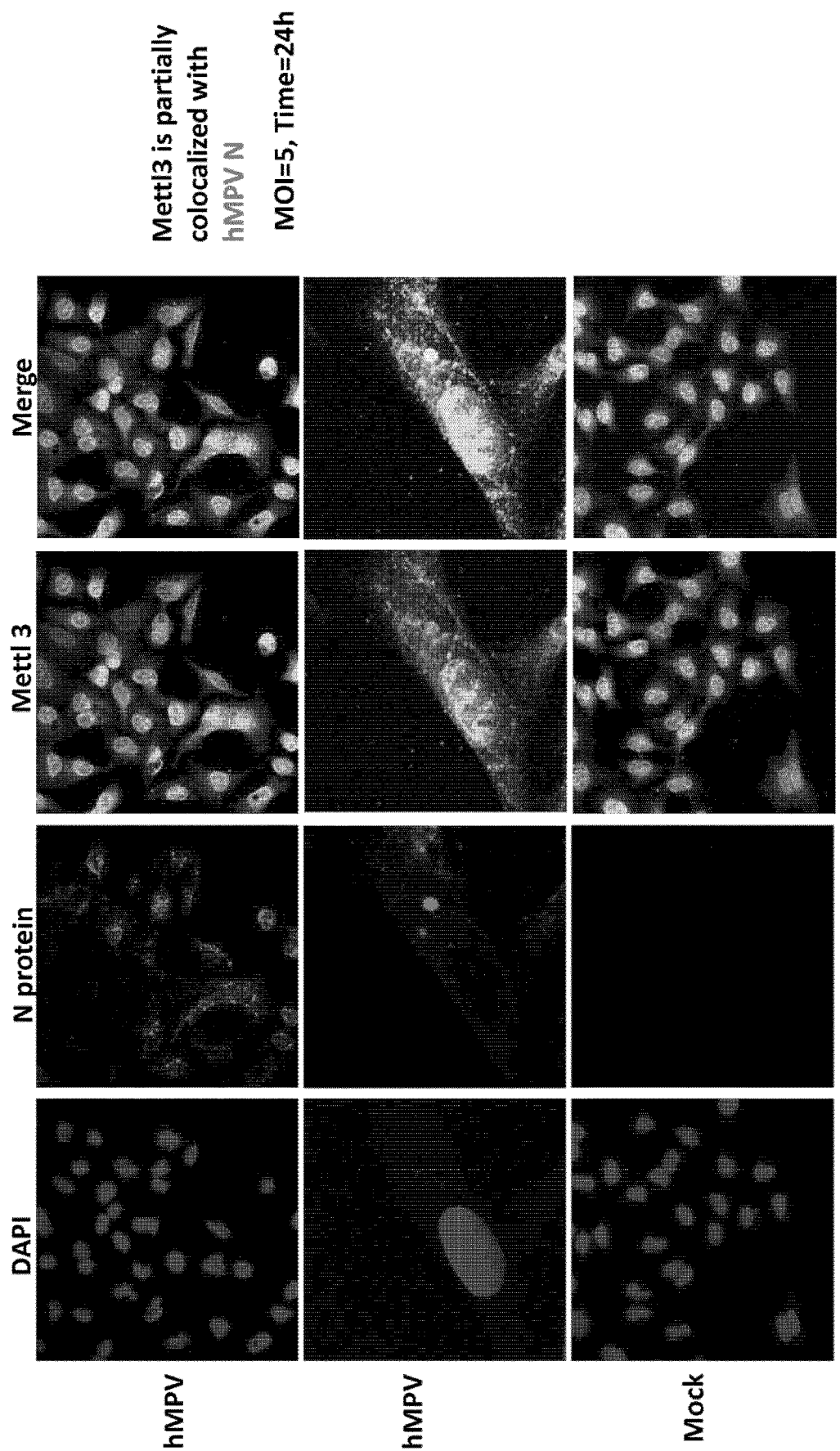
Figure 48:
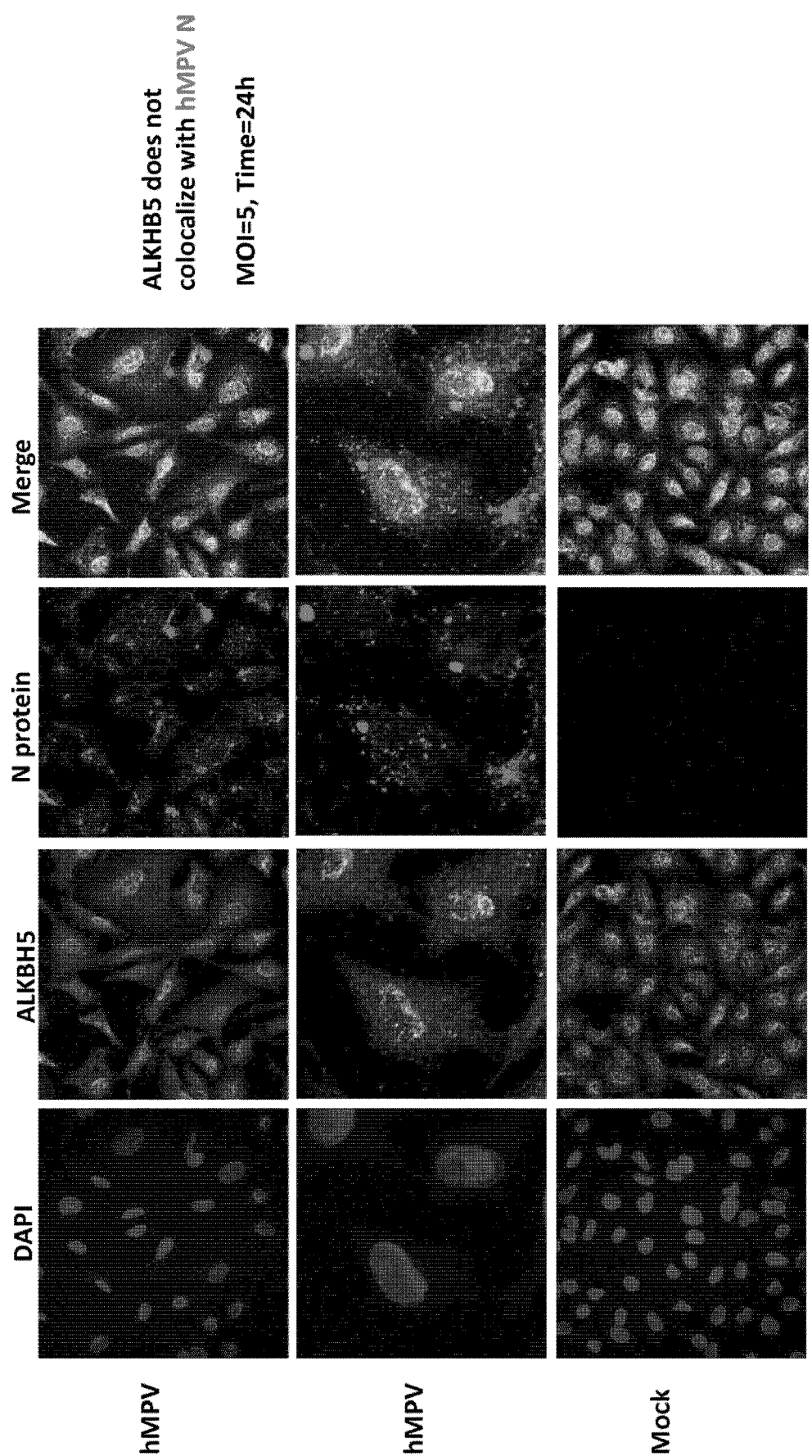
FIG. 48. The effects of hMPV infection on distribution of m$^6$A eraser proteins in cells. A549 cells were infected by rhMPV at an MOI of 5.0. At 24 h post-infection, mock- or rhMPV-infected cells were stained with anti-ALKBH5 antibody and anti-hMPV N protein antibody, and were analyzed by confocal microscope. Nuclei were labeled with DAPI. Representative results from three independent experiments are shown.
Figure 49A:
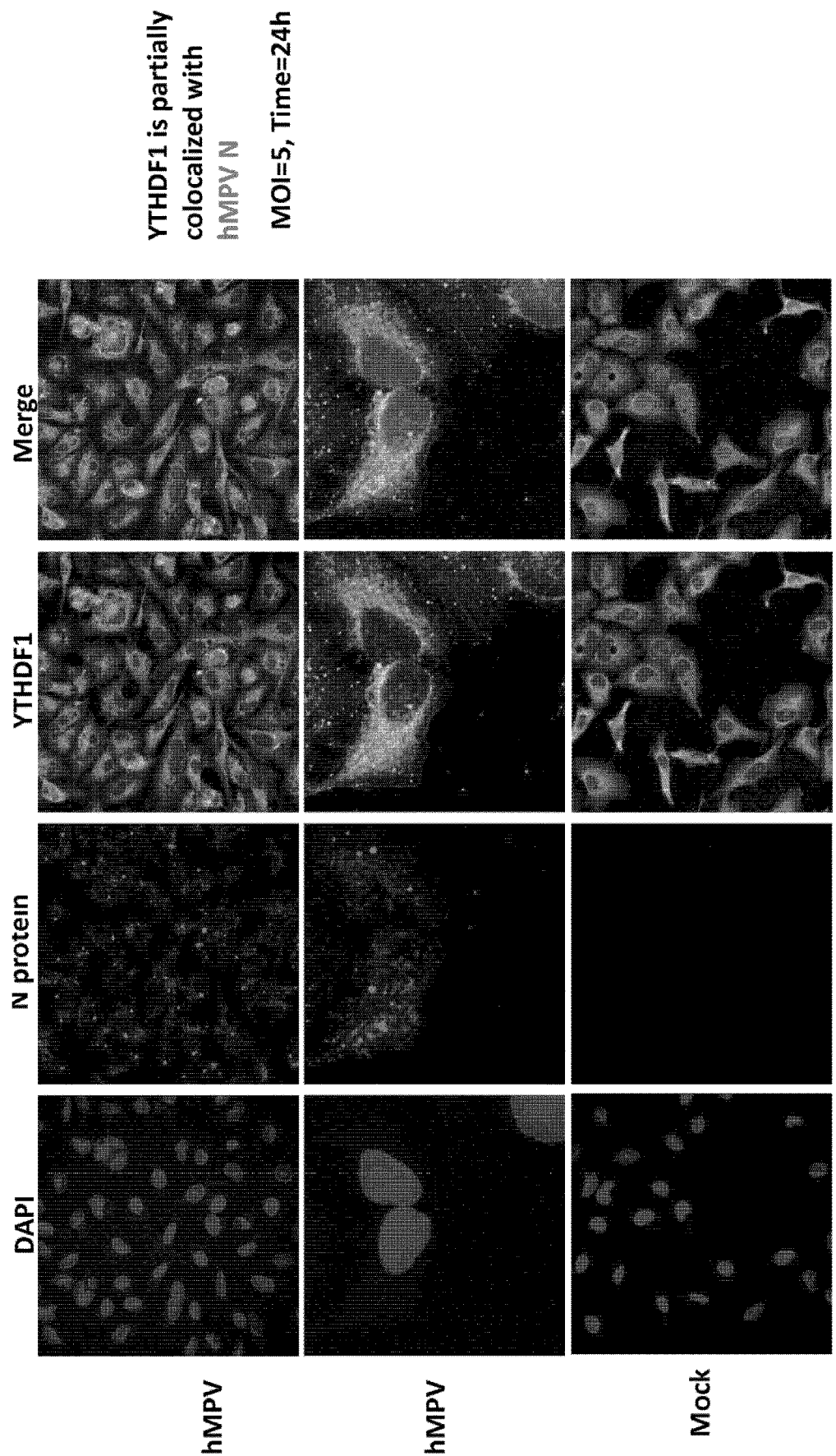
FIG. 49A-C. Distribution of m$^6$A reader proteins in mock and hMPV-infected A549 cells. A549 cells were infected with rhMPV at an MOI of 5.0. At 24 h post-infection, mock- or rhMPV-infected cells were stained with anti-reader or writer antibody and anti-hMPV N protein antibody, and analyzed by confocal microscopy. Nuclei were labeled with DAPI. (A) YTHDF1; (B) YTHDF2; and (C) YTHDF 3.
Figure 49B:
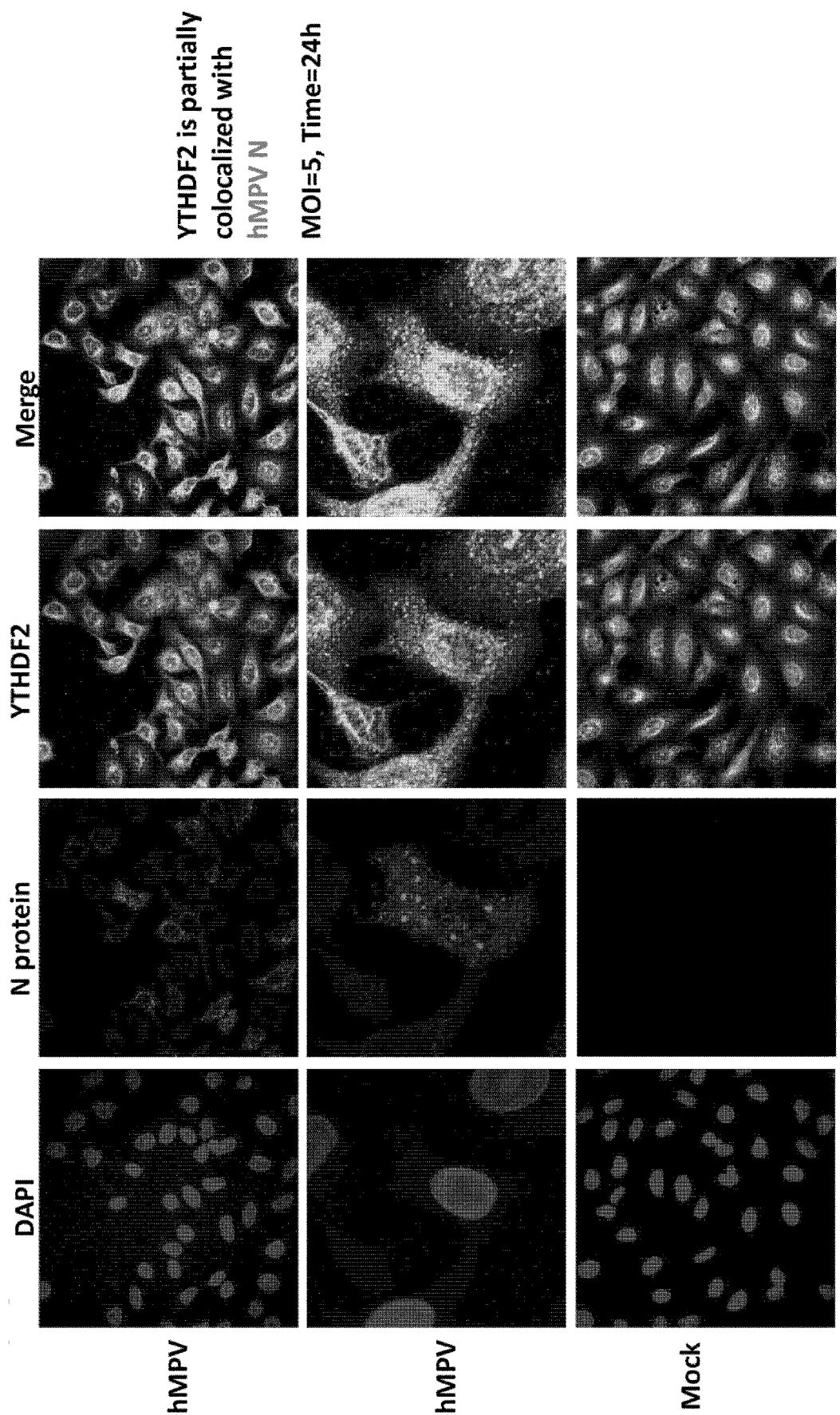
Figure 49C:
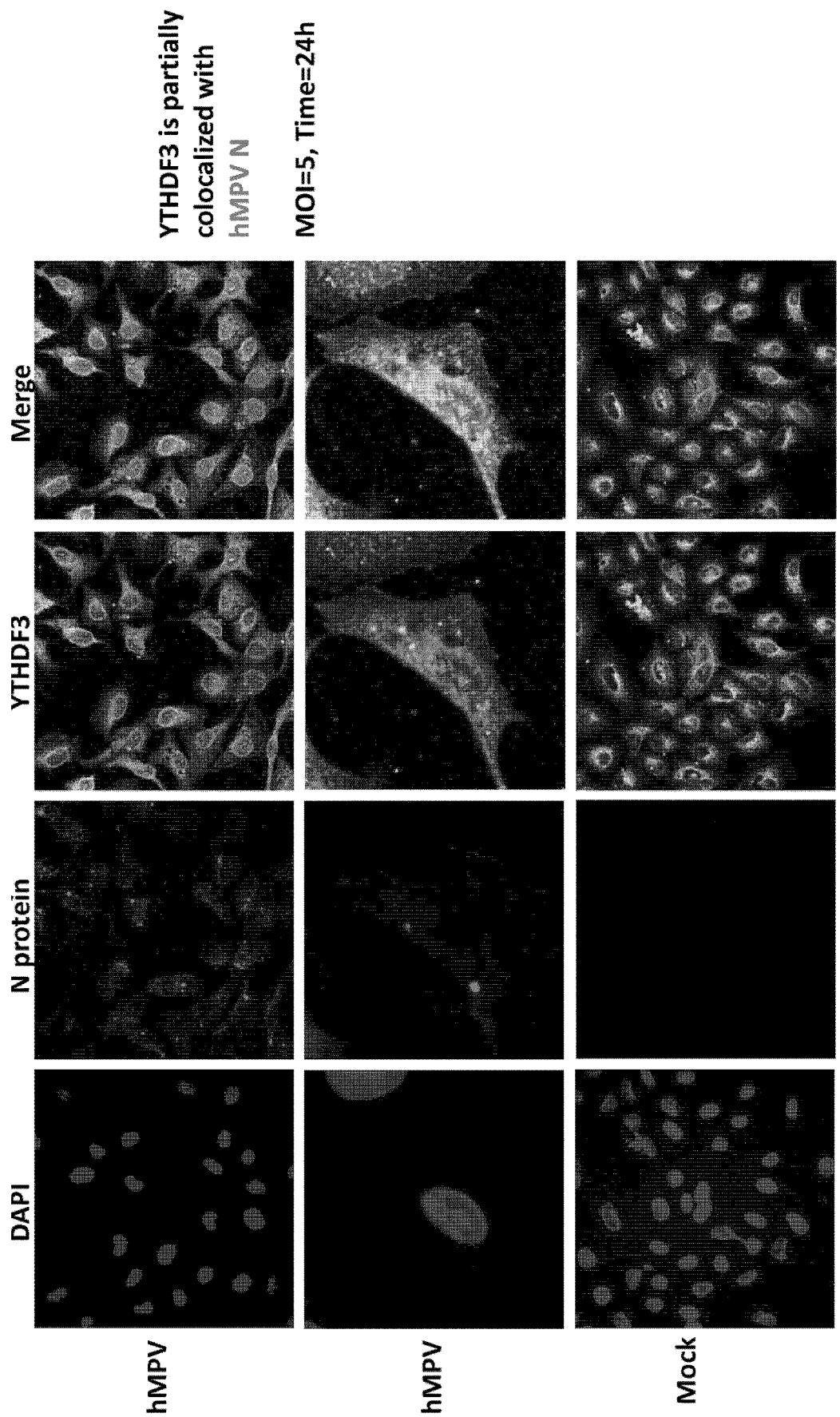
Figure 50:
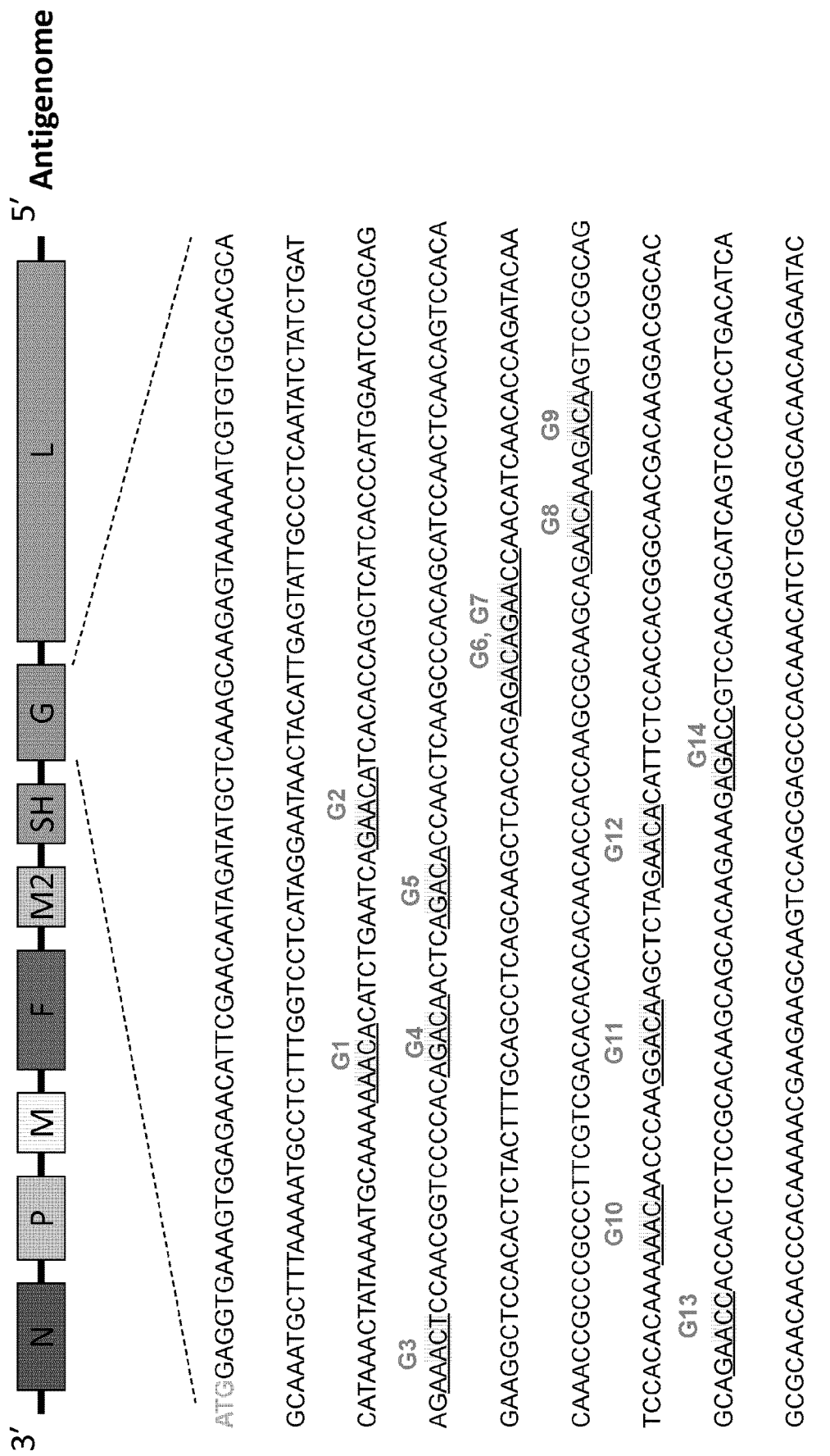
FIG. 50. Mutagenesis strategy in putative m$^6$A site in the G gene region in hMPV ant mids encoding YTHDF1, 2, 3, or YTHDC1. At 24 h post-transfection, cells were further transfected with 1 µg of pCAGGS-G. At 24 h post-transfection, total cell extracts were harvested and subjected to Western blot using antibody against hMPV G protein. (B) siRNA knockdown of $m^6A$ reader proteins reduces G expression. A549 cells were transfected with siRNA targeting YTHDF1, 2, 3, or YTHDC1. At 24 h post-transfection, cells were further transfected with 1 µg of pCAGGS-G. At 24 h post-transfection, cell lysates were harvested for Western blot analysis. (C) Transient expression of $m^6A$ writer proteins enhances G expression. A549 cells were transfected with 1 µg of plasmids encoding METTLE3 and/or METTL14. At 24 h post-transfection, cells were further transfected with 1 µg of pCAGGS-G. At 24 h post-transfection, total cell extracts were harvested and subjected to Western blot using antibody against hMPV G protein. (D) siRNA knockdown of $m^6A$ writer proteins reduces G expression. A549 cells were transfected with siRNA targeting METTLE3 and/or METTL14. At 24 h post-transfection, cells were further transfected with 1 µg of pCAGGS-G. At 24 h post-transfection, cell lysates were harvested for Western blot analysis. (E) Mutations in m6A sites in G reduces G expression. A549 cells were transfected with 1 µg of each plasmid. At 48 h post-transfection, cell lysates were harvested for Western blot analysis.
Figure 51:
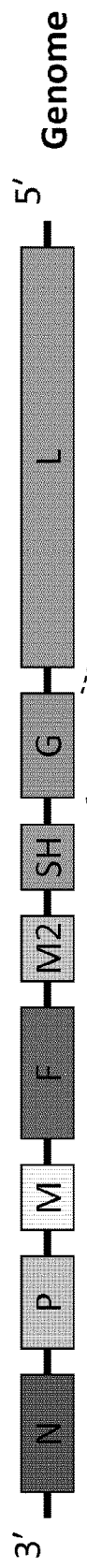
Figure 52:
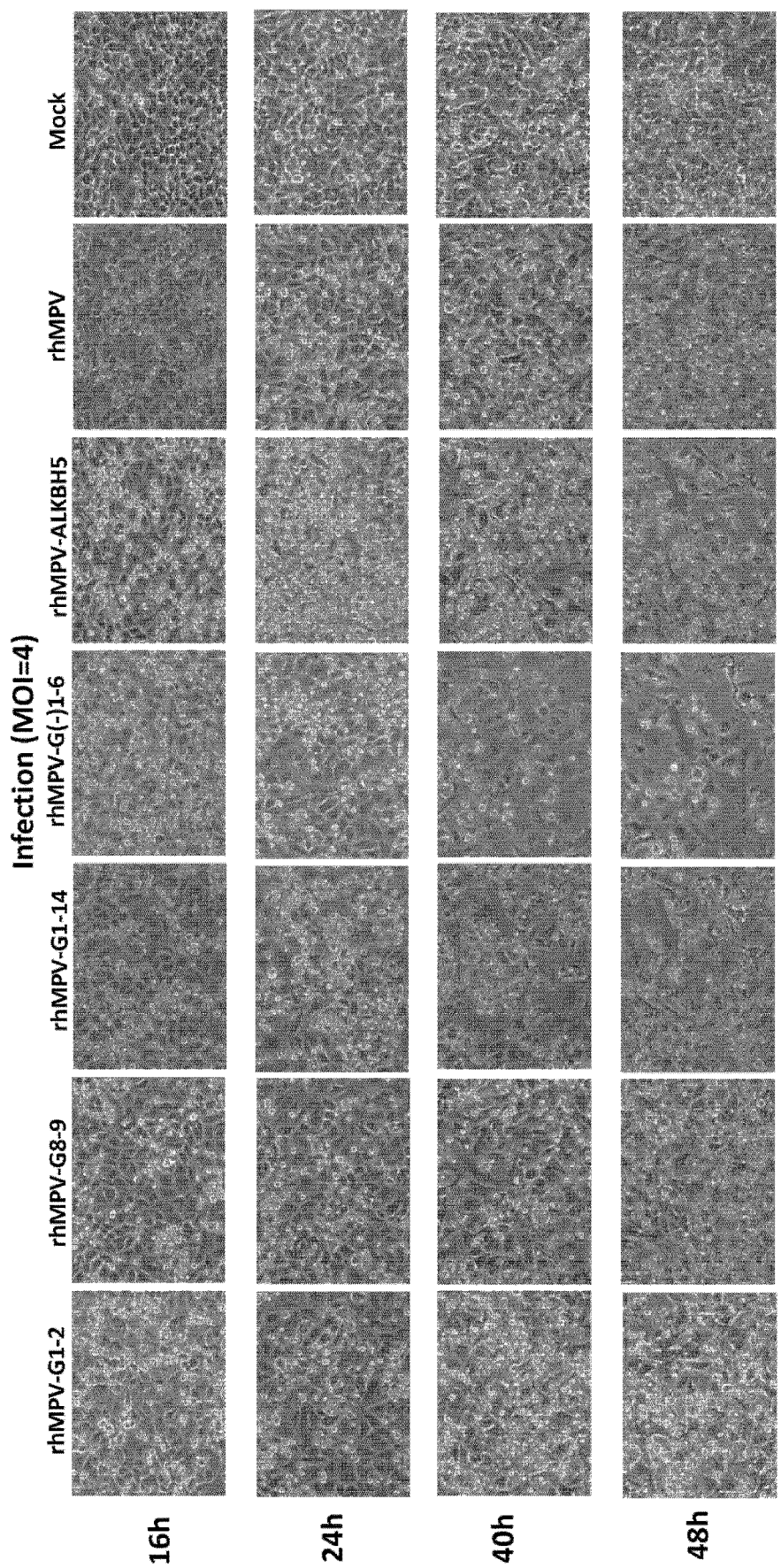
Figure 54:
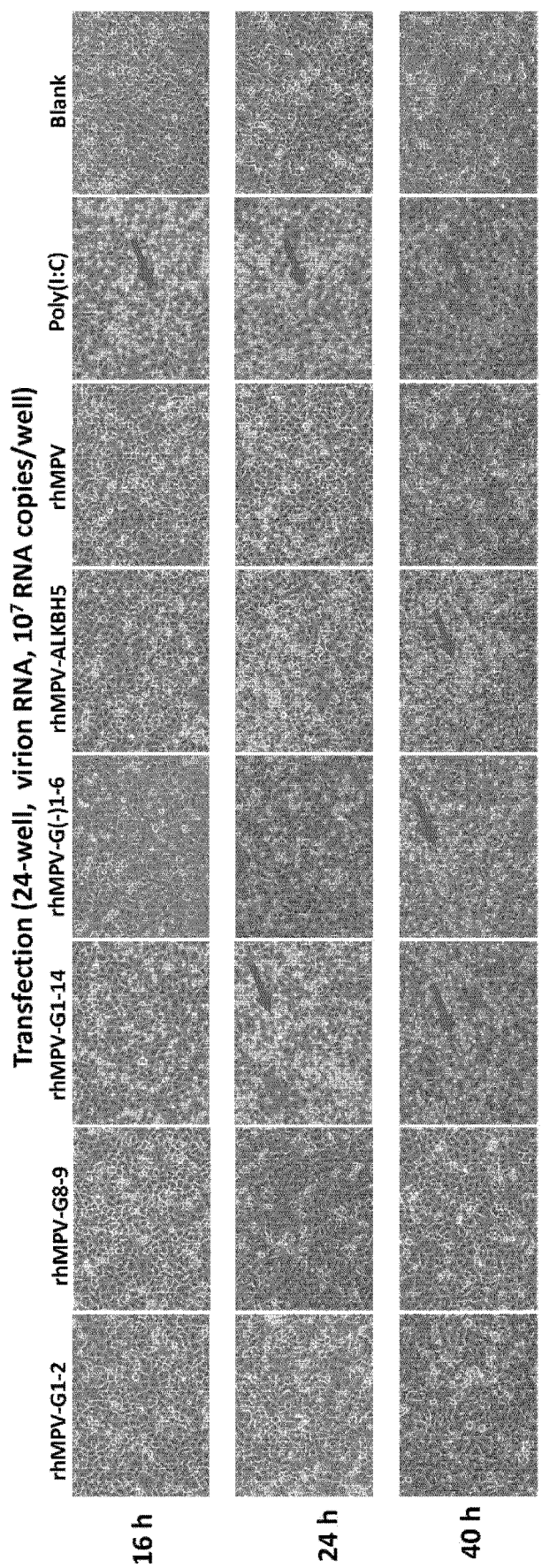

It is generally believed that host RNA methyltransferases, METTL3 and METTL14, are localized in the nucleus (25). The fact that hMPV replicates entirely in the cytoplasm suggested that these proteins may also be present in the cytoplasm. To test this possibility, hMPV-infected A549 cells were stained with antibodies against the hMPV N protein together with individual m$^6$A-related proteins, and analyzed by confocal microscopy. The majority of METTL3 and METTL14 proteins were localized in the nucleus (FIG. 30G and FIG. 47). However, a small fraction of these two proteins were detected in the cytoplasm of both mock and hMPV infected cells. This small amount of host RNA methyltransferases may be sufficient to catalyze m$^6$A modification of the hMPV RNAs. Interestingly, viral N protein and Mettl14 had a strong co-localization in inclusion bodies, the site where hMPV replication and RNP assembly occurs (FIG. 30G and FIG. 47A). In addition, N protein was partially co-localized with METTL3 (FIG. 47B). However, viral N protein had little co-localization with the eraser proteins (ALKBH5) (FIG. 48). The inventors also examined the localization of m$^6$A reader proteins in mock- and hMPV-infected cells. The majority of m$^6$A binding proteins (YTHDF1, YTHDF2, and YTHDF3) were found in the cytoplasm of both mock- and hMPV-infected cells (FIG. 49). HMPV infection did not significantly alter the distribution of m$^6$A writer and reader protein compared to mock-infected cells. In addition, viral N protein was partially co-localized with all three reader proteins (FIG. 49).

Abrogation of m$^6$A Sites in the G Gene Results in Attenuation of hMPV in Cell Culture.

Figure 34A:
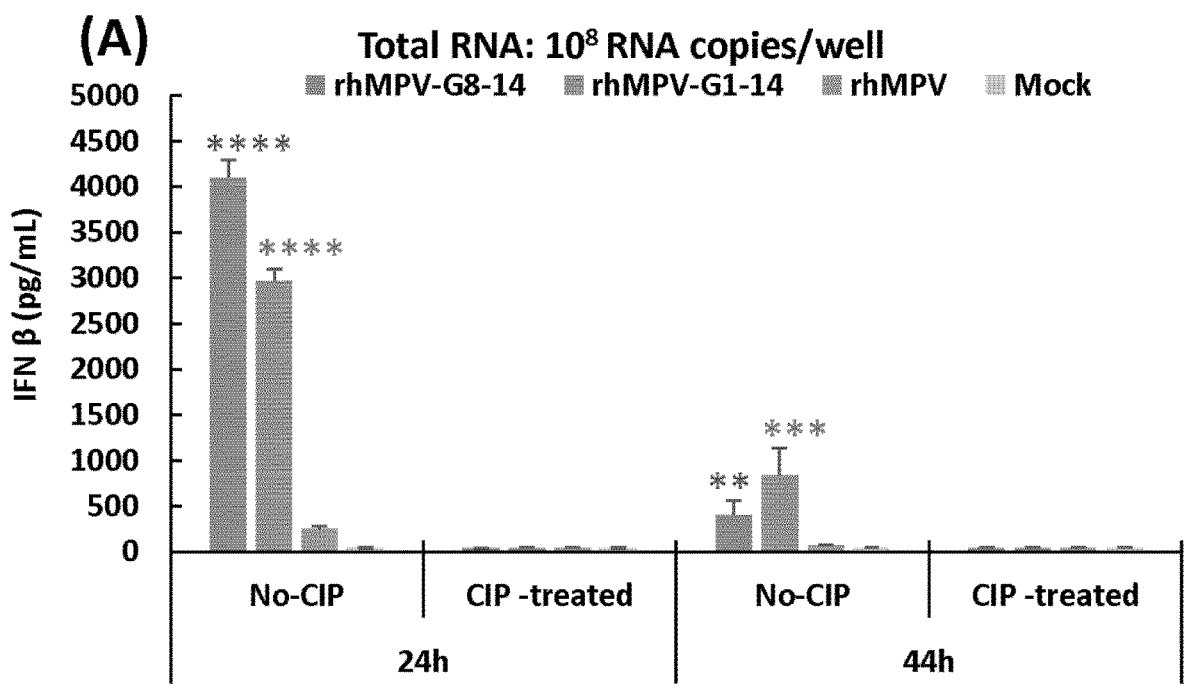

Since the m$^6$A-seq showed that the G gene has the strongest m$^6$A enrichment in the antigenome, genome, and among hMPV mRNAs, the inventors decided to focus on less viral N and G proteins were detected in the $m^6A$-deficient rhMPVs-infected cells compared to the parental rhMPV-infected cells (FIG. 32D). Thus, the $m^6A$-deficient rhMPVs had significant replication defects in A549 cells.

To determine whether these hMPV mutants are defective in $m^6A$ methylation, total RNA was purified from rhMPV-infected A549 cells and pulled down using $m^6A$ antibody-conjugated magnetic beads by the MeRIP method. For rhMPVs with mutations in the antigenome, $m^6A$ methylation of both antigenome and G mRNA should be affected. As expected, antigenome and G mRNA from $m^6A$-deficient rhMPVs had significant defects in binding to $m^6A$-specific antibody compared to those from rhMPV (FIG. 32E). As controls, no significant difference in $m^6A$ binding was observed for genome (FIG. 32E). The inventors also quantified the $m^6A$ content in virion RNA extracted from each recombinant virus by $m^6A$ RNA Methylation Assay Kit. As expected, virion RNA of rhMPV-G1-14 containing 14 mutations in $m^6A$ sites had reduced $m^6A$ content compared to virion RNA of rhMPV-G1-2 and G8-9 containing only two $m^6A$ site mutations (FIG. 32F). These results suggest that $m^6A$-deficient rhMPVs indeed produce antigenome, G mRNA, or genome that are deficient in $m^6A$ methylation.

The inventors also generated an important control virus (rhMPV-ALKBH5) that is naturally defective in $m^6A$ methylation. Briefly, A549 cells were transfected with a plasmid encoding AlkBH5 (a $m^6A$ eraser protein), followed by infection with rhMPV, and hMPV virions were harvested and purified. Virion RNA of rhMPV-ALKBH5 was significantly defective in $m^6A$ content (FIG. 32F), presumably because some of the $m^6A$ modifications in virion RNA have been removed by ALKBH5. Thus, these RNAs are 'naturally' deficient in $m^6A$ methylation, as their nucleotide sequences are not changed.

The function of $m^6A$ methylation is mediated by $m^6A$ reader proteins. Thus, the inventors also determined whether these hMPV mutants affect the binding efficiency of virion RNA to $m^6A$ reader proteins. For this purpose, RNA was isolated from highly purified virus particles. As shown in FIG. 32G and FIG. 53, the binding efficiency of antigenome from rhMPV-G1-14 and rhMPV-G8-14 to YTHDF1 and YTHDF2 was significantly reduced, only retaining approximately 12-34% of their binding relative to the rhMPV RNA. However, the antigenome of rhMPV-G1-2 and G8-9 retained 80-90% of their binding activity to YTHDF1 and YTHDF2. Therefore, the antigenome of rhMPVs with more $m^6A$ site mutations was more defective in binding to the $m^6A$ reader proteins. These results also provided additional evidence that the antigenome of $m^6A$-deficient rhMPVs is deficient in $m^6A$ methylation.

$m^6A$-Deficient rhMPVs Trigger a Significantly Higher Type I Interferon Response.

The $m^6A$-seq showed that hMPV infection caused broad alterations in the expression of genes involved in innate immunity. Thus, the inventors determined the dynamics of type I interferon (IFN-I) response of these $m^6A$-deficient rhMPVs in virus-infected cells. Briefly, A549 cells were infected by each recombinant virus at an MOI of 4.0, and IFN-α and IFN-β protein levels in cell culture supernatants were determined at 16, 24, and 40 h post-inoculation by ELISA. All $m^6A$-deficient rhMPVs induced significantly higher IFN-α (FIG. 33A) and IFN-β (FIG. 33B) than the parental rhMPV. IFN-α level gradually increased with late time points for all recombinant viruses. However, the largest differences on IFN-β level between $m^6A$-deficient rhMPVs and parental rhMPV was observed at 16 h post-infection. Interestingly, it appears that rhMPV-G1-2 and G8-9 (with 2 $m^6A$ site mutations) had stronger IFN responses than rhMPV-G1-14 (with 14 $m^6A$ site mutations). Thus, the inventors decided to further characterize their IFN responses. The inventors compared the dynamics of IFN-β response of these hMPV mutants in A549 cells at a lower MOI (1.0) (FIG. 33C). Under this condition, rhMPV-G1-14 induced significantly more IFN-β than rhMPV-G1-2 and G8-9.

The inventors also determined IFN production in a human macrophage cell line (THP-1). The increase of IFN-α and IFN-β in TPH-1 was much more dramatic than in A549 cells: a 20-50-fold increase for both IFN-α (FIG. 33D) and IFN-β (FIG. 33E) in rhMPV-G1-14 and G8-14-infected cells compared to those infected with the parental rhMPV. The inventors compared the dynamics of the IFN-β response to rhMPV-G1-14, G1-2, and G8-9 in THP-1 at MOI of 4.0 (FIG. 33D) and 1.0 (FIG. 33E). At both MOIs, rhMPV-G1-14 induced significantly higher IFN-β than rhMPV-G1-2 and G8-9 at 16 and 24 h post-infection.

The inventors next compared the IFN responses to rhMPV-G(−)1-6 and rhMPV-G1-14. It was found that rhMPV-G(−)1-6 had significantly higher IFN responses in both A549 cells (FIG. 33F) and THP-1 cells (FIG. 33G) compared to rhMPV although their IFN responses were relatively less than that of rhMPV-G1-14.

Taken together, these results demonstrate that (i) inactivation of $m^6A$ sites in the G region in antigenome and G gene in genome of hMPV results in enhanced IFN-I induction; and (ii) hMPV with natural deficiency in $m^6A$ methylation leads to an enhanced IFN-I induction.

$m^6A$-Deficient hMPV Antigenome and Genome but not the G mRNA Triggers a Higher Type I IFN Response.

To further investigate the mechanism underlying the enhanced IFN-I response associated with $m^6A$-deficient hMPVs, the inventors transfected A549 cells with RNAs isolated from virus-infected cells or virions. Under these conditions, there would be no viral replication but there would be viral protein translation. Total RNAs purified from rhMPV, rhMPV-G8-14, rhMPV-G1-14-infected A549 cells would include viral genome, antigenome and mRNAs, and host RNAs. Equal amounts of total RNA isolated from rhMPV-G8-14 and rhMPV-G1-14-infected A549 cells which are deficient in viral RNA $m^6A$ modification triggered a significantly higher IFN response than those RNAs isolated from rhMPV-infected A549 cells ($P<0.05$) (FIG. 34A). No type I interferon response was detected in A549 cells transfected with mock-infected cell RNA. This IFN production was abrogated when the RNAs were dephosphorylated by CIP treatment (FIG. 34A), consistent with the previous observation that the 5'-phosphorylated viral genome RNA is the ligand for cytoplasmic RNA sensors. Since RNAs from hMPV or hMPV-infected cells cannot initiate replication, it is likely that the $m^6A$-deficient viral RNAs contributed to the enhanced type I IFN response. Next, total RNAs from hMPV-infected cells were incubated with a polyadenylated G mRNA-specific probe, and viral G mRNA was isolated. Transfection of G mRNA samples into A549 cells only induced a minimal amount of IFN-β compared to virion RNA (FIG. 34C, compared to FIGS. 34A and B). To completely eliminate any effect of contamination of viral genome, antigenome or triphosphorylated RNA, the G mRNA was treated with CIP followed by transfection into A549 cells. As expected, G mRNA from rhMPV-G8-14, rhMPV-G1-14, and rhMPV failed to stimulate IFN induction, and there was no significant difference among these groups (P>0.05) (FIG. 34C), demonstrating that $m^6A$-deficient G mRNA did not contribute to the enhanced type I IFN response.

Figure 39A:
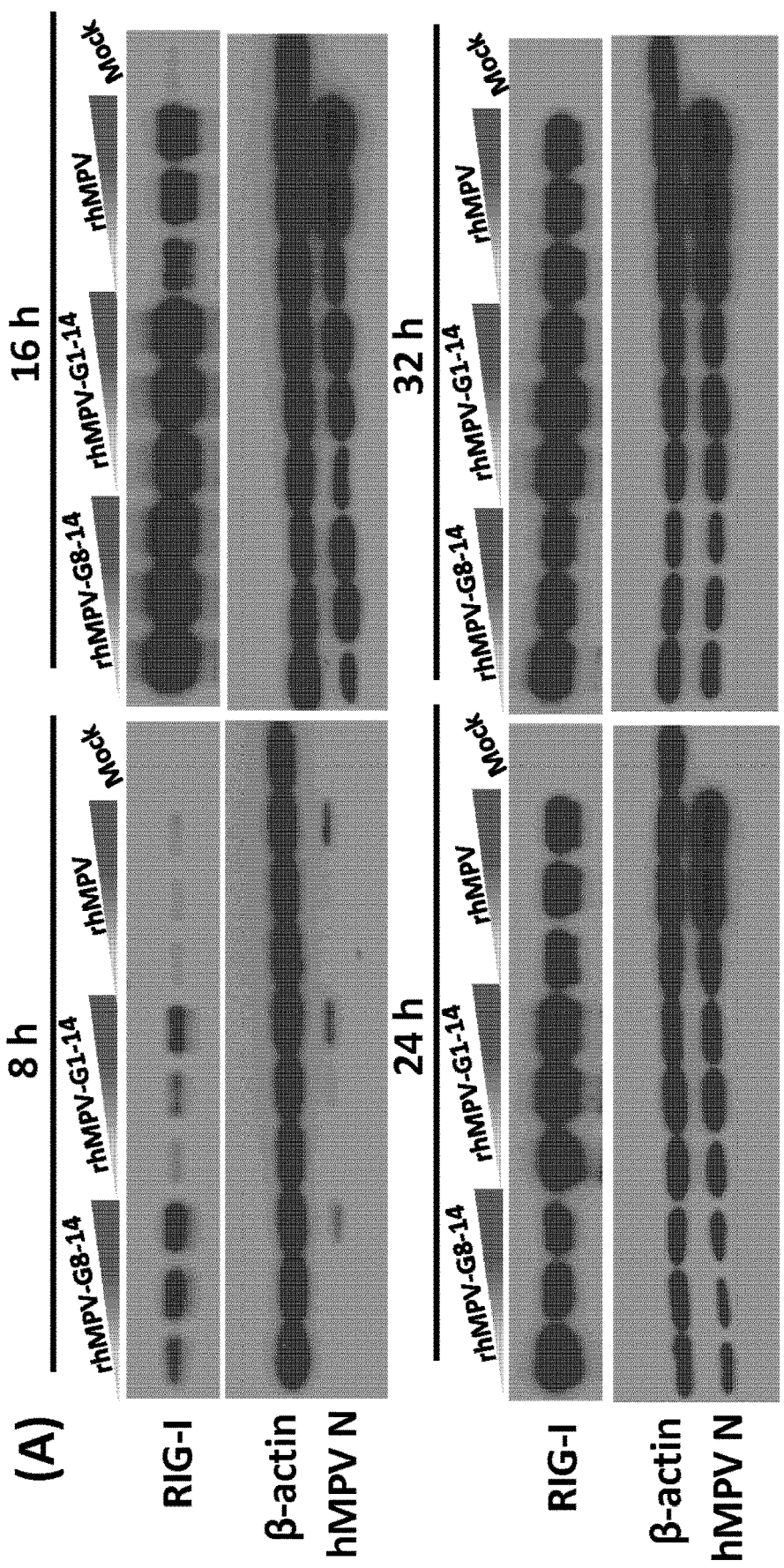
Figure 39B:
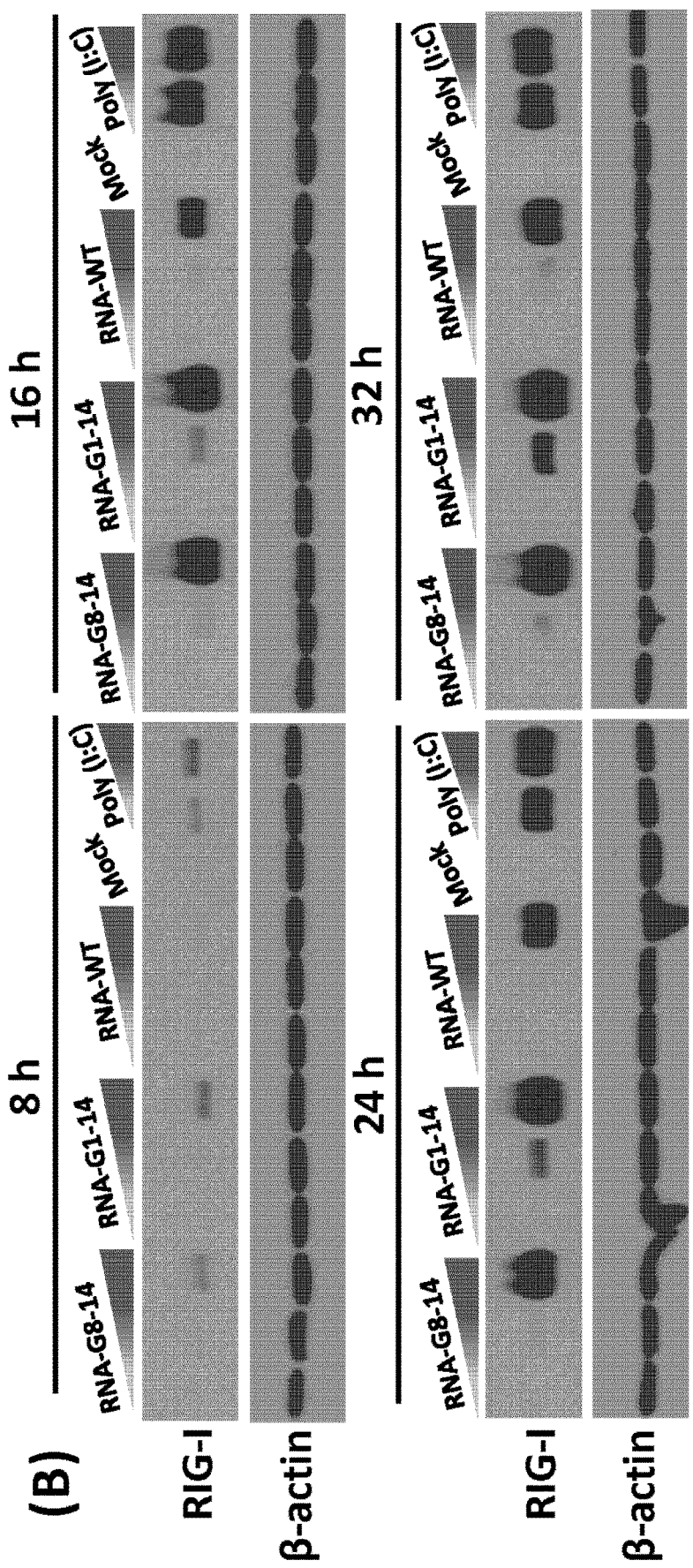
Figure 39C:
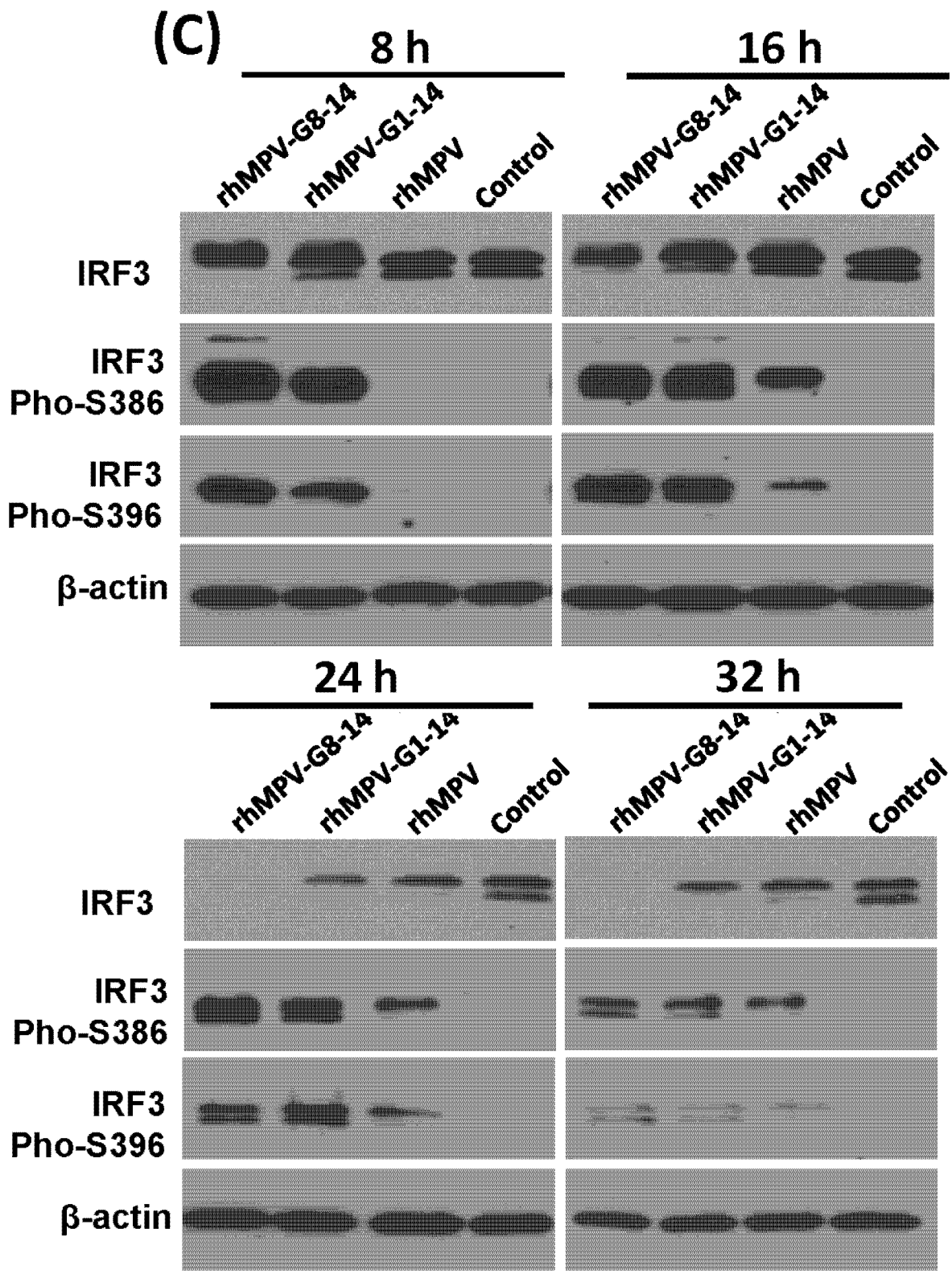
Figure 39D:
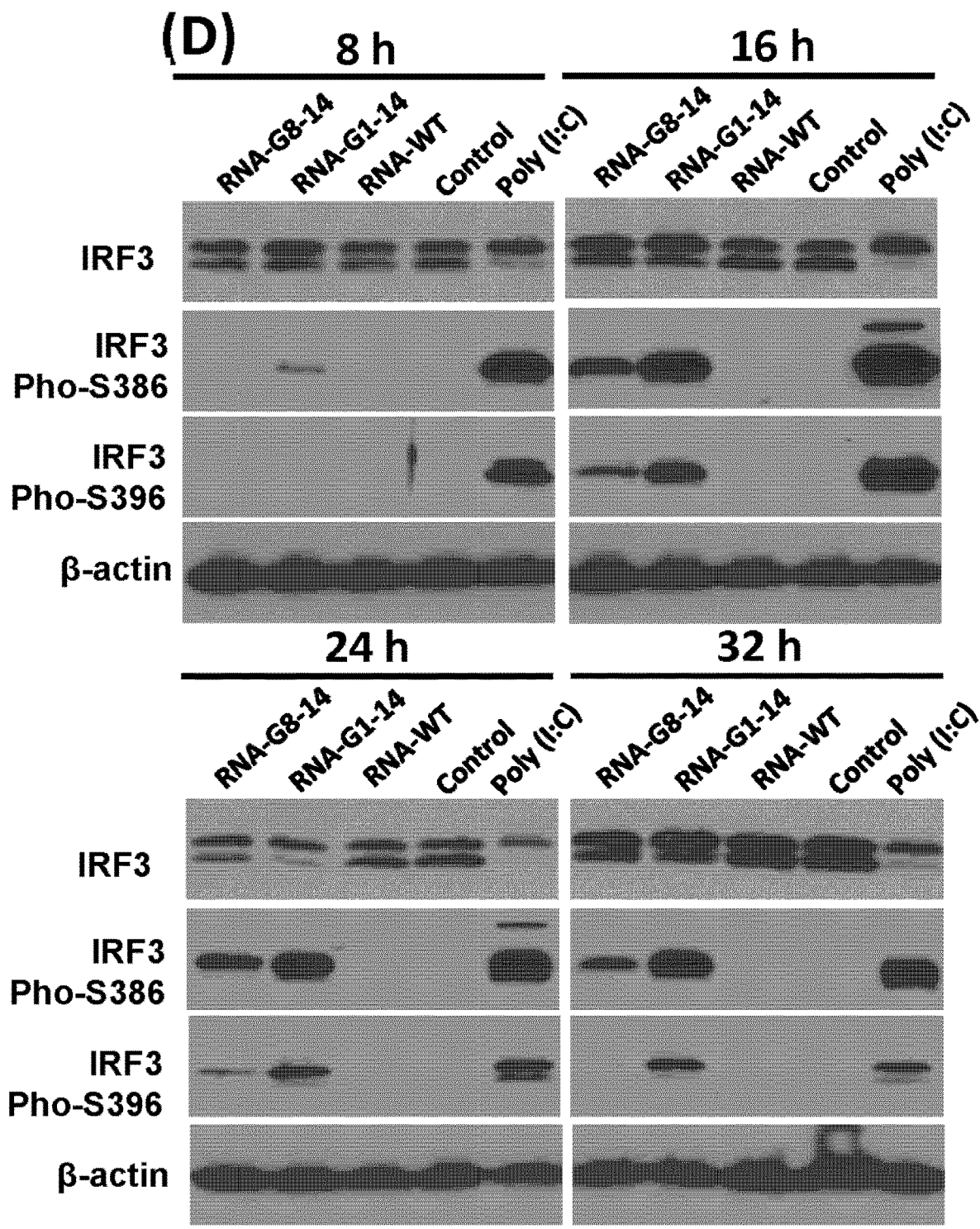

Finally, to directly demonstrate whether the $m^6A$-deficient antigenome is involved in the enhanced IFN response, the inventors isolated hMPV genome and antigenome from highly purified virions and assessed it for the induction of IFN expression. Transfection of virion RNAs of rhMPV-G8-14 and rhMPV-G1-14 stimulated significantly higher IFN induction in A549 cells than RNAs of rhMPV (P<0.05) (FIG MOI of 5.0, phosphorylation of IRF3 was measured using antibody specific to two different phosphorylation sites, S386 and S396. Phosphorylation of IRF3 was significantly higher in rhMPV-G18-14 and G1-14-infected cells than the rhMPV-infected cells (FIG. 39C). Similarly, the inventors observed a significantly higher IRF3 phosphorylation in A549 cells transfected with virion RNA derived from rhMPV-G8-14 and G1-14 than those transfected with virion RNA from rhMPV (FIG. 39D). Higher IRF3 phosphorylation at S386 and S396 were also observed for rhMPV-G (−)1-6 and rhMPV-ALKBH5 compared to rhMPV (FIG. 39G). In addition, CIP treatment of virion RNA of rhMPV-G8-14, G1-14, and rhMPV completely abolished IRF3 phosphorylation (FIG. 39F), which is consistent with the results that CIP treatment abolished RIG-I expression and IFN production. Thus, these results showed that $m^6A$ deficient hMPVs led to a significantly higher amount of IRF3 phosphorylation, which is consistent with the fact that they induced higher expression of type I IFN.

Enhanced Recognition of $m^6A$-Deficient Antigenome by Cytoplasmic RNA Sensor RIG-I.

The inventors next directly compared the binding affinity of $m^6A$-containing and -deficient antigenome to RIG-I protein. The inventors first used biotinylated virion RNA to pull down endogenously expressed RIG-I in A549 cell extract. To do this, 109 copies of virion RNA with or without CIP treatment was biotinylated and subsequently conjugated to the Streptavidin beads. The RNA-associated beads were washed three times and incubated with A549 cell lysates containing endogenously overexpressed RIG-I. RIG-I that co-isolated with the biotinylated RNA via Streptavidin beads was detected by Western blotting. As shown in FIG. 40A, virion RNA of rhMPV-G8-14 and rhMPV-G1-14 pulled down significantly more RIG-I protein compared to virion RNA of rhMPV. After removal of triphosphate by CIP, virion RNA from rhMPV and rhMPV mutants failed to pull down RIG-I. This result demonstrated that $m^6A$-deficient virion RNA enhanced the ability to pull down RIG-I protein.

As a complementary approach, the inventors used RIG-I protein to pull down virion RNA. To do this, total cell lysates from A549 cells overexpressing Flag-tagged RIG-I was incubated with anti-Flag M2 magnetic beads. The RIG-I conjugated magnetic beads (FIG. 40B) were further incubated with $2\times10^8$ copies of virion RNA (either with or without CIP treatment) or $2\times10^9$ copies of N or G mRNA. The beads were washed three times and RNA bound to the RIG-I conjugated-beads was quantified by real-time RT-PCR. Antigenome (without CIP) of rhMPV-G1-14 and rhMPV-G8-14 had approximately 90- and 33-fold increases in binding to RIG-I compared to those of rhMPV (FIG. 40C). After removal of the triphosphate by CIP, the binding of antigenome to RIG-I was significantly abrogated, consistent with the fact that triphosphorylated RNA is the ligand for RIG-I (FIG. 40C). As controls, the capped viral mRNAs (N and G) had a minimal level of binding to RIG-I. In addition, N and G mRNAs from rhMPV-G1-14 and rhMPV-G8-14 had a similar level of binding efficiency compared to those of rhMPV (FIG. 40C). This observation is in agreement with the fact that capped mRNA is not recognized by RIG-I. Therefore, these results demonstrated that $m^6A$-deficient antigenome RNA significantly increases binding affinity to RIG-I.

To further confirm that $m^6A$-deficient RNA has an increased binding affinity to RIG-I, the inventors performed an in vitro RNA competitive binding assay. Briefly, highly purified RIG-I protein (FIG. 40D) were incubated with virion RNA mixture consisting of different ratios of biotinylated rhMPV1-14- and rhMPV-RNA (conjugated to Dynabeads® MyOne™ Streptavidin C1 beads) in the presence of AMP-PNP, an analogue of ATP. The beads were washed three times and subjected to Western blot against RIG-I. As shown in FIG. 40E, the amount of pulldown RIG-I increased when more $m^6A$-deficient RNA (rhMPV-G1-14) was used in the competition assay.

$m^6A$-Deficient Virion RNA Facilitates RIG-I Conformational Changes.

To gain further mechanistic insight into how $m^6A$-deficient RNA leads to RIG-I mediated IFN signaling, the inventors examined the conformational changes of RIG-I upon binding to RNA ligand. The RIG-I protein is comprised of three major domains, the caspase activation and recruitment domains (CARDs), a helicase domain (Helicase) that binds to ATP and interacts with RNA, and a C-terminal domain (CTD) which is a triphosphate recognition and RNA binding domain (58) (FIG. 41A). In the absence of ligand RNA, RIG-I is in an autorepressed conformation (FIG. 41B). Upon binding of the 5'ppp-RNA ligand to the RIG-I CTD, it enables subsequent ATP binding and hydrolysis and helicase:RNA interactions (59). This induces a RIG-I conformational change that releases the CARDs for K63-linked polyubiquitination and binding of unanchored K63-linked ubiquitin chains (59). These combined activities result in the interaction of CARDs with the adapter protein MAVS, causing MAVS oligomerization and subsequent downstream signaling (FIG. 41B).

The inventors hypothesized that $m^6A$-deficient hMPV RNA facilitates the RIG-I conformational change for downstream signaling. To test this hypothesis, the inventors adopted 30 limited proteolysis of RIG-I:RNA complexes using trypsin, which has been often used for examining the RIG-I conformational changes (60, 61). To do this, excess hMPV virion RNA (with or without $m^6A$ methylation) and AMP-PNP were added to highly purified RIG-I protein and the mixtures were incubated at 37° C. for 30 min to allow RIG-I:RNA complexes to form. Subsequently, trypsin was added to the mixture to partially digest the complexes. At different time points, the protease activity was stopped by adding SDS loading buffer. Tryptic protein fragments were separated by SDS-PAGE, and RIG-I-specific fragments were detected by Western blot using an anti-helicase domain antibody against RIG-I (Abcam). As shown in FIG. 41C, in the absence of ligand RNA, trypsin treatment of the full-length RIG-I protein (approximately 110 kDa) yielded a 55-kDa RIG-I fragment (helicase domain), representing the trypsin sensitivity of autorepressed RNA-free RIG-I conformation. As positive controls, trypsin treatment of poly (I:C) bound RIG-I yielded an 80-kDa fragment (CARD-Helicase domain) which represents the trypsin resistance of the RNA-bound RIG-I (FIG. 41D). Next, the inventors compared the trypsin sensitivity of RIG-I upon binding of virion RNA for each of the hMPV mutants. As shown in FIG. 41E, RNA of rhMPV-G1-14 and G8-14 yielded significantly more 80-kDa fragment than RNA of rhMPV-G1-2, G8-9, or rhMPV. In addition, the inventors performed a competition assay in which different ratios of RNAs rhMPV-G1-14 and rhMPV were mixed and incubated with RIG-I and AMP-PNP, followed by trypsin treatment. The RIG:RNA mixture containing more rhMPV-G1-14 RNA yielded significantly more of the trypsin-resistant 80-kDa RIG-I fragment (FIG. 41F). Collectively, these data suggest that the 5'ppp-on the genome is essential for RIG-I binding, but the $m^6A$-deficient virion RNA either enhances RIG-I binding or facilitates the conformational change of RIG-I in the RIG-I:RNA complex which is known to enhanced downstream IFN induction.

Restoration of the Replication of m⁶A-Deficient rhMPVs in RIG-I and MAVS Knockout A549 Cells.

Figure 56:
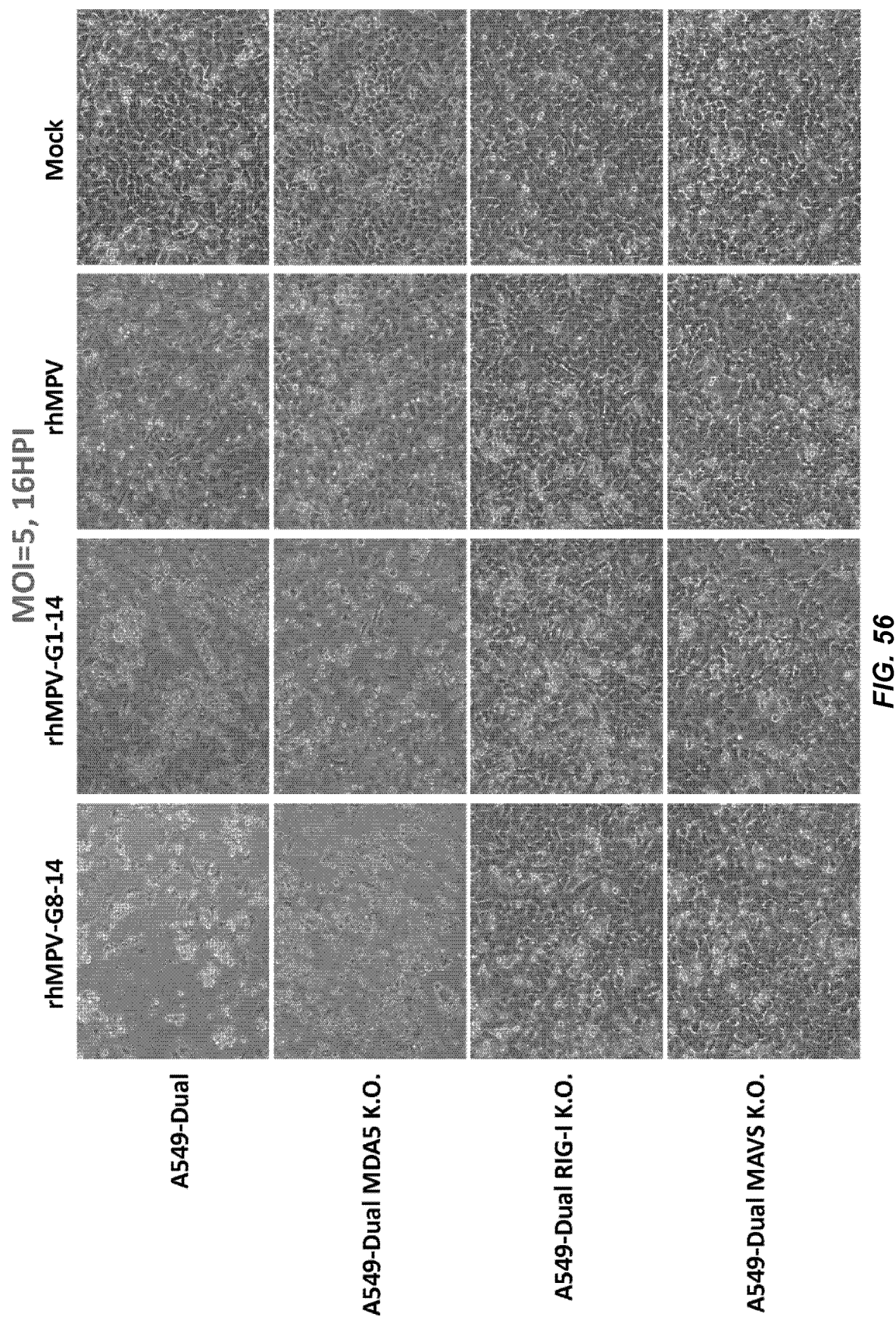

If RIG-I is indeed involved in recognition of nonself RNA, the growth of m⁶A-deficient rhMPVs should be restored when RIG-I and its adaptor MAVS proteins are depleted. Thus, the inventors performed a single step growth curve of m⁶A-deficient rhMPVs in wt, MDA5, RIG-I, and MAVS knockout A549 cells. Compared to rhMPV, both rhMPV-G1-14 and rhMPV-G8-14 had a significant defect in growth in wild type A549 cells (FIG. 42A). Interestingly, the growth of rhMPV-G1-14 was restored in RIG-I (FIG. 17C) and MAVs (FIG. 42D) knockout A549 cells although it had a delay in replication kinetics in early time points. Also, the growth of rhMPV-G8-14 was partially restored in RIG-I and MAVS knockout A549 cells. In contrast, the growth of neither rhMPV-G1-14 nor rhMPV-G8-14 was restored in MDA5 knockout cells (FIG. 42B), similar to the wt cell line. Interestingly, rhMPV-G1-14 and rhMPV-G8-14 displayed earlier cell death in wild type and MDA5 knockout A549 cells than in RIG-I and MAVs knockout A549 cells (FIG. 56). These results further support the notion that RIG-I but not MDA5 is involved in recognition of m⁶A-deficient antigenome RNA.

Contribution of Other Functions of m⁶A Methylation to the Attenuated Phenotype of m⁶A-Deficient rhMPVs.

Although the peak titer of m⁶A-deficient hMPVs can be rescued in RIG-I and MAVS knockout cells, m⁶A-deficient hMPVs exhibited delayed replication kinetics at early time points. This suggests that innate sensing may not be the only factor which leads to the attenuation of m⁶A-deficient hMPVs. Previous studies have shown that m⁶A plays important roles in RNA stability and mRNA translation (29, 31). During the experiment, the inventors found that virion RNA extracted from m⁶A-deficient hMPVs was easily degraded when the RNA samples were stored in −80° C. These degraded RNA samples failed to trigger a higher IFN response, as fresh RNA did (data not shown), suggesting that viral m⁶A is important for RNA stability.

In hMPV-infected cells, the inventors found that G protein synthesis from m⁶A-deficient hMPVs decreased compared to rhMPV, suggesting that the m⁶A in G mRNA may be important for its stability or translation. To further test this hypothesis, the inventors first determined the impact of G protein expression by overexpression or knockdown of host m⁶A writer and reader proteins. To do this, pCAGGS expressing the hMPV G gene was constructed (pCAGGS-G). A549 cells were transfected with plasmids encoding YTHDF1-3, YTHDC1, METTL3, and METTL14, and 20 h later were transfected with pCAGGS-G. Interestingly, G protein expression dramatically increased in A549 cells that transiently overexpress m⁶A reader proteins (FIG. 57A) and writer proteins (FIG. 57C). Conversely, G protein expression was significantly reduced when individual, endogenous reader (YTHDF1-3 and YTHDC1) (FIG. 57B) and writer (METTL3 and METTL14) (FIG. 57D) were knocked down by siRNA. Thus, m⁶A reader and writer proteins increase the expression of hMPV G protein from m⁶A-modified G mRNA. As a second approach, the inventors mutated m⁶A sites in the G mRNA and determined the G protein expression. These pCAGGS-G mutants were transfected into A549 cells and the effect of these mutations on G protein expression was analyzed by Western blot. Mutants pCAGGS-G1-14 and pCAGGS-G8-14 had a significant reduction in G protein expression compared to pCAGGS-G (FIG. 57E). Thus, abrogation of m⁶A site in G mRNA diminished G protein translation. Taken together, m⁶A in virion RNA plays a major role in the innate immune recognition and RNA stability whereas m⁶A in mRNA is important for protein translation.

m⁶A-Deficient rhMPVs Induces Higher Type I Interferon In Vivo.

The m⁶A-deficient rhMPVs induced significantly higher type I IFN in cell culture infections. The inventors next determined whether they also induce higher type I IFN in vivo using cotton rats, the best available small animal model for hMPV. Six-week-old SPF cotton rats were inoculated intranasally with $2.0 \times 10^5$ PFU of rhMPV or m⁶A-deficient rhMPV mutants (rhMPV-G8-14 and rhMPV-G1-14) or PBS. At day 2 post-inoculation, cotton rats were terminated, bronchoalveolar lavage (BAL) was collected from the right lung and tested for IFN-β bioactivity. Briefly, CCRT cells were incubated with serially diluted BAL or human IFN-β, followed by infection with rVSV-GFP. The IFN-β level in BAL was calculated based on the inhibitory effect on rVSV-GFP infection using human IFN-β as the standard. Under these conditions, IFN-β bioactivity of BAL samples from rhMPV and PBS-inoculated cotton rats was below the detection limit (FIG. 43A). In contrast, IFN-β of BAL from rhMPV-G8-14 and rhMPV-G1-14 had average IFN-β bioactivity of 150.2 (P<0.0001) and 175.3 U/ml (P<0.01) respectively (FIG. 43A). This result demonstrated that m⁶A-deficient rhMPVs induced higher type I IFN responses in vivo compared to rhMPV.

m⁶A-Deficient rhMPVs are Significantly Attenuated in Replication in Cotton Rats.

The m⁶A-deficient rhMPVs were significantly attenuated in cell culture. The inventors next determined whether they are attenuated in vivo using cotton rats as a model. Six-week-old SPF cotton rats were inoculated intranasally with $2.0 \times 10^5$ PFU of rhMPV or m⁶A-deficient rhMPV mutant (rhMPV-G1-2, rhMPV-G8-9, and rhMPV-G1-14). At day 4 post-inoculation, cotton rats were terminated, and viral replication was determined. The average viral titers in lungs and nasal turbinates of rhMPV-inoculated cotton rats were $10^{5.08}$ and $10^{5.16}$ PFU/g tissue, respectively. Recombinant rhMPV-G1-2, rhMPV-G8-9, and rhMPV-G1-14 had 1.80, 2.03, and 2.7 log virus reductions in lungs compared to rhMPV, respectively (FIG. 43B). Particularly, rhMPV-G1-14 was only slightly above the detection limit for virus replication in the lungs. These m⁶A-deficient hMPV mutants also had significant reductions (0.30-0.71 log, P<0.05) in viral replication in the nasal turbinates of cotton rats although the level of reduction was less than in the lungs (1.8-2.7 log) (FIG. 43B). No infectious virus was detected in either nasal turbinates or lungs in mock-infected cotton rats. These results demonstrated that m⁶A-deficient rhMPVs are more attenuated in replication in the lower respiratory tract than in the upper respiratory tract of cotton rats. The lungs of hMPV-infected cotton rats were also examined histologically (FIG. 43C). The parental hMPV caused moderate histologic lesions characterized by interstitial pneumonia, mononuclear cell infiltration, and edematous thickening of the bronchial submucosa. In contrast, fewer histological changes were found in the lungs of cotton rats infected with m⁶A-deficient rhMPVs. Thus, m⁶A-deficient rhMPVs were less pathogenic in cotton rats. Collectively, these results demonstrate that depletion of m⁶A sites in viral G gene significantly decreased hMPV replication and pathogenesis in vivo.

m⁶A-Deficient rhMPVs Provided Complete Protection Against hMPV Infection.

Figure 43D:
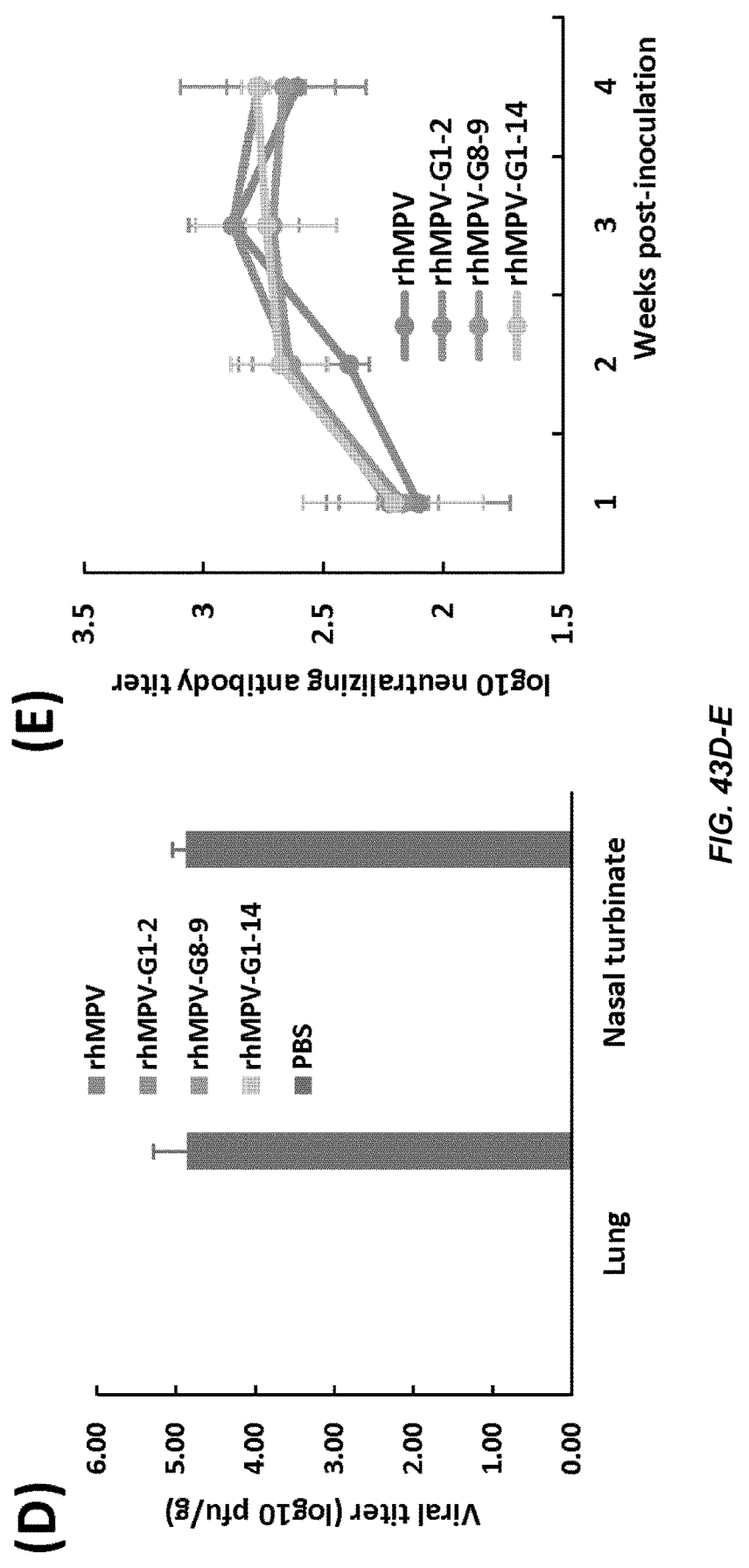

Since m⁶A-deficient rhMPVs are significantly attenuated in vitro and in vivo, the inventors next determined whether they were immunogenic in cotton rats. Briefly, 6-week-old female cotton rats were intranasally immunized with 2.0× $10^5$ PFU of rhMPV or $m^6$A-deficient rhMPV mutants. After immunization, weekly serum was collected from each cotton rat. At week 4 post-immunization, cotton rats were challenged with 2.0×$10^5$ PFU of rhMPV, terminated at day 4 after challenge, and viral titers in lungs and nasal turbinate were determined. For the unvaccinated challenged group, $10^{4.86}$ and $10^{4.87}$ PFU/g tissue were detected in the lungs and nasal turbinates, respectively (FIG. 43D). In contrast, cotton rats immunized with rhMPV, rhMPV-G1-2, rhMPV-G8-9, and rhMPV-G1-14 were completely protected from virus replication in both lungs and nasal turbinates (FIG. 43D). Also, rhMPV-G1-14 triggered significantly higher neutralizing antibody titers at weeks 1 and 2 than parental rhMPV (P<0.05) (FIG. 43E). At week 4, all $m^6$A deficient rhMPVs had levels of antibody similar to rhMPV (FIG. 43E). Thus, $m^6$A-deficient rhMPV retained wild type or even higher levels of immunogenicity and provided complete protection against hMPV infection.

C. Discussion

The most prevalent epigenetic modification in all types of RNAs, rRNA, tRNA, snRNA, and mRNAs is $m^6$A methylation. Viruses are obligatory intracellular parasites; their RNAs are also $m^6$A methylated during replication in host cells. The presence of $m^6$A in viral mRNA clearly enhances translation and mRNA stability (29, 31). However, the biological function of $m^6$A in the viral genome and its replicative intermediate RNA has been mysterious. Using hMPV as a model, the inventors have demonstrated that $m^6$A methylation of the antigenome and genome acts as a molecular signature for discriminating self from nonself RNA through the RNA sensor RIG-I. Several lines of evidence support this finding. First, the hMPV genome, antigenome, and mRNAs acquire $m^6$A methylation during infection and hMPV infection enhances the expression of genes involved in innate immunity. Second, $m^6$A methylation enhances hMPV replication and gene expression, and $m^6$-deficient hMPVs are attenuated. Third, $m^6$A-mutated rhMPVs, naturally $m^6$A-deficient hMPV, and their antigenome and/or genome RNA triggered a higher type I IFN response. Fourth, $m^6$A methylation protects the antigenome and genome from recognition by RIG-I thereby inhibiting RIG-I-dependent production of type I interferon in virus-infected cells and virion RNA-transfected cells. Fifth, $m^6$A methylation of the viral antigenome and genome contributes to the evasion of the interferon-mediated restriction of viral replication. Finally, the deficiency of $m^6$A methylation in the viral antigenome and genome RNA enhances the activation of the RIG-I pathway including RIG-I expression, RIG-I binding affinity, RIG-I conformational change, and IRF3 phosphorylation. The replication of $m^6$A-deficient rhMPVs was restored when the RIG-I and MAVs signal pathways were knocked out. The data demonstrate that hMPV acquires $m^6$A methylation in antigenome and genome as a means of mimicking host RNA to avoid the detection of innate immunity.

Figure 44:
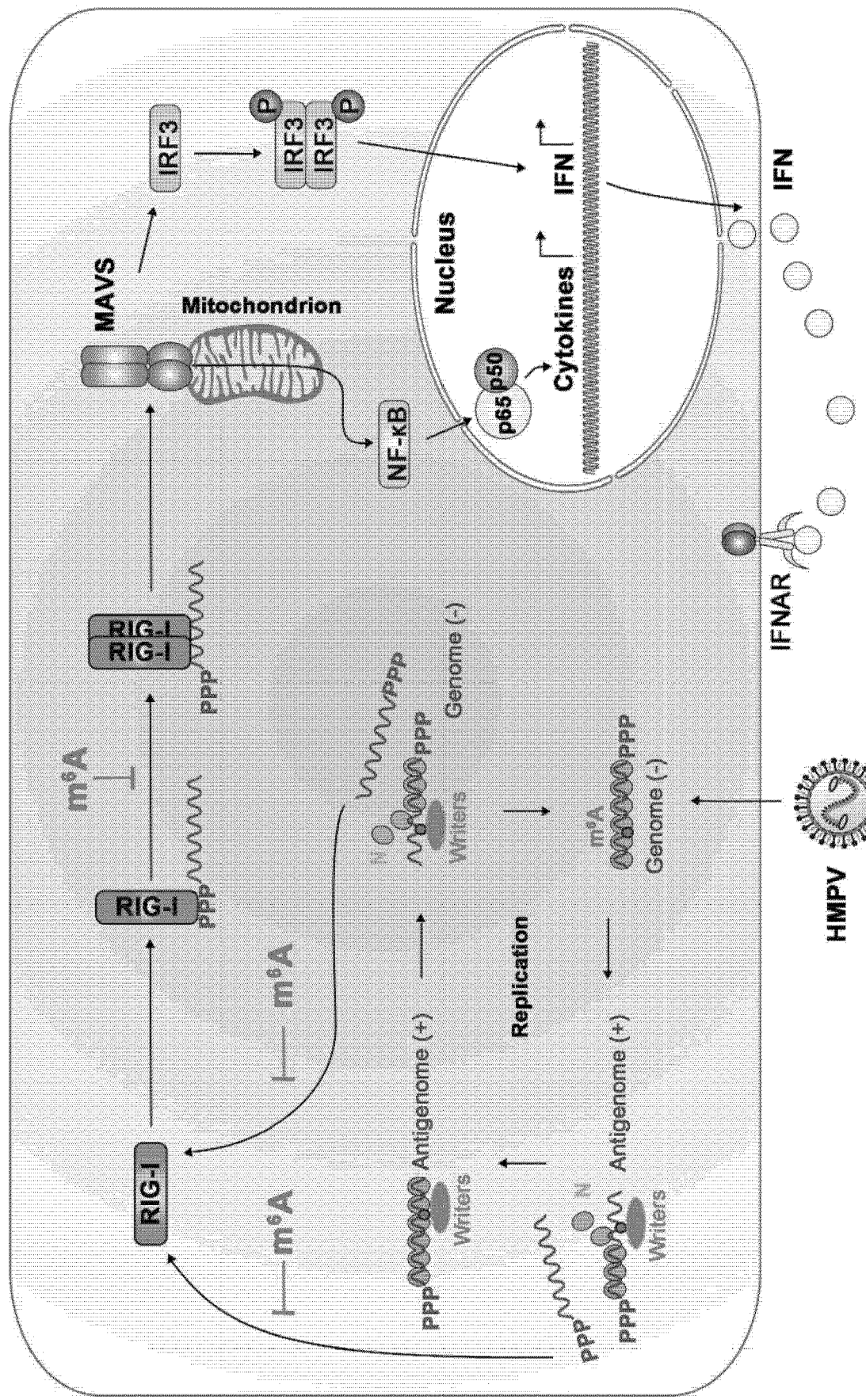
FIG. 44. Model for RIG-I mediated IFN signaling pathway. Upon hMPV entry, the RNP complex is delivered into the cytoplasm where RNA synthesis and viral replication occur. During replication, the RdRP initiates at the extreme 3' end of the genome and synthesizes a full-length complementary antigenome, which subsequently serves as template for synthesis of full-length progeny genomes. The newly synthesized genome and antigenome was methylated by $m^6A$ writer proteins and encapsidated by viral N protein. Viral genome and antigenome are recognized by cytoplasmic RNA sensor RIG-I and induces signaling to the downstream adaptor protein MAVS which subsequently activates IRF3 and NF-κB pathways, leading to the production of type-I IFN and proinflammatory cytokines. The internal $m^6A$ methylation inhibits RIG-I mediated IFN signaling pathway.

A model consistent with these findings is depicted in FIG. 44. Upon virus entry, the ribonucleoprotein (RNP) complex, composed of the genome wrapped in the nucleocapsid (N) protein, associated with the viral RNA-dependent RNA polymerase (RdRP), is delivered into the cytoplasm where viral transcription and replication occur. During transcription, the RdRP sequentially transcribes the 8 viral genes into 9 mRNAs which are $m^6$A methylated and translated into 9 proteins, including the N protein. During replication, the RdRP initiates at the extreme 3' end of the genome and synthesizes a full-length complementary antigenome, which is methylated by $m^6$A writer proteins and subsequently encapsidated by soluble N protein in a helical nucleocapsid with 9 to 10 bases/rotation of the helix (62). This N-antigenomic RNA serves as template for synthesis of full-length progeny genomes, which are also $m^6$A methylated and encapsidated by soluble N protein. RNA $m^6$A methylation likely occurs prior to or concomitant with encapsidation, supported by the observation that N is partially co-localizes with METTL3 and strongly co-localizes with METTL14 in inclusion bodies where new RNP is assembled and active viral replication occurs. The antigenome and genome are 5' triphosphorylated. Those that are not $m^6$A methylated are recognized as a "nonself RNA" by RIG-I. The deficiency of $m^6$A in virion RNA induces higher RIG-I expression, an enhanced RIG-I binding affinity and an enhanced ability to trigger the conformational change in RIG-I that corresponds to enhanced signaling to the downstream adaptor protein MAVS, activating IRF3 and NF-κB pathways, leading to higher production of type-I IFN and proinflammatory cytokines. In contrast, although the wild type hMPV virion RNA can be recognized by RIG-I due to the 5'ppp, the internal $m^6$A modification appears to interfere with the high affinity binding of the RNA with the RIG-I helicase domain. Without this separate RNA interaction, the low binding affinity association with 5'ppp does not appear to efficiently induce the RIG-I mediated IFN signaling pathway. In addition, RIG-I is a 5'-triphosphate-dependent translocase, traveling from the 5'-ppp into the RNA chain to trigger oligomerization (63, 64). Recently, it was found that the translocation of RIG-I and the following RIG-I oligomerization is hindered by internal 2'-O methylation in dsRNA (65). Thus, it is likely that $m^6$A methylation may also serve as a "brake" or "throttle" to prevent RIG-I translocation and oligomerization, leading to downstream signaling (FIG. 41B).

One aspect of this scenario would seem to be unlikely, that the $m^6$A-modified genome or antigenome, tightly encapsidated by the N protein, would be accessible to RIG-I. And even if RIG-I could bind to the terminal 5'ppp, how would it be able to reach further into the RNA to find a non-methylated $m^6$A site? A more likely scenario might be that all of the genomes and antigenomes that are synthesized are not encapsidated. Particularly early in the infectious cycle, when the concentration of the N protein is low, some of these full-length RNA genomes and antigenomes may not be encapsidated, enabling RIG-I access to both the 5'ppp and RNA downstream from it. Unencapsidated full-length genome or antigenome RNAs would likely be fragile, as they are susceptible to cytoplasmic RNases. However, only a 5' fragment would be necessary to activate RIG-I in this scenario.

The $m^6$A-seq analysis showed that all three species of viral RNA are $m^6$A methylated and the strongest $m^6$A peaks are located in the G gene mRNA and the region corresponding to the G gene in both genome and antigenome, leading the inventors to mutate these $m^6$A sites. The inventors modified the positive-strand RNA, disrupting $m^6$A sites of both the G mRNA (transcription product) and antigenome (replication intermediate). The inventors also mutated the $m^6$A sites in the G gene in negative-sense genome RNA. By overexpressing $m^6$A eraser protein, the inventors generated hMPV that is naturally defective in $m^6$A methylation in its antigenome and genome. In all cases, these $m^6$A-deficient rhMPVs and their virion RNAs induced significantly higher type I IFN responses. Both genome and antigenome ssRNAs contain 5' triphosphate, a known ligand for RIG-I (4, 13). Removal of the 5' triphosphate abrogated the RIG-I expression, RIG-I binding, IRF3 phosphorylation, and IFN response of both wild type antigenome and m$^6$A-deficient antigenome, suggesting that 5' triphosphate is absolutely required for RIG-I signaling. However, when m$^6$A sites in the antigenome and genome were mutated or naturally removed by eraser proteins, the expression of RIG-I and the binding affinity of RIG-I for the m$^6$A-deficient virion RNA was significantly enhanced compared to the wild type virion RNA, leading to a higher type I IFN response. Thus, marking antigenome and genome RNA with m$^6$A methylation allows it to escape detection by RIG-I. The m$^6$A sites in both genome and antigenome are involved in innate immune recognition.

Unlike genome and antigenome, hMPV mRNAs are capped and G-N-7 and ribose 2'-O are methylated at the 5' end and the mRNA is polyadenylated at the 3' end. Neither modification is recognized by RIG-I or MDA5. Previously, it was shown that viral mRNA lacking 2'-O methylation can be detected by MDA5 and the IFIT family, highlighting that 2'-O methylation also serves as a molecular marker for host innate immunity to discriminate self from nonself mRNA. Here the inventors found that m$^6$A deficient G mRNA with G-N-7 and ribose 2'-O methylation is not recognized by RIG-I or MDA5, suggesting that m$^6$A methylation in mRNA does not play a role in innate immunity. However, the data suggest that m$^6$A methylation of viral mRNA plays an important role in enhancing mRNA translation. First, overexpression of m$^6$A reader and writer proteins enhanced G protein expression whereas knockdown of these proteins inhibited G expression. Second, G protein expression was inhibited when m$^6$A sites in G mRNA were mutated.

The inventors found that m$^6$A-deficient hMPVs triggered significantly higher type I interferon responses compared to the parental hMPV, thereby contributing to the restriction of viral replication. In addition, both m$^6$A-deficient rhMPV and isolated antigenome and/or genome RNA induced higher expression of RIG-I. However, IFN response was completely abrogated when RIG-I or MAVs but not MDA5 were knocked out from A549 cells. The binding affinity of RIG-I to m$^6$A-deficient RNAs significantly increased compared to the m$^6$A-sufficient RNAs. This suggests that RIG-I played a dominant role in recognizing m$^6$A-deficient rhMPV and antigenome. This conclusion was further supported by the fact that the replication of m$^6$A-deficient hMPVs was completely or partially restored in A549 cells when RIG-I or MAVs but not MDA5 were knocked out. In addition, the inventors found that m$^6$A-deficient rhMPV and antigenome triggered a higher NF-κB driven SEAP activity. These results suggest that m$^6$A-deficient RNA contributes to the enhanced activation of transcription factors belonging to the NF-κB and IRF families which lead to the enhanced expression of IFN.

Overall, the degrees of the defects in RNA m$^6$A methylation are highly correlated with the levels of type I IFN responses and the levels of signaling molecules involved in the RIG-I mediated pathway. Antigenome of rhMPV-G1-14 contains more m$^6$A site mutations than the antigenome of rhMPV-G1-2 and G8-9. Consistent with higher defects in m$^6$A methylation, the antigenome of rhMPV-G1-14 induced significantly higher RIG-I expression, more RIG-I conformational changes, and more IFN production than the antigenome of rhMPV-G1-2 and G8-9 when their virion RNAs were transfected into A549 cells. Interestingly, in virus-infected cells, rhMPV-G1-2 and G8-9 induced more IFN than rhMPV-G1-14 under some conditions (e.g. MOI of 4.0 in A549 cells). The inventors interpret this discrepancy as being due to the complicated nature of IFN regulation during hMPV infection, involving viral RNA replication, protein synthesis, and alteration of host gene expression. In contrast, virion RNA transfection avoids these complicating factors, examining more directly the effects of m$^6$A methylation of RNA on IFN production. Importantly, in addition to the RIG-I pathway, several other signaling pathways including MDA5 and TLR3/TLR4/TLR7 are triggered during hMPV infection (57, 72) and may play a role. Also, several viral proteins (G, M2-2, SH, and P) have been shown to inhibit these pathways (57, 72). Since the G gene region has the strongest m$^6$A peaks in the hMPV genome, deletion of the G gene from the genome would result in a natural m$^6$A-deficient virus. Thus, it is possible that m$^6$A-deficient genome and antigenome produced by rhMPV-AG activated the RIG-I signaling pathway, rather than the loss of G protein expression suppressing RIG-I. Purified virion RNA from m$^6$A deficient rhMPVs, which did not contain any viral proteins, directly triggered higher RIG-I expression and a more robust IFN response. In addition, compensation for the reduced G protein expression did not inhibit the IFN response of these m$^6$A-deficient rhMPVs.

Viral RNA m$^6$A methylation and its functions is an emerging field that has only been explored over the past two years. Detailed mechanisms by which m$^6$A controls virus replication and gene expression are still poorly understood. The inventors demonstrated that the multiple biological functions of m$^6$A methylation collectively contribute to enhanced hMPV replication and gene expression. First, during replication, the newly synthesized genome and replicative intermediate (antigenome) are m$^6$A methylated by m$^6$A writer proteins to prevent their detection by the innate immune system. Second, during transcription, viral mRNAs are also m$^6$A methylated which enhances their translation which in turn may enhance virus spread. However, viral m$^6$A appears to play an antiviral role in several flaviviruses such as HCV and Zika virus via an unknown mechanism(s) (40, 41). Resolving why m$^6$A has a pro-viral function in some viruses whereas it has an antiviral function in other viruses may facilitate a strategy to develop m$^6$A as an antiviral drug target.

One important application of this work is in the development of live attenuated vaccine candidates for hMPV by reducing m$^6$A methylation in viral RNAs. Currently, hMPV is the second leading causative agent of acute respiratory disease in infants, children, and the elderly (76, 77), behind RSV. Despite major efforts, there is no FDA-approved vaccine for hMPV (77). Inactivated vaccines are not suitable for hMPV because they cause enhanced lung damage upon re-infection with the same virus (78). In contrast, enhanced lung damage has not been observed for live attenuated vaccine candidates (55, 79). Thus, a live attenuated vaccine is one of the most promising candidates for hMPV (80). However, it has been a challenge to identify a live attenuated vaccine strain that has an optimal balance between attenuation and immunogenicity. Since viral m$^6$A acts in a pro-viral manner for hMPV, it should be feasible to generate an m$^6$A-deficient rhMPV strain that is sufficiently attenuated yet retains high immunogenicity. In this study, the inventors showed that depletion of m$^6$A sites in G mRNA resulted in a recombinant virus (rhMPV-G1-14) that is sufficiently attenuated in replication in the lungs but only had a mild defect in replication in nasal turbinate. Cotton rats immunized with this m$^6$A-deficient hMPV expressed a high level of neutralizing antibody and were completely protected against challenge with parental rhMPV, highlighting the potential of utilizing an m6A-deficient hMPV mutant as a live vaccine candidate. This phenotype is similar to that of the cold-adapted attenuated viruses, which replicate in upper but not lower respiratory tracts. Cold-adapted (ca) temperature sensitive (ts) influenza virus vaccine has been licensed for use in humans since 1980 (81, 82).

A distinct advantage of targeting $m^6A$ sites for virus attenuation is that $m^6A$-deficient hMPV mutants are capable of inducing a significantly higher type I IFN response compared to rhMPV. A higher IFN response will likely enhance adaptive immunity. Targeting different combinations of the many viral $m^6A$ sites could identify combinations with the optimal balance between attenuation and immunogenicity. A virus with mutations in multiple $m^6A$ sites would have enhanced genetic stability because reversion at any one site would have only a minor fitness gain. In fact, all $m^6A$-deficient hMPV mutants were genetically stable; with no revertants or additional mutations detected after fifteen passages in A549 cells. In addition, $m^6A$-deficient hMPV mutants grew to reasonably high titers in cell culture, especially in IFN-deficient cells, making vaccine production economically feasible. Thus, inhibition of viral $m^6A$ methylation is a novel approach to attenuating hMPV for the rational design of live attenuated vaccines.

In summary, the inventors discovered that the presence of $m^6A$ in virion RNA serves as a molecular signature for discrimination of self from non-self RNA by the cytoplasmic RNA sensor RIG-I. This work highlights that possibility of using $m^6A$ as a novel approach for the development of antiviral drugs and live attenuated vaccines for pneumoviruses.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications described herein are specifically incorporated by reference for all purposes.

REFERENCES

The following references, to the extent that they provide exemplary procedural or other details supplementary to those set forth herein, are specifically incorporated herein by reference.

Example 1 References

1. Yue, Y., J. Liu, and C. He, RNA N6-methyladenosine methylation in post-transcriptional gene expression regulation. Genes Dev, 2015. 29(13): p. 1343-55.
2. Roundtree, I. A., et al., Dynamic RNA Modifications in Gene Expression Regulation. Cell, 2017. 169(7): p. 1187-1200.
3. Desrosiers, R., K. Friderici, and F. Rottman, Identification of methylated nucleosides in messenger RNA from Novikoff hepatoma cells. Proc Natl Acad Sci USA, 1974. 71(10): p. 3971-5.
4. Lavi, S. and A. J. Shatkin, Methylated simian virus 40-specific RNA from nuclei and cytoplasm of infected BSC-1 cells. Proc Natl Acad Sci USA, 1975. 72(6): p. 2012-6.
5. Perry, R. P., et al., The methylated constituents of L cell messenger RNA: evidence for an unusual cluster at the 5' terminus. Cell, 1975. 4(4): p. 387-94.
6. Wei, C. M., A. Gershowitz, and B. Moss, Methylated nucleotides block 5' terminus of HeLa cell messenger RNA. Cell, 1975. 4(4): p. 379-86.
7. Jia, G., et al., N6-methyladenosine in nuclear RNA is a major substrate of the obesity-associated FTO. Nat Chem Biol, 2011. 7(12): p. 885-7.
8. Zheng, G., et al., ALKBH5 is a mammalian RNA demethylase that impacts RNA metabolism and mouse fertility. Mol Cell, 2013. 49(1): p. 18-29.
9. Meyer, K. D., et al., Comprehensive analysis of mRNA methylation reveals enrichment in 3' UTRs and near stop codons. Cell, 2012. 149(7): p. 1635-46.
10. Linder, B., et al., Single-nucleotide-resolution mapping of m6A and m6Am throughout the transcriptome. Nat Methods, 2015. 12(8): p. 767-72.
11. Dominissini, D., et al., Transcriptome-wide mapping of N(6)-methyladenosine by m(6)A-seq based on immunocapturing and massively parallel sequencing. Nat Protoc, 2013. 8(1): p. 176-89.
12. Meyer, K. D. and S. R. Jaffrey, The dynamic epitranscriptome: N6-methyladenosine and gene expression control. Nat Rev Mol Cell Biol, 2014. 15(5): p. 313-26.
13. Vu, L. P., et al., The N6-methyladenosine (m6A)-forming enzyme METTL3 controls myeloid differentiation of normal hematopoietic and leukemia cells. Nat Med, 2017.
14. Jaffrey, S. R. and M. G. Kharas, Emerging links between m6A and misregulated mRNA methylation in cancer. Genome Med, 2017. 9(1): p. 2.
15. Wang, X., et al., N(6)-methyladenosine Modulates Messenger RNA Translation Efficiency. Cell, 2015. 161(6): p. 1388-99.
16. Zhao, B. S., et al., m6A-dependent maternal mRNA clearance facilitates zebrafish maternal-to-zygotic transition. Nature, 2017. 542(7642): p. 475-478.
17. Liu, J., et al., A METTL3-METTL14 complex mediates mammalian nuclear RNA N6-adenosine methylation. Nat Chem Biol, 2014. 10(2): p. 93-5.
18. Ping, X. L., et al., Mammalian WTAP is a regulatory subunit of the RNA N6-methyladenosine methyltransferase. Cell Res, 2014. 24(2): p. 177-89.
19. Dominissini, D., et al., Topology of the human and mouse m6A RNA methylomes revealed by m6A-seq. Nature, 2012. 485(7397): p. 201-6.
20. Wang, X., et al., N6-methyladenosine-dependent regulation of messenger RNA stability. Nature, 2014. 505 (7481): p. 117-20.
21. Shi, H., et al., YTHDF3 facilitates translation and decay of N6-methyladenosine-modified RNA. Cell Res, 2017. 27(3): p. 315-328.
22. Li, A., et al., Cytoplasmic m6A reader YTHDF3 promotes mRNA translation. Cell Res, 2017. 27(3): p. 444-447.
23. Kane, S. E. and K. Beemon, Precise localization of m6A in Rous sarcoma virus RNA reveals clustering of methylation sites: implications for RNA processing. Mol Cell Biol, 1985. 5(9): p. 2298-306.
24. Canaani, D., et al., Identification and mapping of N6-methyladenosine containing sequences in simian virus 40 RNA. Nucleic Acids Res, 1979. 6(8): p. 2879-99.

25. Sommer, S., et al., The methylation of adenovirus-specific nuclear and cytoplasmic RNA. Nucleic Acids Res, 1976. 3(3): p. 749-65.
26. Moss, B., et al., 5'-Terminal and internal methylated nucleosides in herpes simplex virus type 1 mRNA. J Virol, 1977. 23(2): p. 234-9.
27. Furuichi, Y., et al., Blocked, methylated 5'-terminal sequence in avian sarcoma virus RNA. Nature, 1975. 257(5527): p. 618-20.
28. Krug, R. M., M. A. Morgan, and A. J. Shatkin, Influenza viral mRNA contains internal N6-methyladenosine and 5'-terminal 7-methylguanosine in cap structures. J Virol, 1976. 20(1): p. 45-53.
29. Kennedy, E. M., et al., Posttranscriptional m(6)A Editing of HIV-1 mRNAs Enhances Viral Gene Expression. Cell Host Microbe, 2016. 19(5): p. 675-85.
30. Lichinchi, G., et al., Dynamics of the human and viral m(6)A RNA methylomes during HIV-1 infection of T cells. Nat Microbiol, 2016. 1: p. 16011.
31. Tirumuru, N., et al., N(6)-methyladenosine of HIV-1 RNA regulates viral infection and HIV-1 Gag protein expression. Elife, 2016. 5.
32. Courtney, D. G., et al., Epitranscriptomic Enhancement of Influenza A Virus Gene Expression and Replication. Cell Host Microbe, 2017. 22(3): p. 377-386 e5.
33. Tsai, K., D. G. Courtney, and B. R. Cullen, Addition of m6A to SV40 late mRNAs enhances viral structural gene expression and replication. PLoS Pathog, 2018. 14(2): p. e1006919.
34. Hesser, C. R., et al., N6-methyladenosine modification and the YTHDF2 reader protein play cell type specific roles in lytic viral gene expression during Kaposi's sarcoma-associated herpesvirus infection. PLoS Pathog, 2018. 14(4): p. e1006995.
35. Ye, F., E. R. Chen, and T. W. Nilsen, Kaposi's Sarcoma-Associated Herpesvirus Utilizes and Manipulates RNA N(6)-Adenosine Methylation To Promote Lytic Replication. J Virol, 2017. 91(16).
36. Tan, B., et al., Viral and cellular N(6)-methyladenosine and N(6),2'-O-dimethyladenosine epitranscriptomes in the KSHV life cycle. Nat Microbiol, 2018. 3(1): p. 108-120.
37. Gokhale, N. S., et al., N6-Methyladenosine in Flaviviridae Viral RNA Genomes Regulates Infection. Cell Host Microbe, 2016. 20(5): p. 654-665.
38. Lichinchi, G., et al., Dynamics of Human and Viral RNA Methylation during Zika Virus Infection. Cell Host Microbe, 2016. 20(5): p. 666-673.
39. Cowton, V. M., D. R. McGivern, and R. Fearns, Unravelling the complexities of respiratory syncytial virus RNA synthesis. J Gen Virol, 2006. 87(Pt 7): p. 1805-21.
40. Fearns, R., M. E. Peeples, and P. L. Collins, Increased expression of the N protein of respiratory syncytial virus stimulates minigenome replication but does not alter the balance between the synthesis of mRNA and antigenome. Virology, 1997. 236(1): p. 188-201.
41. Ruigrok, R. W., T. Crepin, and D. Kolakofsky, Nucleoproteins and nucleocapsids of negative-strand RNA viruses. Curr Opin Microbiol, 2011. 14(4): p. 504-10.
42. Afonso, C. L., et al., Taxonomy of the order Mononegavirales: update 2016. Arch Virol, 2016. 161(8): p. 2351-60.
43. Collins, P. L. and B. S. Graham, Viral and host factors in human respiratory syncytial virus pathogenesis. J Virol, 2008. 82(5): p. 2040-55.
44. Nair, H., et al., Global burden of acute lower respiratory infections due to respiratory syncytial virus in young children: a systematic review and meta-analysis. Lancet, 2010. 375(9725): p. 1545-55.
45. van den Hoogen, B. G., et al., A newly discovered human pneumovirus isolated from young children with respiratory tract disease. Nat Med, 2001. 7(6): p. 719-24.
46. Edwards, K. M., et al., Burden of human metapneumovirus infection in young children. N Engl J Med, 2013. 368(7): p. 633-43.
47. Kolakofsky, D. and A. Bruschi, Antigenomes in Sendai virions and Sendai virus-infected cells. Virology, 1975. 66(1): p. 185-91.
48. Liu, L., et al., QNB: differential RNA methylation analysis for count-based small-sample sequencing data with a quad-negative binomial model. BMC Bioinformatics, 2017. 18(1): p. 387.
49. Kennedy, E. M., et al., Posttranscriptional m(6)A Editing of HIV-1 mRNAs Enhances Viral Gene Expression. Cell Host Microbe, 2017. 22(6): p. 830.
50. Whelan, S. P., J. N. Barr, and G. W. Wertz, Transcription and replication of nonsegmented negative-strand RNA viruses. Curr Top Microbiol Immunol, 2004. 283: p. 61-119.
51. Johnson, S. M., et al., Respiratory Syncytial Virus Uses CX3CR1 as a Receptor on Primary Human Airway Epithelial Cultures. PLoS Pathog, 2015. 11(12): p. e1005318.
52. de Clercq, E. and J. A. Montgomery, Broad-spectrum antiviral activity of the carbocyclic analog of 3-deazaadenosine. Antiviral Res, 1983. 3(1): p. 17-24.
53. Wyde, P. R., et al., Evaluation of the toxicity and antiviral activity of carbocyclic 3-deazaadenosine against respiratory syncytial and parainfluenza type 3 viruses in tissue culture and in cotton rats. Antiviral Res, 1990. 14(4-5): p. 215-25.
54. Boyoglu-Barnum, S., et al., Mutating the CX3C Motif in the G Protein Should Make a Live Respiratory Syncytial Virus Vaccine Safer and More Effective. J Virol, 2017. 91(10).
55. Teng, M. N. and P. L. Collins, The central conserved cystine noose of the attachment G protein of human respiratory syncytial virus is not required for efficient viral infection in vitro or in vivo. J Virol, 2002. 76(12): p. 6164-71.
56. Teng, M. N., S. S. Whitehead, and P. L. Collins, Contribution of the respiratory syncytial virus G glycoprotein and its secreted and membrane-bound forms to virus replication in vitro and in vivo. Virology, 2001. 289(2): p. 283-96.
57. Vanover, D., et al., RSV glycoprotein and genomic RNA dynamics reveal filament assembly prior to the plasma membrane. Nat Commun, 2017. 8(1): p. 667.
58. Durbin, A. F., et al., RNAs Containing Modified Nucleotides Fail To Trigger RIG-I Conformational Changes for Innate Immune Signaling. MBio, 2016. 7(5).
59. Mayers, D. L., et al., Anti-human immunodeficiency virus 1 (HIV-1) activities of 3-deazaadenosine analogs: increased potency against 3'-azido-3'-deoxythymidine-resistant HIV-1 strains. Proc Natl Acad Sci USA, 1995. 92(1): p. 215-9.
60. Kim, D., B. Langmead, and S. L. Salzberg, HISAT: a fast spliced aligner with low memory requirements. Nat Methods, 2015. 12(4): p. 357-60.
61. Ma, L., et al., Evolution of transcript modification by N6-methyladenosine in primates. Genome Res, 2017. 27(3): p. 385-392.

62. Cui, X., et al., Guitar: An R/Bioconductor Package for Gene Annotation Guided Transcriptomic Analysis of RNA-Related Genomic Features. Biomed Res Int, 2016. 2016: p. 8367534.
63. Collins, P. L., et al., Production of infectious human respiratory syncytial virus from cloned cDNA confirms an essential role for the transcription elongation factor from the 5' proximal open reading frame of the M2 mRNA in gene expression and provides a capability for vaccine development. Proc Natl Acad Sci USA, 1995. 92(25): p. 11563-7.
64. Tripp, R. A., Jones, L. P., Haynes, L. M., Zheng, H., Murphy, P. M., and Anderson, L. J. CX3C chemokine mimicry by respiratory syncytial virus G glycoprotein. Nat Immunol, 2001. 2(8):732-8.

Example 2 References

1. Takeuchi O, Akira S. 2009. Innate immunity to virus infection. Immunological Reviews 227:75-86.
2. Loo Y M, Gale M, Jr. 2007. Viral regulation and evasion of the host response. Current Topics in Microbiology and Immunology 316:295-313.
3. Chow K T, Gale M, Jr., Loo Y M. 2018. RIG-I and Other RNA Sensors in Antiviral Immunity. Annual Review of Immunology 36:667-694.
4. Hornung V, Ellegast J, Kim S, Brzozka K, Jung A, Kato H, Poeck H, Akira S, Conzelmann K K, Schlee M, Endres S, Hartmann G. 2006. 5'-Triphosphate RNA is the ligand for RIG-I. Science 314:994-997.
5. Pichlmair A, Schulz O, Tan C P, Naslund T I, Liljestrom P, Weber F, Reis e Sousa C. 2006. RIG-I-mediated antiviral responses to single-stranded RNA bearing 5'-phosphates. Science 314:997-1001.
6. Saito T, Owen D M, Jiang F, Marcotrigiano J, Gale M, Jr. 2008. Innate immunity induced by composition-dependent RIG-I recognition of hepatitis C virus RNA. Nature 454:523-527.
7. Uzri D, Gehrke L. 2009. Nucleotide sequences and modifications that determine RIG-I/RNA binding and signaling activities. Journal of Virology 83:4174-4184.
8. Schlee M, Roth A, Hornung V, Hagmann C A, Wimmenauer V, Barchet W, Coch C, Janke M, Mihailovic A, Wardle G, Juranek S, Kato H, Kawai T, Poeck H, Fitzgerald K A, Takeuchi O, Akira S, Tuschl T, Latz E, Ludwig J, Hartmann G. 2009. Recognition of 5' triphosphate by RIG-I helicase requires short blunt double-stranded RNA as contained in panhandle of negative-strand virus. Immunity 31:25-34.
9. Kato H, Takeuchi O, Mikamo-Satoh E, Hirai R, Kawai T, Matsushita K, Hiiragi A, Dermody T S, Fujita T, Akira S. 2008. Length-dependent recognition of double-stranded ribonucleic acids by retinoic acid-inducible gene-I and melanoma differentiation-associated gene 5. The Journal of Experimental Medicine 205:1601-1610.
10. Runge S, Sparrer K M, Lassig C, Hembach K, Baum A, Garcia-Sastre A, Soding J, Conzelmann K K, Hopfner K P. 2014. In vivo ligands of MDA5 and RIG-I in measles virus-infected cells. PLoS Pathogens 10:e1004081.
11. Shuman S. 2002. What messenger RNA capping tells us about eukaryotic evolution. Nature reviews. Molecular Cell Biology 3:619-625.
12. Furuichi Y, LaFiandra A, Shatkin A J. 1977. 5'-Terminal structure and mRNA stability. Nature 266:235-239.
13. Hyde J L, Diamond M S. 2015. Innate immune restriction and antagonism of viral RNA lacking 2-O methylation. Virology 479-480:66-74.
14. Li J, Wang J T, Whelan S P. 2006. A unique strategy for mRNA cap methylation used by vesicular stomatitis virus. Proceedings of the National Academy of Sciences of the United States of America 103:8493-8498.
15. Ray D, Shah A, Tilgner M, Guo Y, Zhao Y, Dong H, Deas T S, Zhou Y, Li H, Shi P Y. 2006. West Nile virus 5'-cap structure is formed by sequential guanine N-7 and ribose 2'-O methylations by nonstructural protein 5. Journal of Virology 80:8362-8370.
16. Chen Y, Su C, Ke M, Jin X, Xu L, Zhang Z, Wu A, Sun Y, Yang Z, Tien P, Ahola T, Liang Y, Liu X, Guo D. 2011. Biochemical and structural insights into the mechanisms of SARS coronavirus RNA ribose 2'-O-methylation by nsp16/nsp10 protein complex. PLoS Pathogens 7:e1002294.
17. Zust R, Cervantes-Barragan L, Habjan M, Maier R, Neuman B W, Ziebuhr J, Szretter K J, Baker S C, Barchet W, Diamond M S, Siddell S G, Ludewig B, Thiel V. 2011. Ribose 2'-O-methylation provides a molecular signature for the distinction of self and non-self mRNA dependent on the RNA sensor Mda5. Nature Immunology 12:137-143.
18. Daffis S, Szretter K J, Schriewer J, Li J, Youn S, Errett J, Lin T Y, Schneller S, Zust R, Dong H, Thiel V, Sen G C, Fensterl V, Klimstra W B, Pierson T C, Buller R M, Gale M, Jr., Shi P Y, Diamond M S. 2010. 2'-O methylation of the viral mRNA cap evades host restriction by IFIT family members. Nature 468:452-456.
19. Abbas Y M, Laudenbach B T, Martinez-Montero S, Cencic R, Habjan M, Pichlmair A, Damha M J, Pelletier J, Nagar B. 2017. Structure of human IFIT1 with capped RNA reveals adaptable mRNA binding and mechanisms for sensing N1 and N2 ribose 2'-O methylations. Proceedings of the National Academy of Sciences of the United States of America 114:E2106-E2115.
20. Yue Y, Liu J, He C. 2015. RNA N6-methyladenosine methylation in post-transcriptional gene expression regulation. Genes & Development 29:1343-1355.
21. Roundtree I A, Evans M E, Pan T, He C. 2017. Dynamic RNA Modifications in Gene Expression Regulation. Cell 169:1187-1200.
22. Desrosiers R, Friderici K, Rottman F. 1974. Identification of methylated nucleosides in messenger RNA from Novikoff hepatoma cells. Proceedings of the National Academy of Sciences of the United States of America 71:3971-3975.
23. Perry R P, Kelley D E, Friderici K, Rottman F. 1975. The methylated constituents of L cell messenger RNA: evidence for an unusual cluster at the 5' terminus. Cell 4:387-394.
24. Wei C M, Gershowitz A, Moss B. 1975. Methylated nucleotides block 5' terminus of HeLa cell messenger RNA. Cell 4:379-386.
25. Liu J, Yue Y, Han D, Wang X, Fu Y, Zhang L, Jia G, Yu M, Lu Z, Deng X, Dai Q, Chen W, He C. 2014. A METTL3-METTL14 complex mediates mammalian nuclear RNA N6-adenosine methylation. Nature Chemical Biology 10:93-95.
26. Ping X L, Sun B F, Wang L, Xiao W, Yang X, Wang W J, Adhikari S, Shi Y, Lv Y, Chen Y S, Zhao X, Li A, Yang Y, Dahal U, Lou X M, Liu X, Huang J, Yuan W P, Zhu X F, Cheng T, Zhao Y L, Wang X, Rendtlew Danielsen J M, Liu F, Yang Y G. 2014. Mammalian WTAP is a regulatory subunit of the RNA N6-methyladenosine methyltransferase. Cell Research 24:177-189.
27. Jia G, Fu Y, Zhao X, Dai Q, Zheng G, Yang Y, Yi C, Lindahl T, Pan T, Yang Y G, He C. 2011. N6-methyladenosine in nuclear RNA is a major substrate of the obesity-associated FTO. Nature Chemical Biology 7:885-887.

28. Zheng G, Dahl J A, Niu Y, Fedorcsak P, Huang C M, Li C J, Vagbo C B, Shi Y, Wang W L, Song S H, Lu Z, Bosmans R P, Dai Q, Hao Y J, Yang X, Zhao W M, Tong W M, Wang X J, Bogdan F, Furu K, Fu Y, Jia G, Zhao X, Liu J, Krokan H E, Klungland A, Yang Y G, He C. 2013. ALKBH5 is a mammalian RNA demethylase that impacts RNA metabolism and mouse fertility. Molecular Cell 49:18-29.

29. Wang X, Zhao B S, Roundtree I A, Lu Z, Han D, Ma H, Weng X, Chen K, Shi H, He C. 2015. N(6)-methyladenosine Modulates Messenger RNA Translation Efficiency. Cell 161:1388-1399.

30. Dominissini D, Moshitch-Moshkovitz S, Schwartz S, Salmon-Divon M, Ungar L, Osenberg S, Cesarkas K, Jacob-Hirsch J, Amariglio N, Kupiec M, Sorek R, Rechavi G. 2012. Topology of the human and mouse m6A RNA methylomes revealed by m6A-seq. Nature 485:201-206.

31. Wang X, Lu Z, Gomez A, Hon G C, Yue Y, Han D, Fu Y, Parisien M, Dai Q, Jia G, Ren B, Pan T, He C. 2014. N6-methyladenosine-dependent regulation of messenger RNA stability. Nature 505:117-120.

32. Frye M, Harada B T, Behm M, He C. 2018. RNA modifications modulate gene expression during development. Science 361:1346-1349.

33. Zhao B S, Wang X, Beadell A V, Lu Z, Shi H, Kuuspalu A, Ho R K, He C. 2017. m(6)A-dependent maternal mRNA clearance facilitates zebrafish maternal-to-zygotic transition. Nature 542:475-478.

34. Lavi S, Shatkin A J. 1975. Methylated simian virus 40-specific RNA from nuclei and cytoplasm of infected BSC-1 cells. Proceedings of the National Academy of Sciences of the United States of America 72:2012-2016.

35. Furuichi Y, Shatkin A J, Stavnezer E, Bishop J M. 1975. Blocked, methylated 5'-terminal sequence in avian sarcoma virus RNA. Nature 257:618-620.

36. Moss B, Gershowitz A, Stringer J R, Holland L E, Wagner E K. 1977. 5'-Terminal and internal methylated nucleosides in herpes simplex virus type 1 mRNA. Journal of Virology 23:234-239.

37. Sommer S, Salditt-Georgieff M, Bachenheimer S, Darnell J E, Furuichi Y, Morgan M, Shatkin A J. 1976. The methylation of adenovirus-specific nuclear and cytoplasmic RNA. Nucleic Acids Research 3:749-765.

38. Dominissini D, Moshitch-Moshkovitz S, Salmon-Divon M, Amariglio N, Rechavi G. 2013. Transcriptome-wide mapping of N(6)-methyladenosine by m(6)A-seq based on immunocapturing and massively parallel sequencing. Nature Protocols 8:176-189.

39. Linder B, Grozhik A V, Olarerin-George A O, Meydan C, Mason C E, Jaffrey S R. 2015. Single-nucleotide-resolution mapping of m6A and m6Am throughout the transcriptome. Nature Methods 12:767-772.

40. Gokhale N S, McIntyre A B R, McFadden M J, Roder A E, Kennedy E M, Gandara J A, Hopcraft S E, Quicke K M, Vazquez C, Willer J, Ilkayeva O R, Law B A, Holley C L, Garcia-Blanco M A, Evans M J, Suthar M S, Bradrick S S, Mason C E, Horner S M. 2016. N6-Methyladenosine in Flaviviridae Viral RNA Genomes Regulates Infection. Cell Host & Microbe 20:654-665.

41. Lichinchi G, Zhao B S, Wu Y, Lu Z, Qin Y, He C, Rana T M. 2016. Dynamics of Human and Viral RNA Methylation during Zika Virus Infection. Cell Host & Microbe 20:666-673.

42. Courtney D G, Kennedy E M, Dumm R E, Bogerd H P, Tsai K, Heaton N S, Cullen B R. 2017. Epitranscriptomic Enhancement of Influenza A Virus Gene Expression and Replication. Cell Host & Microbe 22:377-386 e375.

43. Tsai K, Courtney D G, Cullen B R. 2018. Addition of m6A to SV40 late mRNAs enhances viral structural gene expression and replication. PLoS Pathogens 14:e1006919.

44. Hesser C R, Karijolich J, Dominissini D, He C, Glaunsinger B A. 2018. N6-methyladenosine modification and the YTHDF2 reader protein play cell type specific roles in lytic viral gene expression during Kaposi's sarcoma-associated herpesvirus infection. PLoS Pathogens 14:e1006995.

45. Tan B, Liu H, Zhang S, da Silva S R, Zhang L, Meng J, Cui X, Yuan H, Sorel O, Zhang S W, Huang Y, Gao S J. 2018. Viral and cellular N(6)-methyladenosine and N(6), 2'-O-dimethyladenosine epitranscriptomes in the KSHV life cycle. Nature Microbiology 3:108-120.

46. Ye F, Chen E R, Nilsen T W. 2017. Kaposi's Sarcoma-Associated Herpesvirus Utilizes and Manipulates RNA N(6)-Adenosine Methylation To Promote Lytic Replication. Journal of Virology 91.

47. Lichinchi G, Gao S, Saletore Y, Gonzalez G M, Bansal V, Wang Y, Mason C E, Rana 30 T M. 2016. Dynamics of the human and viral m(6)A RNA methylomes during HIV-1 infection of T cells. Nature Microbiology 1:16011.

48. Kennedy E M, Bogerd H P, Kornepati A V, Kang D, Ghoshal D, Marshall J B, Poling B C, Tsai K, Gokhale N S, Horner S M, Cullen B R. 2016. Posttranscriptional m(6)A Editing of HIV-1 mRNAs Enhances Viral Gene Expression. Cell Host & Microbe 19:675-685.

49. Tirumuru N, Zhao B S, Lu W, Lu Z, He C, Wu L. 2016. N(6)-methyladenosine of HIV-1 RNA regulates viral infection and HIV-1 Gag protein expression. eLife 5.

50. Herfst S, de Graaf M, Schickli J H, Tang R S, Kaur J, Yang C F, Spaete R R, Haller A A, van den Hoogen B G, Osterhaus A D, Fouchier R A. 2004. Recovery of human metapneumovirus genetic lineages a and B from cloned cDNA. Journal of Virology 78:8264-8270.

51. Zhang Y, Wei Y, Li J. 2012. Development and optimization of a direct plaque assay for human and avian metapneumoviruses. J Virol Methods 185:61-68.

52. Kim D, Pertea G, Trapnell C, Pimentel H, Kelley R, Salzberg S L. 2013. TopHat2: accurate alignment of transcriptomes in the presence of insertions, deletions and gene fusions. Genome Biology 14:R36.

53. Tripathi S, Pohl M O, Zhou Y, Rodriguez-Frandsen A, Wang G, Stein D A, Moulton H M, DeJesus P, Che J, Mulder L C, Yanguez E, Andenmatten D, Pache L, Manicassamy B, Albrecht R A, Gonzalez M G, Nguyen Q, Brass A, Elledge S, White M, Shapira S, Hacohen N, Karlas A, Meyer T F, Shales M, Gatorano A, Johnson J R, Jang G, Johnson T, Verschueren E, Sanders D, Krogan N, Shaw M, Konig R, Stertz S, Garcia-Sastre A, Chanda S K. 2015. Meta- and Orthogonal Integration of Influenza "OMICs" Data Defines a Role for UBR4 in Virus Budding. Cell Host & Microbe 18:723-735.

54. Cai H, Zhang Y, Ma Y, Sun J, Liang X, Li J. 2015. Zinc binding activity of human metapneumovirus M2-1 protein is indispensable for viral replication and pathogenesis in vivo. Journal of Virology 89:6391-6405.

55. Zhang Y, Wei Y, Zhang X, Cai H, Niewiesk S, Li J. 2014. Rational design of human metapneumovirus live attenuated vaccine candidates by inhibiting viral mRNA cap methyltransferase. Journal of Virology 88:11411-11429.
56. Kolakofsky D, Bruschi A. 1975. Antigenomes in Sendai virions and Sendai virus-infected cells. Virology 66:185-191.
57. Kolli D, Bao X, Casola A. 2012. Human metapneumovirus antagonism of innate immune responses. Viruses 4:3551-3571.
58. Kolakofsky D, Kowalinski E, Cusack S. 2012. A structure-based model of RIG-I activation. RNA 18:2118-2127.
59. Zeng W, Sun L, Jiang X, Chen X, Hou F, Adhikari A, Xu M, Chen Z J. 2010. Reconstitution of the RIG-I pathway reveals a signaling role of unanchored polyubiquitin chains in innate immunity. Cell 141:315-330.
60. Durbin A F, Wang C, Marcotrigiano J, Gehrke L. 2016. RNAs Containing Modified Nucleotides Fail To Trigger RIG-I Conformational Changes for Innate Immune Signaling. mBio 7.
61. Jiang F, Ramanathan A, Miller M T, Tang G Q, Gale M, Jr., Patel S S, Marcotrigiano J. 2011. Structural basis of RNA recognition and activation by innate immune receptor RIG-I. Nature 479:423-427.
62. Green T J, Zhang X, Wertz G W, Luo M. 2006. Structure of the vesicular stomatitis virus nucleoprotein-RNA complex. Science 313:357-360.
63. Myong S, Cui S, Cornish P V, Kirchhofer A, Gack M U, Jung J U, Hopfner K P, Ha T. 2009. Cytosolic viral sensor RIG-I is a 5'-triphosphate-dependent translocase on double-stranded RNA. Science 323:1070-1074.
64. Zheng J, Wang C, Chang M R, Devarkar S C, Schweibenz B, Crynen G C, Garcia-Ordonez R D, Pascal B D, Novick S J, Patel S S, Marcotrigiano J, Griffin P R. 2018. HDX-M S reveals dysregulated checkpoints that compromise discrimination against self RNA during RIG-I mediated autoimmunity. Nature Communications 9:5366.
65. Devarkar S C, Schweibenz B, Wang C, Marcotrigiano J, Patel S S. 2018. RIG-I Uses an ATPase-Powered Translocation-Throttling Mechanism for Kinetic Proofreading of RNAs and Oligomerization. Molecular Cell 72:355-368 e354.
66. Kariko K, Buckstein M, Ni H, Weissman D. 2005. Suppression of RNA recognition by Toll-like receptors: the impact of nucleoside modification and the evolutionary origin of RNA. Immunity 23:165-175.
67. Sioud M, Furset G, Cekaite L. 2007. Suppression of immunostimulatory siRNA-driven innate immune activation by 2'-modified RNAs. Biochemical and Biophysical Research Communications 361:122-126.
68. Coots R A, Liu X M, Mao Y, Dong L, Zhou J, Wan J, Zhang X, Qian S B. 2017. m(6)A Facilitates eIF4F-Independent mRNA Translation. Molecular Cell 68:504-514 e507.
69. Rubio R M, Depledge D P, Bianco C, Thompson L, Mohr I. 2018. RNA m(6) A modification enzymes shape innate responses to DNA by regulating interferon beta. Genes & Development 32:1472-1484.
70. Zheng Q, Hou J, Zhou Y, Li Z, Cao X. 2017. The RNA helicase DDX46 inhibits innate immunity by entrapping m(6)A-demethylated antiviral transcripts in the nucleus. Nature Immunology 18:1094-1103.
71. Winkler R, Gillis E, Lasman L, Safra M, Geula S, Soyris C, Nachshon A, Tai-Schmiedel J, Friedman N, Le-Trilling VTK, Trilling M, Mandelboim M, Hanna J H, Schwartz S, Stern-Ginossar N. 2019. m(6)A modification controls the innate immune response to infection by targeting type I interferons. Nature Immunology 20:173-182.
72. Cespedes P F, Palavecino C E, Kalergis A M, Bueno S M. 2016. Modulation of Host Immunity by the Human Metapneumovirus. Clinical Microbiology Reviews 29:795-818.
73. Bao X, Liu T, Shan Y, Li K, Garofalo R P, Casola A. 2008. Human metapneumovirus glycoprotein G inhibits innate immune responses. PLoS Pathogens 4:e1000077.
74. Kolli D, Bao X, Liu T, Hong C, Wang T, Garofalo R P, Casola A. 2011. Human metapneumovirus glycoprotein G inhibits TLR4-dependent signaling in monocyte-derived dendritic cells. Journal of Immunology 187:47-54.
75. Biacchesi S, Skiadopoulos M H, Yang L, Lamirande E W, Tran K C, Murphy B R, Collins P L, Buchholz U J. 2004. Recombinant human Metapneumovirus lacking the small hydrophobic S H and/or attachment G glycoprotein: deletion of G yields a promising vaccine candidate. Journal of Virology 78:12877-12887.
76. van den Hoogen B G, de Jong J C, Groen J, Kuiken T, de Groot R, Fouchier R A, Osterhaus A D. 2001. A newly discovered human pneumovirus isolated from young children with respiratory tract disease. Nature Medicine 7:719-724.
77. Schildgen V, van den Hoogen B, Fouchier R, Tripp R A, Alvarez R, Manoha C, Williams J, Schildgen O. 2011. Human Metapneumovirus: lessons learned over the first decade. Clinical Microbiology Reviews 24:734-754.
78. Yim K C, Cragin R P, Boukhvalova M S, Blanco J C, Hamlin M E, Boivin G, Porter D D, Prince G A. 2007. Human metapneumovirus: enhanced pulmonary disease in cotton rats immunized with formalin-inactivated virus vaccine and challenged. Vaccine 25:5034-5040.
79. Buchholz U J, Nagashima K, Murphy B R, Collins P L. 2006. Live vaccines for human metapneumovirus designed by reverse genetics. Expert Review of Vaccines 5:695-706.
80. Wen S C, Williams J V. 2015. New Approaches for Immunization and Therapy against Human Metapneumovirus. Clinical and Vaccine Immunology: CVI 22:858-866.
81. Reeve P, Almond J W, Felsenreich V, Pibermann M, Maassab H F. 1980. Studies with a cold-recombinant A/Victoria/3/75 (H3N2) virus. I. biologic, genetic, and biochemical characterization. The Journal of Infectious Diseases 142:850-856.
82. Murphy B R, Holley H P, Jr., Berquist E J, Levine M M, Spring S B, Maassab H F, Kendal A P, Chanock R M. 1979. Cold-adapted variants of influenza A virus: evaluation in adult seronegative volunteers of A/Scotland/840/74 and A/Victoria/3/75 cold-adapted recombinants derived from the cold-adapted A/Ann Arbor/6/60 strain. Infection and Immunity 23:253-259.

The invention claimed is:

1. An attenuated negative-sense single-stranded RNA virus of the family Pneumoviridae comprising sequence alterations in the viral genome or antigenome corresponding to the G gene encoding one or more $N^6$-methyladenosine (m6A) consensus sites, wherein the alterations result in reduction of m6A modifications of viral mRNA, antigenome or genome.

2. The attenuated virus of claim 1, wherein the sequence alterations change at least two nucleotides of at least one m6A consensus site.

3. The attenuated virus of claim 1, wherein at least one sequence alteration comprises a change of an adenine or a cytosine in an m6A consensus site in virus mRNA and/or the virus antigenome.

4. The attenuated virus of claim 3, wherein there are at least two sequence alterations and the two sequence alterations comprise a change of an adenine and cytosine in the same m6A consensus site in virus mRNA and/or the virus antigenome.

5. The attenuated virus of claim 1, wherein at least one of the sequence alterations changing an m6A consensus site does not alter the amino acid sequence of an encoded polypeptide.

6. The attenuated virus of claim 5, wherein the virus comprises alterations in encoded m6A consensus sites in at least three different positions in the genome or antigenome.

7. The attenuated virus of claim 1, wherein the virus is respiratory syncytial virus (RSV).

8. The attenuated RSV of claim 7, wherein the mutated m6A consensus sites are in regions 392-467 nt, 567-660 nt, and/or 716-795 nt of the G gene in reference to SEQ ID NO: 1.

9. The attenuated RSV of claim 8, wherein mutated consensus sites are in regions 392-467 nt, 567-660 nt, and 716-795 nt of the G gene in reference to SEQ ID NO: 1.

10. The attenuated virus of claim 1, wherein the virus comprises metapneumovirus (MPV).

11. The attenuated virus of claim 10, wherein mutated m6A consensus sites comprise one or more consensus sites selected from the following consensus sites in the MPV antigenome: site 1, 171-AAm$^6$AC»TA-175; site 2, 187-GAm$^6$A»GCA-191; site 3, 227-AAm$^6$ACT»G-231; site 4, 246-AGm$^6$AC»TA-250; site 5, 255-AGm$^6$AC»TA-259; site 6, 341-AGm$^6$ACA»G-345; site 7, 346-GAm$^6$A»GCC-351; site 8, 422-GAm$^6$ACA»G-426; site 9, 428-AGm$^6$ACA»G-432; site 10, 453-AAm$^6$AC»TA-457; site 11, 464-GGm$^6$ACA»G-468; site 12, 476-GAm$^6$ACA»G-480; site 13, 518-GAm$^6$ACC»G-522; and site 14, 553-AGm$^6$A»GCC-557 in reference to SEQ ID NO: 3.

12. The attenuated virus of claim 11, wherein mutated m6A consensus sites comprise one or more consensus sites selected from the following consensus sites in the MPV genome: site 1, 237-G»CGm$^6$TC»GC-241; site 2, 290-AG»Am$^6$TCC»A-294; site 3, 433-AGm$^6$T»C CC-437; site 4, 441-A»C Gm$^6$TC»GC-445; site 5, 570-AGm$^6$ T»C CC-574; and site 6, 616-AG»Am$^6$TCC»G-620 in reference to the complement of SEQ ID NO: 3.

13. The attenuated virus of claim 1, wherein the alterations do not change an encoded amino acid.

14. The attenuated virus of claim 1, wherein replication of the attenuated virus is at least 3-fold reduced compared to a virus without mutations in the viral genome encoding one or more N$^6$-methyladenosine (m6A) consensus sites in viral mRNA, the viral antigenome, or the viral genome.

15. A method for increasing immunity to a negative-sense single-stranded RNA virus of the family Pneumoviridae in a patient comprising administering to the patient a composition comprising the attenuated virus of claim 1.

16. The method of claim 15, wherein the patient is a pediatric patient.

17. The method of claim 15, wherein the patient does not have symptoms of a viral infection.

18. A method for producing an attenuated negative-sense single-stranded RNA virus of the family Pneumoviridae comprising infecting a cell line with the attenuated virus of claim 1; culturing the cell line under conditions to promote virus replication; and collecting virus particles.

19. The method of claim 18, wherein culturing the cell line under conditions to promote virus replication comprises culturing under serum-free conditions.

20. The method of claim 18, wherein the cell line comprises cells that are reduced in endogenous expression of one or more m6A writer proteins.

21. The method of claim 20, wherein the writer proteins comprise methyltransferase-like 3 (METTL3) and/or methyltransferase-like 14 (METTL14).

22. The method of claim 18, wherein the cell line comprises cells that are in reduced in expression of one or more m6A eraser proteins.

23. The method of claim 22, wherein the eraser proteins comprise fat mass and obesity-associated (FTO) and/or AlkB homolog 5 (ALKBH5).

24. The attenuated virus of claim 1, wherein the virus comprises respiratory syncytial virus (RSV) or metapneumovirus (MPV).

25. The attenuated virus of claim 1, wherein at least one sequence alteration comprises a change of a cytosine in an m6A consensus site in virus mRNA and/or the virus antigenome.

* * * * *

SEQUENCE LISTING

<160> NUMBER OF SEQ ID NOS: 31

<210> SEQ ID NO 1
<211> LENGTH: 897
<212> TYPE: DNA
<213> ORGANISM: Human orthopneumovirus

<400> SEQUENCE: 1
atgtccaaaa acaaggacca acgcaccgct aagacattag aaaggacctg ggacactctc 60
aatcatttat tattcatatc atcgtgctta tataagttaa atcttaaatc tgtagcacaa 120
atcacattat ccattctggc aatgataatc tcaacttcac ttataattgc agccatcata 180
ttcatagcct cggcaaacca caaagtcaca ccaacaactg caatcataca agatgcaaca 240
agccagatca agaacacaac cccaacatac ctcacccaga atcctcagct tggaatcagt 300
ccctctaatc cgtctgaaat tacatcacaa atcaccacca tactagcttc aacaacacca 360
ggagtcaagt caaccctgca atccacaaca gtcaagacca aaaacacaac aacaactcaa 420
acacaaccca gcaagcccac cacaaaacaa cgccaaaaca aaccaccaag caaacccaat 480
aatgattttc actttgaagt gttcaacttt gtaccctgca gcatatgcag caacaatcca 540
acctgctggg ctatctgcaa aagaatacca aacaaaaaac caggaaagaa aaccactacc 600
aagcccacaa aaaaaccaac cctcaagaca accaaaaaag atcccaaacc tcaaaccact 660
aaatcaaagg aagtacccac caccaagccc acagaagagc caaccatcaa caccaccaaa 720
acaaacatca taactacact actcacctcc aacaccacag gaaatccaga actcacaagt 780
caaatggaaa ccttccactc aacttcctcc gaaggcaatc caagcccttc tcaagtctct 840
acaacatccg agtacccatc acaaccttca tctccaccca acacaccacg ccagtag 897

<210> SEQ ID NO 2
<211> LENGTH: 15104
<212> TYPE: DNA
<213> ORGANISM: Human orthopneumovirus

<400> SEQUENCE: 2
ttgcataaac caaaaaaatg gggcaaataa gaatttgata agtaccactt aaatttaact 60
cccttggtta gagatgggca gcaattcatt gagtatgata aaagttagat tacaaaattt 120
gtttgacaat gatgaagtag cattgttaaa aataacatgc tatactgata aattaataca 180
tttaactaat gctttggcta aggcagtgat acatacaatc aaattgaatg gcattgtgtt 240
tgtgcatgtt attacaagta gtgatatttg ccctaataat aatattgtag taaaatccaa 300
tttcacaaca atgccagtac tacaaaatgg aggttatata tgggaaatga tggaattaac 360
acattgctct caacctaatg gtctactaga tgacaattgt gaaattaaat tctccaaaaa 420
actaagtgat tcaacaatga ccaattatat gaatcaatta tctgaattac ttggatttga 480
tcttaatcca taaattataa ttaatatcaa ctagcaaatc aatgtcacta acaccattag 540
ttaatataaa acttaacaga agacaaaaat ggggcaaata aatcaattca gccaacccaa 600
ccatggacac aacccacaat gataatacac cacaaagact gatgatcaca gacatgagac 660
cgttgtcact tgagaccata ataacatcac taaccagaga catcataaca cacaaattta 720
tatacttgat aaatcatgaa tgcatagtga gaaaacttga tgaaagacag gccacattta 780
cattcctggt caactatgaa atgaaactat tacacaaagt aggaagcact aaatataaaa 840
aatatactga atacaacaca aaatatggca ctttccctat gccaatattc atcaatcatg 900
atgggttctt agaatgcatt ggcattaagc ctacaaagca tactcccata atatacaagt 960

```
atgatctcaa tccataaatt tcaacacaat attcacacaa tctaaaacaa caactctatg    1020
cataactata ctccatagtc cagatggagc ctgaaaatta tagtaattta aaacttaagg    1080
agagatataa gatagaagat ggggcaaata caaccatggc tcttagcaaa gtcaagttga    1140
atgatacact caacaaagat caacttctgt catccagcaa atacaccatc caacggagca    1200
caggagatag tattgatact cctaattatg atgtgcagaa acacatcaat aagttatgtg    1260
gcatgttatt aatcacagaa gatgctaatc ataaattcac tgggttaata ggtatgttat    1320
atgcgatgtc taggttagga agagaagaca ccataaaaat actcagagat gcgggatatc    1380
atgtaaaagc aaatggagta gatgtaacaa cacatcgtca agacattaat ggaaaagaaa    1440
tgaaatttga agtgttaaca ttggcaagct taacaactga aattcaaatc aacattgaga    1500
tagaatctag aaaatcctac aaaaaaatgc taaaagaaat gggagaggta gctccagaat    1560
acaggcatga ctctcctgat tgtgggatga taatattatg tatagcagca ttagtaataa    1620
ctaaattagc agcaggggac agatctggtc ttacagccgt gattaggaga gctaataatg    1680
tcctaaaaaa tgaaatgaaa cgttacaaag gcttactacc caaggacata gccaacagct    1740
tctatgaagt gtttgaaaaa catccccact ttatagatgt ttttgttcat tttggtatag    1800
cacaatcttc taccagaggt ggcagtagag ttgaagggat ttttgcagga ttgtttatga    1860
atgcctatgg tgcagggcaa gtgatgttac ggtggggagt cttagcaaaa tcagttaaaa    1920
atattatgtt aggacatgct agtgtgcaag cagaaatgga acaagttgtt gaggtttatg    1980
aatatgccca aaaattgggt ggtgaagcag gattctacca tatattgaac aacccaaaag    2040
catcattatt atctttgact caatttcctc acttctccag tgtagtatta ggcaatgctg    2100
ctggcctagg cataatggga gagtacagag gtacaccgag gaatcaagat ctatatgatg    2160
cagcaaaggc atatgctgaa caactcaaag aaaatggtgt gattaactac agtgtactag    2220
acttgacagc agaagaacta gaggctatca acatcagct taatccaaaa gataatgatg    2280
tagagctttg agttaataaa aaatgggca ataaatcat catggaaaag tttgctcctg    2340
aattccatgg agaagatgca acaacaggg ctactaaatt cctagaatca ataaagggca    2400
aattcacatc acccaaagat cccaagaaaa agatatgtat catatctgtc aactcaatag    2460
atatagaagt aaccaaagaa agccctataa catcaaattc aactattatc aacccaacaa    2520
atgagacaga tgatactgca gggaacaagc ccaattatca agaaaaacct ctagtaagtt    2580
tcaaagaaga ccctacacca agtgataatc cttttctaa actatacaaa gaaaccatag    2640
aaacatttga taacaatgaa gaagaatcca gctattcata cgaagaaata aatgatcaga    2700
caaacgataa tataacagca agattagata ggattgatga aaaattaagt gaaatactag    2760
gaatgcttca cacattagta gtggcaagtg caggacctac atctgctcgg gatggtataa    2820
gagatgccat ggttggttta agagaagaaa tgatagaaaa aatcagaact gaagcattaa    2880
tgaccaatga cagattagaa gctatggcaa gactcaggaa tgaggaaagt gaaaagatgg    2940
caaaagacac atcagatgaa gtgtctctca atccaacatc agagaaattg aacaacctat    3000
tggaagggaa tgatagtgac aatgatctat cacttgaaga tttctgatta gttaccaatc    3060
ttcacatcaa cacacaatac caacagaaga ccaacaaact aaccaaccca atcatccaac    3120
caaacatcca tccgccaatc agccaaacag ccaacaaaac aaccagccaa tccaaaacta    3180
accacccgga aaaatctat aatatagtta caaaaaagg aaagggtgcg cgctgggca    3240 aatatggaaa catacgtgaa caagcttcac gaaggctcca catacacagc tgctgttcaa    3300
```

```
tacaatgtct tagaaaaaga cgatgaccct gcatcactta caatatgggt gcccatgttc    3360
caatcatcta tgccagcaga tttacttata aaagaactag ctaatgtcaa catactagtg    3420
aaacaaatat ccacacccaa gggaccttca ctaagagtca tgataaactc aagaagtgca    3480
gtgctagcac aaatgcccag caaatttacc atatgcgcta atgtgtcctt ggatgaaaga    3540
agcaaactag catatgatgt aaccacaccc tgtgaaatca aggcatgtag tctaacatgc    3600
ctaaaatcaa aaaatatgtt gactacagtt aaagatctca ctatgaagac actcaaccct    3660
acacatgata ttattgcttt atgtgaattt gaaaacatag taacatcaaa aaaagtcata    3720
ataccaacat acctaagatc catcagtgtc agaaataaag atctgaacac acttgaaaat    3780
ataacaacca ctgaattcaa aaatgctatc acaaatgcaa aaatcatccc ttactcagga    3840
ttactattag tcatcacagt gactgacaac aaaggagcat tcaaatacat aaagccacaa    3900
agtcaattca tagtagatct tggagcttac ctagaaaaag aaagtatata ttatgttacc    3960
acaaattgga agcacacagc tacacgattt gcaatcaaac ccatggaaga ttaaccttt     4020 tcctctacat cagtgtgtta attcatacaa actttctacc tacattcttc acttcaccat    4080
cacaatcaca aacactctgt ggttcaacca atcaaacaaa acttatctga agtcccagat    4140
catcccaagt cattgtttat cagatctagt actcaaataa gttaataaaa aatatacaca    4200
tggcgatcga catggggcaa ataatcattg gaggaaatcc aactaatcac aatatctgtt    4260
aacatagaca agtccacaca ccatacagaa tcaaccaatg gaaaatacat ccataacaat    4320
agaattctca agcaaattct ggccttactt tacactaata cacatgatca caacaataat    4380
ctctttgcta atcataatct ccatcatgat gcaatacta aacaaacttt gtgaatataa     4440
cgtattccat aacaaaacct tgagttaccc aagagctcgc gtcaacacat agcattagtt    4500
aattaaaaat tagggcccaa caatgaacta ggatatcaag actaacaata acattggggc    4560
aaatgcaaac atgtccaaaa acaaggacca acgcaccgct aagacattag aaaggacctg    4620
ggacactctc aatcatttat tattcatatc atcgtgctta tataagttaa atcttaaatc    4680
tgtagcacaa atcacattat ccattctggc aatgataatc tcaacttcac ttataattgc    4740
agccatcata ttcatagcct cggcaaacca caaagtcaca ccaacaactg caatcataca    4800
agatgcaaca agccagatca agaacacaac cccaacatac ctcacccaga atcctcagct    4860
tggaatcagt ccctctaatc cgtctgaaat tacatcacaa atcaccacca tactagcttc    4920
aacaacacca ggagtcaagt caaccctgca atccacaaca gtcaagacca aaaacacaac    4980
aacaactcaa acacacccca gcaagcccac cacaaaacaa cgccaaaaca accaccaag     5040 caaacccaat aatgattttc actttgaagt gttcaacttt gtaccctgca gcatatgcag    5100
caacaatcca acctgctggg ctatctgcaa aagaatacca acaaaaaaac caggaaagaa    5160
aaccactacc aagcccacaa aaaaaccaac cctcaagaca accaaaaaag atcccaaacc    5220
tcaaaccact aaatcaaagg aagtacccac caccaagccc acagaagagc aaccatcaa     5280 caccaccaaa acaaacatca aactacact actcacctcc aacaccacag gaaatccaga    5340
actcacaagt caaatggaaa ccttccactc aacttcctcc gaaggcaatc caagcccttc    5400
tcaagtctct acaacatccg agtacccatc acaaccttca tctccaccca acacaccacg    5460
ccagtagtta cttaaaaaca tattatcaca aaaggccttg accaaccgcg gagaatcaaa    5520
ataaactctg gggcaaataa caatggagtt gctaatcctc aaagcaaatg caattaccac    5580
aatcctcact gcagtcacat tttgttttgc ttctggtcaa aacatcactg aagaatttta    5640
tcaatcaaca tgcagtgcag ttagcaaagg ctatcttagt gctctgagaa ctggttggta    5700
```

```
taccagtgtt ataactatag aattaagtaa tatcaagaaa aataagtgta atggaacaga     5760
tgctaaggta aaattgataa aacaagaatt agataaatat aaaaatgctg taacagaatt     5820
gcagttgctc atgcaaagca cacaagcaac aaacaatcga gccagaagag aactaccaag     5880
gtttatgaat tatacactca acaatgccaa aaaaccaat gtaacattaa gcaagaaaag       5940 gaaagaaga tttcttggtt ttttgttagg tgttggatct gcaatcgcca gtggcgttgc       6000
tgtatctaag gtcctgcacc tagaagggga agtgaacaag atcaaagtg ctctactatc       6060 cacaaacaag gctgtagtca gcttatcaaa tggagttagt gttttaacca gcaaagtgtt     6120
agacctcaaa aactatatag ataaacaatt gttacctatt gtgaacaagc aaagctgcag     6180
catatcaaat atagaaactg tgatagagtt ccaacaaaag aacaacagac tactagagat     6240
taccagggaa tttagtgtta atgcaggcgt aactacacct gtaagcactt acatgttaac     6300
taatagtgaa ttattgtcat taatcaatga tatgcctata acaaatgatc agaaaaagtt     6360
aatgtccaac aatgttcaaa tagttagaca gcaaagttac tctatcatgt ccataataaa     6420
agaggaagtc ttagcatatg tagtacaatt accactatat ggtgttatag atacaccctg     6480
ttggaaacta cacacatccc ctctatgtac aaccaacaca aaagaagggg ccaacatctg     6540
tttaacaaga actgacagag gatggtactg tgacaatgca ggatcagtat ctttcttccc     6600
acaagctgaa acatgtaaag ttcaatcaaa tcgagtattt tgtgacacaa tgaacagttt     6660
aacattacca agtgaagtaa atctctgcaa tgttgacata ttcaacccca aatatgattg     6720
taaaattatg acttcaaaaa cagatgtaag cagctccgtt atcacatctc taggagccat     6780
tgtgtcatgc tatggcaaaa ctaaatgtac agcatccaat aaaaatcgtg gaatcataaa     6840
gacattttct aacgggtgcg attatgtatc aaataaaggg gtggacactg tgtctgtagg     6900
taacacatta tattatgtaa ataagcaaga aggtaaaagt ctctatgtaa aaggtgaacc     6960
aataataaat ttctatgacc cattagtatt cccctctgat gaatttgatg catcaatatc     7020
tcaagtcaac gagaagatta accagagcct agcatttatt cgtaaatccg atgaattatt     7080
acataatgta aatgctggta aatccaccac aaatatcatg ataactacta taattatagt     7140
gattatagta atattgttat cattaattgc tgttggactg ctcttatact gtaaggccag     7200
aagcacacca gtcacactaa gcaaagatca actgagtggt ataaataata ttgcatttag     7260
taactaaata aaaatagcac ctaatcatgt tcttacaatg gttactatc tgctcataga     7320 caacccatct gtcattggat tttcttaaaa tctgaacttc atcgaaactc tcatctataa     7380
accatctcac ttacactatt taagtagatt cctagtttat agttatataa aacacaattg     7440
catgccactc gagcttacca tctgtaaaaa tgaaaactgg ggcaaatatg tcacgaagga     7500
atccttgcaa atttgaaatt cgaggtcatt gcttaaatgg taagaggtgt cattttagtc     7560
ataattattt tgaatggcca ccccatgcac tgcttgtaag acaaaacttt atgttaaaca     7620
gaatacttaa gtctatggat aaaagtatag ataccttatc agaaataagt ggagctgcag     7680
agttggacag aacagaagag tatgctcttg tgtagttgg agtgctagag agttatatag     7740
gatcaataaa caatataact aaacaatcag catgtgttgc catgagcaaa ctcctcactg     7800
aactcaatag tgatgatatc aaaagctga gggacaatga agagctaaat tcacccaaga     7860
taagagtgta caatactgtc atatcatata ttgaaagcaa caggaaaaac aataaacaaa     7920
ctatccatct gttaaaaaga ttgccagcag acgtattgaa gaaaaccatc aaaaacacat     7980
tggatatcca taagagcata accatcaaca acccaaaaga atcaactgtt agtgatacaa     8040
```

```
atgaccatgc caaaaataat gatactacct gacaaatatc cttgtagtat aacttccata    8100
ctaataacaa gtagatgtag agttactatg tataatcaaa agaacacact atatttcaat    8160
caaaacaacc caaataacca tatgtactca ccgaatcaaa cattcaatga aatccattgg    8220
acctctcaag aattgattga cacaattcaa aattttctac aacatctagg tattattgag    8280
gatatatata caatatatat attagtgtca taacactcaa ttctaacact caccacatcg    8340
ttacattatt aattcaaaca attcaagttg tgggacaaaa tggatcccat tattaatgga    8400
aattctgcta atgtttatct aaccgatagt tatttaaaag gtgttatctc tttctcagag    8460
tgtaatgctt taggaagtta catattcaat ggtccttatc tcaaaaatga ttataccaac    8520
ttaattagta gacaaaatcc attaatagaa cacatgaatc taaagaaact aaatataaca    8580
cagtccttaa tatctaagta tcataaaggt gaaataaaat tagaagaacc tacttatttt    8640
cagtcattac ttatgacata caagagtatg acctcgtcag aacagattgc taccactaat    8700
ttacttaaaa agataataag aagagctata gaaataagtg atgtcaaagt ctatgctata    8760
ttgaataaac tagggcttaa agaaaaggac aagattaaat ccaacaatgg acaagatgaa    8820
gacaactcag ttattacgac cataatcaaa gatgatatac tttcagctgt taaagataat    8880
caatctcatc ttaaagcaga caaaaatcac tctacaaaac aaaaagacac aatcaaaaca    8940
acactcttga gaaaattgat gtgttcaatg caacatcctc catcatggtt aatacattgg    9000
tttaacttat acacaaaatt aaacaacata ttaacacagt atcgatcaaa tgaggtaaaa    9060
aaccatgggt ttacattgat agataatcaa actcttagtg gatttcaatt tattttgaac    9120
caatatggtt gtatagttta tcataaggaa ctcaaaagaa ttactgtgac aacctataat    9180
caattcttga catggaaaga tattagcctt agtagattaa atgtttgttt aattacatgg    9240
attagtaact gcttgaacac attaaataaa agcttaggct taagatgcgg attcaataat    9300
gttatcttga cacaactatt cctttatgga gattgtatac taaagctatt tcacaatgag    9360
gggttctaca taataaaaga ggtagaggga tttattatgt ctctaatttt aaatataaca    9420
gaagaagatc aattcagaaa acgattttat aatagtatgc tcaacaacat cacagatgct    9480
gctaataaag ctcagaaaaa tctgctatca agagtatgtc atacattatt agataagaca    9540
gtgtccgata atataataaa tggcagatgg ataattctat taagtaagtt ccttaaatta    9600
attaagcttg caggtgacaa taaccttaac aatctgagtg aactatattt tttgttcaga    9660
atatttggac acccaatggt agatgaaaga caagccatgg atgctgttaa aattaattgc    9720
aatgagacca aattttactt gttaagcagt ctgagtatgt taagaggtgc ctttatatat    9780
agaattataa aagggtttgt aaataattac aacagatggc ctactttaag aaatgctatt    9840
gttttaccct taagatggtt aacttactat aaactaaaca cttatccttc tttgttggaa    9900
cttacagaaa gagatttgat tgtgttatca ggactacgtt tctatcgtga gtttcggttg    9960
cctaaaaaag tggatcttga aatgattata aatgataaag ctatatcacc tcctaaaaat    10020
ttgatatgga ctagtttccc tagaaattac atgccatcac acatacaaaa ctatatagaa    10080
catgaaaaat taaaattttc cgagagtgat aaatcaagaa gagtattaga gtattattta    10140
agagataaca aattcaatga atgtgattta tacaactgtg tagttaatca agttatctc     10200
aacaaccta atcatgtggt atcattgaca ggcaaagaaa gagaactcag tgtaggtaga    10260
atgtttgcaa tgcaaccggg aatgttcaga caggttcaaa tattggcaga gaaaatgata    10320
gctgaaaaca ttttacaatt cttttcctgaa agtcttacaa gatatggtga tctagaacta    10380
caaaaaatat tagaactgaa agcaggaata agtaacaaat caaatcgcta caatgataat    10440
```

```
tacaacaatt acattagtaa gtgctctatc atcacagatc tcagcaaatt caatcaagca    10500
tttcgatatg aaacgtcatg tatttgtagt gatgtgctgg atgaactgca tggtgtacaa    10560
tctctatttt cctggttaca tttaactatt cctcatgtca caataatatg cacatatagg    10620
catgcacccc cctatatagg agatcatatt gtagatctta acaatgtaga tgaacaaagt    10680
ggattatata gatatcacat gggtggcatc gaagggtggt gtcaaaaact atggaccata    10740
gaagctatat cactattgga tctaatatct ctcaaaggga aattctcaat tactgcttta    10800
attaatggtg acaatcaatc aatagatata agcaaaccaa tcagactcat ggaaggtcaa    10860
actcatgctc aagcagatta tttgctagca ttaaatagcc ttaaattact gtataaagag    10920
tatgcaggca taggccacaa attaaaagga actgagactt atatatcacg agatatgcaa    10980
tttatgagta aaacaattca acataacggt gtatattacc cagctagtat aaagaaagtc    11040
ctaagagtgg gaccgtggat aaacactata cttgatgatt tcaaagtgag tctagaatct    11100
ataggtagtt tgacacaaga attagaatat agaggtgaaa gtctattatg cagtttaata    11160
tttagaaatg tatggttata taatcagatt gctctacaat taaaaaatca tgcattatgt    11220
aacaataaac tatatttgga catattaaag gttctgaaac acttaaaaac ctttttttaat   11280 cttgataata ttgatacagc attaacattg tatatgaatt tacccatgtt atttggtggt    11340
ggtgatccca acttgttata tcgaagtttc tatagaagaa ctcctgactt cctcacagag    11400
gctatagttc actctgtgtt catacttagt tattatacaa accatgactt aaaagataaa    11460
cttcaagatc tgtcagatga tagattgaat aagttcttaa catgcataat cacgtttgac    11520 aaaaaccta atgctgaatt cgtaacattg atgagagatc ctcaagcttt agggtctgag    11580
agacaagcta aaattactag cgaaatcaat agactggcag ttacagaggt tttgagtaca    11640
gctccaaaca aaatattctc caaaagtgca caacattata ctactacaga gatagatcta    11700
aatgatatta tgcaaaatat agaacctaca tatcctcatg ggctaagagt tgtttatgaa    11760
agtttaccct tttataaagc agagaaaata gtaaatctta tatcaggtac aaaatctata    11820
actaacatac tggaaaaaac ttctgccata gacttaacag atattgatag agccactgag    11880
atgatgagga aaaacataac tttgcttata aggatacttc cattggattg taacagagat    11940
aaaagagaga tattgagtat ggaaaaccta agtattactg aattaagcaa atatgttagg    12000
gaaagatctt ggtctttatc caatatagtt ggtgttacat cacccagtat catgtataca    12060
atggacatca aatatactac aagcactata tctagtggca taattataga gaaatataat    12120
gttaacagtt taacacgtgg tgagagagga cccactaaac catgggttgg ttcatctaca    12180
caagagaaaa aaacaatgcc agtttataat agacaagtct taaccaaaaa acagagagat    12240
caaatagatc tattagcaaa attggattgg gtgtatgcat ctatagataa caaggatgaa    12300
ttcatggaag aactcagcat aggaaccctt gggttaacat atgaaaaggc caagaaatta    12360
tttccacaat atttaagtgt caattatttg catcgcctta cagtcagtag tagaccatgt    12420
gaattccctg catcaatacc agcttataga acaacaaatt atcactttga cactagccct    12480
attaatcgca tattaacaga aaagtatggt gatgaagata ttgacatagt attccaaaac    12540
tgtataagct ttggccttag tttaatgtca gtagtagaac aatttactaa tgtatgtcct    12600
aacagaatta ttctcatacc taagcttaat gagatacatt tgatgaaacc tcccatattc    12660
acaggtgatg ttgatattca caagttaaaa caagtgatac aaaaacagca tatgttttta    12720
ccagacaaaa taagtttgac tcaatatgtg gaattattct aagtaataa aacactcaaa    12780
```

```
tctggatctc atgttaattc taatttaata ttggcacata aaatatctga ctattttcat    12840
aatacttaca ttttaagtac taatttagct ggacattgga ttctgattat acaacttatg    12900
aaagattcta aaggtatttt tgaaaaagat tggggagagg gatatataac tgatcatatg    12960
tttattaatt tgaaagtttt cttcaatgct tataagacct atctcttgtg ttttcataaa    13020
ggttatggca aagcaaagct ggagtgtgat atgaacactt cagatcttct atgtgtattg    13080
gaattaatag acagtagtta ttggaagtct atgtctaagg tattttaga acaaaaagtt    13140 atcaaataca ttcttagcca agatgcaagt ttacatagag taaaaggatg tcatagcttc    13200
aaattatggt ttcttaaacg tcttaatgta gcagaattca cagtttgccc ttgggttgtt    13260
aacatagatt atcatccaac acatatgaaa gcaatattaa cttatataga tcttgttaga    13320
atgggattga taaatataga tagaatacac attaaaaata aacacaaatt caatgatgaa    13380
ttttatactt ctaatctctt ctacattaat tataacttct cagataatac tcatctatta    13440
actaaacata taaggattgc taattctgaa ttagaaaata attacaacaa attatatcat    13500
cctacaccag aaaccctaga gaatatacta gccaatccga ttaaaagtaa tgacaaaaag    13560
acactgaatg actattgtat aggtaaaaat gttgactcaa taatgttacc attgttatct    13620
aataagaagc ttattaaatc gtctgcaatg attagaacca attacagcaa acaagatttg    13680
tataatttat tccctatggt tgtgattgat agaattatag atcattcagg caatacagcc    13740
aaatccaacc aactttacac tactacttcc caccaaatat ccttagtgca caatagcaca    13800
tcactttact gcatgcttcc ttggcatcat attaatagat tcaattttgt atttagttct    13860
acaggttgta aaattagtat agagtatatt ttaaagatc ttaaaattaa agatcccaat    13920
tgtatagcat tcataggtga aggagcaggg aatttattat tgcgtacagt agtggaactt    13980
catcctgaca taagatatat ttacagaagt ctgaaagatt gcaatgatca tagtttacct    14040
attgagtttt taaggctgta caatggacat atcaacattg attatggtga aaatttgacc    14100
attcctgcta cagatgcaac caacaacatt cattggtctt atttacatat aaagtttgct    14160
gaacctatca gtctttttgt ctgtgatgcc gaattgtctg taacagtcaa ctggagtaaa    14220
attataatag aatggagcaa gcatgtaaga aagtgcaagt actgttcctc agttaataaa    14280
tgtatgttaa tagtaaaata tcatgctcaa gatgatattg atttcaaatt agacaatata    14340
actatattaa aaacttatgt atgcttaggc agtaagttaa agggatcgga ggtttactta    14400
gtccttacaa taggtcctgc gaatatattc ccagtattta atgtagtaca aaatgctaaa    14460
ttgatactat caagaaccaa aaatttcatc atgcctaaga aagctgataa agagtctatt    14520
gatgcaaata ttaaaagttt gataccctt ctttgttacc ctataacaaa aaaaggaatt    14580
aatactgcat tgtcaaaact aaagagtgtt gttagtggag atactactatc atattctata    14640 gctggacgta atgaagtttt cagcaataaa cttataaatc ataagcatat gaacatctta    14700
aaatggttca atcatgtttt aaatttcaga tcaacagaac taaactataa ccatttatat    14760
atggtagaat ctacatatcc ttacctaagt gaattgttaa acagcttgac aaccaatgaa    14820
cttaaaaaac tgattaaaat cacaggtagt ctgttataca actttcataa tgaataatga    14880
ataaagatct tataataaaa attcccatag ctatacacta acactgtatt caattatagt    14940
tattaaaaat taaaaatcgt acgattttt aaataacttt tagtgaacta atcctaaagt    15000
tatcatttta atcttggagg aataaattta aaccctaatc taattggttt atatgtgtat    15060
taactaaatt acgagatatt agttttgac actttttttc tcgt                     15104
```

<210> SEQ ID NO 3
<211> LENGTH: 711
<212> TYPE: DNA
<213> ORGANISM: Human metapneumovirus

<400> SEQUENCE: 3

```
atggaggtga aagtggagaa cattcgaaca atagatatgc tcaaagcaag agtaaaaaat      60
cgtgtggcac gcagcaaatg ctttaaaaat gcctctttgg tcctcatagg aataactaca     120
ttgagtattg ccctcaatat ctatctgatc ataaactata aaatgcaaaa aaacacatct     180
gaatcagaac atcacaccag ctcatcaccc atggaatcca gcagagaaac tccaacggtc     240
cccacagaca actcagacac caactcaagc cacagcatc caactcaaca gtccacagaa      300
ggctccacac tctactttgc agcctcagca agctcaccag agacagaacc aacatcaaca     360
ccagatacaa caaaccgccc gcccttcgtc gacacacaca acaccacc aagcgcaagc       420
agaacaaaga caagtccggc agtccacaca aaaaacaacc caaggacaag ctctagaaca     480
cattctccac cacgggcaac gacaaggacg gcacgcagaa ccaccactct ccgcacaagc     540
agcacaagaa agagaccgtc cacagcatca gtccaacctg catcagcgc aacaacccac      600
aaaaacgaag aagcaagtcc agcgagccca caaacatctg caagcacaac aagaatacaa     660
aggaaaagcg tggaggccaa cacatcaaca acatacaacc aaaactagtta a             711
```

<210> SEQ ID NO 4
<211> LENGTH: 13350
<212> TYPE: DNA
<213> ORGANISM: Human metapneumovirus

<400> SEQUENCE: 4

```
gtataaatta gattccaaaa aaatatggga caagtgaaaa tgtctcttca agggattcac      60
ctgagtgatt tatcatacaa gcatgctata ttaaaagagt ctcagtacac aataaaaaga     120
gatgtgggta caacaactgc agtgacaccc tcatcattgc aacaagaaat aacactgttg     180
tgtggagaaa ttctgtatgc taaacatgct gactacaaat atgctgcaga ataggaata     240
caatatatta gcacagcttt aggatcagag agagtgcagc agattctgag gaactcaggc     300
agtgaagtcc aagtggtctt aaccagaacg tactctctgg ggaaaattaa aaacaataaa     360
ggagaagatt tacagatgtt agacatacac ggggtagaga gagctgggt agaagagata      420
gacaaagaag caaggaaaac aatggcaacc ttgcttaagg aatcatcagg taatatccca    480
caaaatcaga ggccctcagc accagacaca cccataatct tattatgtgt aggtgcctta     540
atattcacta aactagcatc aaccatgaa gtgggactag agaccacagt cagaagggct      600
aaccgtgtac taagtgatgc actcaagaga taccctagaa tggacatacc aaagattgcc     660
agatccttct atgacttatt tgaacaaaaa gtgtatcaca gaagtttgtt cattgagtat     720
ggcaaagcat taggctcatc atctacaggc agcaaagcag aaagtctatt tgttaatata     780
ttcatgcaag cttatgggc cggtcaaaca atgctaaggt gggggtcat tgccaggtca      840
tccaacaata taatgttagg acatgtatcc gtccaagctg agttaaaaca ggtcacagaa     900
gtctatgact ggtgcgaga atgggccct gaatctggac ttctacattt aaggcaaagc       960
ccaaaagctg gactgttatc actagccaac tgtcccaact tgcaagtgt tgttctcgga    1020
aatgcctcag gcttaggcat aatcggtatg tatcgaggga gagtaccaaa cacagaatta   1080
ttttcagcag ctgaaagtta tgccaaaagt ttgaaagaaa gcaataaaat aaatttctct    1140
tcattaggac ttacagatga agagaaagag gctgcagaac atttcttaaa tgtgagtgac    1200
```

```
gacagtcaaa atgattatga gtaattaaaa aagtgggaca agtcaaaatg tcattccctg    1260
aaggaaaaga tattcttttc atgggtaatg aagcagcaaa attagcagaa gctttccaga    1320
aatcattaag aaaaccaggt cataaaagat ctcaatctat tataggagaa aaagtgaata    1380
ctgtatcaga acattggaa ttacctacta tcagtagacc tgcaaaacca accataccgt    1440
cagaaccaaa gttagcatgg acagataaag gtggggcaac caaaactgaa ataaagcaag    1500
caatcaaagt catggatccc attgaagaag aagagtctac cgagaagaag gtgctaccct    1560
ccagtgatgg gaaaacccct gcagaaaaga aactgaaacc atcaactaac accaaaaga    1620 aggtttcatt tacaccaaat gaaccaggga aatatacaaa gttggaaaaa gatgctctag    1680
atttgctctc agataatgaa gaagaagatg cagaatcttc aatcttaacc tttgaagaaa    1740
gagatacttc atcattaagc attgaggcca gattggaatc aatagaggag aaattaagca    1800
tgatattagg gctattaaga acactcaaca ttgctacagc aggacccaca gcagcaagag    1860
atgggatcag agatgcaatg attggcgtaa gagaggaatt aatagcagac ataataaagg    1920
aagctaaagg gaaagcagca gaaatgatgg aagaggaaat gagtcaacga tcaaaaatag    1980
gaaatggtag tgtaaaatta acagaaaaag caaaagagct caacaaaatt gttgaagatg    2040
aaagcacaag tggagaatcc gaagaagaag aagaaccaaa agacacacaa gacaatagtc    2100
aagaagatga catttaccag ttaattatgt agtttaataa aaataaacaa tgggacaagt    2160
aaaaatggag tcctacctag tagacaccta tcaaggcatt ccttacacag cagctgttca    2220
agttgatcta atagaaaagg acctgttacc tgcaagccta acaatatggt tccctttgtt    2280
tcaggccaac acaccaccag cagtgctgct cgatcagcta aaaaccctga caataaccac    2340
tctgtatgct gcatcacaaa atggtccaat actcaaagtg aatgcatcag cccaaggtgc    2400
agcaatgtct gtacttccca aaaaatttga agtcaatgcg actgtagcac tcgatgaata    2460
tagcaaactg gaatttgaca aactcacagt ctgtgaagta aaaacagttt acttaacaac    2520
catgaaacca tacgggatgg tatcaaaatt tgtgagctca gccaaatcag ttggcaaaaa    2580
aacacatgat ctaatcgcac tatgtgattt tatggatcta gaaaagaaca cacctgttac    2640
aataccagca ttcatcaaat cagtttcaat caaagagagt gagtcagcta ctgttgaagc    2700
tgctataagc agtgaagcag accaagctct aacacaggcc aaaattgcac cttatgcggg    2760
attaattatg atcatgacta tgaacaatcc caaaggcata ttcaaaaagc ttggagctgg    2820
gactcaagtc atagtagaac taggagcata tgtccaggct gaaagcataa gcaaaatatg    2880
caagacttgg agccatcaag ggacaagata tgtcttgaag tccagataac aaccaagcac    2940
cttggccaag agctactaac cctatctcat agatcataaa gtcaccattc tagttatata    3000
aaaatcaagt tagaacaaga attaaatcaa tcaagaacgg acaaataaa aatgtcttgg    3060 aaagtggtga tcattttttc attgttaata acacctcaac acggtcttaa agagagctac    3120
ttagaagagt catgtagcac tataactgaa ggatatctca gtgttctgag gcaggttgg    3180 tacaccaatg ttttacact ggaggtaggc gatgtagaga accttacatg tgccgatgga    3240
cccagcttaa taaaacaga attagacctg accaaaagtg cactaagaga gctcagaaca    3300
gtttctgctg atcaactggc aagagaggag caaattgaaa atcccagaca atctagattc    3360
gttctaggag caatagcact cggtgttgca actgcagctg cagttacagc aggtgttgca    3420
attgccaaaa ccatccggct tgaaagtgaa gtaacagcaa ttaagaatgc cctcaaaaag    3480
accaatgaag cagtatctac attggggaat ggagttcgtg tgttggcaac tgcagtgaga    3540
gagctgaaag atttttgtgag caagaatcta acacgtgcaa tcaacaaaaa caagtgcgac    3600
```

```
attgctgacc tgaaaatggc cgttagcttc agtcaattca acagaaggtt cctaaatgtt    3660
gtgcggcaat tttcagacaa cgctggaata acaccagcaa tatctttgga cttaatgaca    3720
gatgctgaac tagccagagc tgtttccaac atgccaacat ctgcaggaca aataaaactg    3780
atgttggaga accgtgcaat ggtaagaaga aaagggttcg gattcctgat aggagtttac    3840
ggaagctccg taatttacat ggtgcaactg ccaatctttg gggttataga cacgccttgc    3900
tggatagtaa aagcagcccc ttcttgttca ggaaaaaagg gaaactatgc ttgcctctta    3960
agagaagacc aaggatggta ttgtcaaaat gcagggtcaa ctgtttacta cccaaatgaa    4020
aaagactgtg aaacaagagg agaccatgtc ttttgcgaca cagcagcagg aatcaatgtt    4080
gctgagcagt caaggagtg caacataaac atatctacta ctaattaccc atgcaaagtt    4140
agcacaggaa gacatcctat cagtatggtt gcactatctc ctcttggggc tttggttgct    4200
tgctacaagg gagtgagctg ttccattggc agcaacagag tagggatcat caagcaactg    4260
aacaaaggct gctcttatat aaccaaccaa gacgcagaca cagtgacaat agacaacact    4320
gtataccagc taagcaaagt tgaaggcgaa cagcatgtta taaaaggaag gccagtgtca    4380
agcagctttg acccagtcaa gtttcctgaa gatcaattca atgttgcact tgaccaagtt    4440
ttcgagagca ttgagaacag tcaggccttg gtggatcaat caaacagaat cctaagcagt    4500
gcagagaaag gaaacactgg cttcatcatt gtaataattc taattgctgt ccttggctct    4560
accatgatcc tagtgagtgt ttttatcata ataagaaaa caaagaaacc cacaggagca    4620
cctccagagc tgagtggtgt cacaaacaat ggcttcatac cacataatta gttaattaaa    4680 aataagtaa attaaaataa attaaaatta aaataaaaa tttgggacaa atcataatgt    4740
ctcgcaaggc tccgtgcaaa tatgaagtgc ggggcaaatg caatagagga agtgagtgca    4800
agtttaacca caattactgg agttggccag atagatactt attaataaga tcaaattatt    4860
tattaaatca acttttaagg aacactgata gagctgatgg cttatcaata atatcaggag    4920
caggcagaga agataggaca caagattttg tcctaggttc caccaatgtg gttcaaggtt    4980
atattgatga taaccaaagc ataacaaaag ctgcagcctg ttacagtcta cataatataa    5040
tcaaacaact acaagaagtt gaagttaggc aggctagaga taacaaacta tctgacagca    5100
aacatgtagc acttcacaac ttagtcctat cttatatgga gatgagcaaa actcctgcat    5160
ctttaatcaa caatctcaag agactgccga gagagaaact gaaaaaatta gcaaagctca    5220
taattgactt atcagcaggt gctgaaaatg actcttcata tgccttgcaa gacagtgaaa    5280
gcactaatca agtgcagtga gcatggtcca gtttttcatta ctatagaggt tgatgacatg    5340
atatggactc acaaggactt aaaagaagct ttatctgatg ggatagtgaa gtctcatact    5400
aacatttaca attgttattt agaaaacata gaaattatat atgtcaaggc ttacttaagt    5460
tagtaaaaac acatcagagt gggataaatg acaatgataa cattagatgt cattaaaagt    5520
gatgggtctt caaaaacatg tactcacctc aaaaaaataa ttaaagacca ctctggtaaa    5580
gtgcttattg tacttaagtt aatattagct ttactaacat ttctcacagt aacaatcacc    5640
atcaattata taaagtggaa aaacaatctg caaatatgcc agtcaaaaac tgaatcagac    5700
aaaaaggact catcatcaaa taccacatca gtcacaacca agactactct aaatcatgat    5760
atcacacagt attttaaaag tttgattcaa aggtatacaa actctgcaat aaacagtgac    5820
acatgctgga aaataaacag aaatcaatgc acaaatataa caacatacaa attttttatgt    5880 tttaaatctg aagacacaaa aaccaacaat tgtgataaac tgacagattt atgcagaaac    5940
```

```
aaaccaaaac cagcagttgg agtgtatcac atagtagaat gccattgtat atacacagtt    6000
aaatggaagt gctatcatta cccaaccgat gaaacccaat cctaaatgtt aacaccagat    6060
taggatccat ccaagtctgt tagttcaaca atttagttat ttaaaaatat tttgaaaaca    6120
agtaagtttc tatgatactt cataataata agtaataatt aattgcttaa tcatcatcac    6180
aacattattc gaaaccataa ctattcaatt taaaaagtaa aaaacaataa catgggacaa    6240
gtagttatgg aggtgaaagt ggagaacatt cgaacaatag atatgctcaa agcaagagta    6300
aaaaatcgtg tggcacgcag caaatgcttt aaaaatgcct ctttggtcct cataggaata    6360
actacattga gtattgccct caatatctat ctgatcataa actataaaat gcaaaaaaac    6420
acatctgaat cagaacatca caccagctca tcacccatgg aatccagcag agaaactcca    6480
acggtcccca cagacaactc agacaccaac tcaagcccac agcatccaac tcaacagtcc    6540
acagaaggct ccacactcta ctttgcagcc tcagcaagct caccagagac agaaccaaca    6600
tcaacaccag atacaacaaa ccgcccgccc ttcgtcgaca cacacacaac accaccaagc    6660
gcaagcagaa caaagacaag tccggcagtc cacacaaaaa acaacccaag acaagctct    6720 agaacacatt ctccaccacg ggcaacgaca aggacggcac gcagaaccac cactctccgc    6780
acaagcagca caagaaagag accgtccaca gcatcagtcc aacctgacat cagcgcaaca    6840
acccacaaaa acgaagaagc aagtccagcg agcccacaaa catctgcaag cacaacaaga    6900
atacaaagga aaagcgtgga ggccaacaca tcaacaacat acaaccaaac tagttaacaa    6960
aaaatacaaa ataactctaa gataaaccat gcagacacca acaatggaga agccaaaaga    7020
caattcacaa tctccccaaa aaggcaacaa caccatatta gctctgccca aatctccctg    7080
gaaaaaacac tcgcccatat accaaaaata ccacaaccac cccaagaaaa aaactgggca    7140
aaacaacacc caagagacaa ataacaatgg atcctctcaa tgaatccact gttaatgtct    7200
atcttcctga ctcatatctt aaaggagtga tttcctttag tgagactaat gcaattggtt    7260
catgtctctt aaaaagacct tacctaaaaa atgacaacac tgcaaaagtt gccatagaga    7320
atcctgttat cgagcatgtt agactcaaaa atgcagtcaa ttctaagatg aaaatatcag    7380
attacaagat agtagagcca gtaaacatgc aacatgaaat tatgaagaat gtacacagtt    7440
gtgagctcac attattaaaa cagtttttaa caaggagtaa aaatattagc actctcaaat    7500
taaatatgat atgtgattgg ctgcagttaa agtctacatc agatgatacc tcaatcctaa    7560
gttttataga tgtagaattt atacctagct gggtaagcaa ttggtttagt aattggtaca    7620
atctcaacaa gttgattctg gaattcagga aagaagaagt aataagaact ggttcaatct    7680
tgtgtaggtc attgggtaaa ttagtttttg ttgtatcatc atatggatgt atagtcaaga    7740
gcaacaaaag caaagagtg agcttcttca catacaatca actgttaaca tggaaagatg    7800
tgatgttaag tagattcaat gcaaattttt gtatatgggt aagcaacagt ctgaatgaaa    7860
atcaagaagg gctagggttg agaagtaatc tgcaaggcat attaactaat aagctatatg    7920
aaactgtaga ttatatgctt agtttatgtt gcaatgaagg tttctcactt gtgaaagagt    7980
tcgaaggctt tattatgagt gaaattctta ggattactga acatgctcaa ttcagtacta    8040
gatttagaaa tactttatta aatggattaa ctgatcaatt aacaaaatta aaaaataaaa    8100
acagactcag agttcatggt accgtgttag aaaataatga ttatccaatg tacgaagttg    8160
tacttaagtt attaggagat actttgagat gtattaaatt attaatcaat aaaaacttag    8220
agaatgctgc tgaattatac tatatatttta gaatattcgg tcacccaatg gtagatgaaa    8280
gagatgcaat ggatgctgtc aaattaaaca atgaaatcac aaaaatcctt aggtgggaga    8340
```

```
gcttgacaga actaagaggg gcattcatat taaggattat caaaggattt gtagacaaca    8400
acaaaagatg gcccaaaatt aaaaacttaa aagtgcttag taagagatgg actatgtact    8460
tcaaagcaaa aagttacccc agtcaacttg aattaagcga acaagatttt ttagagcttg    8520
ctgcaataca gtttgaacaa gagttttctg tccctgaaaa aaccaacctt gagatggtat    8580
taaatgataa agctatatca cctcctaaaa gattaatatg gtctgtgtat ccaaaaaatt    8640
acttacctga gaaaataaaa aatcgatatc tagaagagac tttcaatgca agtgatagtc    8700
tcaaaacaag aagagtacta gagtactatt tgaaagataa taaattcgac caaaagaac    8760
ttaaaagtta tgttgttaaa caagaatatt taaatgataa ggatcatatt gtctcgctaa    8820
ctggaaaaga aagagaatta agtgtaggta gaatgtttgc tatgcaacca ggaaaacagc    8880
gacaaataca aatattggct gaaaaattgt tagctgataa tattgtacct tttttcccag    8940
aaaccttaac aaagtatggt gatctagatc ttcagagaat aatggaaatc aaatcggaac    9000
tttcttctat taaaactaga agaaatgata gttataataa ttacattgca agagcatcca    9060
tagtaacaga tttaagtaag ttcaaccaag cctttaggta tgaaactaca gcgatctgtg    9120
cggatgtagc agatgaacta catggaacac aaagcctatt ctgttggtta catcttatcg    9180
tccctatgac aacaatgata tgtgcctata gacatgcacc accagaaaca aaaggtgaat    9240
atgatataga taagatagaa gagcaaagtg gtttatatag atatcatatg ggtggtattg    9300
aaggatggtg tcaaaaactc tggacaatgg aagctatatc tctattagat gttgtatctg    9360
taaaaacacg atgtcaaatg acatctttat taaacggtga caaccaatca atagatgtaa    9420
gtaaaccagt taagttatct gagggtttag atgaagtgaa agcagattat agcttggctg    9480
taaaaatgtt aaaagaaata agagatgcat acagaaatat aggccataaa cttaaagaag    9540
gggaaacata tatatcaaga gatcttcagt ttataagtaa ggtgattcaa tctgaaggag    9600
taatgcatcc taccoctata aaaaagatct taagagtggg accatggata aacacaatat    9660
tagatgacat taaaaccagt gcagagtcaa tagggagtct atgtcaggaa ttagaattta    9720
gggggggaaag cataatagtt agtctgatat taaggaattt ttggctgtat aatttataca    9780
tgcatgaatc aaagcaacac cccctagcag ggaagcagtt attcaaacaa ctaaataaaa    9840
cattaacatc agtgcagaga ttttttgaaa taaaaaagga aaatgaagta gtagatctat    9900
ggatgaacat accaatgcag tttggaggag gagatccagt agtcttctat agatcttct    9960
atagaaggac ccctgatttt ttaactgaag caatcagtca tgtggatatt ctgttaagaa   10020
tatcagccaa cataagaaat gaagcgaaaa taagtttctt caaagcctta ctgtcaatag   10080
aaaaaaatga acgtgctaca ctgacaacac taatgagaga tcctcaagct gttggctcag   10140
agcgacaagc aaaagtaaca agtgatatca atagaacagc agttaccagc atcttaagtc   10200
tttctccaaa tcaactttc agcgatagtg ctatacacta cagtagaaat gaagaagagg   10260
tcggaatcat tgctgacaac ataacacctg tttatcctca tggactgaga gttttgtatg   10320
aatcattacc tttcataaa gctgaaaaag ttgtgaatat gatatcagga acgaaatcca   10380
taaccaactt attacagaga acatctgcta ttaatggtga agatattgac agagctgtat   10440
ccatgatgct ggagaaccta ggattattat ctagaatatt gtcagtagtt gttgatagta   10500
tagaaattcc aaccaaatct aatggtaggc tgatatgttg tcagatatct agaaccctaa   10560
gggagacatc atgaataat atggaaatag ttggagtaac atccccctagc atcactacat   10620
gcatggatgt catatatgca actagctctc atttgaaagg gataatcatt gaaaagttca   10680
```

```
gcactgacag aactacaaga ggtcaaagag gtccaaagag cccttgggta gggtcgagca   10740
ctcaagagaa aaaattagtt cctgtttata acagacaaat tctttcaaaa caacaaagag   10800
aacagctaga agcaattgga aaaatgagat gggtatataa agggacacca ggtttaagac   10860
gattactcaa taagatttgt cttggaagtt taggcattag ttacaaatgt gtaaaacctt   10920
tattacctag gtttatgagt gtaaatttcc tacacaggtt atctgtcagt agtagaccta   10980
tggaattccc agcatcagtt ccagcttata gaacaacaaa ttaccatttt gacactagtc   11040
ctattaatca agcactaagt gagagatttg ggaatgaaga tattaatttg gtcttccaaa   11100
atgcaatcag ctgtggaatt agcataatga gtgtagtaga acaattaact ggtaggagtc   11160
caaaacagtt agttttaata cctcaattag aagaaataga cattatgcca ccaccagtgt   11220
ttcaagggaa attcaattat aagctagtag ataagataac ttctgatcaa catatcttca   11280
gtccagacaa aatagatatg ttaacactgg ggaaaatgct catgcccact ataaaaggtc   11340
agaaaacaga tcagttcctg aacaagagag agaattattt ccatgggaat aatcttattg   11400
agtctttgtc agcagcgtta gcatgtcatt ggtgtgggat attaacagag caatgtatag   11460
aaaataatat tttcaagaaa gactggggtg acgggttcat atcggatcat gcttttatgg   11520
acttcaaaat attcctatgt gtctttaaaa ctaaactttt atgtagttgg gggtcccaag   11580
ggaaaaacat taaagatgaa gatatagtag atgaatcaat agataaactg ttaaggattg   11640
ataatacttt ttggagaatg ttcagcaagg ttatgtttga atcaaaggtt aagaaaagga   11700
taatgttata tgatgtaaaa tttctatcat tagtaggtta tagggtttt aagaattggt   11760 ttatagaaca gttgagatca gctgagttgc atgaggtacc ttggattgtc aatgccgaag   11820
gtgatctggt tgagatcaag tcaattaaaa tctatttgca actgatagag caaagtttat   11880
ttttaagaat aactgttttg aactatacag atatggcaca tgctctcaca agattaatca   11940
gaaagaagtt gatgtgtgat aatgcactat taactccgat tccatcccca atggttaatt   12000
taactcaagt tattgatcct acagaacaat tagcttattt ccctaagata acatttgaaa   12060
ggctaaaaaa ttatgacact agttcaaatt atgctaaagg aaagctaaca aggaattaca   12120
tgatactgtt gccatggcaa catgttaata gatataactt tgtctttagt tctactggat   12180
gtaaagttag tctaaaaaca tgcattggaa aacttatgaa agatctaaac cctaaagttc   12240 tgtacttat tggagaaggg gcaggaaatt ggatggccag aacagcatgt gaatatcctg   12300
acatcaaatt tgtatacaga agtttaaaag atgaccttga tcatcattat cctttggaat   12360
accagagagt tataggagaa ttaagcagga aatagatag cggtgaaggg ctttcaatgg   12420
aaacaacaga tgcaactcaa aaaactcatt gggatttgat acacagagta agcaaagatg   12480
ctttattaat aactttatgt gatgcagaat ttaaggacag agatgatttt tttaagatgg   12540
taattctatg gaggaaacat gtattatcat gcagaatttg cactacttat gggacagacc   12600
tctatttatt cgcaaagtat catgctaaag actgcaatgt aaaattaccc tttttttgtga   12660 gatcagtagc cacctttatt atgcaaggta gtaaactgtc aggctcagaa tgctacatac   12720
tcttaacact aggccaccac aacaatttac cctgccatgg agaaatacaa aattctaaga   12780
tgaaaatagc agtgtgtaat gattttatg ctgcaaaaaa acttgacaat aaatctattg   12840
aagccaactg taaatcactt ttatcagggc taagaatacc gataaataag aaagaattaa   12900
atagacagag aaggttatta acactacaaa gcaaccattc ttctgtagca acagttggag   12960
gtagcaaggt catagagtct aaatggttaa caaacaaggc aaaacacaata attgattggt   13020 tagaacatat tttaaattct ccaaaaggtg aattaaatta tgatttttt gaagcattag   13080
```

```
aaaatactta ccctaatatg attaaactaa tagataatct agggaatgca gagataaaaa    13140
aactgatcaa agtaactgga tatatgcttg taagtaaaaa atgaaaaatg ataaaaatga    13200
taaaataggt gacaacttca tactattcca aagtaatcat ttgattatgc aattatgtaa    13260
tagttaatta aaaactaaaa atcaaaagtt agaaactaac aactgtcatt aagtttatta    13320
aaaataagaa attataattg gatgtatacg                                     13350
```

```
<210> SEQ ID NO 5
<211> LENGTH: 18
<212> TYPE: DNA
<213> ORGANISM: Human orthopneumovirus

<400> SEQUENCE: 5
tcaagaccaa aaacacaa                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcaagacgaa aaatacaa                                                  18

<210> SEQ ID NO 7
<211> LENGTH: 31
<212> TYPE: DNA
<213> ORGANISM: Human orthopneumovirus

<400> SEQUENCE: 7
accaaacaaa aaaccaggaa agaaaaccac t                                   31

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
accaaataaa aagccaggaa agaaaacgac t                                   31

<210> SEQ ID NO 9
<211> LENGTH: 15
<212> TYPE: DNA
<213> ORGANISM: Human orthopneumovirus

<400> SEQUENCE: 9
ccaaaacaaa catca                                                     15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccaaaacgaa tatca                                                     15
```

<210> SEQ ID NO 11
<211> LENGTH: 711
<212> TYPE: DNA
<213> ORGANISM: Human metapneumovirus

<400> SEQUENCE: 11

```
atggaggtga aagtggagaa cattcgaaca atagatatgc tcaaagcaag agtaaaaaat    60
cgtgtggcac gcagcaaatg ctttaaaaat gcctctttgg tcctcatagg aataactaca   120
ttgagtattg ccctcaatat ctatctgatc ataaactata aaatgcaaaa aaacacatct   180
gaatcagaac atcacaccag ctcatcaccc atggaatcca gcagagaaac tccaacggtc   240
cccacagaca actcagacac caactcaagc ccacagcatc caactcaaca gtccacagaa   300
ggctccacac tctactttgc agcctcagca agctcaccag agacagaacc aacatcaaca   360
ccagatacaa caaaccgccc gcccttcgtc gacacacaca caacaccacc aagcgcaagc   420
agaacaaaga caagtccggc agtccacaca aaaaacaacc caaggacaag ctctagaaca   480
cattctccac cacgggcaac gacaaggacg gcacgcagaa ccaccactct ccgcacaagc   540
agcacaagaa agagaccgtc cacagcatca gtccaacctg acatcagcgc aacaacccac   600
aaaaacgaag aagcaagtcc agcgagccca caaacatctg caagcacaac aagaatacaa   660
aggaaaagcg tggaggccaa cacatcaaca acatacaacc aaactagtta a            711
```

<210> SEQ ID NO 12
<211> LENGTH: 712
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
ttaactagtt tggttgtatg ttgttgatgt gttggcctcc acgcttttcc tttgtattct    60
tgttgtgctt gcagatgttt gtgggctcgc tggacttgct tcttcgtttt tgtgggttgt   120
tgcgctgatg tcaggttgga ctgatgctgt ggacggtctc tttcttgtgc tgcttgtgcg   180
gagagtggtg gttctgcgtg ccgtccttgt cgttgcccgt ggtggagaat gtgttctaga   240
gcttgtcctt gggttgtttt tttgtgtgga ctgccggact tgtctttgtt ctgcttgcgc   300
ttggtggtgt tgtgtgtgtg tcgacgaagg gcgggcggtt tgttgtatct ggtgttgatg   360
ttggttctgt ctctggtgag cttgctgagg ctgcaaagta gagtgtggag ccttctgtgg   420
actgttgagt tggatgctgt gggcttgagt tggtgtctga gttgtctgtg gggaccgttg   480
gagtttctct gctggattcc atgggtgatg agctggtgtg atgttctgat tcagatgtgt   540
tttttttgcat tttatagttt atgatcagat agatattgag ggcaatactc aatgtagtta   600
ttcctatgag gaccaaagag gcatttttaa agcatttgct gcgtgccaca cgattttta    660
ctcttgcttt gagcatatct attgttcgaa tgttctccac tttcacctcc at           712
```

<210> SEQ ID NO 13
<211> LENGTH: 11
<212> TYPE: DNA
<213> ORGANISM: Human orthopneumovirus

<400> SEQUENCE: 13

```
ctcaaacaca a                                                          11
```

```
<210> SEQ ID NO 14
<211> LENGTH: 26
<212> TYPE: DNA
<213> ORGANISM: Human orthopneumovirus

<400> SEQUENCE: 14
acaaaacaac gccaaaacaa accacc                                          26

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctcaaacgca a                                                          11

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acaaagcaac gccaaaataa gccacc                                          26

<210> SEQ ID NO 17
<211> LENGTH: 24
<212> TYPE: DNA
<213> ORGANISM: Human orthopneumovirus

<400> SEQUENCE: 17
aaaaaaccaa ccctcaagac aacc                                            24

<210> SEQ ID NO 18
<211> LENGTH: 18
<212> TYPE: DNA
<213> ORGANISM: Human orthopneumovirus

<400> SEQUENCE: 18
cccaaacctc aaaccact                                                   18

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaaagccaa ccctcaagac gacc                                            24

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
```
cccaagcctc aaacgact                                                    18

<210> SEQ ID NO 21
<211> LENGTH: 30
<212> TYPE: DNA
<213> ORGANISM: Human orthopneumovirus

<400> SEQUENCE: 21
ccagaactca caagtcaaat ggaaaccttc                                       30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccagagctca caagtcaaat ggaaacgttc                                       30

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tttttttttt tttttttttt ttt                                              23

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccgcgtctag ttgttcatga a                                                21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaggacgttc ccaatagcca a                                                21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atggattaaa tcagtatcta a                                                21

<210> SEQ ID NO 27

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctgcaagtat gttcactatg a                                           21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaggatgagt taatagctaa a                                           21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaacaagtac ttcttcggcg a                                           21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aaatagccgc tgcttgtgag a                                           21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acgtgacacg ttcggagaa                                              19
```